United States Patent
Dichtel et al.

(10) Patent No.: US 9,855,545 B2
(45) Date of Patent: *Jan. 2, 2018

(54) POROUS CYCLODEXTRIN POLYMERIC MATERIALS AND METHODS OF MAKING AND USING SAME

(71) Applicant: Cornell University, Ithaca, NY (US)

(72) Inventors: William R. Dichtel, Wilmette, IL (US); Alaaeddin Alsbaiee, King of Prussia, PA (US); Brian J. Smith, Ithaca, NY (US); Juan Hinestroza, Ithaca, NY (US); Diego Alzate-Sanchez, Ithaca, NY (US); Leilei Xiao, Ithaca, NY (US); Yuhan Ling, Ithaca, NY (US); Damian Helbling, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,206

(22) Filed: Mar. 3, 2017

(65) Prior Publication Data

US 2017/0173560 A1    Jun. 22, 2017

Related U.S. Application Data

(63) Continuation of application No. 15/134,030, filed on Apr. 20, 2016, now Pat. No. 9,624,314.

(60) Provisional application No. 62/149,975, filed on Apr. 20, 2015.

(51) Int. Cl.

| | |
|---|---|
| C08B 37/16 | (2006.01) |
| B01J 20/24 | (2006.01) |
| B01J 20/289 | (2006.01) |
| B01J 20/28 | (2006.01) |
| C02F 1/28 | (2006.01) |
| B01D 53/02 | (2006.01) |
| B01D 15/40 | (2006.01) |
| G01N 30/14 | (2006.01) |
| G01N 30/30 | (2006.01) |
| G01N 33/02 | (2006.01) |
| C02F 103/06 | (2006.01) |
| C02F 101/30 | (2006.01) |

(52) U.S. Cl.
CPC .............. *B01J 20/24* (2013.01); *B01D 15/40* (2013.01); *B01D 53/025* (2013.01); *B01J 20/289* (2013.01); *B01J 20/28033* (2013.01); *C02F 1/285* (2013.01); *C08B 37/0012* (2013.01); *G01N 30/14* (2013.01); *G01N 30/30* (2013.01); *G01N 33/02* (2013.01); *B01D 2253/202* (2013.01); *B01D 2253/306* (2013.01); *B01D 2253/308* (2013.01); *B01D 2253/31* (2013.01); *B01D 2257/708* (2013.01); *C02F 2101/305* (2013.01); *C02F 2103/06* (2013.01)

(58) Field of Classification Search
CPC .......... B01J 20/24; B01J 20/26; B01J 20/267; B01D 15/08–15/428; B01D 53/02–53/1493; G01N 30/14; G01N 33/02; C08B 37/0012
See application file for complete search history.

(56) References Cited

U.S. PATENT DOCUMENTS

| | | |
|---|---|---|
| 4,958,015 A | 9/1990 | Zemel et al. |
| 5,104,547 A | 4/1992 | Cabrera et al. |
| 9,505,850 B2 | 11/2016 | Sakata et al. |
| 2005/0154198 A1 | 7/2005 | Trotta et al. |
| 2006/0009592 A1 | 1/2006 | Ochs et al. |
| 2016/0271580 A1 | 9/2016 | Trotta et al. |

FOREIGN PATENT DOCUMENTS

WO        9625438 A1        8/1996

OTHER PUBLICATIONS

Alsbaiee, A., et al., Rapid removal of organic micropollutants from water by a porous beta-cyclodextrin polymer, Nature, Dec. 21, 2015, vol. 529, pp. 190-194.

Oishi, Y., et al., Preparation and Properties of Fluorine-Containing Aromatic Polyamides from Tetrafluorophthayoyl Chlorides and Aromatic Diamines, Journal of Polymer Science: Part A: Polymer Chemistry, 1989, vol. 27, pp. 3393-3403.

*Primary Examiner* — Leigh C Maier

(74) *Attorney, Agent, or Firm* — Hodgson Russ LLP

(57) ABSTRACT

A nucleophilic substitution reaction to crosslink cyclodextrin (CD) polymer with rigid aromatic groups, providing a high surface area, mesoporous CD-containing polymers (P-CDPs). The P-CDPs can be used for removing organic contaminants from water. By encapsulating pollutants to form well-defined host-guest complexes with complementary selectivities to activated carbon (AC) sorbents. The P-CDPs can rapidly sequester pharmaceuticals, pesticides, and other organic micropollutants, achieving equilibrium binding capacity in seconds with adsorption rate constants 15-200 times greater than ACs and nonporous CD sorbents. The CD polymer can be regenerated several times, through a room temperature washing procedure, with no loss in performance.

30 Claims, 71 Drawing Sheets

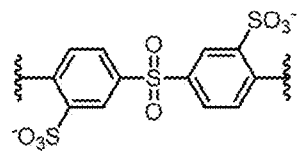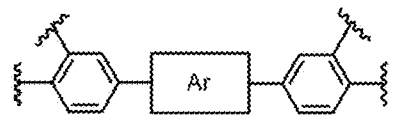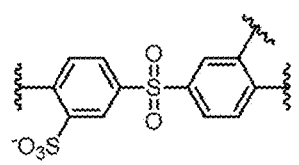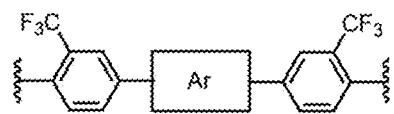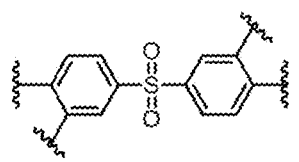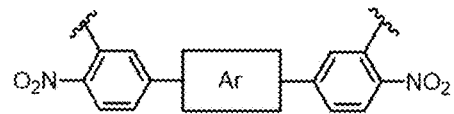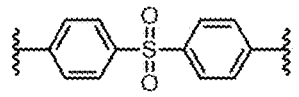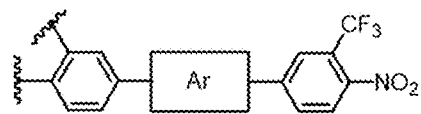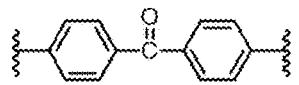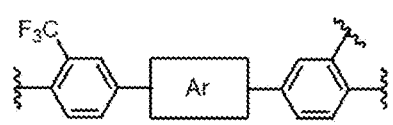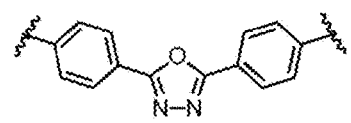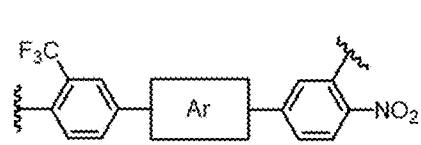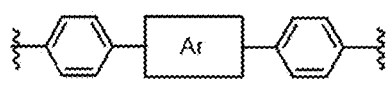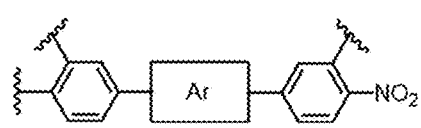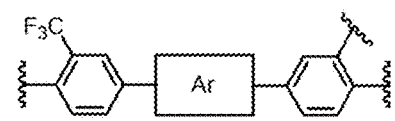
FIG. 1

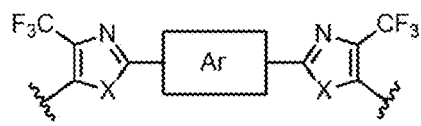
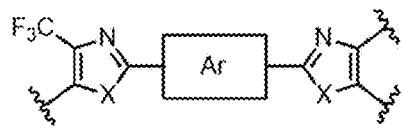
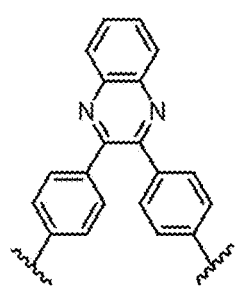
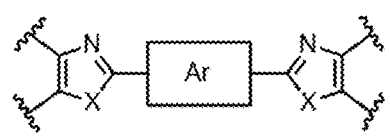
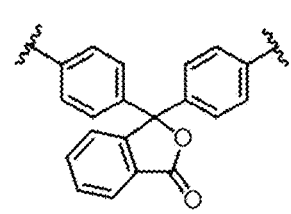
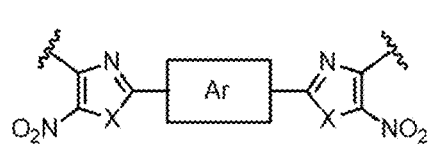
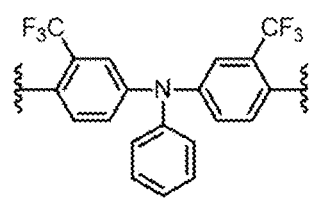
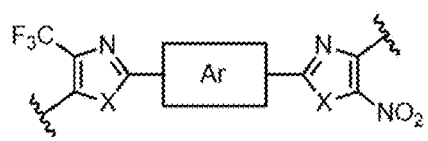
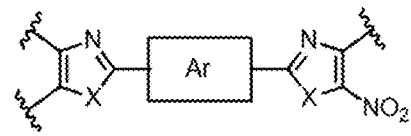
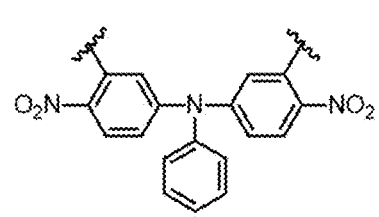
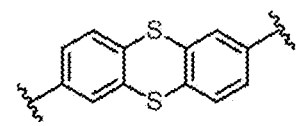
FIG. 2

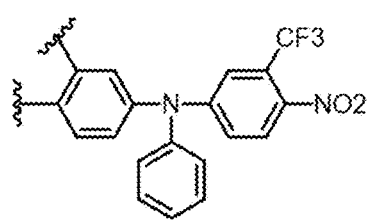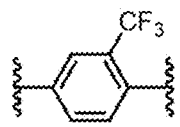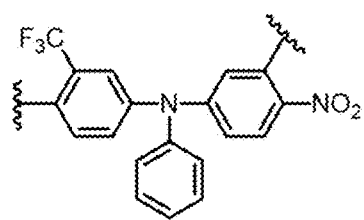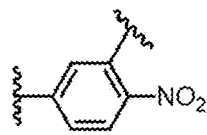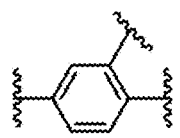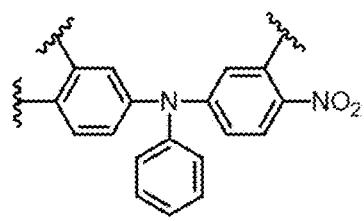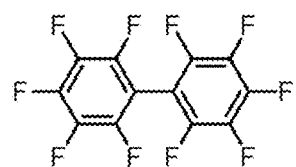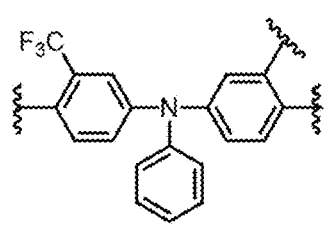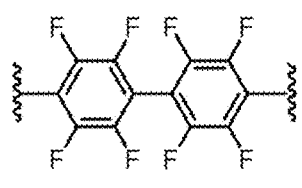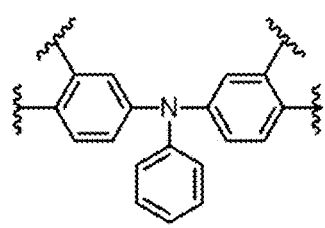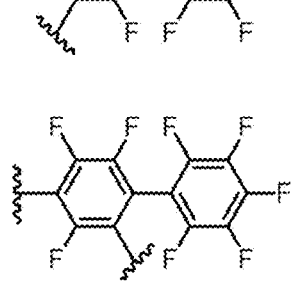
FIG. 3

| Pollutant | logK$_{ow}$[a] | logD[b] | MW (g/mol) | pKa | C$_s$ (g/L)[c] | Min z L (Å)[d] | Max z L (Å)[e] |
|---|---|---|---|---|---|---|---|
| BPA | 3.6 | 3.6 | 228.3 | 9.7 | 0.12 | 12.4 | 8.6 |
| BPS | 1.6 | 1.7 | 250.3 | 7.6[f] | 0.38[f] | 12.8 | 7.0 |
| metolachlor | 3.2 | 3.2 | 283.8 | 1.4[f] | 0.53 | 12.1 | 9.0 |
| ethinyl estradiol | 4.1 | 3.9 | 296.4 | 10.4 | 0.002 | 13.9 | 8.0 |
| propranolol | 2.6 | 1.1 | 259.3 | 9.5 | 0.050 (ref) | 15.4 | 8.3 |
| 2-naphthol (2-NO) | 2.7 | 2.9 | 144.2 | 9.5 | 0.76 | 9.6 | 4.0 |
| 1-naphthyl amine (1-NA) | 2.2 | 2.3 | 143.2 | 3.9 | 1.7 | 9.5 | 4.1 |
| 2,4-dichlorophenol (DCP) | 2.8 | 3.0 | 163.0 | 7.9 | 4.5 | 8.8 | 4.2 |

[a] Log octanol-water partition coefficient. Predicted using KOWWIN v1.67 software implemented in ChemSpider Database.
[b] Log distribution coefficient at pH = 7.4. Predicted using ACD/Labs Percepta software implemented in ChemSpider Database.
[c] Solubility in water. Experimental values.
[d] Minimal molecular z length. Defined as the length of the conformer perpendicular to its minimal projection area. Generated using ChemAxon software implemented in ChemSpider Database.
[e] Maximum molecular z length. Defined as the length of the conformer perpendicular to its maximal projection area. Generated using ChemAxon software implemented in ChemSpider Database.
[f] Calculated using Advanced Chemistry Development (ACD/Labs) Software V11.02, as implemented in the SciFinder CAS Database.

FIG. 48

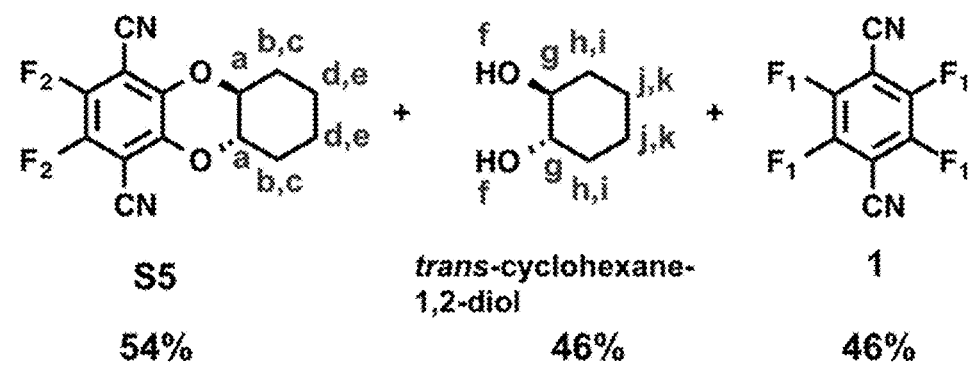
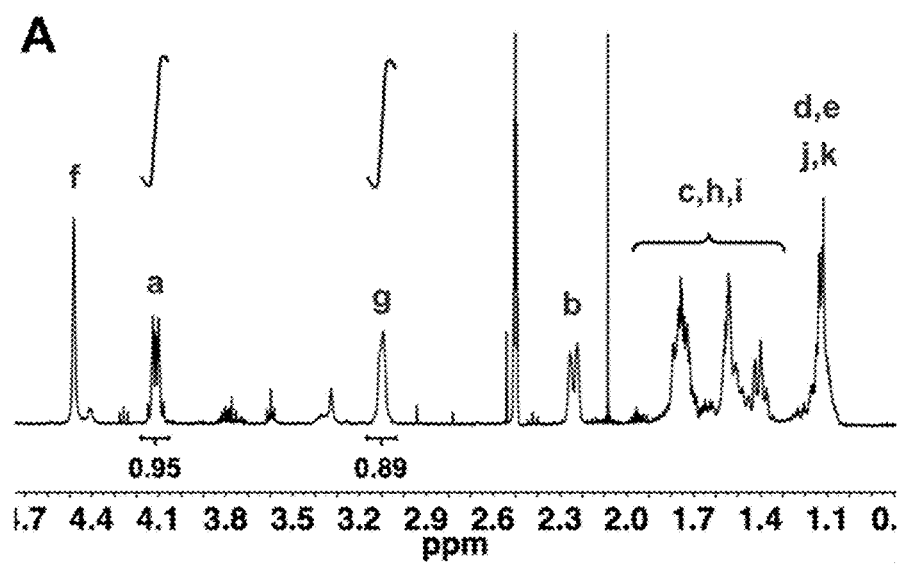
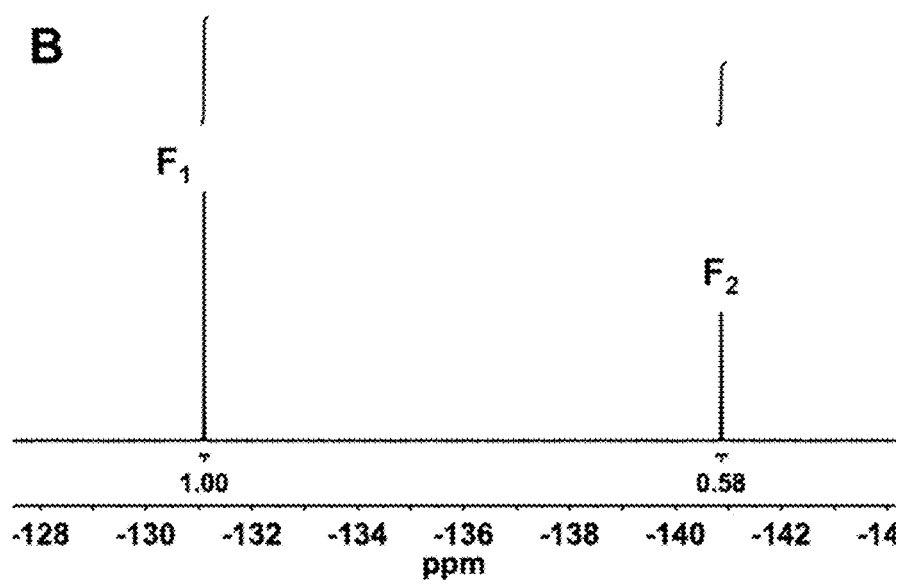
FIG. 77

| Compound Name | Supplier | Chemical Formula | pKa | LogKow | Charge State at pH = 7.4 | McGowan Volume |
|---|---|---|---|---|---|---|
| 2,4-D | Aldrich | C8H6Cl2O3 | 3.0±0.1 | 2.50 | - | 1.38 |
| Abacavir | Aldrich | C14H18N6O | 14.9±0.1 | 0.39 | n | 2.09 |
| Acebutolol | Aldrich | C18H28N2O4 | 13.8±0.2 | 1.53 | + | 2.76 |
| Acetaminophen | USP | C8H9NO2 | 9.9±0.1 | 0.91 | n | 1.17 |
| Acetochlor | Aldrich | C14H20ClNO2 | 1.3±0.5 | 3.50 | n | 2.14 |
| Albuterol | Aldrich | C13H21NO3 | 10.0±0.3 | 0.34 | + | 1.98 |
| Allopurinol | Aldrich | C5H4N4O | 9.2±0.5 | 0.35 | n | 0.88 |
| Amphetamine | Aldrich | C9H13N | 9.9±0.1 | 1.8 | + | 1.24 |
| Atenolol | Aldrich | C14H22N2O3 | 13.9±0.2 | 0.43 | + | 2.18 |
| Atenolol Acid | Aldrich | C14H21N1O4 | 4.4±0.1 | -1.24 | z | 2.14 |
| Atrazine | Aldrich | C8H14Cl1N5 | 2.3±0.1 | 1.76 | n | 1.62 |
| Benzotriazole-methyl-1H | Aldrich | C7H7N3 | 8.7±0.4 | 1.81 | n | 1.01 |
| Bromacil | Aldrich | C9H13BrN2O2 | 8.8±0.4 | 1.69 | z | 1.63 |
| Bupropion | Cerilliant | C13H18ClNO | | 3.27 | + | 1.94 |
| Caffeine | USP | C8H10N4O2 | 0.5±0.7 | -0.55 | n | 1.36 |
| Carbamazepine | Aldrich | C15H12N2O | 13.9±0.2 | 2.77 | n | 1.81 |
| Carbaryl | Aldrich | C12H11NO2 | 12.0±0.5 | 2.96 | n | 1.54 |
| Carbofuran | Aldrich | C12H15NO3 | 12.3±0.5 | 1.30 | n | 1.69 |
| Chloridazon | Aldrich | C10H8Cl1N3O1 | 0.7±0.2 | 1.11 | n | 1.52 |
| Chloroxylenol | Aldrich | C8H9ClO | 9.8±0.2 | 3.30 | n | 1.18 |
| Cimetidine | Aldrich | C10H16N6S | 14.1±0.1 | -0.29 | n | 1.96 |
| Clofibric Acid | Aldrich | C10H11ClO3 | 3.2±0.1 | 2.90 | - | 1.54 |
| Codeine | Cerilliant | C18H21NO3 | 13.4±0.2 | 1.34 | + | 2.21 |
| Cotinine | Cerilliant | C10H12N2O | 4.7±0.1 | 0.21 | n | 1.39 |
| DEET | Aldrich | C12H17NO | -1.4±0.7 | 2.50 | n | 1.68 |
| Diazinon | Aldrich | C12H21N2O3P1S1 | 1.2±0.3 | 4.19 | n | 2.31 |

FIG. 80

| Compound Name | Supplier | Chemical Formula | pKa | LogKow | Charge State at pH = 7.4 | McGowan Volume |
|---|---|---|---|---|---|---|
| Diclofenac | Aldrich | C14H11Cl2N1O2 | 4.2±0.1 | 4.60 | - | 2.03 |
| Dimethoate | Aldrich | C5H12NO3PS2 | 14.4±0.5 | -1.48 | n | 1.58 |
| Diuron | Aldrich | C9H10Cl2N2O1 | 13.6±0.7 | 2.30 | n | 1.60 |
| Efavirenz | Aldrich | C14H9ClF3NO2 | 10.2±0.4 | 5.15 | n | 1.89 |
| Erythromycin | Aldrich | C37H67NO13 | 13.1±0.7 | 2.60 | + | 5.77 |
| Estrone | Aldrich | C18H22O2 | 10.3±0.4 | 4.31 | n | 2.16 |
| Famotidine | Aldrich | C8H15N7O2S3 | 7.5±0.4 | -1.95 | + | 2.26 |
| Fluconazole | Aldrich | C13H12F2N6O | 11.0±0.3 | 0.56 | n | 2.01 |
| Fluoxetine | Aldrich | C17H18F3NO | 10.1±0.1 | 4.17 | + | 2.24 |
| Gemfibrozil | Aldrich | C15H22O3 | 4.8± 0.5 | 4.39 | - | 2.12 |
| Hydrocodone | Cerilliant | C18H21NO3 | 8.5±0.2 | 1.96 | + | 2.21 |
| Ibuprofen | Arcos Organics | C13H18O2 | 4.4±0.1 | 3.84 | - | 1.78 |
| Imidacloprid | Aldrich | C9H10ClN5O2 | 7.2±0.2 | -0.59 | z | 1.68 |
| Iopromid | Aldrich | C18H24I3N3O8 | 10.6±0.7 | -0.44 | z | 3.82 |
| Ioxynil | Aldrich | C7H3I2NO | 5.0±0.2 | 3.38 | - | 1.45 |
| Isoproturon | Aldrich | C12H18N2O1 | 15.1±0.7 | 2.57 | n | 1.78 |
| Ketoprofen | Aldrich | C16H14O3 | 4.2±0.1 | 3.61 | - | 1.98 |
| Linuron | Aldrich | C9H10Cl2N2O2 | 12.1±0.7 | 2.30 | n | 1.66 |
| Malaoxon | Aldrich | C10H19O7PS | N.A | 0.97 | n | 2.21 |
| MCPA | Aldrich | C9H9ClO3 | 3.1±0.1 | 2.41 | - | 1.39 |
| Mecoprop | Aldrich | C10H11ClO3 | 3.2±0.1 | 2.98 | - | 1.54 |
| Meprobamate | Cerilliant | C9H18N2O4 | 13.1±0.5 | 0.93 | n | 1.73 |
| Methomyl | Aldrich | C5H10N2O2S | 13.3±0.5 | 0.72 | n | 1.21 |
| Metolachlor | Aldrich | C15H22ClNO2 | 1.5±0.5 | 3.45 | n | 2.28 |
| Metoprolol | Aldrich | C15H25NO3 | 13.9±0.2 | 1.76 | + | 2.26 |
| Metribuzin | Aldrich | C8H14N4O1S1 | -0.2±0.2 | 1.96 | n | 1.62 |
| Molinate | Aldrich | C9H17NOS | -1.2±0.2 | 2.34 | n | 1.55 |
| Morphine | Cerilliant | C17H19O3 | 9.5±0.4 | 0.90 | + | 2.06 |
| Nadolol | Aldrich | C17H27NO4 | 13.9±0.2 | 0.87 | + | 2.49 |
| Naproxen | Aldrich | C14H14O3 | 4.8±0.3 | 2.99 | - | 1.78 |
| Oxcarbazepine | Aldrich | C15H12N2O2 | 13.7±0.2 | 1.82 | n | 1.87 |
| Oxybenzone | Aldrich | C14H12O3 | 7.6±0.4 | 3.62 | - | 1.74 |
| Paraxanthine | Aldrich | C7H8N4O2 | 8.5±0.5 | 0.09 | n | 1.22 |

FIG. 80 (continued)

| Compound Name | Supplier | Chemical Formula | pKa | LogKow | Charge State at pH = 7.4 | McGowan Volume |
|---|---|---|---|---|---|---|
| Penciclovir | Aldrich | C10H15N5O3 | 14.4±0.1 | -1.69 | n | 1.80 |
| Pentoxyfylline | Aldrich | C13H18N4O3 | 0.5±0.7 | 0.23 | n | 2.08 |
| PFBA | Aldrich | C4HF7O2 | 0.4±0.1 | 2.31 | - | 0.87 |
| PFOA | Aldrich | C8HF15O2 | 0.5±0.1 | 5.11 | - | 1.58 |
| Phenytoin | Aldrich | C15H12N2O2 | 8.3±0.1 | 3.40 | z | 1.87 |
| Progesterone | Aldrich | C21H30O2 | N.A | 4.15 | n | 2.62 |
| Prometon | Aldrich | C10H19N5O | 4.4±0.41 | 1.75 | n | 1.84 |
| Propachlor | Aldrich | C11H14ClNO | 0.3±0.5 | 2.39 | n | 1.66 |
| Ranitidine | USP | C13H22N4O3S | 8.4±0.3 | 0.99 | z | 2.40 |
| Siduron | Aldrich | C14H20N2O | 12.4±0.4 | 3.27 | n | 1.95 |
| Simazine | Aldrich | C7H12ClN5 | 2.7±0.1 | 0.63 | n | 1.48 |
| Sitagliptin | Aldrich | C16H15F6N5O | 7.2±0.1 | 1.26 | + | 2.44 |
| Sucralose | Aldrich | C12H19Cl3O8 | 12.5±0.7 | -0.47 | n | 2.42 |
| Sulfamethoxazole | Aldrich | C10H11N3O3S | 5.8±0.5 | 0.79 | - | 1.72 |
| Sulfathiazole | Aldrich | C9H9N3O2S2 | 7.2±0.1 | 0.98 | - | 1.69 |
| TCEP | Aldrich | C6H12Cl3O4P | N.A | 2.11 | n | 1.76 |
| Testosterone | Aldrich | C19H28O2 | 15.1±0.6 | 3.37 | n | 2.38 |
| Tramadol | Cerilliant | C16H25NO2 | 14.5±0.4 | 2.45 | + | 2.23 |
| Tributyl Phosphate | Aldrich | C12H27O4P | N.A | 4.09 | n | 2.24 |
| Triclosan | Aldrich | C12H7Cl3O2 | 7.8±0.4 | 4.98 | n | 1.81 |
| Trimethoprim | Aldrich | C14H18N4O3 | 7.0±0.1 | 0.89 | + | 2.18 |
| Valsartan | USP | C24H29N5O3 | 3.6±0.1 | 5.27 | - | 3.41 |
| Venlafaxine | USP | C17H27NO2 | 14.8±0.2 | 2.74 | + | 2.37 |
| Warfarin | Aldrich | C19H16O4 | 4.5±1.0 | 3.52 | - | 2.31 |

FIG. 80 (continued)

| Compound Name | Exact Mass | Ionization Mode | Retention Time, (min) | Limit of Quantification, (ng/l) |
|---|---|---|---|---|
| 2,4-D | 219.97 | Negative | 14.03 | 10.00 |
| Abacavir | 286.15 | Positive | 9.25 | 5.00 |
| Acebutolol | 336.20 | Positive | 10.11 | 5.00 |
| Acetaminophen | 151.06 | Positive | 8.32 | 10.00 |
| Acetochlor | 269.12 | Positive | 16.20 | 10.00 |
| Albuterol | 239.15 | Positive | 8.12 | 5.00 |
| Allopurinol | 136.04 | Positive | 7.35 | 200.00 |
| Amphetamine | 135.10 | Positive | 9.30 | 5.00 |
| Atenolol | 266.16 | Positive | 8.16 | 5.00 |
| Atenolol Acid | 267.15 | Positive | 9.24 | 5.00 |
| Atrazine | 215.09 | Positive | 13.17 | 5.00 |
| Benzotriazole-methyl-1H | 133.06 | Positive | 11.12 | 5.00 |
| Bromacil | 260.02 | Positive | 12.03 | 10.00 |
| Bupropion | 239.11 | Positive | 10.92 | 5.00 |
| Caffeine | 194.08 | Positive | 9.44 | 5.00 |
| Carbamazepine | 236.09 | Positive | 12.55 | 5.00 |
| Carbaryl | 201.08 | Positive | 12.52 | 10.00 |
| Carbofuran | 221.11 | Positive | 12.02 | 5.00 |
| Chloridazon | 221.04 | Positive | 10.62 | 5.00 |
| Chloroxylenol | 156.03 | Negative | 15.26 | 200.00 |
| Cimetidine | 252.12 | Positive | 8.31 | 5.00 |
| Clofibric Acid | 214.04 | Negative | 14.70 | 10.00 |
| Codeine | 299.15 | Positive | 8.52 | 10.00 |
| Cotinine | 176.09 | Positive | 6.93 | 50.00 |
| DEET | 191.13 | Positive | 13.31 | 5.00 |
| Diazinon | 304.10 | Positive | 17.47 | 5.00 |
| Diclofenac | 295.02 | Positive | 17.36 | 10.00 |
| Dimethoate | 229.00 | Positive | 10.52 | 5.00 |
| Diuron | 232.02 | Positive | 13.88 | 10.00 |
| Efavirenz | 315.03 | Positive | 17.39 | 10.00 |
| Erythromycin | 733.46 | Positive | 13.20 | 200.00 |
| Estrone | 270.16 | Positive | 11.72 | 5.00 |
| Famotidine | 337.04 | Positive | 8.29 | 10.00 |
| Fluconazole | 306.10 | Positive | 10.43 | 50.00 |
| Fluoxetine | 309.13 | Positive | 14.06 | 10.00 |
| Gemfibrozil | 250.16 | Positive | 19.30 | 10.00 |
| Hydrocodone | 299.15 | Positive | 8.82 | 5.00 |
| Ibuprofen | 206.13 | Positive | 17.76 | 10.00 |
| Imidacloprid | 255.05 | Positive | 10.06 | 5.00 |
| Iopromid | 790.87 | Positive | 8.43 | 5.00 |
| Ioxynil | 370.83 | Negative | 14.26 | 5.00 |
| Isoproturon | 206.14 | Positive | 13.56 | 5.00 |
| Ketoprofen | 254.09 | Positive | 14.30 | 10.00 |

FIG. 81

| Compound Name | Exact Mass | Ionization Mode | Retention Time, (min) | Limit of Quantification, (ng/l) |
|---|---|---|---|---|
| Linuron | 248.01 | Positive | 14.87 | 10.00 |
| Malaoxon | 314.06 | Positive | 12.06 | 5.00 |
| MCPA | 200.02 | Negative | 14.37 | 5.00 |
| Mecoprop | 214.04 | Negative | 15.60 | 5.00 |
| Meprobamate | 218.13 | Positive | 11.28 | 10.00 |
| Methomyl | 162.05 | Positive | 9.20 | 5.00 |
| Metolachlor | 283.13 | Positive | 16.35 | 5.00 |
| Metoprolol | 267.18 | Positive | 10.23 | 5.00 |
| Metribuzin | 214.09 | Positive | 11.99 | 5.00 |
| Molinate | 187.10 | Positive | 15.37 | 5.00 |
| Morphine | 285.14 | Positive | 7.52 | 10.00 |
| Nadolol | 309.19 | Positive | 9.40 | 5.00 |
| Naproxen | 230.09 | Positive | 14.83 | 5.00 |
| Oxcarbazepine | 252.09 | Positive | 11.61 | 10.00 |
| Oxybenzone | 228.08 | Positive | 16.72 | 50.00 |
| Paraxanthine | 180.06 | Positive | 8.78 | 10.00 |
| Penciclovir | 253.12 | Positive | 8.34 | 5.00 |
| Pentoxyfylline | 278.14 | Positive | 10.54 | 5.00 |
| PFBA | 213.99 | Negative | 10.70 | 10.00 |
| PFOA | 413.97 | Negative | 16.99 | 5.00 |
| Phenytoin | 252.09 | Positive | 12.36 | 5.00 |
| Progesterone | 314.22 | Positive | 17.29 | 10.00 |
| Prometon | 225.16 | Positive | 11.62 | 5.00 |
| Propachlor | 211.08 | Positive | 13.39 | 5.00 |
| Ranitidine | 314.14 | Positive | 8.24 | 10.00 |
| Siduron | 232.16 | Positive | 14.84 | 10.00 |
| Simazine | 201.08 | Positive | 11.92 | 5.00 |
| Sitagliptin | 407.12 | Positive | 10.42 | 10.00 |
| Sucralose | 396.01 | Negative | 9.90 | 5.00 |
| Sulfamethoxazole | 253.05 | Positive | 10.00 | 10.00 |
| Sulfathiazole | 255.01 | Positive | 8.58 | 10.00 |
| TCEP | 283.95 | Positive | 12.19 | 5.00 |
| Testosterone | 288.21 | Positive | 15.40 | 5.00 |
| Tramadol | 263.19 | Positive | 10.11 | 5.00 |
| Tributyl Phosphate | 266.16 | Positive | 18.87 | 5.00 |
| Triclosan | 287.95 | Negative | 19.36 | 10.00 |
| Trimethoprim | 290.14 | Positive | 9.21 | 5.00 |
| Valsartan | 435.23 | Positive | 15.60 | 10.00 |
| Venlafaxine | 277.20 | Positive | 11.28 | 10.00 |
| Warfarin | 308.10 | Positive | 15.27 | 5.00 |

FIG. 81 (continued)

| Compound Name | $K_{obs}$, [g mg$^{-1}$ min$^{-1}$] | | Removal – 5 min, [%] | | Removal – 30 min, [%] | | Instant Uptake, [%] | |
|---|---|---|---|---|---|---|---|---|
| | CCAC | P-CDP | CCAC | P-CDP | CCAC | P-CDP | CCAC | P-CDP |
| 2,4-D | 11.0 | 0.0 (72.9) | 43.3 ± 3.4 | 2.2 ± 5.0 | 76.8 ± 1.6 | 4.7 ± 3.0 | 43.4 ± 4.1 | 3.7 ± 4.8 |
| Abacavir | 14.0 | 141.8 | 56.2 ± 2.7 | 90.4 ± 3.9 | 88.1 ± 1.9 | 94.6 ± 0.3 | 50.8 ± 0.3 | 98.9 ± 5.2 |
| Acebutolol | 1.9 | 586.88 | 61.2 ± 4.4 | 64.1 ± 16.1 | 97 ± 0.6 | 82.6 ± 10.1 | 72.5 ± 0.0 | 99.9 ± 5.2 |
| Acetaminophen | 13.9 | 0.0 (-772.6) | 32.4 ± 7.6 | 6.8 ± 2.8 | 56.1 ± 6.9 | 0.6 ± 1.8 | 57.8 ± 9.0 | 0.0 ± 3.9 |
| Acetochlor | 13.0 | 61.9 | 59.7 ± 4.5 | 51.7 ± 4.1 | 90.9 ± 0.8 | 59.3 ± 2.1 | 53.5 ± 5.7 | 66.0 ± 4.5 |
| Albuterol | 0 (-1775.1) | 151.0 | 0.0 ± 9.0 | 74.2 ± 3.9 | 0.2 ± 6.1 | 79.2 ± 4.3 | 23.5 ± 1.9 | 91.8 ± 10.0 |
| Allopurinol | 26.4 | 37.3 | 32.9 ± 11.0 | 1.1 ± 13.1 | 47.5 ± 4.8 | 6.3 ± 3.6 | 53 ± 13.1 | 0 ± 7.0 |
| Amphetamine | 0 (-4485.5) | 73712.2 | 0 ± 7.1 | 75.5 ± 16.5 | 0 ± 11.2 | 72.4 ± 9.9 | 33.4 ± 0.7 | 97.1 ± 9.0 |
| Atenolol | 5.0 | 182.8 | 16.7 ± 8.1 | 83.3 ± 6.6 | 45.2 ± 4.3 | 88.5 ± 2.1 | 44.4 ± 0.6 | 97.1 ± 5.8 |
| Atenolol_Acid | 16.3 | 85.7 | 34.6 ± 1.5 | 76.4 ± 3.9 | 57.8 ± 3.6 | 82.3 ± 2.0 | 42.3 ± 1.2 | 94.2 ± 4.8 |
| Atrazine | 14.7 | 177.1 | 44.6 ± 1.5 | 17.6 ± 4.8 | 75.7 ± 1.7 | 22.2 ± 4.9 | 43.7 ± 4.8 | 29.2 ± 6.0 |
| Benzotriazole-methyl-1H | 21.0 | 281.1 | 60.4 ± 1.8 | 15.5 ± 2.1 | 82.9 ± 1.0 | 18.2 ± 5.0 | 56.2 ± 4.4 | 27.1 ± 5.6 |
| Bromacil | 16.9 | 612.7 | 39.4 ± 2.6 | 8.7 ± 4.3 | 64.2 ± 2.8 | 8.8 ± 6.07 | 44.7 ± 4.1 | 6.9 ± 4.4 |
| Bupropion hcl | 3.1 | 5184.7 | 20.7 ± 2.6 | 59.6 ± 13.1 | 67.0 ± 6.4 | 71.6 ± 4.1 | 46.6 ± 0.1 | 99.7 ± 5.8 |
| Caffeine | 13.0 | 207.9 | 44.7 ± 19.0 | 0.7 ± 6.7 | 77.5 ± 3.4 | 5.5 ± 6.5 | 61.1 ± 12.1 | 0.0 ± 6.4 |
| Carbamazepine | 13.0 | 335.1 | 56.2 ± 5.4 | 15.1 ± 2.9 | 86.3 ± 1.4 | 18.0 ± 3.6 | 56.3 ± 1.8 | 26.6 ± 4.7 |
| Carbaryl | 16.8 | 1485.8 | 49.0 ± 1.8 | 11.3 ± 3.9 | 77.2 ± 1.5 | 12.7 ± 6.3 | 49.6 ± 1.8 | 17.7 ± 7 |
| Carbofuran | 15.2 | 0.0 (-980.1) | 40.3 ± 1.9 | 4.8 ± 1.6 | 67.3 ± 2.2 | 3.2 ± 5.6 | 45.3 ± 1.8 | 4.9 ± 5.5 |
| Chloridazon | 14.3 | 364.9 | 56.6 ± 5.7 | 23.9 ± 2.6 | 86.3 ± 1.6 | 25.4 ± 2.9 | 54.7 ± 6.2 | 29.6 ± 5.9 |

FIG. 82

| Compound Name | $K_{obs}$, [g mg⁻¹ min⁻¹] | | Removal – 5 min, [%] | | Removal – 30 min, [%] | | Instant Uptake, [%] | |
|---|---|---|---|---|---|---|---|---|
| Chloroxylenol | 10.6 | 52.8 | 47.4 ± 4.9 | 10.1 ± 15.5 | 77.9 ± 1.0 | 19 ± 16.4 | 45.4 ± 7.2 | 7.5 ± 3.6 |
| Cimetidine | 18.7 | 100.9 | 58.8 ± 6.9 | 86.5 ± 5.3 | 85.5 ± 1.3 | 92.4 ± 0.5 | 56.5 ± 0.5 | 99.8 ± 3.1 |
| Clofibric Acid | 16.8 | 0.0 (-112.9) | 36.8 ± 3.1 | 2.5 ± 5.6 | 60.4 ± 0.5 | 4.5 ± 7.3 | 35.4 ± 1.2 | 2.3 ± 2.4 |
| Codeine | 19.8 | 1501.2 | 22.2 ± 6.9 | 90.6 ± 12.7 | 59.8 ± 4.2 | 94.3 ± 1.3 | 41.2 ± 0.3 | 100 ± 5.7 |
| Cotinine | 17.8 | 239.3 | 32.1 ± 9.5 | 26.8 ± 5.1 | 50.3 ± 1.7 | 25.2 ± 4.0 | 40.6 ± 5.6 | 42 ± 6.3 |
| DEET | 16.8 | 577.9 | 39.0 ± 1.1 | 12.1 ± 2.8 | 66.7 ± 3.1 | 13 ± 2.9 | 42.6 ± 3.2 | 20.5 ± 4.6 |
| Diazinon | 26.3 | 194.7 | 72.5 ± 1.4 | 90.3 ± 5.3 | 96.8 ± 0.0 | 94.6 ± 0.9 | 60.3 ± 0.4 | 98.4 ± 6.3 |
| Diclofenac | 6.4 | 46.4 | 48.0 ± 3.7 | 32.4 ± 4.4 | 88.1 ± 1.5 | 40.4 ± 2.8 | 43.1 ± 3.5 | 77.8 ± 3.9 |
| Dimethoate | 11.1 | 0.0 (-248.1) | 21.5 ± 22.0 | 7.0 ± 4.4 | 55.6 ± 8.5 | 4.9 ± 8.2 | 50.3 ± 10.2 | 9.3 ± 9.3 |
| Diuron | 21.8 | 122.4 | 75.9 ± 2.0 | 81.6 ± 3.5 | 96.7 ± 0.3 | 86.8 ± 1.0 | 63.6 ± 1.5 | 93.4 ± 5.6 |
| Efavirenz | 25.1 | 170.6 | 65.2 ± 4.3 | 82.0 ± 6.0 | 95.7 ± 0.4 | 87.9 ± 1.0 | 56.8 ± 1.3 | 95.0 ± 6.4 |
| Erythromycin | 14.4 | 171.9 | 39.1 ± 8.2 | 60.6 ± 13.2 | 92.6 ± 2.8 | 79.4 ± 3.7 | 68.4 ± 0.0 | 100 ± 6.8 |
| Estrone | 16.8 | 67.4 | 66.2 ± 2.9 | 55.5 ± 5.3 | 96.2 ± 0.5 | 64.9 ± 4.1 | 61.1 ± 4.2 | 73.4 ± 3.9 |
| Famotidine | 26.1 | 107.4 | 74.2 ± 4.0 | 87.4 ± 6.2 | 95.5 ± 0.3 | 93.1 ± 0.7 | 63.4 ± 0.3 | 99.3 ± 2.5 |
| Fluconazole | 11.8 | 329.4 | 43.5 ± 2.4 | 6.5 ± 4.7 | 74.3 ± 1.7 | 7.8 ± 2.7 | 51.8 ± 3.4 | 5.7 ± 5.5 |
| Fluoxetine hcl | 2563.0 | 137.0 | 12.3 ± 37.0 | 46.8 ± 10.7 | 71.2 ± 7.7 | 66.3 ± 6.4 | 79.2 ± 0.0 | 100 ± 5.53 |
| Gemfibrozil | 8.1 | 143.0 | 54.6 ± 4.3 | 76.1 ± 7.7 | 93.9 ± 1.3 | 79.2 ± 5.4 | 47.7 ± 0.6 | 97.8 ± 4.2 |
| Hydrocodone | 16.7 | 1506.9 | 22.2 ± 6.9 | 89.8 ± 14.8 | 59.8 ± 4.2 | 94.1 ± 1.7 | 40.3 ± 0.3 | 98.6 ± 5.6 |
| Ibuprofen | 2.9 | 43.7 | 20.9 ± 4.1 | 9.1 ± 7.5 | 62.5 ± 3.9 | 25.5 ± 10.7 | 38.2 ± 9.3 | 48.7 ± 6.6 |
| Imidacloprid | 15.1 | 224.8 | 56.8 ± 1.6 | 26.9 ± 3.3 | 85.8 ± 1.6 | 29.3 ± 2.6 | 53.1 ± 3.9 | 39.4 ± 4.4 |
| Iopromid | 5.0 | 73.9 | 32.0 ± 10.5 | 6.9 ± 6.5 | 72.4 ± 7.7 | 7.7 ± 7.3 | 57.5 ± 13.2 | 1.8 ± 2.4 |
| Ioxynil | 6.8 | 9915.0 | 47.2 ± 4.7 | 7.3 ± 4.8 | 85.9 ± 0.2 | 8.2 ± 3.4 | 50.8 ± 3.9 | 57.5 ± 2.6 |
| Isoproturon | 15.3 | 84.6 | 55.9 ± 3.4 | 61.0 ± 4.1 | 86.1 ± 1.5 | 67.9 ± 2.1 | 54.3 ± 4.5 | 75.1 ± 4.3 |

FIG. 82 (continued)

| Compound Name | $K_{obs}$, [g mg⁻¹ min⁻¹] | | Removal – 5 min, [%] | | Removal – 30 min, [%] | | Instant Uptake, [%] | |
|---|---|---|---|---|---|---|---|---|
| Ketoprofen | 8.6 | 268.7 | 49.8 ± 5.1 | 23.8 ± 2.9 | 87.2 ± 1.3 | 25.3 ± 4.5 | 43.8 ± 5.1 | 68.7 ± 4.4 |
| Linuron | 24.4 | 143.3 | 77.3 ± 3.7 | 89.0 ± 4.1 | 97.5 ± 0.1 | 93.4 ± 0.7 | 64.3 ± 0.6 | 97.2 ± 5.0 |
| Malaoxon | 12.7 | 359.4 | 46.8 ± 1.9 | 24.4 ± 3.0 | 78.0 ± 2.2 | 25.6 ± 3.9 | 49.3 ± 4.7 | 44.0 ± 4.8 |
| MCPA | 11.9 | 0.0 (255.6) | 43.8 ± 2.6 | 0.0 ± 4.6 | 74.8 ± 0.9 | 1.2 ± 5.6 | 42.2 ± 2.9 | 7.6 ± 3.6 |
| Mecoprop | 11.2 | 0.0 (1997.2) | 38.8 ± 1.2 | 0.0 ± 2.3 | 74.0 ± 1.6 | 0.0 ± 7.0 | 40.6 ± 3.8 | 3.7 ± 2.4 |
| Meprobamate | 15.9 | 0.0 (-405.0) | 34.9 ± 4.7 | 5.1 ± 6.1 | 57.5 ± 2.2 | 2.2 ± 4.3 | 48.1 ± 8.3 | 3.1 ± 7.7 |
| Methomyl | 17.6 | 0.0 (-98.6) | 24.7 ± 7.6 | 0.0 ± 10.3 | 47.1 ± 6.3 | 0.0 ± 11.4 | 53.9 ± 10.3 | 0.0 ± 3.7 |
| Metolachlor | 11.9 | 59.5 | 58.6 ± 2.9 | 56.7 ± 4.6 | 91.1 ± 1.2 | 64.3 ± 2.2 | 53.6 ± 5.0 | 71.4 ± 4.2 |
| Metoprolol | 1.7 | 1633.2 | 40.0 ± 3.9 | 85.8 ± 20.1 | 83.3 ± 3.1 | 91.1 ± 2.8 | 60.6 ± 0.1 | 99.7 ± 6.0 |
| Metribuzin | 18.8 | 435.3 | 36.8 ± 0.9 | 12.7 ± 3.2 | 58.9 ± 2.5 | 13.6 ± 4.5 | 41.9 ± 3.8 | 17.8 ± 5.5 |
| Molinate | 15.5 | 212.6 | 52.7 ± 2.5 | 32.4 ± 2.8 | 79.3 ± 1.8 | 35.9 ± 3.4 | 51.0 ± 5.7 | 47.7 ± 4.9 |
| Morphine | 3.1 | 162.1 | 15.2 ± 13.0 | 80.5 ± 5.2 | 41.8 ± 3.0 | 86.3 ± 2.9 | 45.3 ± 1.0 | 96.1 ± 3.0 |
| Nadolol | 2.2 | 197.6 | 31.1 ± 1.8 | 85.9 ± 7.8 | 69.5 ± 5.0 | 91.4 ± 2.0 | 56.0 ± 0.3 | 98.5 ± 4.9 |
| Naproxen | 10.5 | 57.3 | 52.5 ± 4.0 | 41.0 ± 6.1 | 89.2 ± 1.0 | 51.7 ± 7.0 | 43.3 ± 2.1 | 88.9 ± 4.9 |
| Oxcarbazepine | 14.5 | 60.3 | 59.9 ± 4.5 | 12.1 ± 11.1 | 90.3 ± 5.0 | 20.8 ± 2.6 | 52.1 ± 1.8 | 14.6 ± 4.9 |
| Oxybenzone | 116.1 | 927.3 | 91.5 ± 2.3 | 94.7 ± 15.4 | 99.4 ± 0.0 | 92.8 ± 6.8 | 76.4 ± 0.2 | 99.6 ± 5.3 |
| Paraxanthine | 15.3 | 0.0 (60.9) | 47.5 ± 8.0 | 0.1 ± 5.2 | 71.8 ± 4.7 | 2.4 ± 7.1 | 58.2 ± 6.7 | 5.6 ± 6.0 |
| Penciclovir | 16.3 | 102.7 | 57.8 ± 6.9 | 87.4 ± 4.9 | 88.2 ± 2.9 | 92.8 ± 0.6 | 59.1 ± 0.2 | 98.6 ± 4.2 |
| Pentoxyfylline | 13.7 | 1780.0 | 62.4 ± 6.9 | 25.6 ± 2.4 | 94.7 ± 0.4 | 23.8 ± 3.9 | 55.9 ± 6.3 | 33.1 ± 5.3 |
| PFBA | 29.0 | 0.0 (6538.3) | 20.5 ± 5.9 | 0.0 ± 5.3 | 32.3 ± 4.4 | 0.3 ± 7.8 | 28.2 ± 5.4 | 8.4 ± 7.7 |
| PFOA | 9.9 | 0.0 (-10733.6) | 39.0 ± 5.5 | 0.0 ± 6.3 | 71.5 ± 1.1 | 0.0 ± 4.0 | 35.4 ± 3.1 | 8.0 ± 4.0 |

FIG. 82 (continued)

| Compound Name | $K_{obs}$, [g mg$^{-1}$ min$^{-1}$] | Removal – 5 min, [%] | | Removal – 30 min, [%] | | Instant Uptake, [%] | |
|---|---|---|---|---|---|---|---|
| Phenytoin | 11.0 | 244.0 | 44.4 ± 12.0 | 19.2 ± 6.2 | 78.9 ± 2.5 | 22.1 ± 5.8 | 47.9 ±4.7 | 31.7 ± 5.9 |
| Progesterone | 43.7 | 222.3 | 84.7 ± 1.7 | 94.1 ± 3.8 | 99.3 ± 0.1 | 97.0 ± 0.1 | 74.2 ± 0.2 | 99.3 ± 4.7 |
| Prometon | 14.4 | 179.5 | 40.4 ± 2.5 | 91.5 ± 4.0 | 73.0 ± 1.8 | 95.1 ± 1.1 | 42.7 ± 0.5 | 97.9 ± 3.8 |
| Propachlor | 17.0 | 2055.4 | 43.6 ± 1.3 | 14.4 ± 4.0 | 70.2 ± 1.8 | 16.0 ± 2.9 | 45.1 ± 6.7 | 23.1 ± 4.6 |
| Ranitidine hcl | 16.5 | 9346.4 | 41.5 ± 4.5 | 71.2 ± 3.6 | 84.4 ± 4.2 | 72.0 ± 0.3 | 42.2 ± 0.2 | 99.3 ± 15 |
| Siduron | 14.3 | 73.7 | 63.2 ± 3.4 | 62.6 ± 3.2 | 92.5 ± 0.9 | 70.2 ± 1.9 | 55.9 ± 3.8 | 78.5 ± 4.7 |
| Simazine | 18.3 | 1477.0 | 68.6 ± 3.7 | 11.3 ± 3.9 | 95.0 ± 0.5 | 12.7 ± 6.3 | 58.2 ± 3.1 | 82.6 ± 6.2 |
| Sitagliptin | 2.0 | 1538.2 | 53.6 ± 3.6 | 62.6 ± 12.3 | 93.7 ± 1.2 | 72.5 ± 2.5 | 69.0 ± 0.0 | 99.9 ± 5.4 |
| Sucralose | 10.3 | 114.0 | 38.6 ± 18 | 13.9 ± 10.9 | 74.5 ± 2.7 | 14.1 ± 10.0 | 53.9 ± 12.2 | 10.8 ± 4.1 |
| Sulfamethoxazole | 10.0 | 341.5 | 35.9 ± 14.0 | 25.7 ± 3.6 | 71.1 ± 4.1 | 26.9 ± 3.8 | 43.4 ± 5.0 | 41.7 ± 4.5 |
| Sulfathiazole | 10.4 | 1097.2 | 50.7 ± 7.7 | 14.3 ± 4.6 | 83.2 ± 2.8 | 15.9 ± 2.7 | 53.0 ± 2.6 | 20.9 ± 3.6 |
| TCEP | 15.1 | 240.2 | 41.2 ± 0.5 | 10.9 ± 2.7 | 66.9 ± 2.4 | 12.8 ± 3.5 | 48.9 ± 5.4 | 15.7 ± 6.1 |
| Testosterone | 16.5 | 74.3 | 71.1 ± 2.9 | 79.5 ± 4.2 | 98.4 ± 0.2 | 86.4 ± 1.3 | 60.8 ± 2.2 | 91.2 ± 4.6 |
| Tramadol | 5.1 | 5239.8 | 11.5 ± 1.8 | 66.6 ± 12.1 | 46.5 ± 6.4 | 81.0 ± 6.7 | 38.1 ± 0.2 | 99.4 ± 5.3 |
| Tributyl phosphate | 12.1 | 55.6 | 60.2 ± 3.1 | 61.4 ± 5.7 | 92.6 ± 1.2 | 70.5 ± 2.1 | 55.0 ± 3.2 | 82.5 ± 5.6 |
| Triclosan | 264.0 | 753.4 | 92 ± 2.3 | 92.3 ± 7.1 | 99.5 ± 0.0 | 95.3 ± 0.8 | 79.6 ± 0.1 | 99.7 ± 2.5 |
| Trimethoprim | 14.3 | 898.8 | 55.5 ± 2.5 | 95.1 ± 10.5 | 90.9 ± 1.5 | 97.9 ± 0.3 | 65.6 ± 0.0 | 100 ± 5.3 |
| Valsartan | 3.8 | 87.2 | 28.5 ± 2.1 | 12.5 ± 3.1 | 73.7 ± 0.8 | 18.0 ± 5.1 | 27.5 ± 2.6 | 73.7 ± 3.4 |
| Venlafaxine hcl | 5.5 | 5259.9 | 13.9 ± 2.5 | 59.8 ± 17.6 | 51.8 ± 6.3 | 72.9 ± 5.2 | 38.9 ± 0.2 | 99.4 ± 6.0 |
| Warfarin | 6.3 | 35.5 | 41.9 ± 4.0 | 46.5 ± 3.6 | 84.3 ± 1.7 | 58.2 ± 2.9 | 37.9 ± 5.2 | 73.2 ± 2.1 |

FIG. 82 (continued)

Scale bars: 1 mm

| Compound Name | LogK∞ | $\alpha^H$ | $\beta^H$ | $\pi^H$ | R | V | Group |
|---|---|---|---|---|---|---|---|
| 2,4-D | 0.45 | 0.50 | 0.60 | 1.24 | 1.09 | 1.38 | Validation |
| Abacavir | 3.12 | 0.76 | 2.85 | 2.29 | 1.78 | 2.09 | Training |
| Acetaminophen | 0.72 | 0.89 | 0.89 | 1.32 | 1.20 | 1.17 | Training |
| Acetochlor | 2.45 | 0.00 | 0.70 | 1.71 | 1.20 | 2.14 | Training |
| Albuterol | 2.21 | 1.08 | 1.90 | 1.45 | 1.31 | 1.98 | Validation |
| Allopurinol | -0.49 | 0.74 | 1.07 | 1.58 | 1.46 | 0.88 | Training |
| Atenolol | 2.79 | 0.45 | 1.72 | 1.54 | 1.48 | 2.18 | Training |
| Atenolol Acid | 3.00 | 0.69 | 1.54 | 1.37 | 1.13 | 2.14 | Validation |
| Atrazine | 1.63 | 0.65 | 2.18 | 1.51 | 1.22 | 1.62 | Training |
| Bromacil | 1.07 | 0.35 | 1.75 | 1.75 | 1.36 | 1.63 | Validation |
| Caffeine | 0.68 | 0.00 | 1.31 | 1.00 | 1.60 | 1.36 | Training |
| Carbamazepine | 1.50 | 0.46 | 0.63 | 1.45 | 1.76 | 1.81 | Training |
| Carbaryl | 1.38 | 0.35 | 0.91 | 1.55 | 1.77 | 1.54 | Validation |
| Carbofuran | 1.18 | 0.35 | 1.03 | 1.76 | 1.25 | 1.69 | Training |
| Chloridazon | 1.76 | 0.18 | 1.32 | 1.76 | 1.63 | 1.52 | Training |
| Chloroxylenol | 0.68 | 0.72 | 0.37 | 0.96 | 0.98 | 1.18 | Validation |
| Cimetidine | 2.85 | 0.59 | 2.27 | 2.41 | 1.43 | 1.96 | Validation |
| Clofibric Acid | 0.64 | 0.50 | 0.66 | 1.11 | 0.93 | 1.54 | Training |
| Codeine | 2.85 | 0.26 | 1.53 | 2.16 | 1.91 | 2.21 | Training |
| Cotinine | 1.56 | 0.00 | 1.21 | 1.46 | 1.15 | 1.39 | Validation |
| DEET | 1.33 | 0.00 | 0.84 | 1.42 | 0.93 | 1.68 | Training |
| Diazinon | 3.35 | 0.00 | 2.56 | 2.57 | 1.22 | 2.31 | Training |
| Diclofenac | 2.64 | 0.59 | 1.34 | 2.10 | 2.06 | 2.03 | Training |
| Dimethoate | 1.01 | 0.35 | 2.44 | 2.41 | 1.31 | 1.58 | Training |
| Estrone | 2.45 | 0.55 | 0.82 | 1.55 | 1.54 | 2.16 | Training |
| Famotidine | 3.47 | 0.73 | 2.09 | 2.79 | 2.50 | 2.26 | Validation |
| Hydrocodone | 2.89 | 0.00 | 1.52 | 2.31 | 1.74 | 2.21 | Validation |
| Ibuprofen | 1.98 | 0.59 | 0.49 | 0.83 | 0.75 | 1.78 | Training |
| Imidacloprid | 1.75 | 0.17 | 1.53 | 1.98 | 1.56 | 1.68 | Training |
| Ioxynil | 1.67 | 0.50 | 0.30 | 1.48 | 2.07 | 1.45 | Validation |
| Ketoprofen | 2.20 | 0.59 | 0.86 | 1.77 | 1.53 | 1.98 | Training |
| Malaoxon | 2.20 | 0.00 | 2.90 | 2.51 | 0.61 | 2.21 | Training |
| MCPA | 0.67 | 0.50 | 0.61 | 1.16 | 0.96 | 1.39 | Validation |

FIG. 96

| Compound Name | LogK$_c$ | $\alpha^H$ | $\beta^H$ | $\pi^H$ | R | V | Group |
|---|---|---|---|---|---|---|---|
| Mecoprop | 0.42 | 0.50 | 0.63 | 1.12 | 0.95 | 1.54 | Training |
| Meprobamate | 0.52 | 0.91 | 0.68 | 0.58 | 0.48 | 1.73 | Training |
| Methomyl | 0.63 | 0.35 | 1.18 | 1.13 | 0.94 | 1.21 | Validation |
| Metolachlor | 2.50 | 0.00 | 0.72 | 1.67 | 1.19 | 2.28 | Training |
| Metribuzin | 1.36 | 0.00 | 1.60 | 1.32 | 1.15 | 1.62 | Validation |
| Morphine | 2.43 | 0.55 | 1.54 | 2.06 | 1.99 | 2.06 | Training |
| Nadolol | 2.84 | 0.70 | 1.87 | 1.62 | 1.51 | 2.49 | Validation |
| Naproxen | 2.56 | 0.59 | 0.74 | 1.40 | 1.52 | 1.78 | Training |
| Oxcarbazepine | 1.83 | 0.35 | 1.00 | 2.03 | 2.01 | 1.87 | Training |
| Paraxanthine | 0.08 | 0.35 | 2.24 | 2.17 | 1.56 | 1.22 | Training |
| Penciclovir | 2.79 | 1.23 | 2.84 | 2.69 | 2.05 | 1.80 | Training |
| Pentoxyfylline | 1.75 | 0.00 | 1.65 | 1.47 | 1.73 | 2.08 | Training |
| PFOA | -0.03 | 0.83 | 0.33 | -0.10 | -0.99 | 1.58 | Validation |
| Phenytoin | 1.67 | 0.60 | 2.02 | 2.19 | 2.23 | 1.87 | Validation |
| Progesterone | 2.96 | 0.00 | 0.89 | 1.43 | 1.19 | 2.62 | Training |
| Propachlor | 1.46 | 0.00 | 0.52 | 1.54 | 1.16 | 1.66 | Training |
| Ranitidine hcl | 2.20 | 0.20 | 1.93 | 1.92 | 1.54 | 2.4 | Training |
| Siduron | 2.62 | 0.44 | 1.20 | 1.36 | 1.34 | 1.95 | Training |
| Simazine | 1.38 | 0.65 | 2.16 | 1.55 | 1.23 | 1.48 | Training |
| Sulfamethoxazole | 1.78 | 0.61 | 1.17 | 2.73 | 1.82 | 1.72 | Training |
| Sulfathiazole | 1.40 | 0.61 | 1.33 | 2.71 | 2.17 | 1.69 | Validation |
| TCEP | 1.21 | 0.00 | 1.83 | 1.91 | 0.51 | 1.76 | Validation |
| Testosterone | 2.99 | 0.35 | 0.86 | 1.28 | 1.22 | 2.38 | Training |
| Tributyl_phosphate | 2.63 | 0.00 | 1.85 | 1.44 | 0.13 | 2.24 | Training |
| Triclosan | 2.72 | 0.41 | 0.26 | 1.84 | 1.81 | 1.81 | Training |
| Trimethoprim | 2.61 | 0.65 | 1.84 | 2.88 | 1.95 | 2.18 | Validation |
| Warfarin | 2.66 | 0.35 | 1.49 | 2.57 | 2.10 | 2.31 | Training |

FIG. 96 (continued)

POROUS CYCLODEXTRIN POLYMERIC MATERIALS AND METHODS OF MAKING AND USING SAME

CROSS-REFERENCE TO RELATED APPLICATIONS

This application is a continuation of U.S. application Ser. No. 15/134,030, filed Apr. 20, 2016, which claims priority to U.S. provisional patent application No. 62/149,975, filed Apr. 20, 2015, the disclosures of which are incorporated herein by reference.

STATEMENT REGARDING FEDERALLY SPONSORED RESEARCH

This invention was made with government support awarded by grant No. CHE-1413862 through the National Science Foundation. The Federal Government has certain rights in this invention.

BACKGROUND

As a consequence of population growth, continued industrialization, and climate change, communities in developed and developing countries face dwindling water supplies and are turning to drinking water resources that have been impacted by agricultural runoff or wastewater discharges. Drinking water, surface water, and groundwater impaired by these anthropogenic activities contain pollutants including trace organic chemicals, known as organic micropollutants, such as pesticides, pharmaceuticals, components of personal care products, and other industrial chemicals. As these pollutants have gained attention and analytical techniques have improved, new emerging organic contaminants have been identified in water resources at a rapid pace. Toxicological data for these chemicals are limited, but significant developmental, reproductive, endocrine disrupting and other chronic health effects have been reported. Also, these pollutants can have negative effects on aquatic ecosystems, which serve as a basis of the food chain. Existing technologies for removing these emerging contaminants can be energy intensive, expensive, and are not always effective. Volatile organic compounds (VOCs) are a broad category of atmospheric contaminants emitted from industrial syntheses, transportation, and commercial products including solvent thinners, paint, cleaners, and lubricants. Several techniques have been applied to remove VOCs from air, most commonly through adsorption and sequestration.

Adsorption processes can be employed to remove specific contaminants or contaminant classes from fluids like air and water. Activated carbons (ACs) are the most widespread sorbents used to remove organic pollutants, and their efficacy derives primarily from their high surface areas, nanostructured pores, and hydrophobicity. However, no single type of AC removes all contaminants well. Because of their poorly defined structure and binding site variation, optimal adsorption selectivities require empirical screening at new installations, precluding rational design and improvement. Furthermore, regenerating spent AC is energy intensive (heating to 500-900° C. or other energy intensive procedures) and does not restore full performance. AC also has a slow pollutant uptake rate, achieving its uptake equilibrium in hours to days, such that more rapid contaminant removal requires excess sorbent. Finally, AC can perform poorly for many emerging contaminants, particularly those that are relatively hydrophilic.

An alternative adsorbent material can be made from polymeric cyclodextrin materials produced from insoluble polymers of β-cyclodextrin (β-CD), which are toroidal macrocycles comprised of seven glucose units whose internal cavities are capable of binding organic compounds. β-CD is an inexpensive and sustainably produced monomer derived from cornstarch that is used extensively to formulate and stabilize pharmaceuticals, flavorants, and fragrances, as well as within chiral chromatography stationary phases. Insoluble β-CD polymers have been formed by crosslinking with epichlorohydrin and other reactive compounds that feature well defined binding sites and high association constants. Insoluble βCD polymers crosslinked with epichlorohydrin have been investigated as alternatives to AC for water purification, but their low surface areas result in inferior sorbent performance relative to ACs.

Thus there is a need for new sorbents that address the deficiencies of AC and will provide more effective sorption and/or sequestration properties, for example in VOC adsorption or water purification applications, with reduced energy inputs. There is a need for an adsorbent that provides rapid contaminant extraction, high total uptake, and facile regeneration and reuse procedures. There is a need for a purification adsorbent that is inexpensive and can be reliably mass produced.

SUMMARY

The present disclosure provides porous, high surface area cyclodextrin polymeric materials. The present disclosure also provides methods of making and using these materials.

In an aspect, the present disclosure provides a porous, high surface area cyclodextrin polymeric material. These materials may also be referred to herein as polymers, polymeric materials, or porous polymeric materials. In various embodiments, the polymeric materials of the present disclosure comprise a plurality of cyclodextrin moieties crosslinked by one or more aryl moieties. In an embodiment, the porous polymeric material does not have an aliphatic ether bond to a crosslinking moiety. In various embodiments, the molar ratio of cyclodextrin moieties to aryl moieties ranges from about 1:1 to about 1:X, wherein X is three times the average number of glucose subunits in the cyclodextrin moieties. In various embodiments, the cyclodextrin moieties comprise β-cyclodextrin. In various embodiments, the porous polymeric material is mesoporous. In various embodiments, the porous polymeric material has a Brunauer-Emmett-Teller (BET) surface area of 50 $m^2/g$ to 2000 $m^2/g$. In various embodiments, the cyclodextrin moieties comprise β-cyclodextrin and the ratio of β-cyclodextrin moieties to crosslinking moieties is 1:1 to 1:21. In various embodiments, the present invention is directed to compositions comprising any of the porous polymeric material described herein. In various embodiments, the composition comprises any of the porous polymeric materials described herein covalently bonded to a support material, wherein the support material can be any cellulosic material, such as cotton, in any form, such as fibers, fabrics, etc. In various embodiments, the present invention is directed to methods of purifying a fluid sample comprising one or more pollutants, typically organic pollutants, wherein the sample is a fluid such as water or other liquids, air or other gases, by adsorbing the pollutants with the porous polymeric material, typically in an amount of at least about 50 et. % of the total amount of said pollutants. In various embodiments, the present invention is directed to methods of determining the presence or absence of compounds, such as pollutants, in a fluid sample as described herein, by contacting any of the porous polymeric materials herein with the fluid, adsorbing the compounds with the porous polymeric material, separating the porous polymeric material from the fluid sample, then releasing the compounds adsorbed on the porous polymeric material, for example by heating or solvent extraction, then determining the presence or absence, and optionally the amount, of compound release from the porous polymeric material. In various embodiments, the present invention is directed to methods of removing compounds from a fluid same (as described herein) by contacting any of the porous polymeric materials herein with the fluid, adsorbing the compounds with the porous polymeric material, separating the porous polymeric material from the fluid sample, then releasing the compounds adsorbed on the porous polymeric material, for example by heating or solvent extraction, and optionally isolating the compounds released from the porous polymeric material. In various embodiments, the porous polymeric compositions of the present invention can be incorporated into clothing, for example to provide deodorizing properties, or to protect the wearer from exposure to organic contaminants in the environments (e.g., as protective gear or vapor masks).

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1-9 depict exemplary crosslinking groups or crosslinkers according to the present disclosure.

FIG. 42 shows UV-visible spectra that indicate the adsorption of BPA on

NAC as a function of time.

Figure 43:
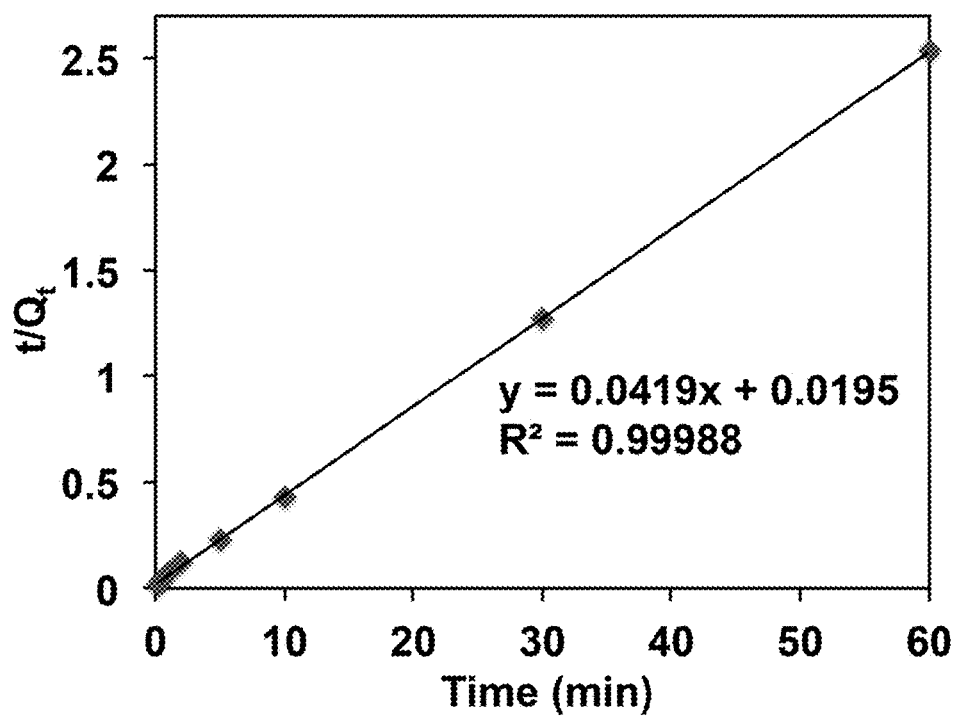

FIG. 43 shows a pseudo-second-order plot of BPA adsorption on NAC.

Figure 44:
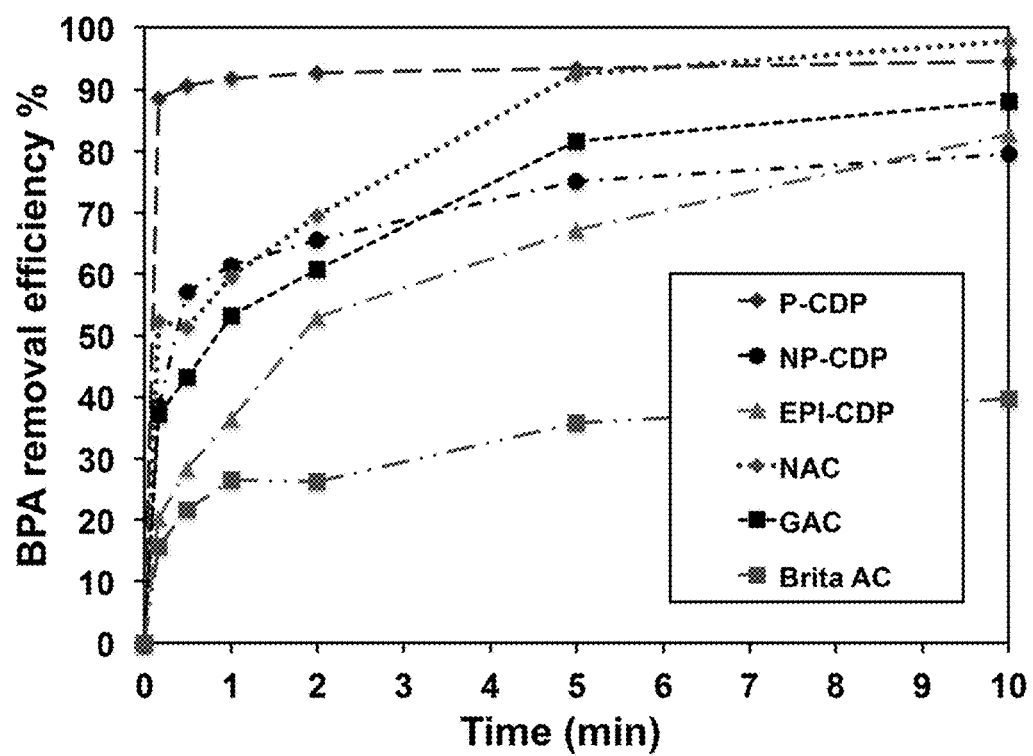

FIG. 44 shows BPA adsorption efficiencies as a function of time for P-CDP, NP-CDP, EPI-CDP, NAC, GAC, and Brita AC.

Figure 45:
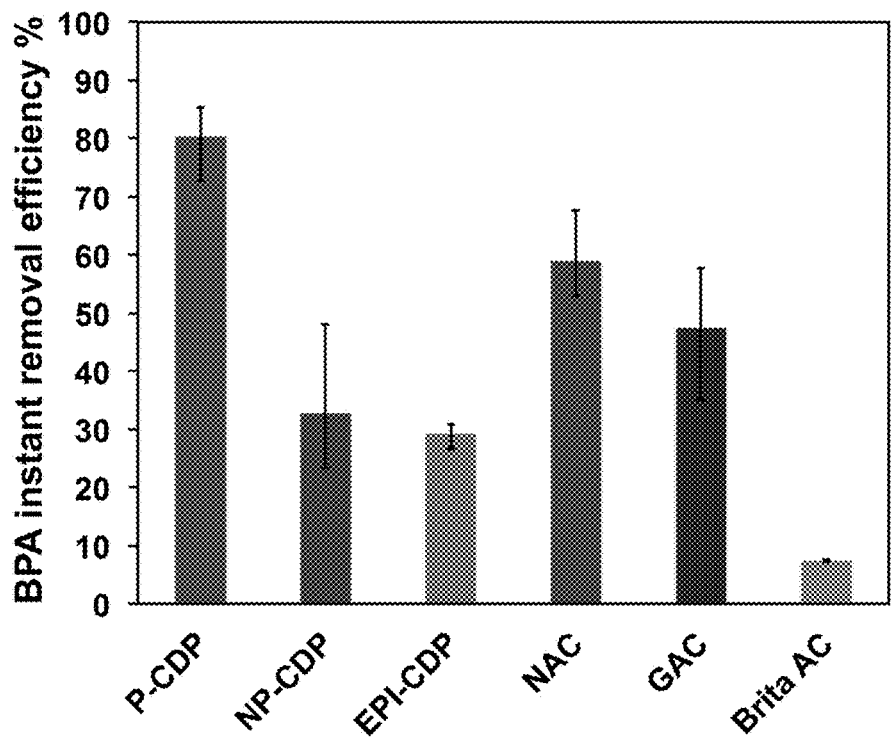

FIG. 45 shows the BPA adsorption efficiencies by P-CDP, NP-CDP, EPI-CDP, NAC, GAC, and Brita AC for a very short contact time with each adsorbent (approximately 1 second).

Figure 46:
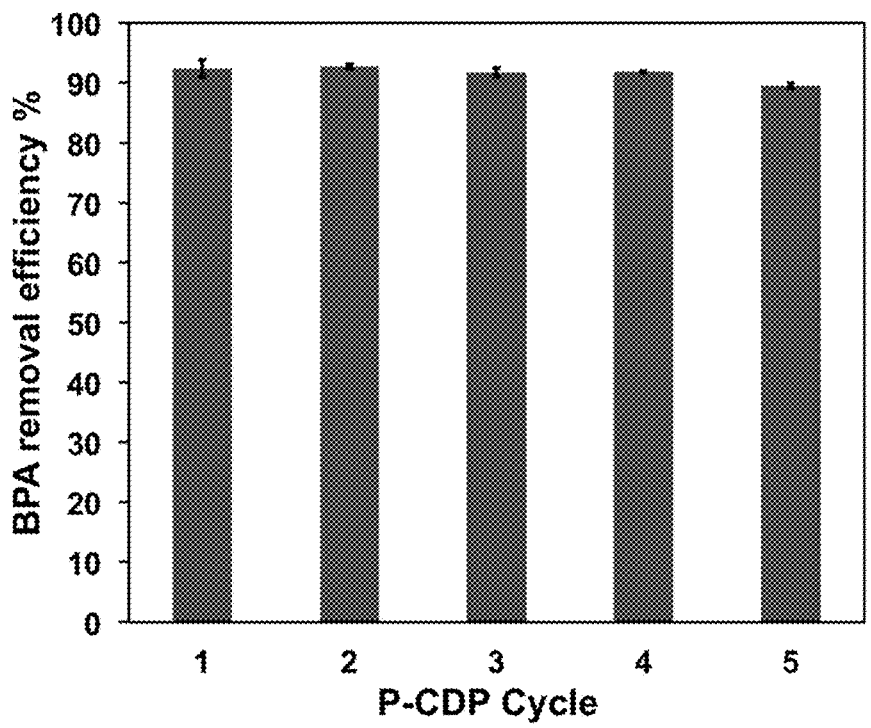

FIG. 46 shows BPA adsorption efficiency by P-CDP for 5 adsorption/desorption cycles.

Figure 47:
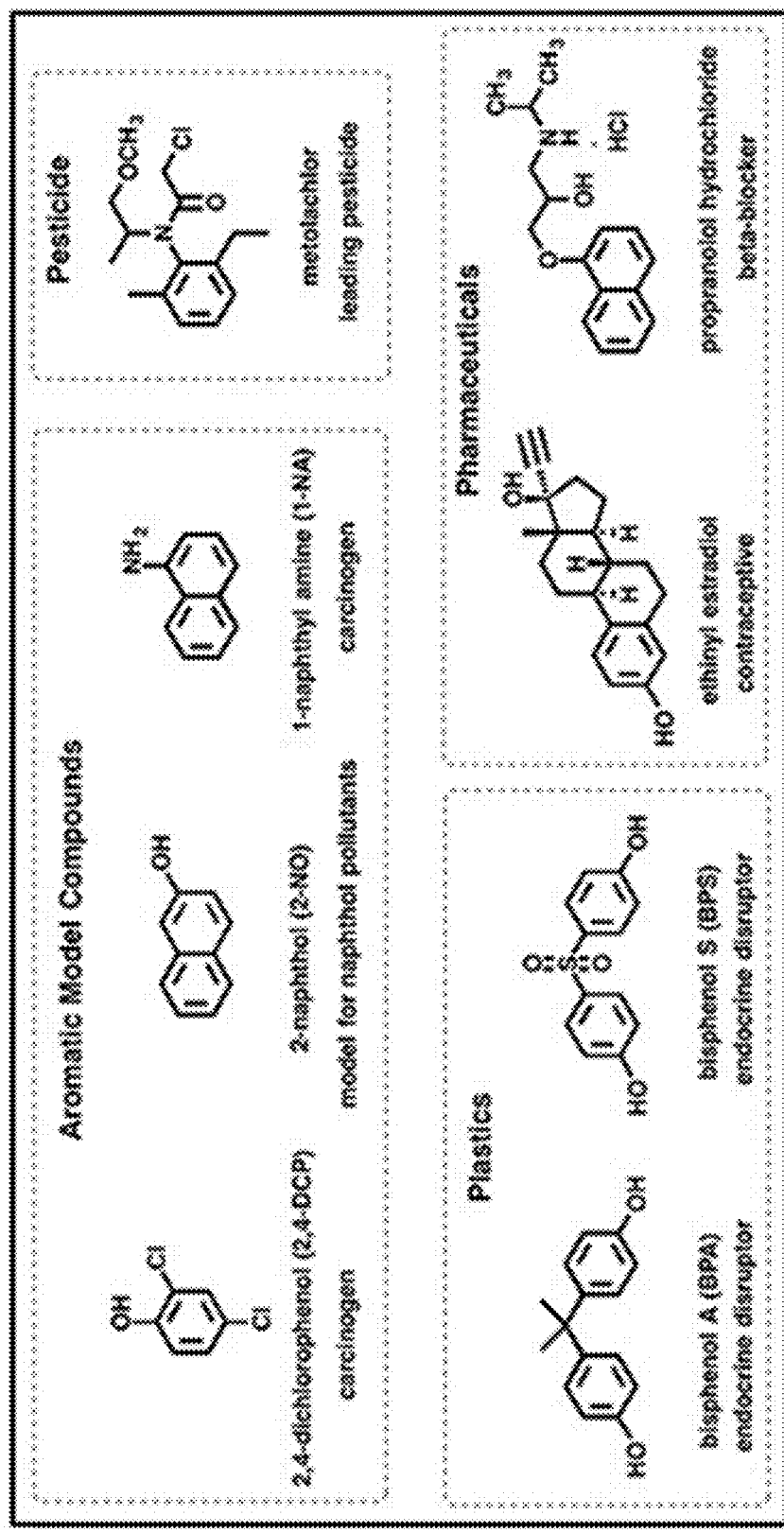

FIG. 47 shows exemplary organic pollutants.

FIG. 48 is a table of molecular descriptor values for micropollutants.

Figure 49:
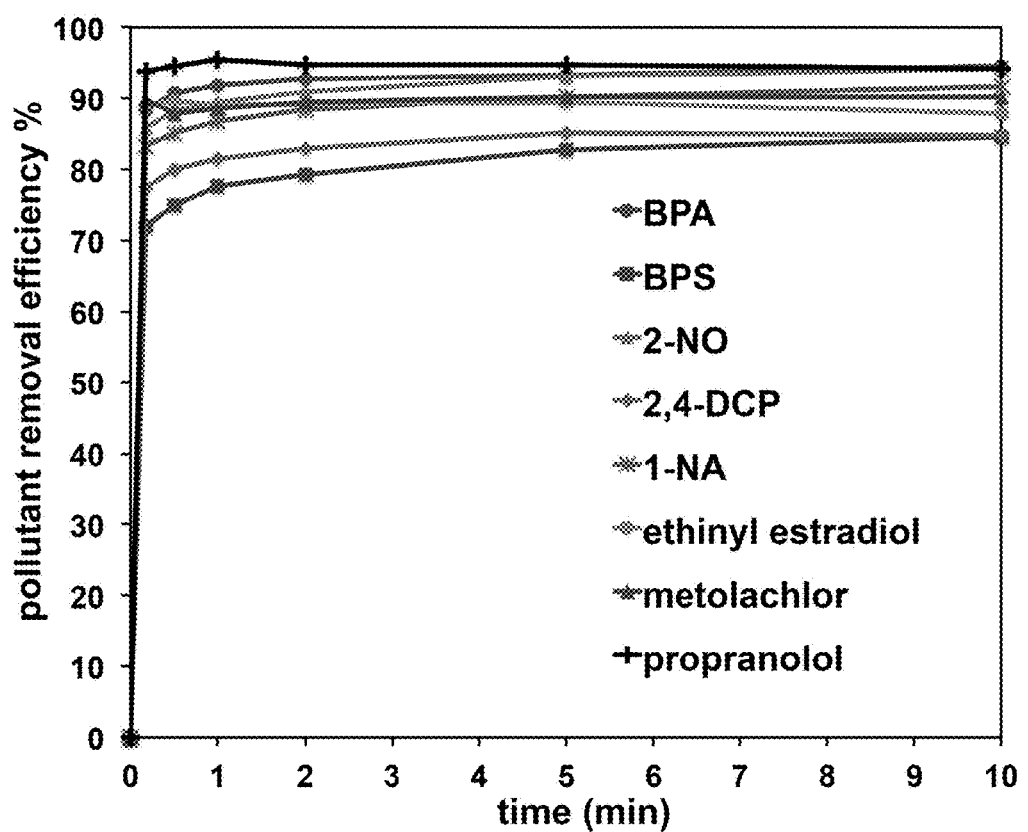

FIG. 49 shows the removal efficiencies of organic contaminants as a function of time by P-CDP.

Figure 50:
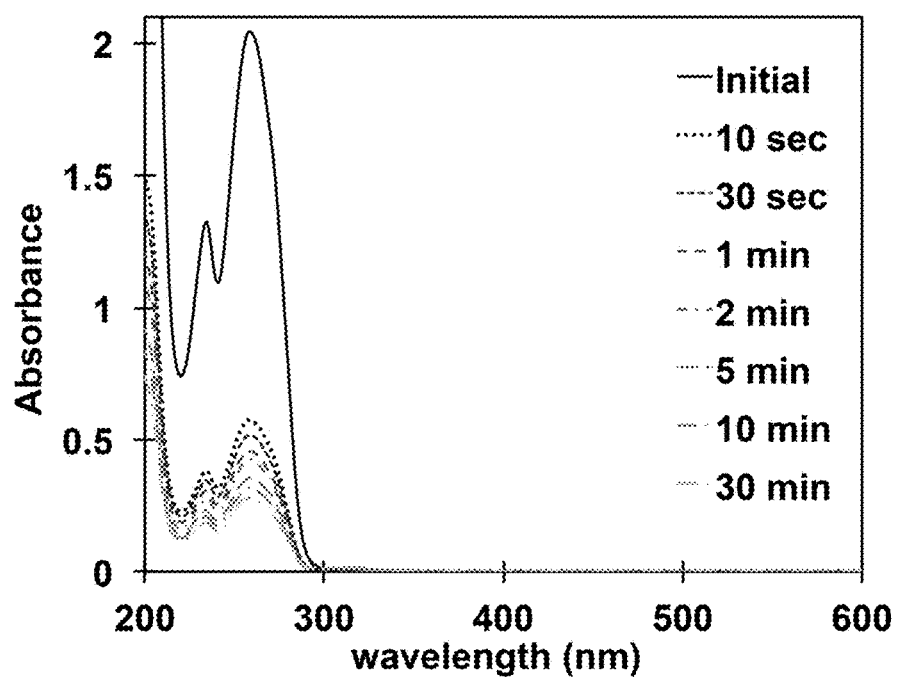

FIG. 50 shows UV-visible spectra that indicate the adsorption of BPS on P-CDP as a function of time.

Figure 51:
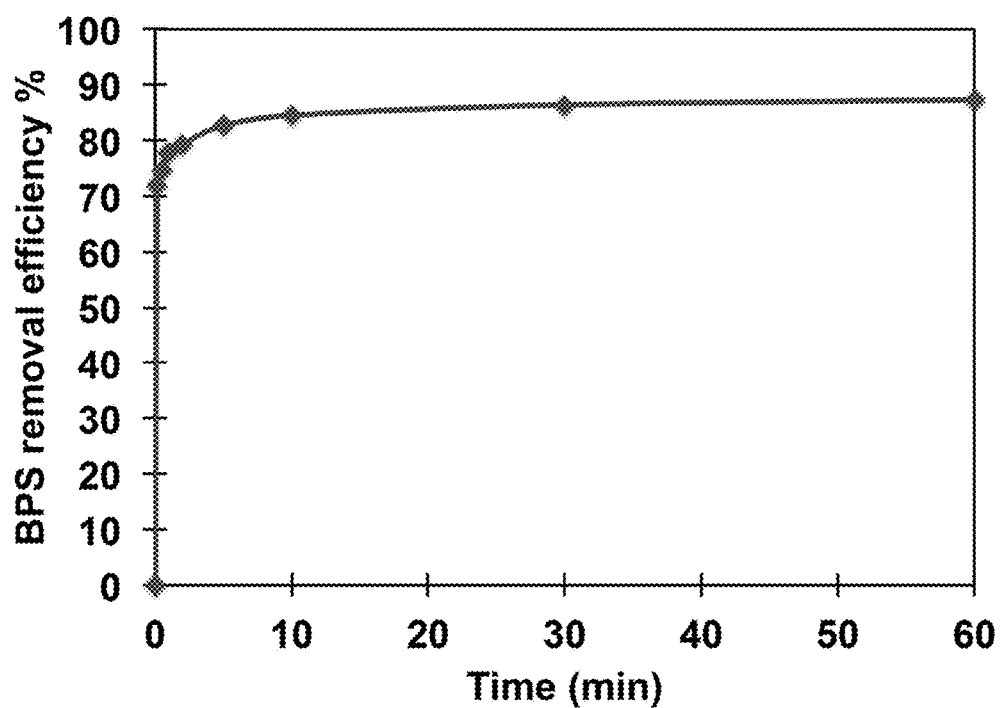

FIG. 51 shows time-dependent adsorption efficiency for BPS by P-CDP.

Figure 52:
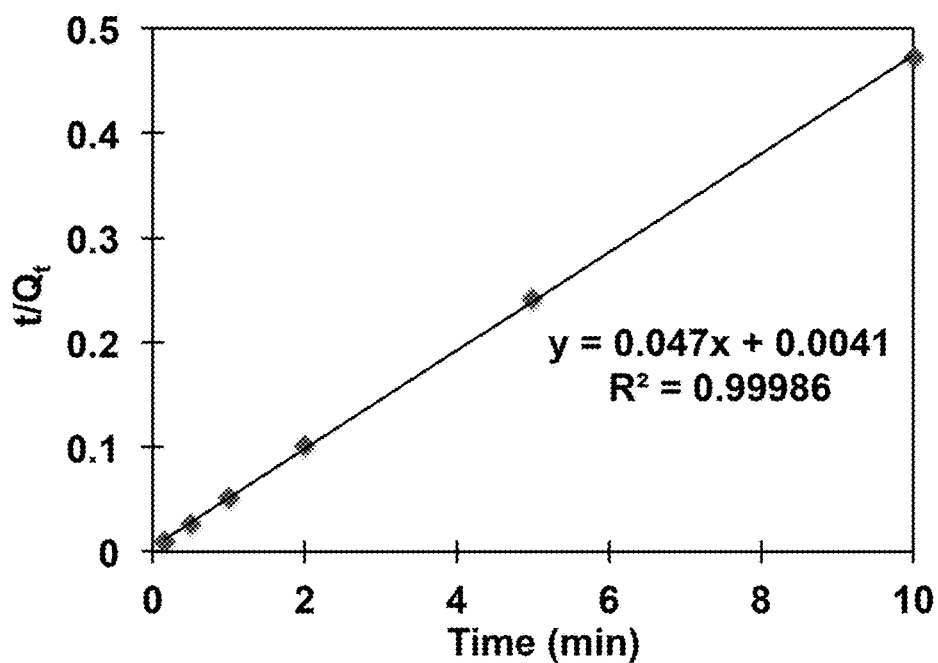

FIG. 52 shows a pseudo-second-order plot of BPS adsorption on P-CDP.

Figure 53:
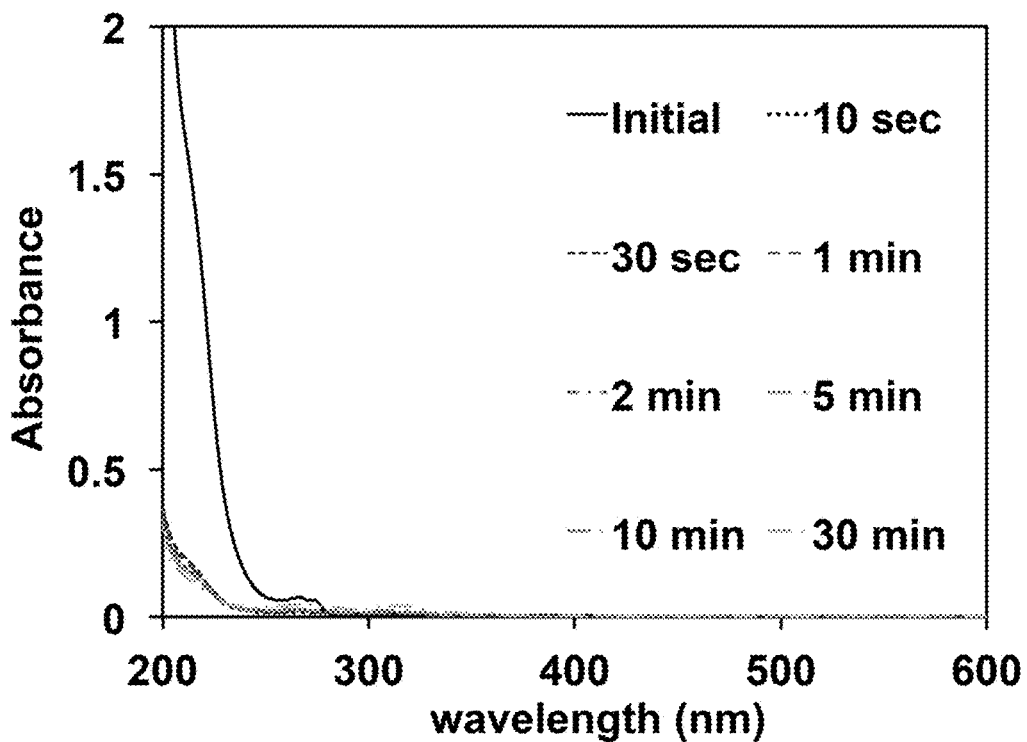

FIG. 53 shows UV-visible spectra that indicate the adsorption of metolachlor on P-CDP as a function of time.

Figure 54:
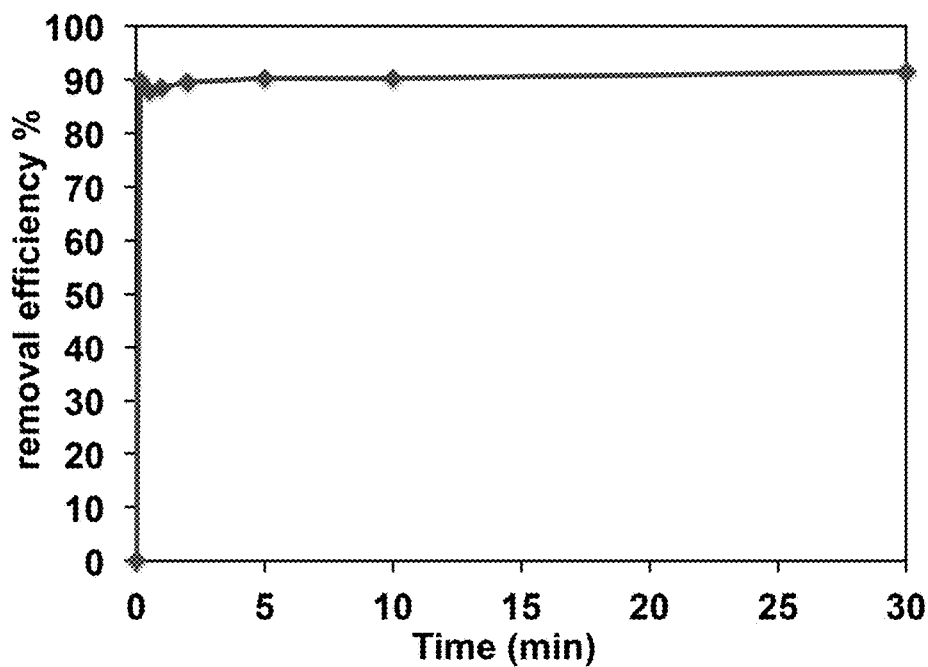

FIG. 54 shows time-dependent adsorption efficiency for metolachlor by P-CDP.

Figure 55:
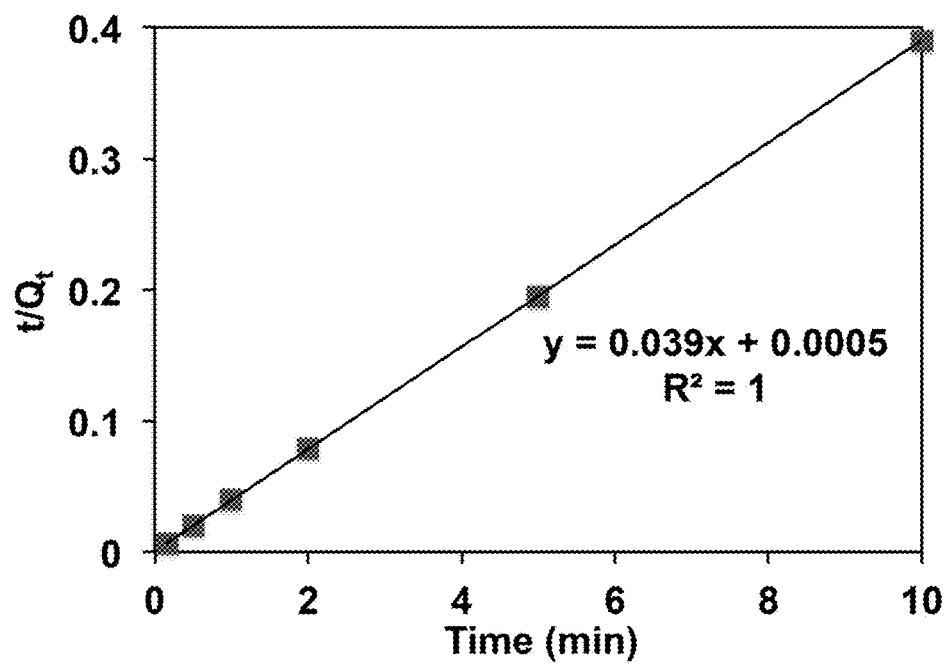

FIG. 55 shows a pseudo-second-order plot of metolachlor adsorption on P-CDP.

Figure 56:
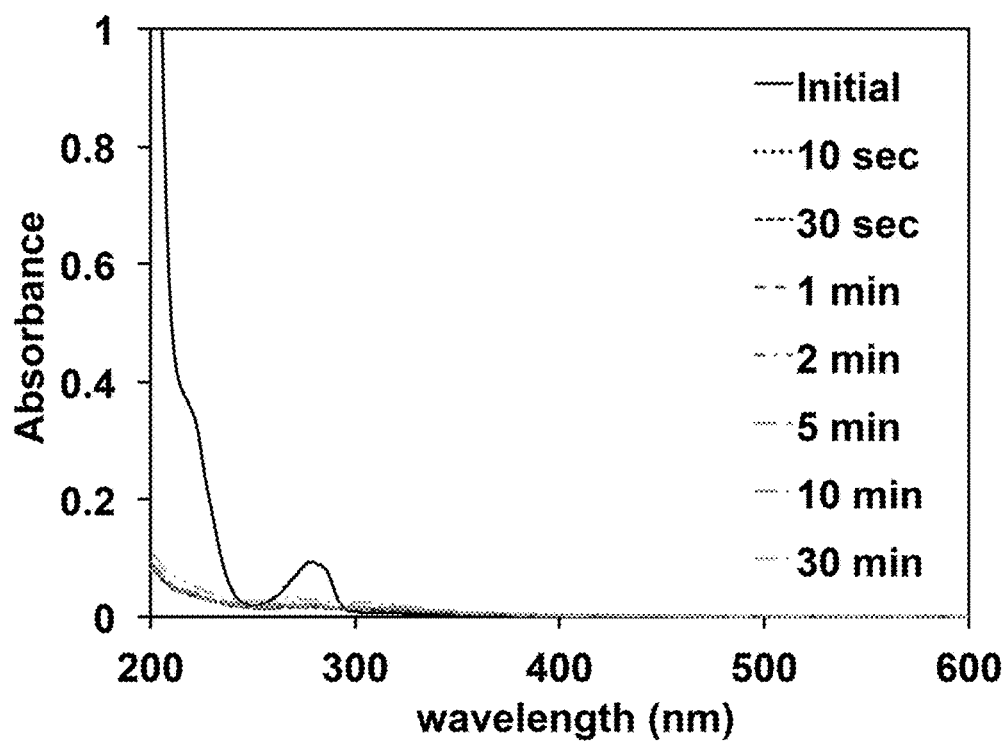

FIG. 56 shows UV-visible spectra that indicate the adsorption of ethinyl estradiol on P-CDP as a function of time.

Figure 57:
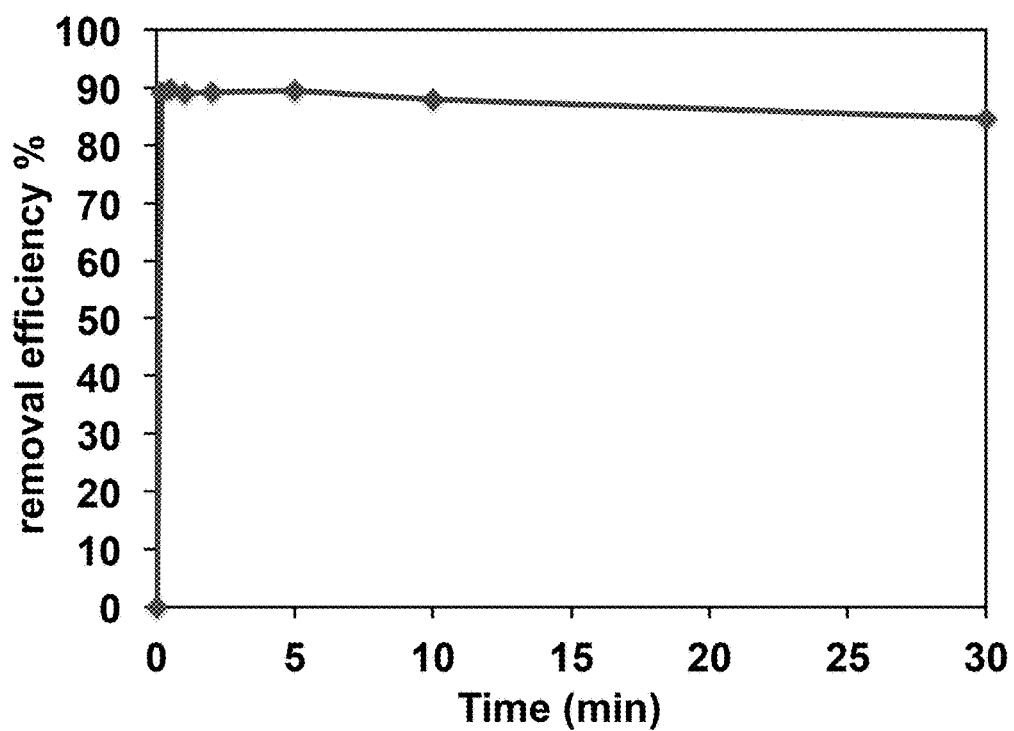

FIG. 57 shows time-dependent adsorption efficiency for ethinyl estradiol by P-CDP.

Figure 58:
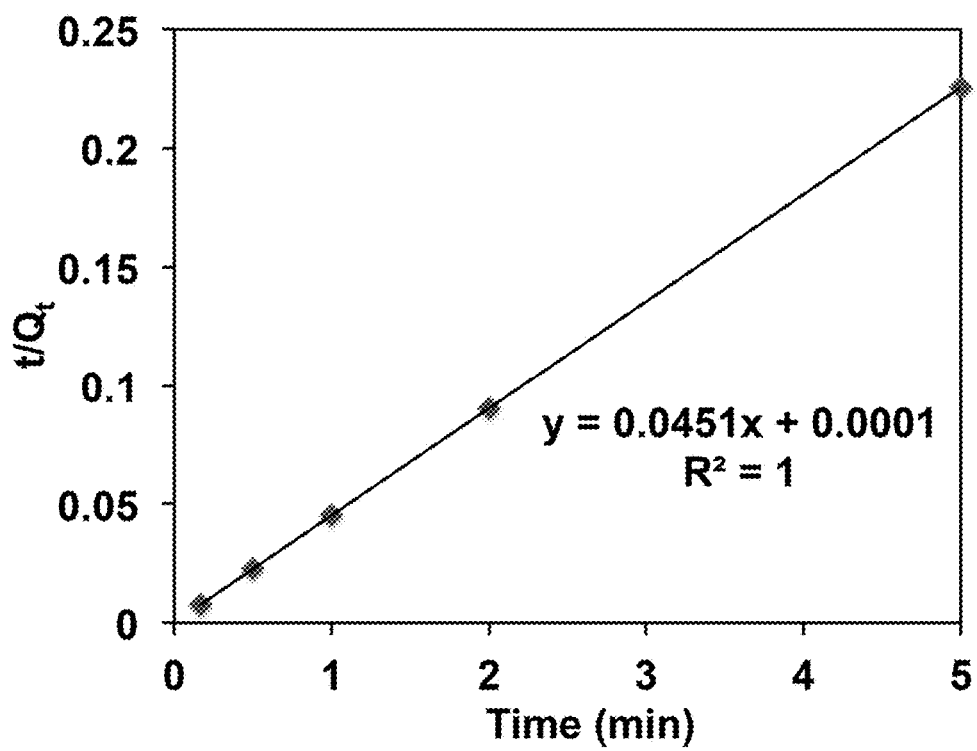

FIG. 58 shows a pseudo-second-order plot of ethinyl estradiol adsorption on P-CDP.

Figure 59:
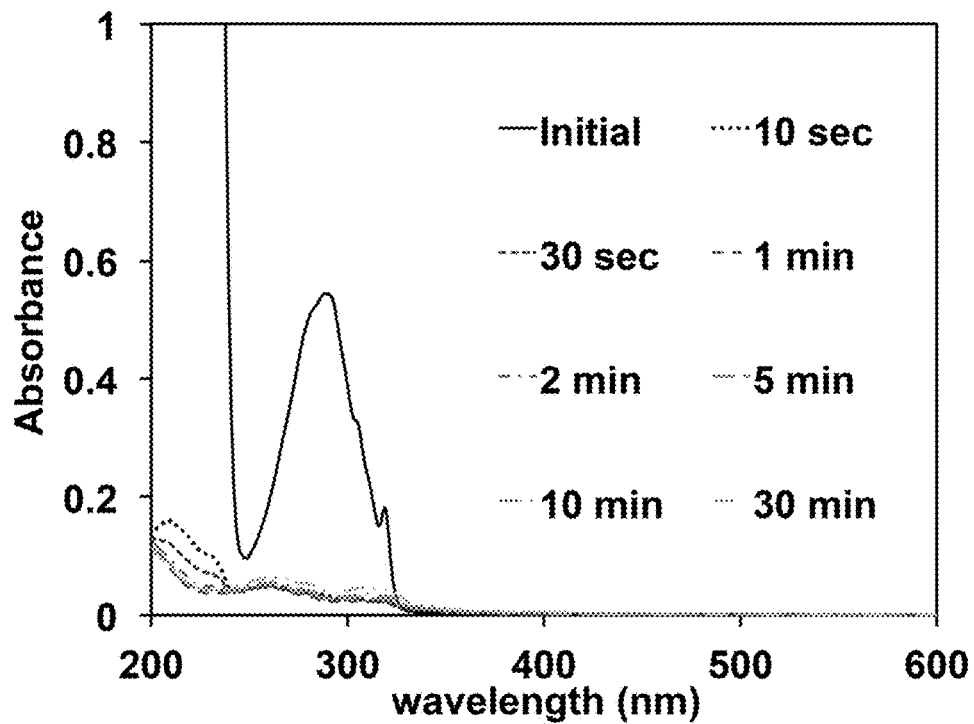

FIG. 59 shows UV-visible spectra that indicate the adsorption of propranolol hydrochloride on P-CDP as a function of time.

Figure 60:
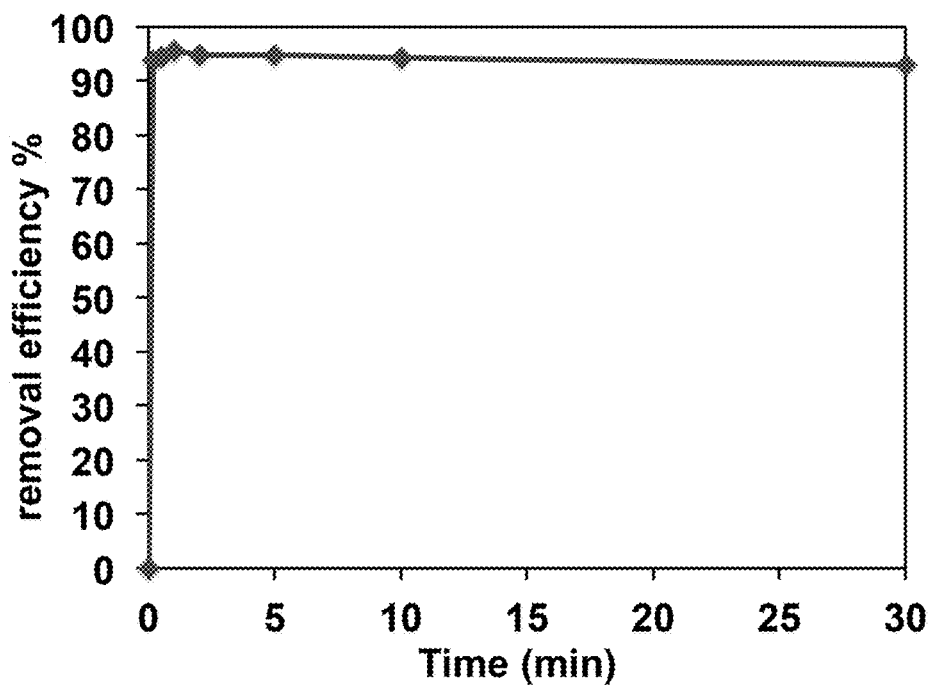

FIG. 60 shows time-dependent adsorption efficiency for propranolol hydrochloride by P-CDP.

Figure 61:
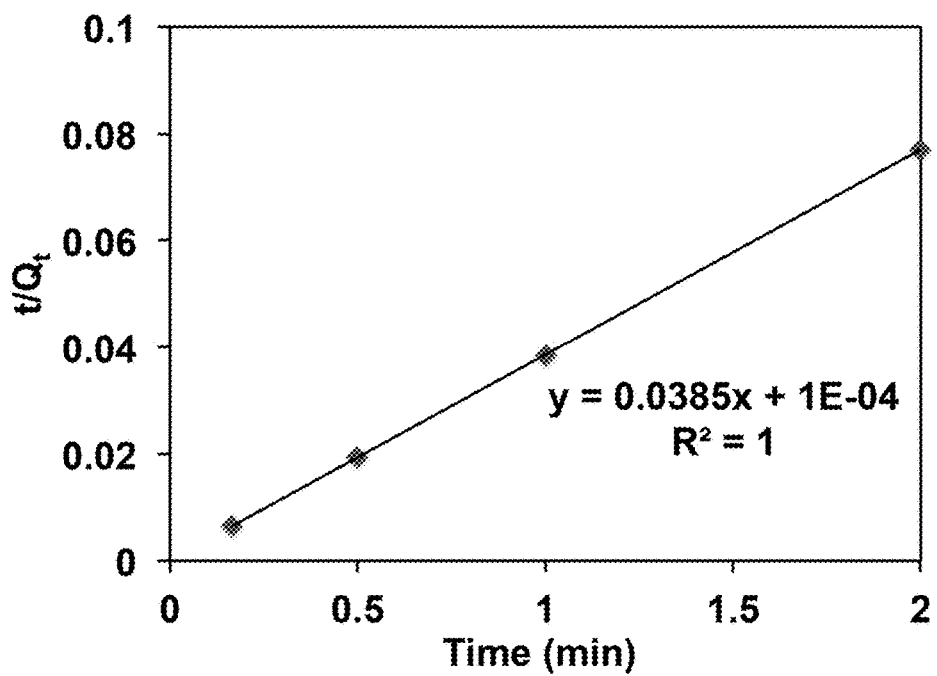

FIG. 61 shows a pseudo-second-order plot of propranolol hydrochloride adsorption on P-CDP.

Figure 62:
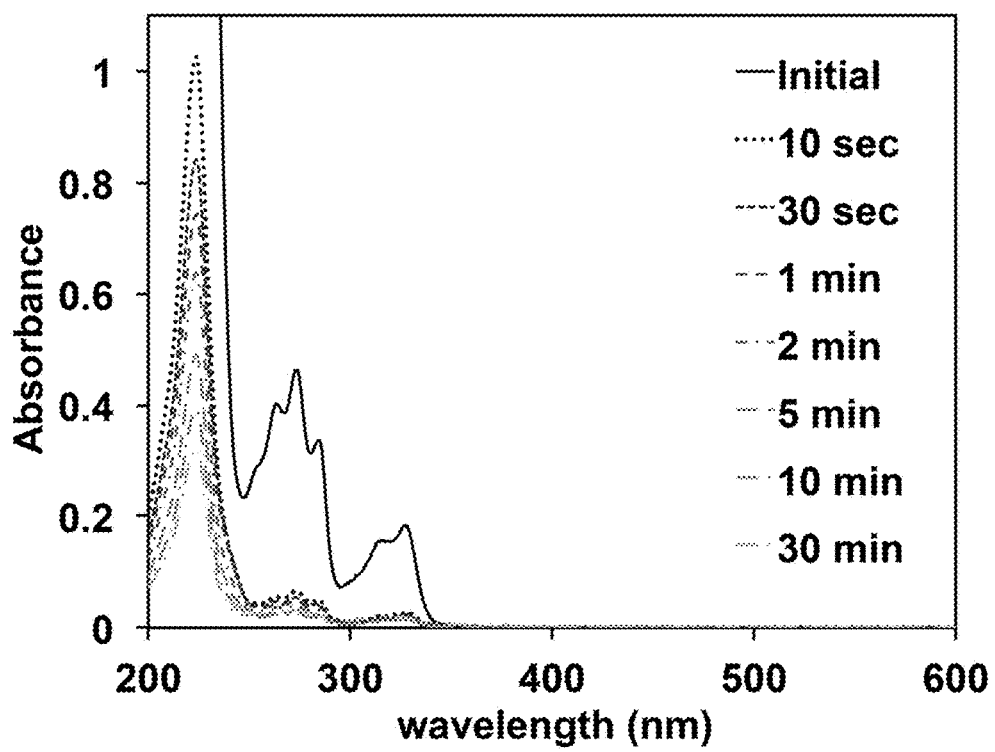

FIG. 62 shows UV-visible spectra that indicate the adsorption of 2-NO on P-CDP as a function of time.

Figure 63:
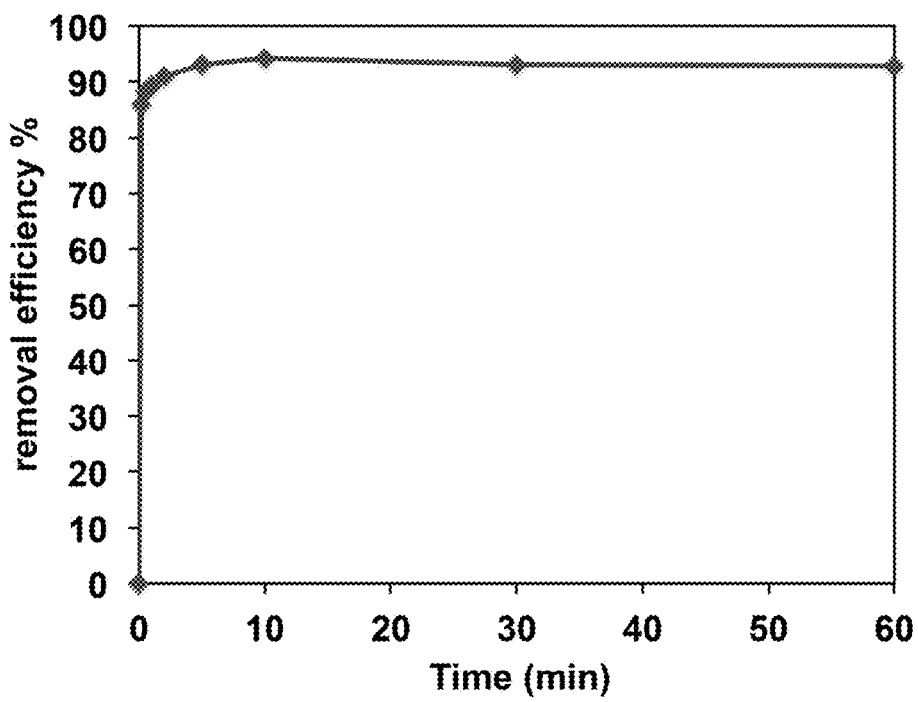

FIG. 63 shows time-dependent adsorption efficiency for 2-NO by P-CDP.

Figure 64:
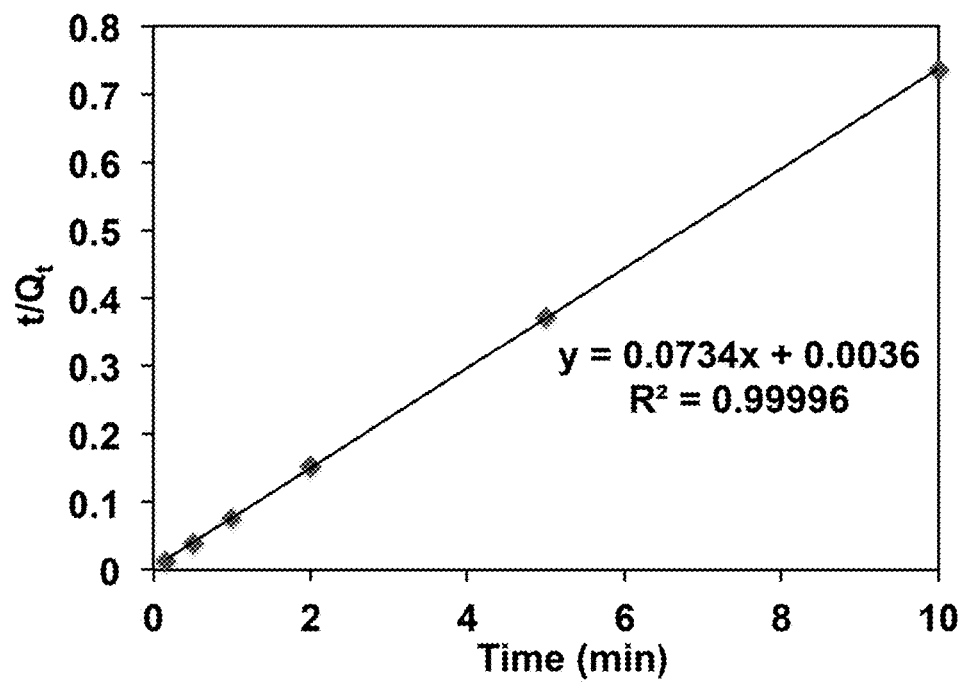

FIG. 64 shows a pseudo-second-order plot of 2-NO adsorption on P-CDP.

Figure 65:
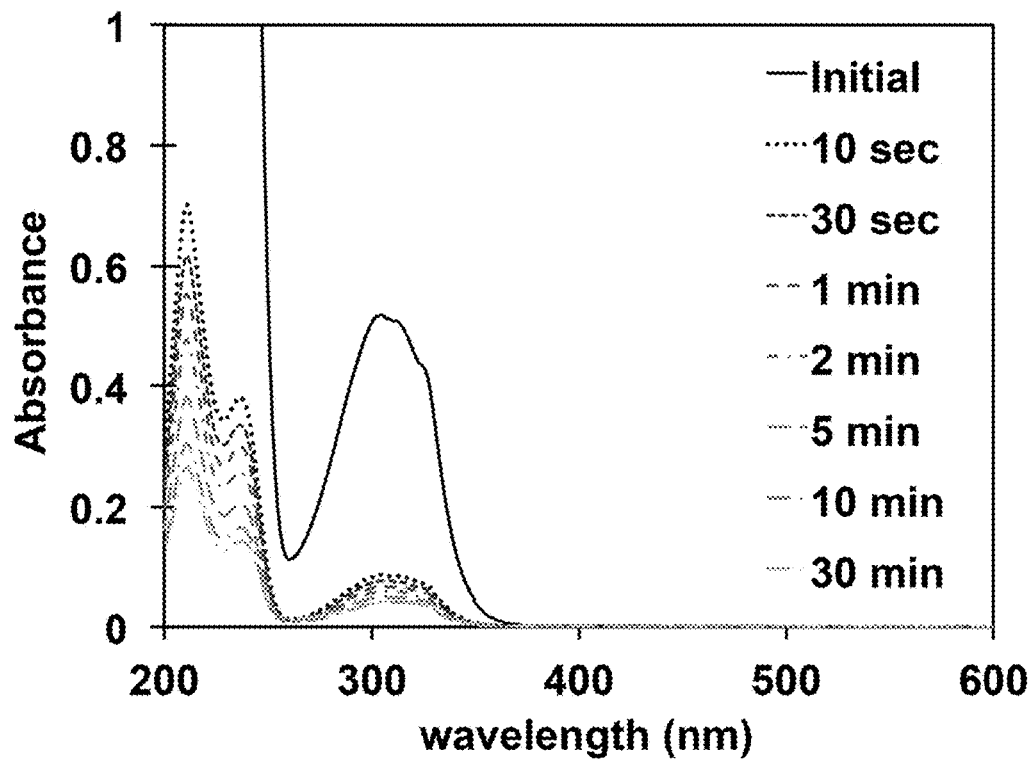

FIG. 65 shows UV-visible spectra that indicate the adsorption of 1-NA on P-CDP as a function of time.

Figure 66:
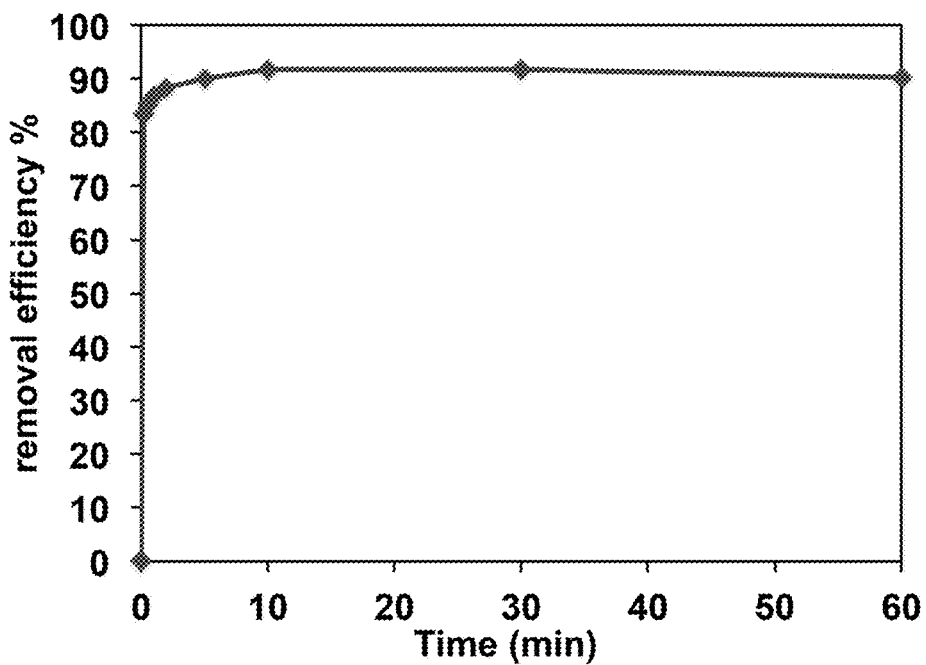

FIG. 66 shows time-dependent adsorption efficiency for 1-NA by P-CDP.

Figure 67:
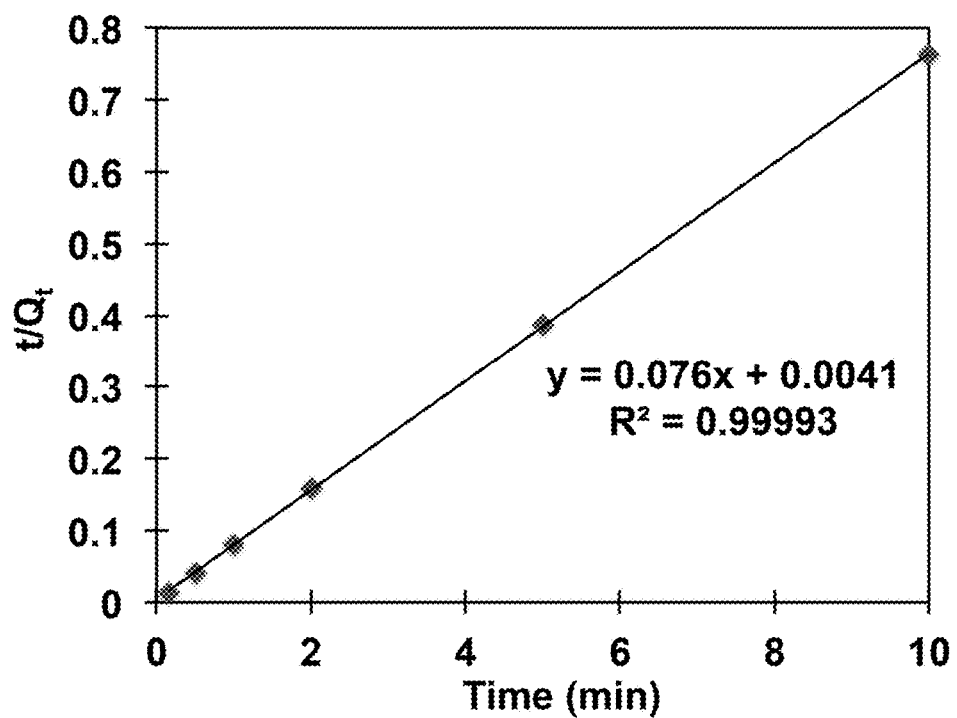

FIG. 67 shows a pseudo-second-order plot of 1-NA adsorption on P-CDP.

Figure 68:
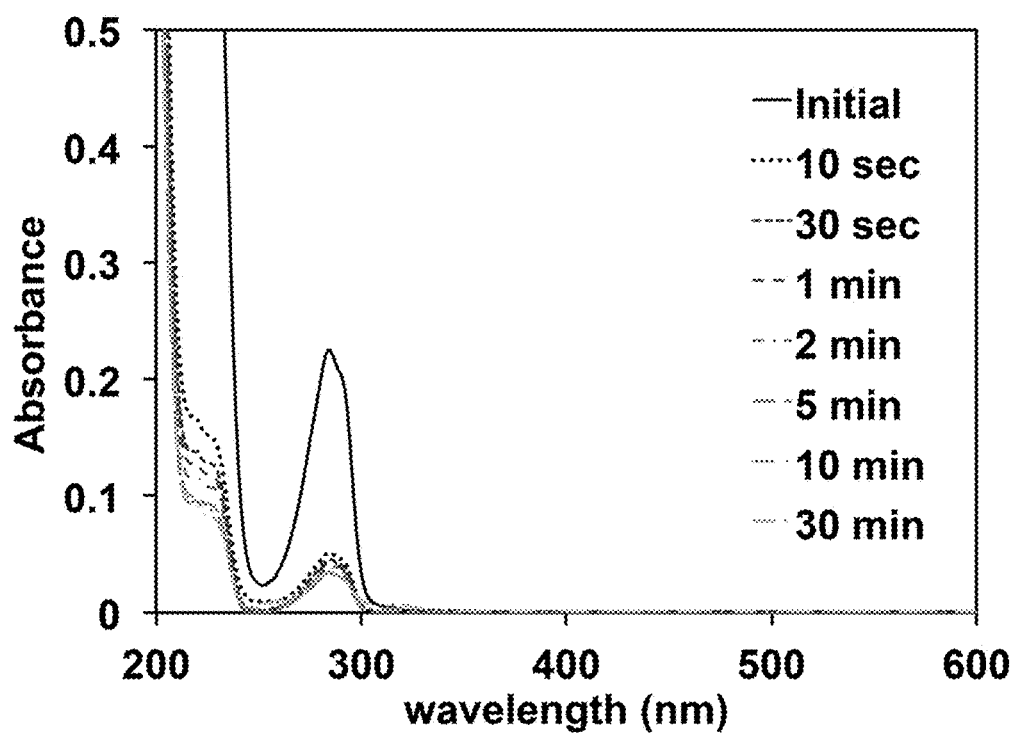

FIG. 68 shows UV-visible spectra that indicate the adsorption of DCP on P-CDP as a function of time.

Figure 69:
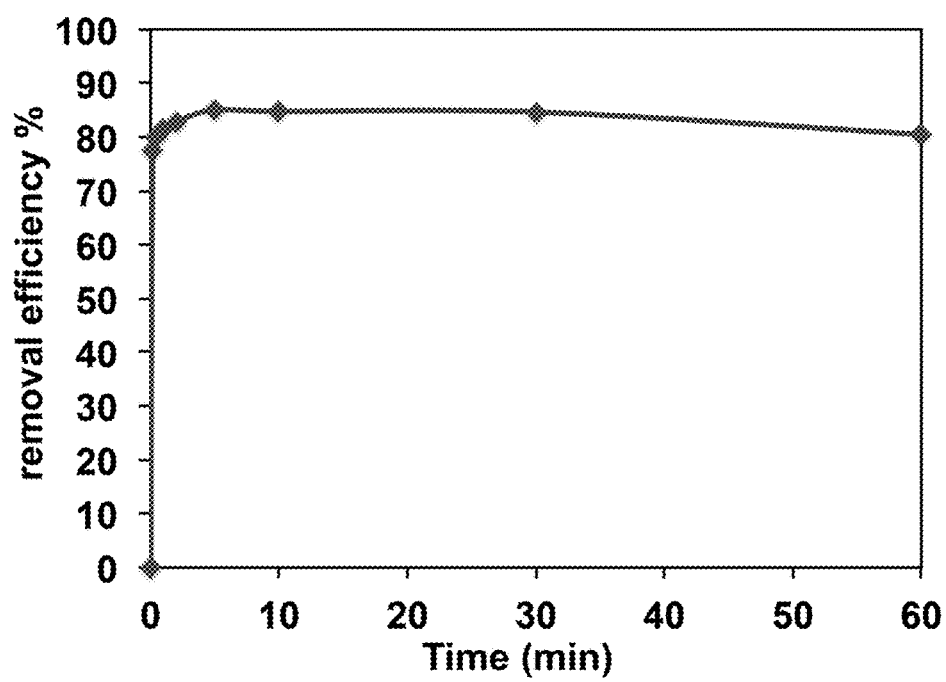

FIG. 69 shows time-dependent adsorption efficiency for DCP by P-CDP.

Figure 70:
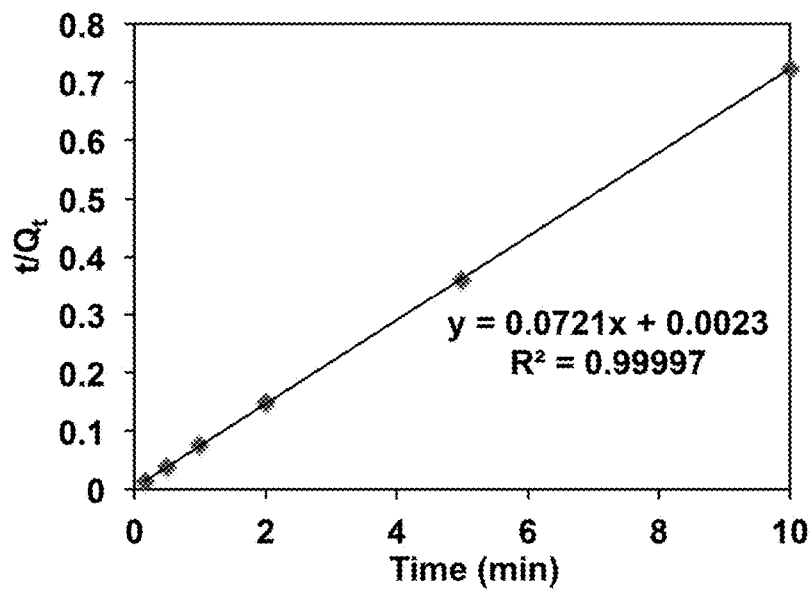

FIG. 70 shows a pseudo-second-order plot of DCP adsorption on P-CDP.

Figure 71:
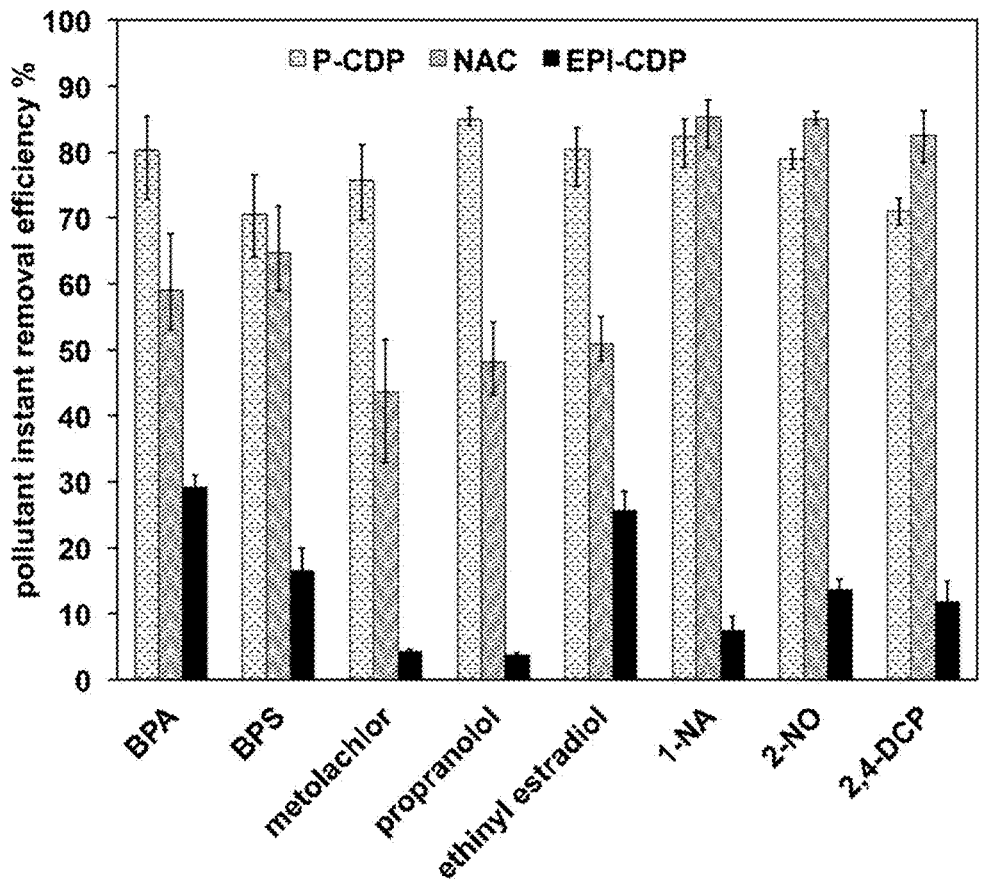

FIG. 71 shows the adsorption efficiencies for various contaminants (at a starting concentration of 0.1 mM) by P-CDP, NAC, and EPI-CDP for a very short contact time with each adsorbent (approximately 1 second).

Figure 72:
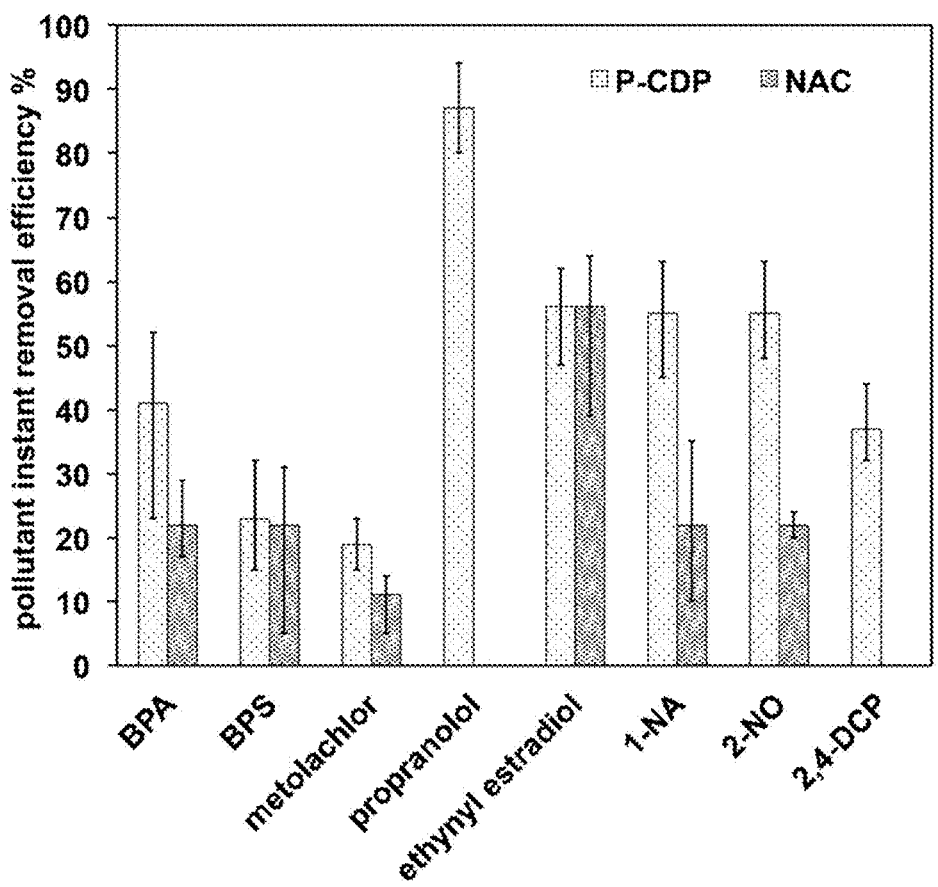

FIG. 72 shows the adsorption efficiencies for various contaminants by P-CDP and NAC for a very short contact time with each adsorbent (approximately 1 second). Individual pollutant concentrations (in units of μg/L) in the mixture were: 100 (BPA); 2.5 (BPS); 5 (metolachlor); 100 (propranolol); 50 (ethinyl estradiol); 5 (1-NA); 25 (2-NO); and 2.5 (2,4-DCP). Data are reported as the average uptake of three independent experiments. Error bars, minimum and maximum uptake.

Figure 73:
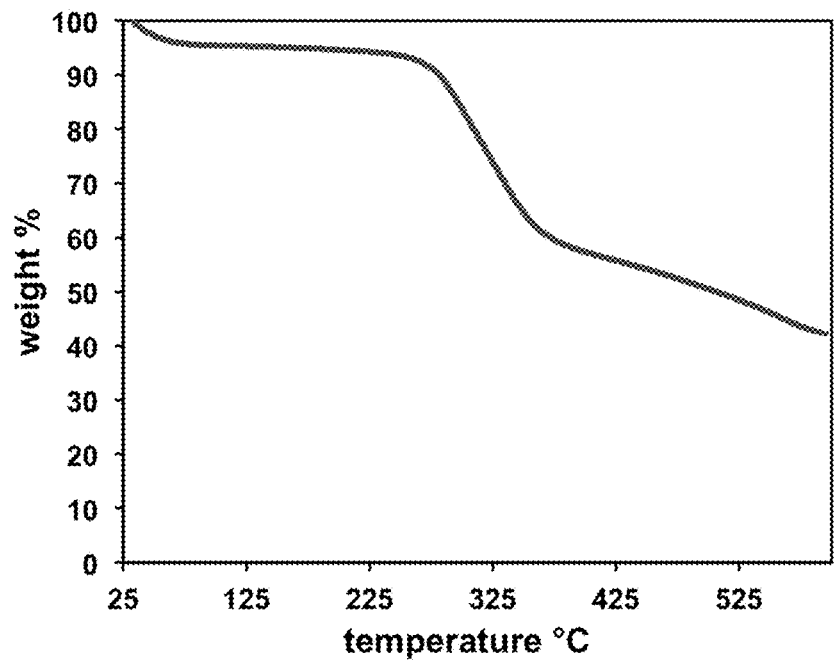

FIG. 73 is a thermogravimetric analysis plot of P-CDP.

Figure 74:
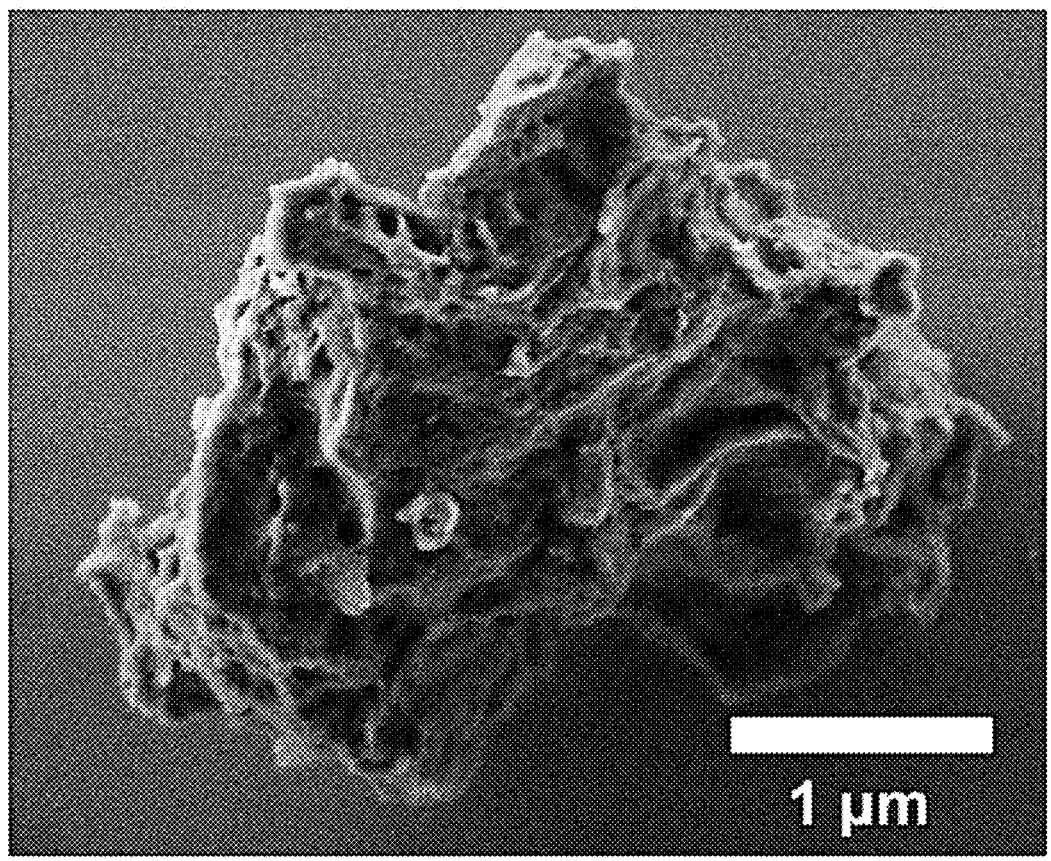

FIG. 74 is a representative scanning electron micrograph of a P-CDP particle.

Figure 75:
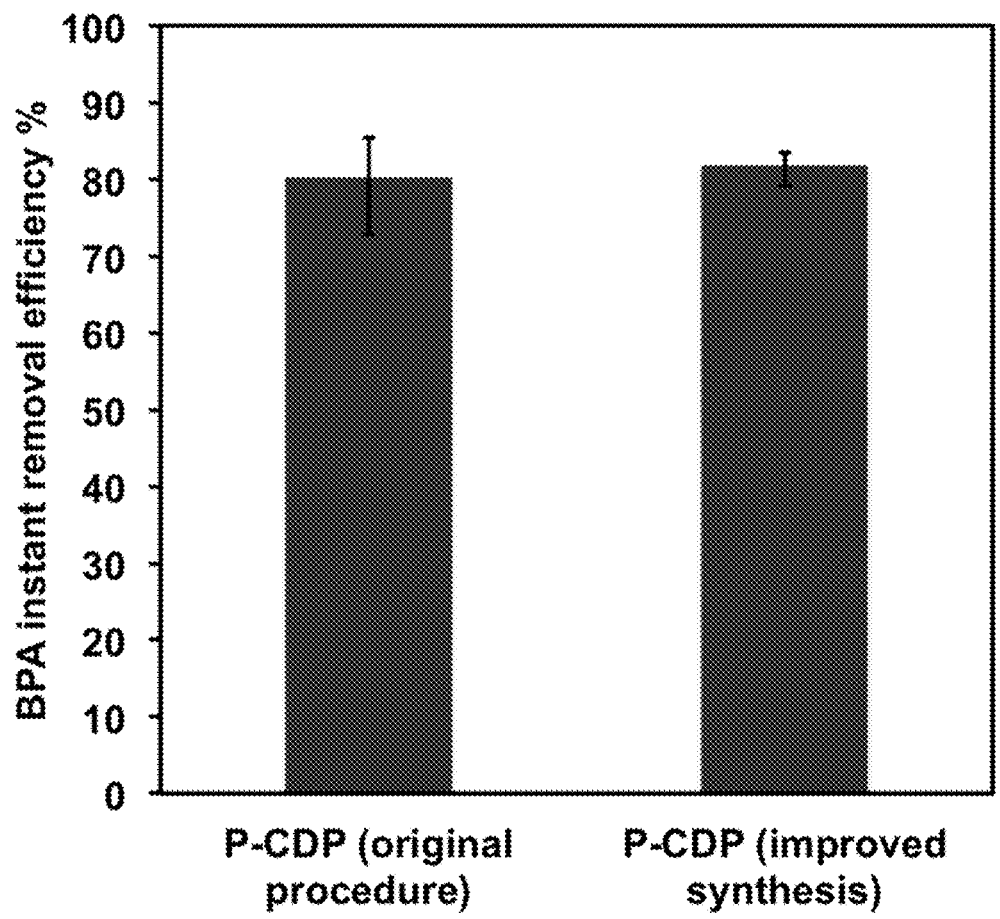

FIG. 75 shows a comparison of BPA instant removal efficiency for P-CDP prepared by different methods.

Figure 76:
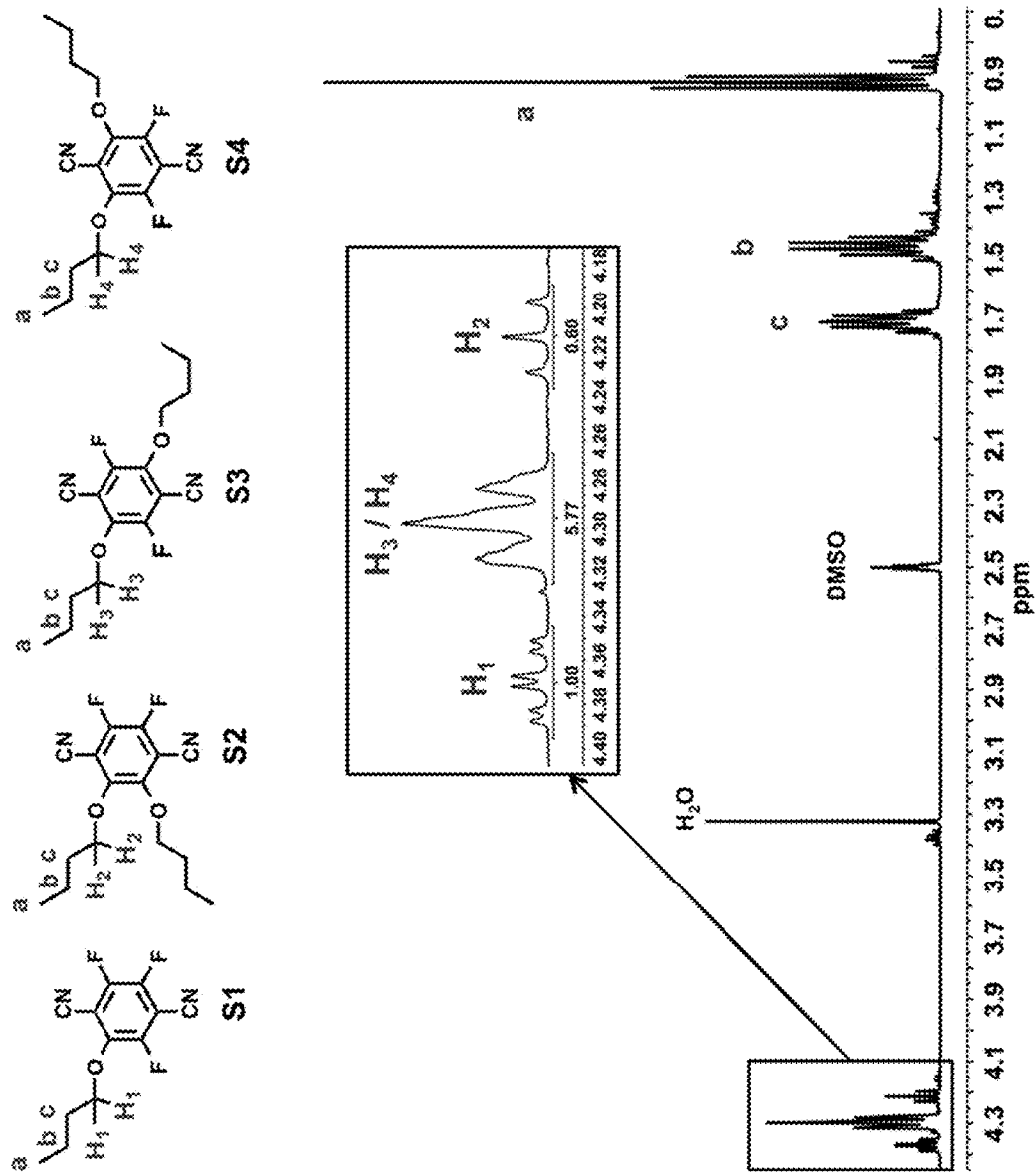

FIG. 76 shows a partial $^1$H NMR spectrum (DMSO-$d_6$, 400 MHz, rt) of the unpurified products of model reaction S2.

FIG. 77 shows partial $^1$ and $^{19}$F NMR spectra showing the formation of mono substituted product S5.

Figure 78:
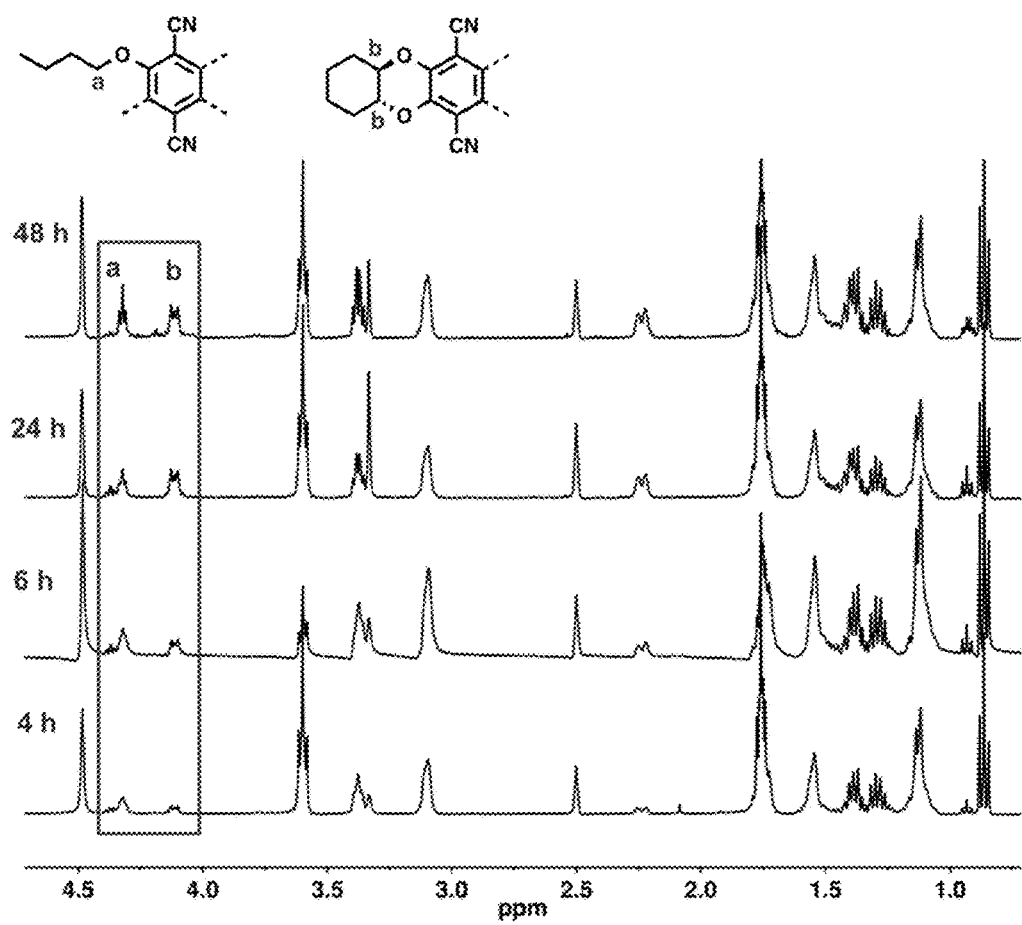

FIG. 78 shows the $^1$H NMR spectra (DMSO-$d_6$, 400 MHz, rt) of aliquots of the competition substitution model reaction S4 collected at various reaction times.

Figure 79:
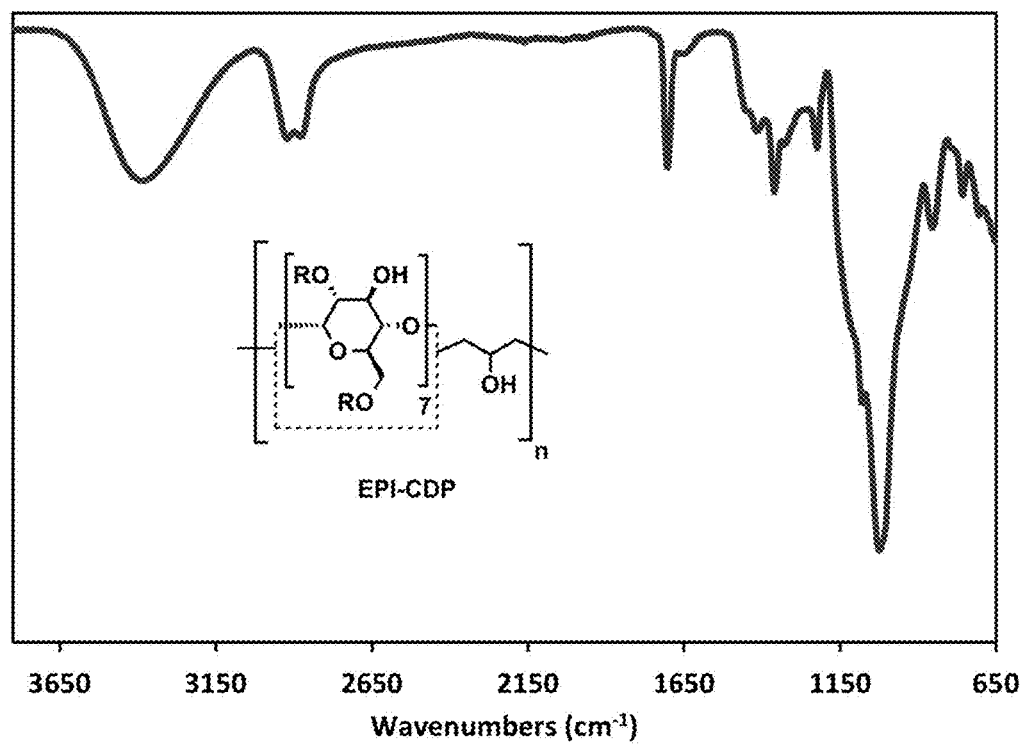

FIG. 79 shows the FT-IR spectrum of as-synthesized EPI-CDP.

FIG. 80 is a table of molecular descriptor values for 83 micropollutants.

FIG. 81 is a table of analytical details for 83 micropollutants.

FIG. 82 describes the major results of the kinetics and instantaneous uptake experiments for 83 micropollutants.

Figure 83:
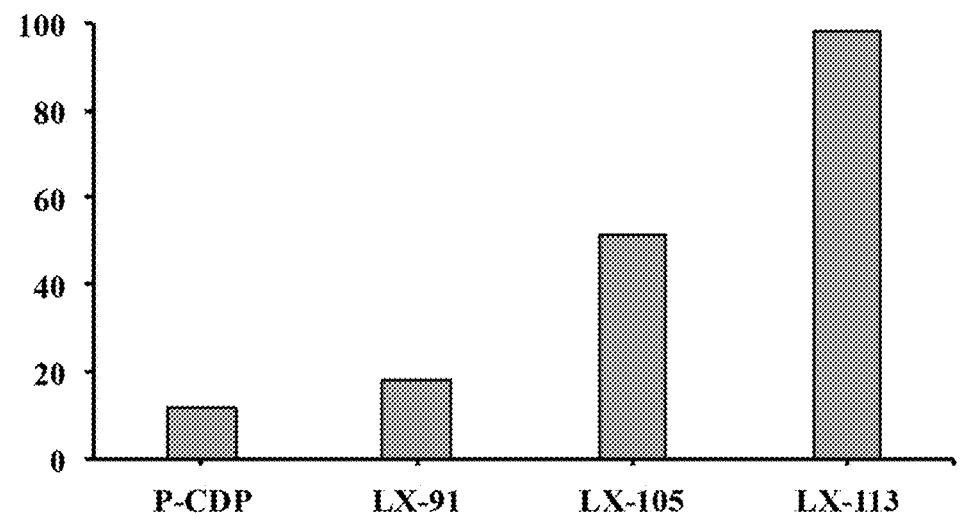

FIG. 83 is a bar graph of equilibrium levels of PFOA removal for cyclodextrin polymers P-CDP, LX-91, LX-105, and LX-113.

Figure 84:
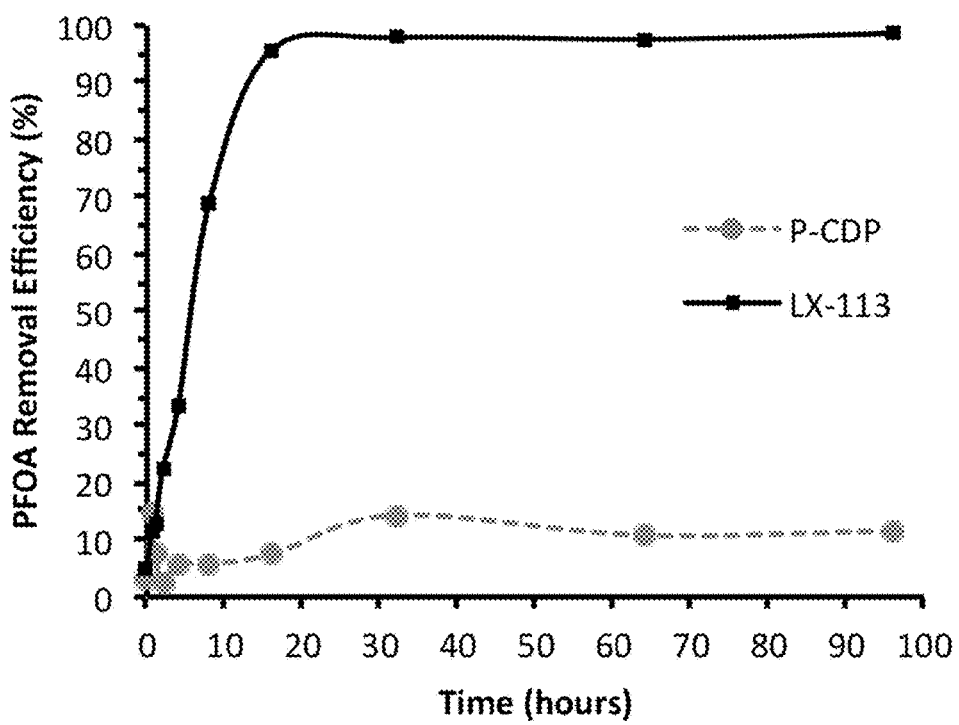

FIG. 84 shows time dependent levels of PFOA removal for LX-113 compared to P-CDP.

Figure 85:
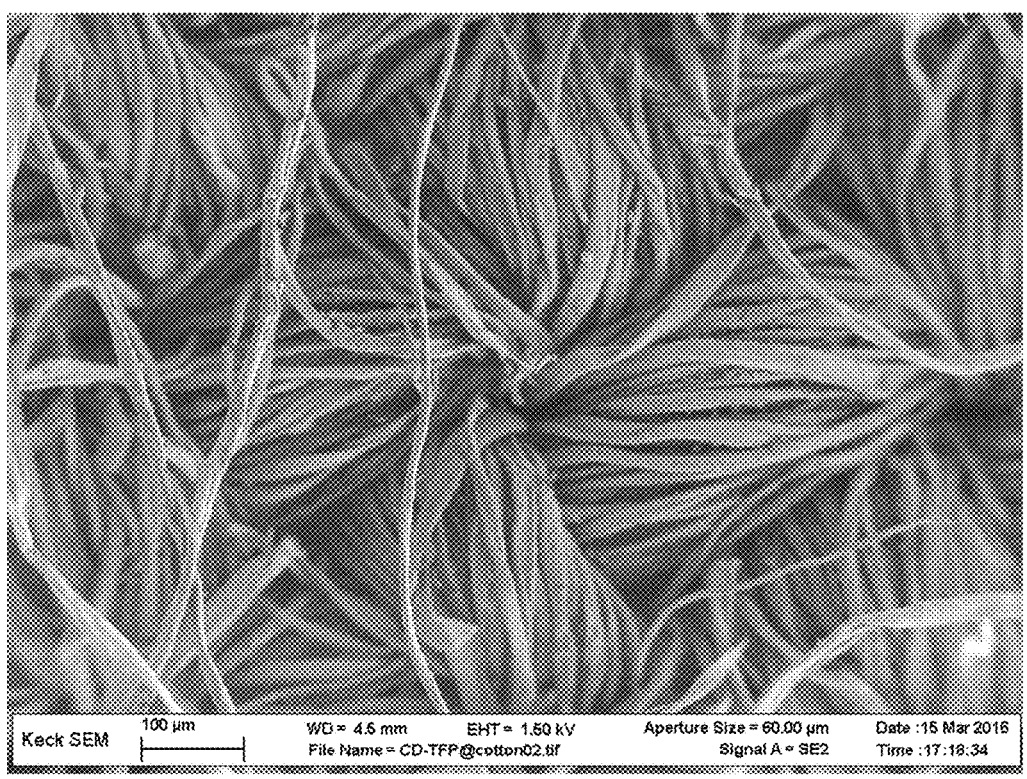

FIG. 85 is an SEM image P-CDP@cotton.

Figure 86:
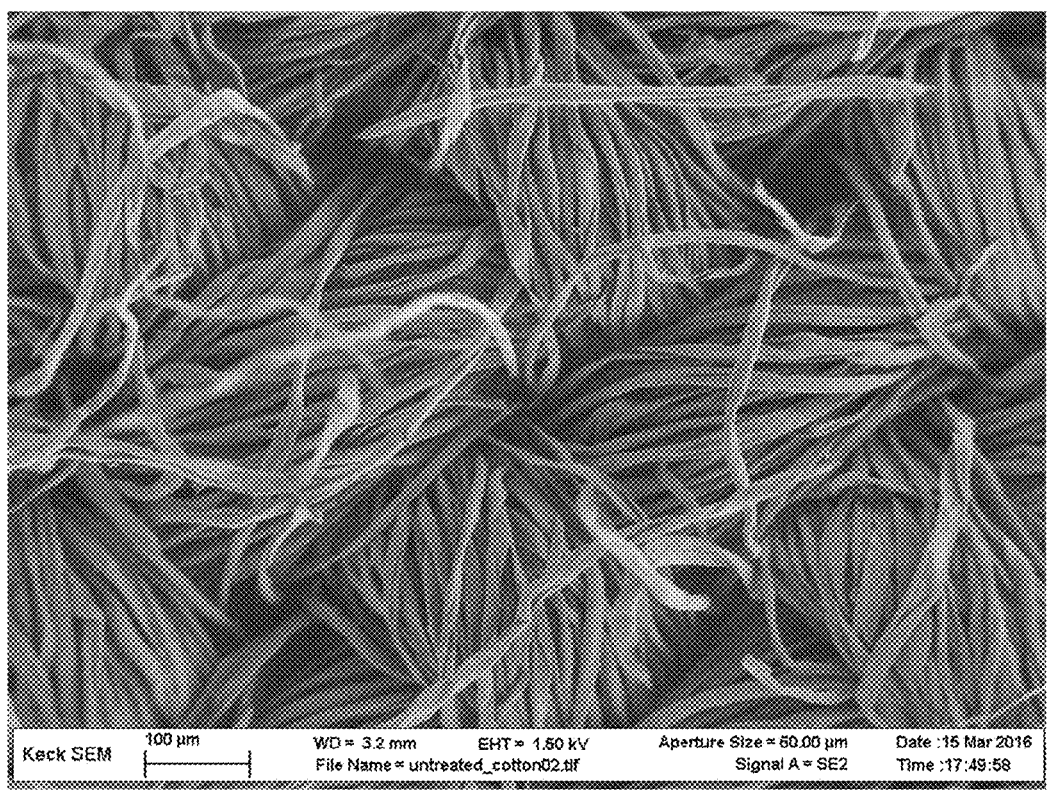

FIG. 86 is an SEM image of untreated cotton.

Figure 87:
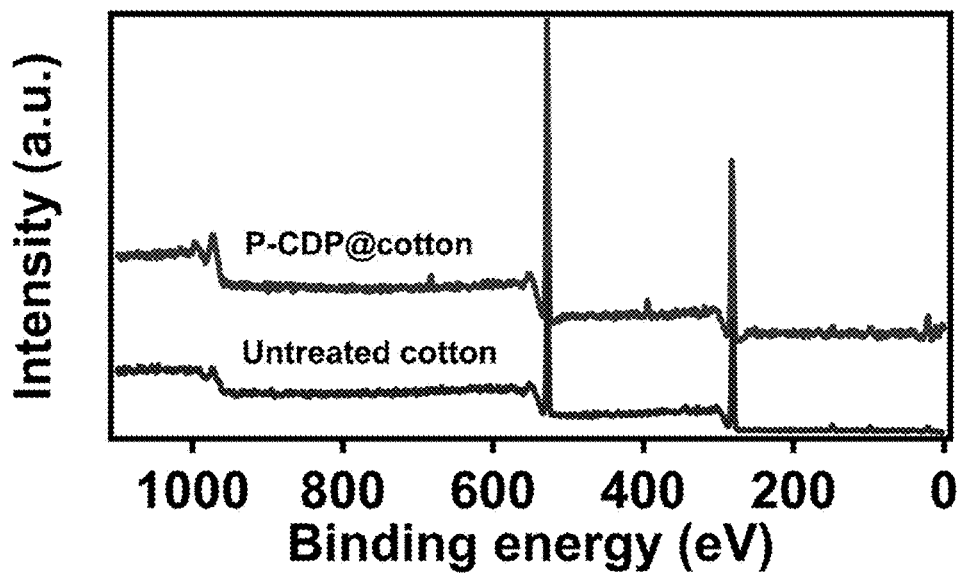

FIG. 87 is an XPS survey of the P-CDP@cotton and untreated cotton.

Figure 88:
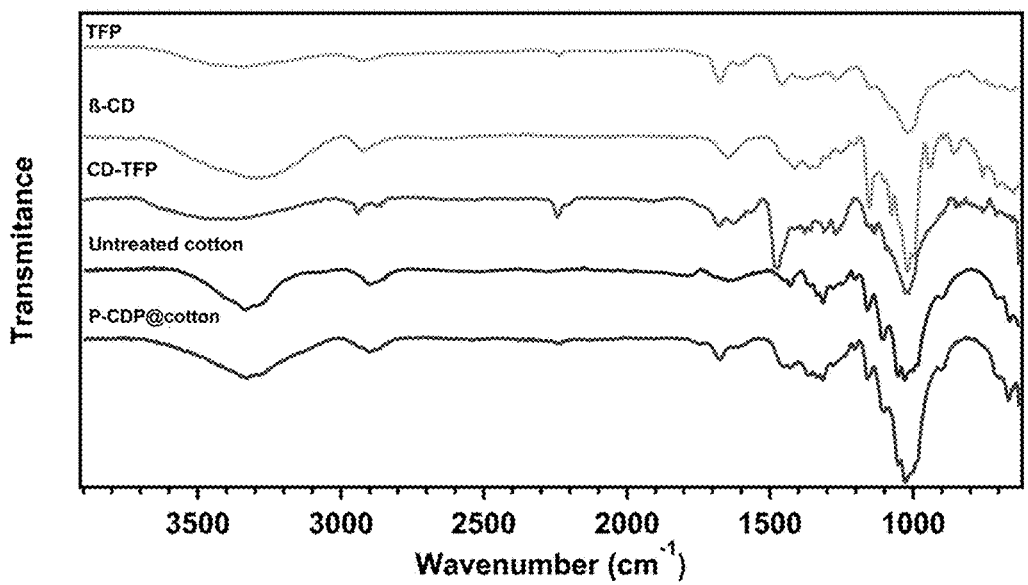

FIG. 88 is a comparison of the infrared spectra of various materials.

Figure 89:
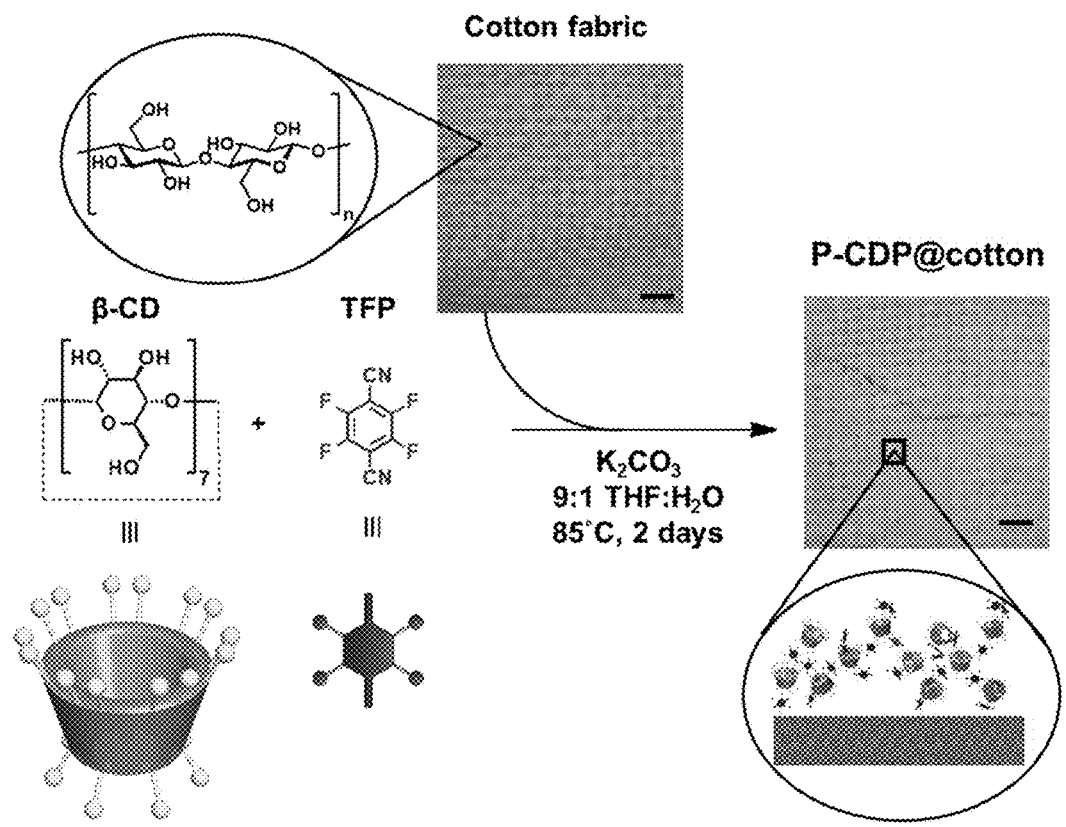

FIG. 89 is a graphic depiction of a P-CDP supported on a cotton fabric substrate (P-CDP@cotton).

Figure 90:
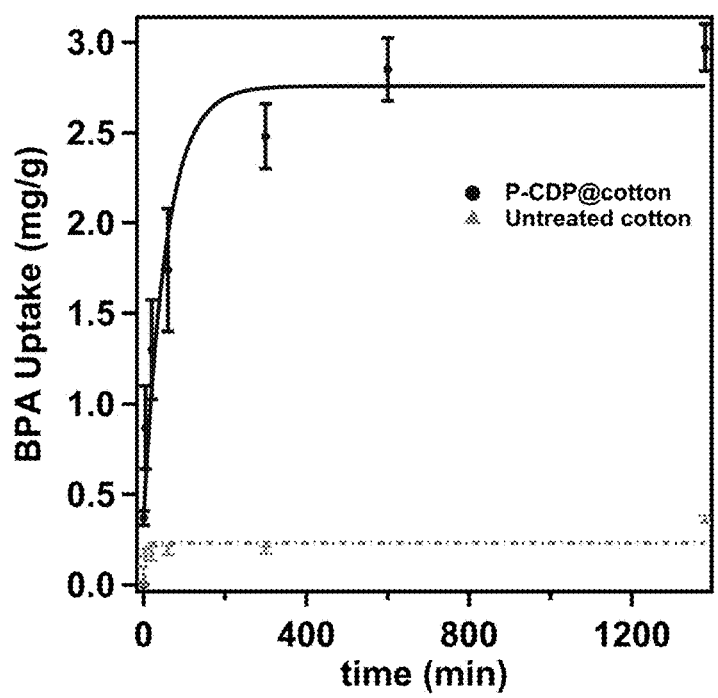

FIG. 90 shows BPA uptake for P-CDP@cotton and untreated cotton fabric as a function of time.

Figure 91:
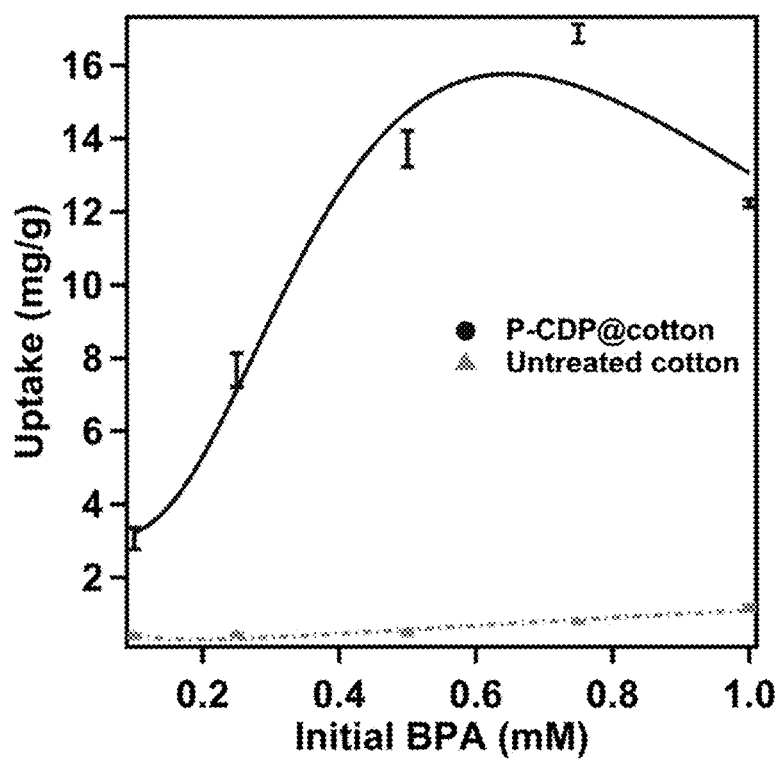

FIG. 91 shows BPA uptake for P-CDP treated and untreated cotton fabric as a function of initial concentration.

Figure 92:
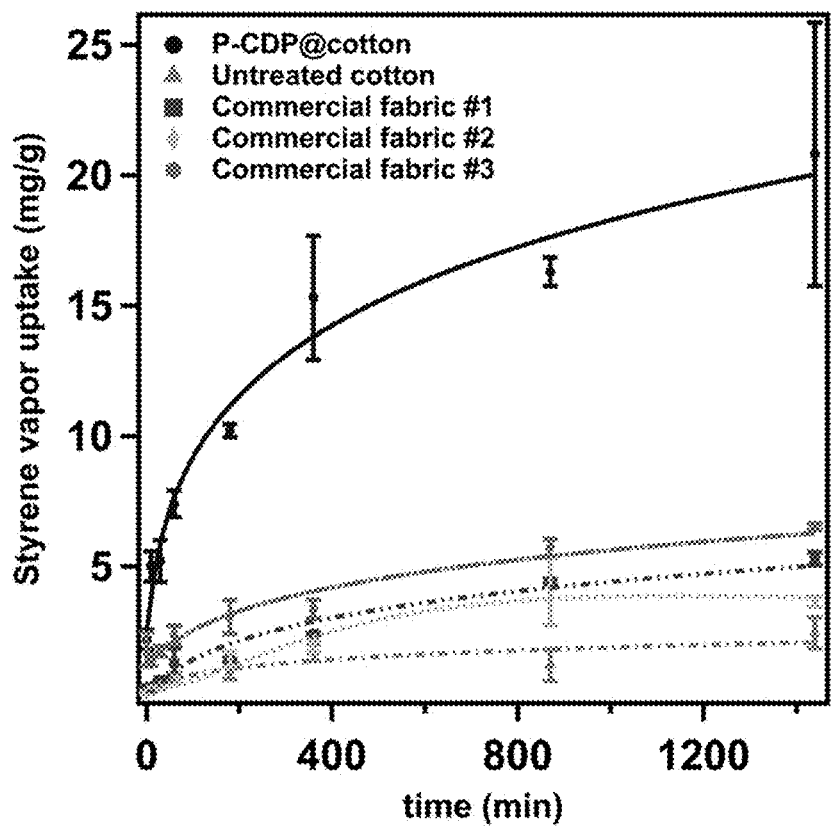

FIG. 92 shows the gas phase adsorption of styrene as a function of time by P-CDP@cotton, untreated cotton, and various commercial fabrics.

Figure 93:
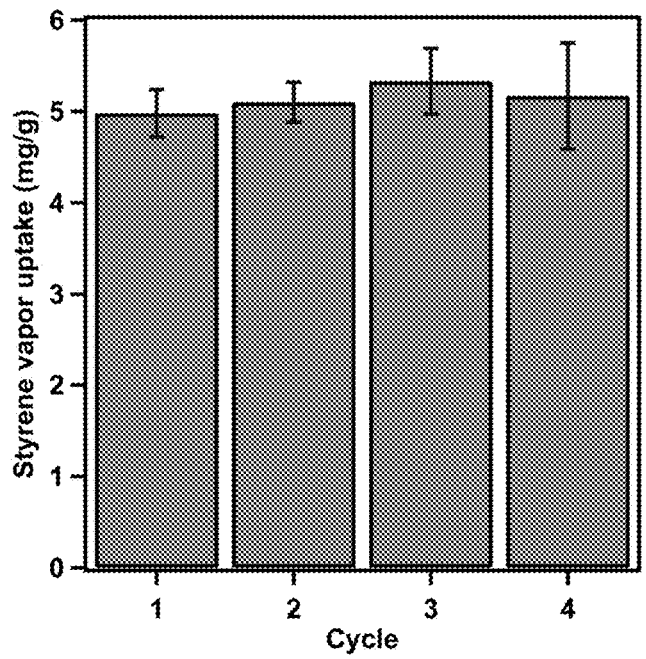

FIG. 93 shows the ability of P-CDP@cotton to adsorb styrene over repeated cycles.

Figure 94:
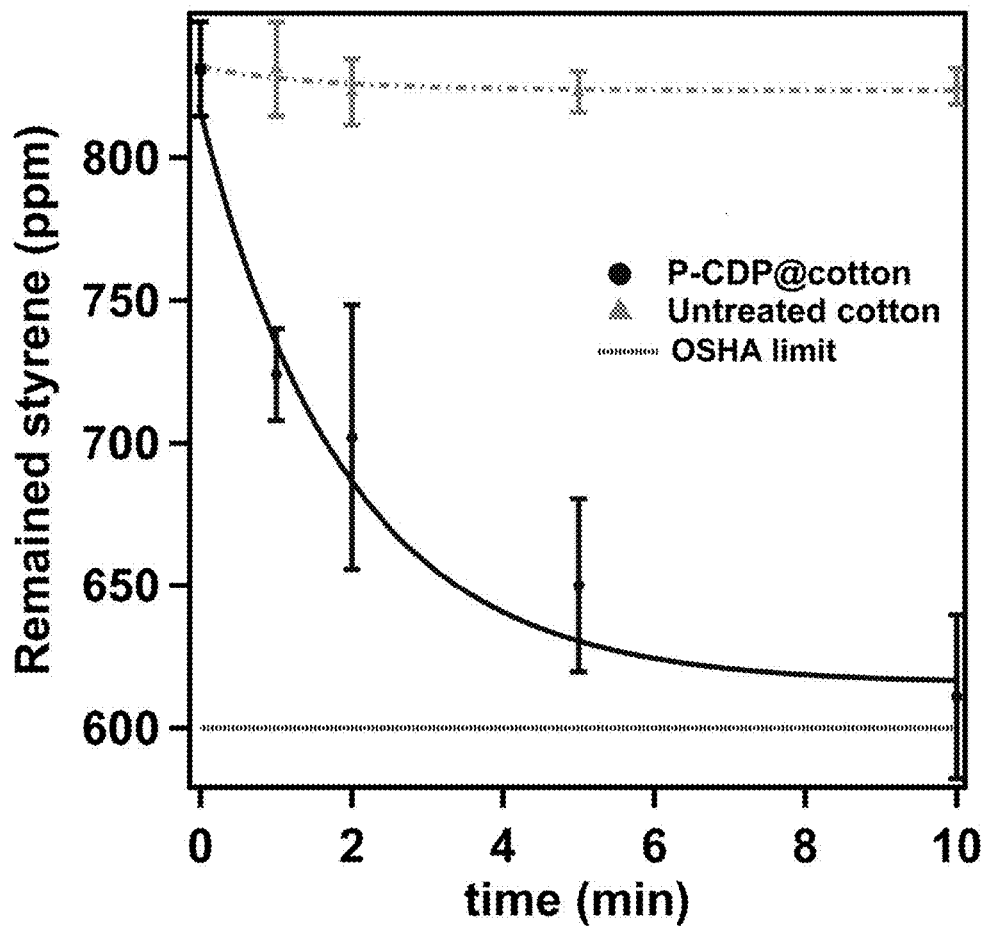

FIG. 94 shows the reduction in gas phase styrene by adsorption P-CDP@cotton and untreated cotton exposed to 850 ppm styrene.

Figure 95:
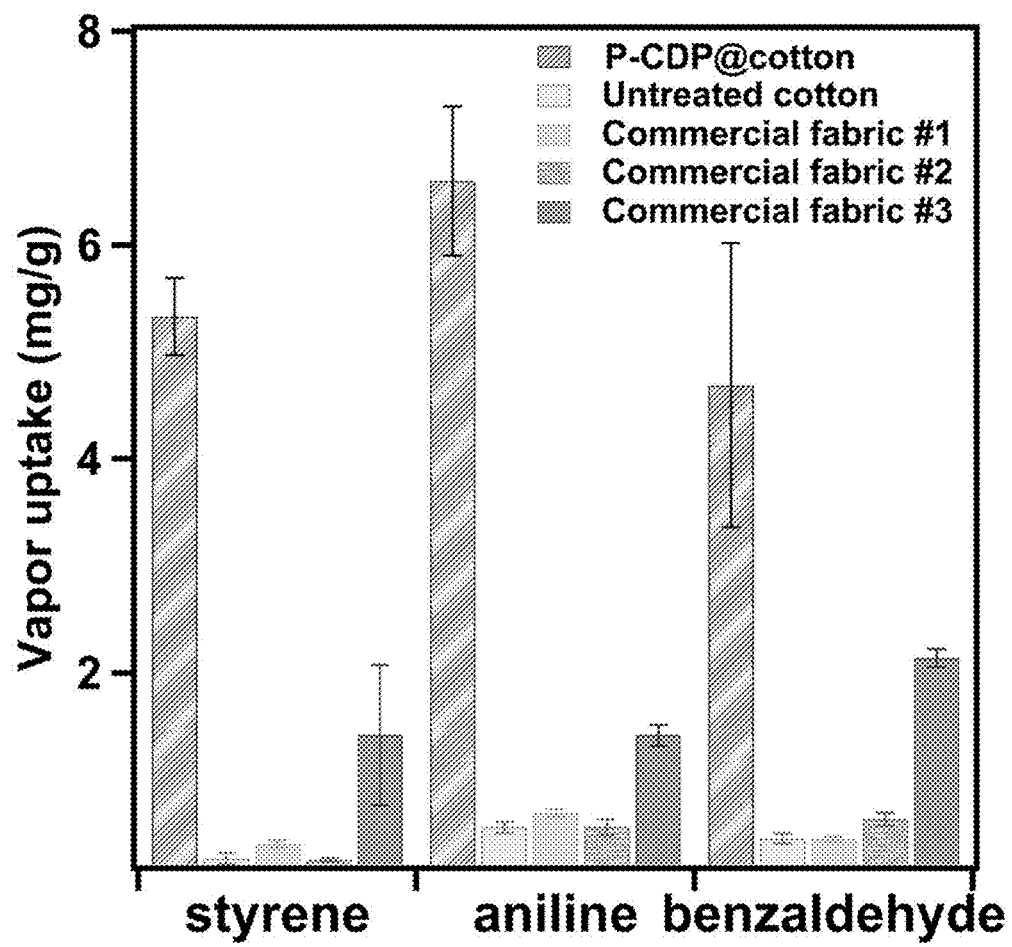

FIG. 95 shows the gas phase uptake of three different gases by P-CDP@cotton compared to untreated cotton and various commercial fabrics.

FIG. 96 shows a table of solvatochromic parameters for 60 micropollutants for LSER model training and validation.

Figure 97:
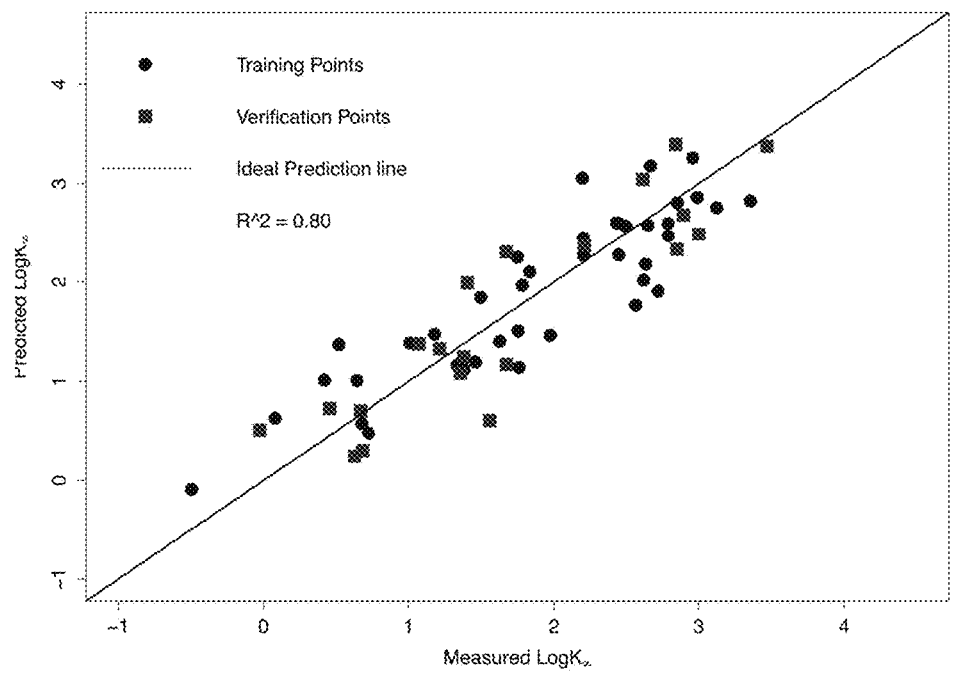

FIG. 97 shows the LSER model derived using the five LSER descriptors.

Figure 98:
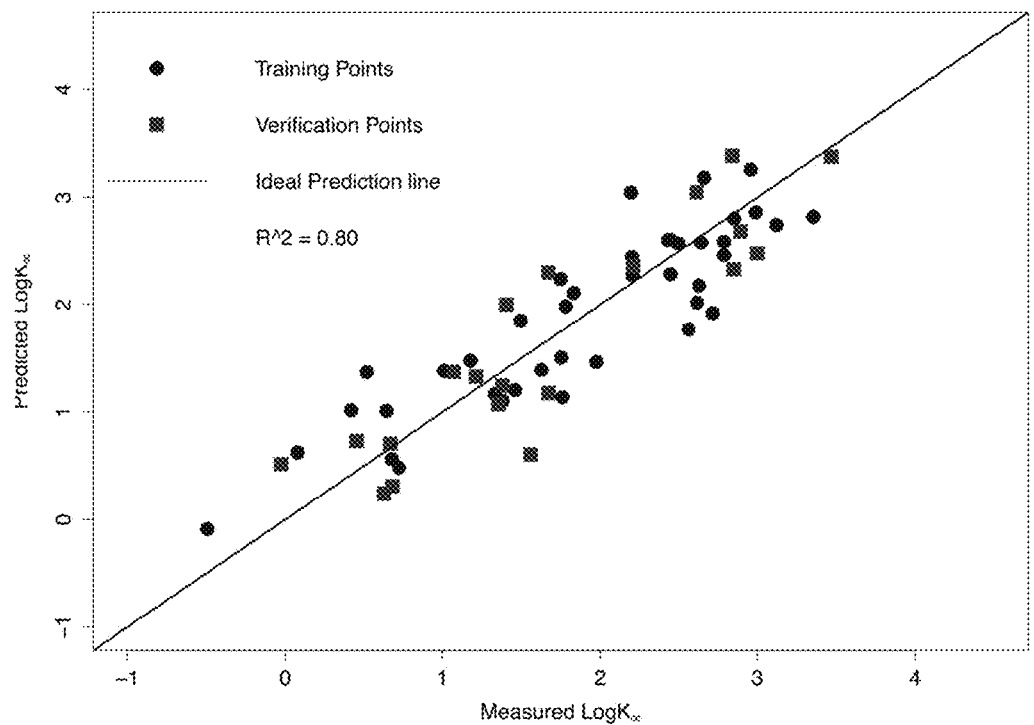

FIG. 98 shows the LSER model derived using the four LSER descriptors.

DETAILED DESCRIPTION

All documents cited herein are incorporated by reference in their entirety for all purposes to the same extent as if each individual document was specifically and individually indicated to be incorporated by reference.

The present disclosure provides porous, typically high surface area cyclodextrin polymeric materials (P-CDP), as well as methods of making and using these materials. The P-CDPs are comprised of insoluble polymers of cyclodextrin, which is an inexpensive, sustainably produced macrocycle of glucose. The polymers of cyclodextrin are comprised of cyclodextrin moieties that are derived from cyclodextrins. The cyclodextrin moiety(s) can be derived from naturally occurring cyclodextrins (e.g., α-, β-, and γ-, comprising 6, 7, and 8 glucose units, respectively) or synthetic cyclodextrins. The cyclodextrin moiety has at least one —O— bond derived from an —OH group on the cyclodextrin from which it is derived. The cyclodextrin moieties can comprise 3-20 glucose units, including 3, 4, 5, 6, 7, 8, 9, 10, 11, 12, 13, 14, 15, 16, 17, 18, 19, and 20 glucose units, inclusive of all ranges therebetween. In many embodiments, the cyclodextrin moieties are derived from starch, and comprise 6-9 glucose units. The polymeric materials may comprise two or more different cyclodextrin moieties. In particular embodiments, the P-CDP is comprised of insoluble polymers of β-cyclodextrin (β-CD).

The P-CDP can also comprise cyclodextrin derivatives or modified cyclodextrins. The derivatives of cyclodextrin consist mainly of molecules wherein some of the OH groups are converted to OR groups. The cyclodextrin derivatives can, for example, have one or more additional moieties that provide additional functionality, such as desirable solubility behavior and affinity characteristics. Examples of suitable cyclodextrin derivative materials include methylated cyclodextrins (e.g., RAMEB, randomly methylated β-cyclodextrins), hydroxyalkylated cyclodextrins (e.g., hydroxypropyl-β-cyclodextrin and hydroxypropyl-γ-cyclodextrin), acetylated cyclodextrins (e.g., acetyl-γ-cyclodextrin), reactive cyclodextrins (e.g., chlorotriazinyl-β-CD), branched cyclodextrins (e.g., glucosyl-β-cyclodextrin and maltosyl-β-cyclodextrin), sulfobutyl-β-cyclodextrin, and sulfated cyclodextrins. For example, the cyclodextrin moiety further comprises a moiety that binds (e.g., with specificity) a metal such as arsenic, cadmium, copper, or lead.

The P-CDP can also comprise cyclodextrin derivatives as disclosed in U.S. Pat. No. 6,881,712 including, e.g., cyclodextrin derivatives with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —$CH_2$—CH(OH)—$CH_3$ or a ⁻$CH_2CH_2$—OH group; branched cyclodextrins such as maltose-bonded cyclodextrins; cationic cyclodextrins such as those containing 2-hydroxy-3-(dimethylamino)propyl ether, wherein R is $CH_2$—CH(OH)—$CH_2$—N$(CH_3)_2$ which is cationic at low pH; quaternary ammonium, e.g., 2-hydroxy-3-(trimethylammonio)propyl ether chloride groups, wherein R is $CH_2$—CH(OH)—$CH_2$—N⁻$(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, April 1994, p. 49 said references being incorporated herein by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

The P-CDP can also comprise a variety of aryl crosslinking moieties. The aryl crosslinking moiety is derived from an aryl compound that can react with a cyclodextrin to form an aryl ether bond. The aryl crosslinking moiety may comprise one or more electron-withdrawing group (e.g., a halide group, such as —Cl and —F, —NO2, and —CN group). The electron-withdrawing groups can be the same or different. Without intending to be bound by any particular theory, it is considered that the electron withdrawing group(s) facilitates a nucleophilic aromatic substitution reaction between the cyclodextrin and aryl compound. In various embodiments, the aryl crosslinking moiety has 0, 1, or 2 cyano groups and, optionally, 0, 1, 2, 3, or 4 halide groups.

The aryl moiety comprises one or more aromatic ring. The aromatic ring(s) comprise 4 to 40 carbons, including 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 carbons, including all ranges therebetween. The aryl moiety can be a fused aromatic ring structure or have at least two aromatic rings linked by a covalent bond (e.g., a biphenyl moiety). The aryl moiety can be a hydrocarbon aryl moiety or heteroaryl moiety. For example, the heteroaryl moiety has one or more heteroatom in an aryl ring or rings. Examples of aryl moieties include phenyl moieties, biphenyl moieties, napthyl moieties, and anthracene moieties. In an embodiment, the aryl moiety is a dicyanophenyl moiety with 0, 1, or 2 halide groups (i.e., substituents).

Examples of suitable aryl moieties include, but are not limited to, the aryl moieties shown in FIGS. 1-6. (In the examples, Ar is an aryl moiety as described herein.)

The porous polymeric material comprises a plurality of cyclodextrin moieties, for example β-cyclodextrin moieties. In an embodiment, the porous polymeric material comprises a plurality of β-cyclodextrin moieties crosslinked by one or more aryl (e.g., dicyano diflurophenyl) moieties. For example, at least two of the plurality of β-cyclodextrin moieties are crosslinked by two or more aryl moieties. One of skill in the art will recognize that the polymeric material of the present disclosure can also include any of the cyclodextrin moieties disclosed herein, for example α- or γ-cyclodextrin moieties in addition to, or instead of the β-cyclodextrin moieties.

The aryl moieties can crosslink the primary and/or secondary groups on the cyclodextrin. The crosslinked cyclodextrin moieties can be covalently bonded to various positions. As an illustrative example, where the aryl crosslinking moiety comprises a phenyl moiety the crosslinking bonds can be to 1,2-, 1,3-, and/or 1,4-positions (relative positions) of the phenyl moiety on the aryl crosslinking moiety, depending on the available bonding sites on the phenyl moiety. Accordingly, the porous polymeric materials can include various regioisomers of the material. In an embodiment, the porous polymeric material comprises one or more regioisomer of the porous polymeric material.

The porous polymeric material of the present disclosure can have pores ranging in size (i.e., the longest dimension (e.g., diameter) of an orifice of a pore) from about 1 nm to about 50 nm, about 1 nm to about 20 nm, about 1 nm to about 10 nm, or about 1 nm to about 5 nm, including about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, or about 50 nm, inclusive of all ranges therebetween. In an embodiment, the porous polymeric material is mesoporous. In an embodiment, the porous polymeric material comprises pores of about 1.5 nm to about 5 nm in size. In various embodiments, about 50% or more, about 80% or more, about 90% or more, about 95% or more, about 99% or more of the pores in the porous polymeric material are about 1 nm to about 50 nm in size. In various embodiments, about 50% or more, about 80% or more, about 90% or more, about 95% or more, about 99% or more of the pores in the porous polymeric material are about 10 nm or less in size.

The porous polymeric material has a relatively large surface area, which substantially improves the adsorption kinetics and/or capacity compared to conventional nonporous cyclodextrin polymers. For example, the porous polymeric materials of the present disclosure can have a surface area ranging from about 50 m$^2$/g to about 2000 m$^2$/g, including all integer m$^2$/g values and ranges therebetween. In particular embodiments, the surface area is about 50 m$^2$/g, about 100 m$^2$/g, about 150 m$^2$/g, about 200 m$^2$/g, about 250 m$^2$/g, about 300 m$^2$/g, about 350 m$^2$/g, about 400 m$^2$/g, about 450 m$^2$/g, about 500 m$^2$/g, about 550 m$^2$/g, about 600 m$^2$/g, about 650 m$^2$/g, about 700 m$^2$/g, about 750 m$^2$/g, about 800 m$^2$/g, about 850 m$^2$/g, about 900 m$^2$/g, about 950 m$^2$/g, about 1000 m$^2$/g, about 1100 m$^2$/g, about 1200 m$^2$/g, about 1300 m$^2$/g, about 1400 m$^2$/g, about 1500 m$^2$/g, about 1600 m$^2$/g, about 1700 m$^2$/g, about 1800 m$^2$/g, about 1900 m$^2$/g, or about 2000 m$^2$/g, inclusive of all ranges therebetween. In various embodiments, the surface area of porous polymeric material is 50 m$^2$/g or greater, 100 m$^2$/g or greater, or 200 m$^2$/g or greater.

The ratio of cyclodextrin moieties to aryl crosslinking moieties is 1:1 to 1:X, where X is three times the average number of glucose subunits in the cyclodextrin moieties of the polymer. In various embodiments, the ratio of cyclodextrin moieties to aryl crosslinking moieties is about 1:1 to about 1:24, including about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, about 1:10, about 1:10.5, about 1:11, about 1:11.5, about 1:12, about 1:12.5, about 1:13, about 1:13.5, about 1:14, about 1:14.5, about 1:15, about 1:15.5, about 1:16, about 1:16.5, about 1:17, about 1:17.5, about 1:18, about 1:18.5, about 1:19, about 1:19.5, about 1:20, about 1:20.5, about 1:21, about 1:21.5, about 1:22, about 1:22.5, about 1:23, about 1:23.5, or about 1:24, including all ranges of ratios therebetween. In an embodiment, the ratio of cyclodextrin moieties to aryl crosslinking moieties is about 1:2.5 to about 1:10.

In an aspect, the present disclosure provides a composition comprising one or more porous polymeric materials of the present disclosure. For example, the composition comprises a support material supporting the porous polymeric materials of the present disclosure. In an embodiment, the composition consists essentially of one or more porous polymeric material.

In an embodiment, a composition comprises one or more porous polymeric material and one or more support materials, where the porous polymeric material is covalently bonded to the support material. Examples of support materials include cellulose (e.g., cellulose fibers), carbon-based materials such as activated carbon, graphene oxide, and oxidized carbon materials, silica, alumina. One of skill in the art will recognize that any material with mechanical or other properties suitable to act as a support, which can covalently bond to the porous polymeric material, can serve as a suitable support material. In an embodiment, the composition is in the form a membrane or a column packing material. In an embodiment, the support is a fiber (e.g., a cellulose fiber). In an embodiment, the support is a porous particulate material (e.g., porous silica and porous alumina).

In an aspect the present disclosure provides methods of making the porous polymeric materials. In an embodiment, the porous polymeric material is made by a method disclosed herein.

The porous polymeric materials of the present disclosure comprise cyclodextrin moieties crosslinked with a suitable crosslinking agent that provides a porous, relatively high surface area polymeric material as described herein. Suitable crosslinking agents can include any, at least difunctional compound capable of reaction with any of the cyclodextrins disclosed herein to form a crosslinked network of cyclodextrin moieties. In order to provide the desired porosity and surface area for the polymeric material, in various embodiments the crosslinking agent should be relatively rigid and inflexible, such as the aryl crosslinkers disclosed herein. One of skill in the art will recognize that crosslinking agents other than aryl crosslinkers can be used, provided they have similar ranges of flexibility. For example, crosslinkers which form crosslinks with no more than about 6 "rotable" bonds (e.g., 2, 3, 4, 5, or 6 rotable bonds) may be suitable. The term rotable refers to bonds in the crosslink having a calculated rotational barrier which is no more than about 80 kJ/mol (298 K), for example in the range of about 10-30 kJ/mol. Such crosslinks have limited mobility, which is believed to aid in the formation of high porosity and surface area materials.

In an embodiment, a method of making a porous polymeric material comprises contacting a cyclodextrin with a crosslinking agent, such as an aryl compound such that the crosslinking agent (e.g., aryl compound) crosslinks at least two cyclodextrin moieties. The crosslinking agent comprises at least two groups (e.g., halide groups, if the crosslinking agent is an aryl compound) that can react with the cyclodextrin to form covalent (e.g., aryl ether bonds). Without intending to be bound by any particular theory, it is considered that the reaction between a cyclodextrin and an aryl compound is a nucleophilic aromatic substitution reaction.

Figure 4:
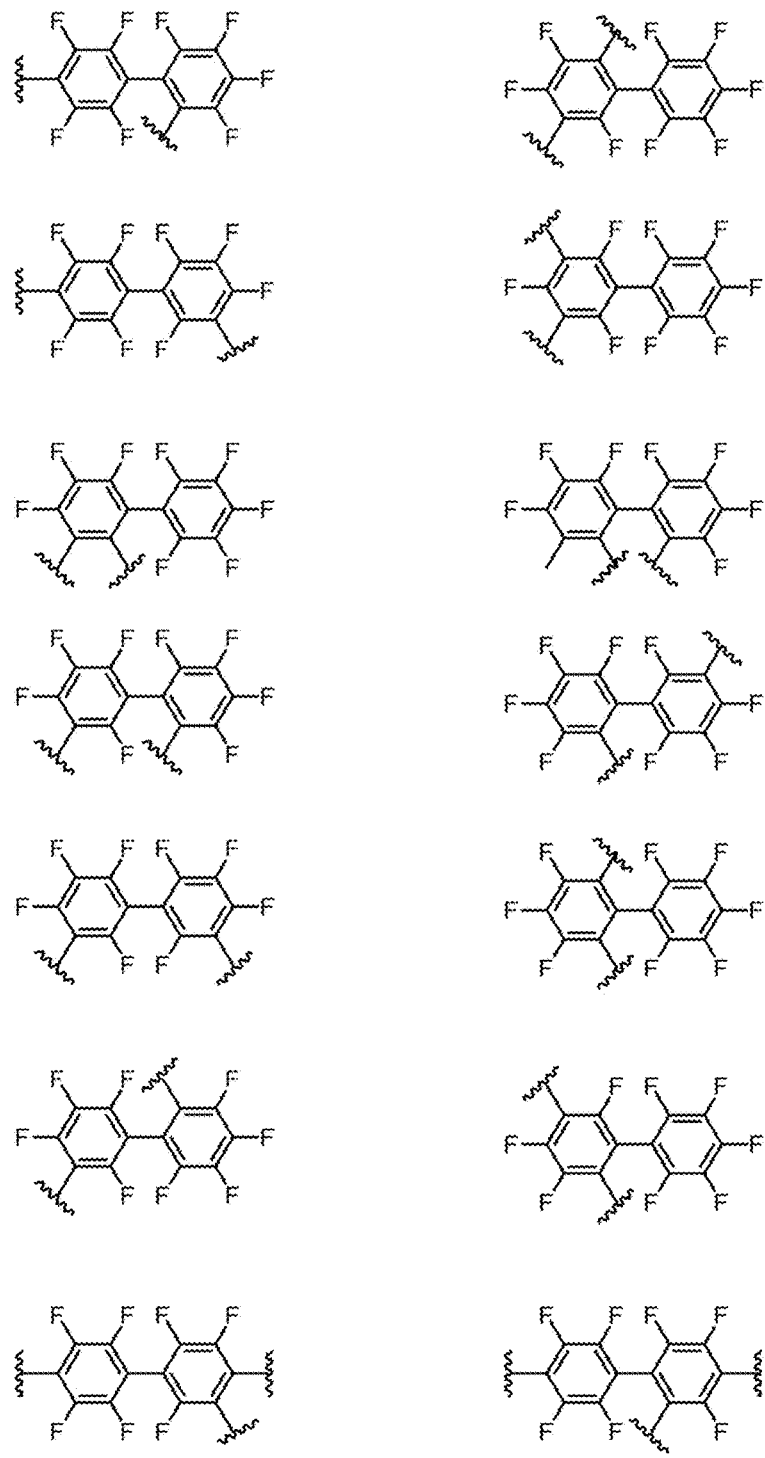
Figure 5:
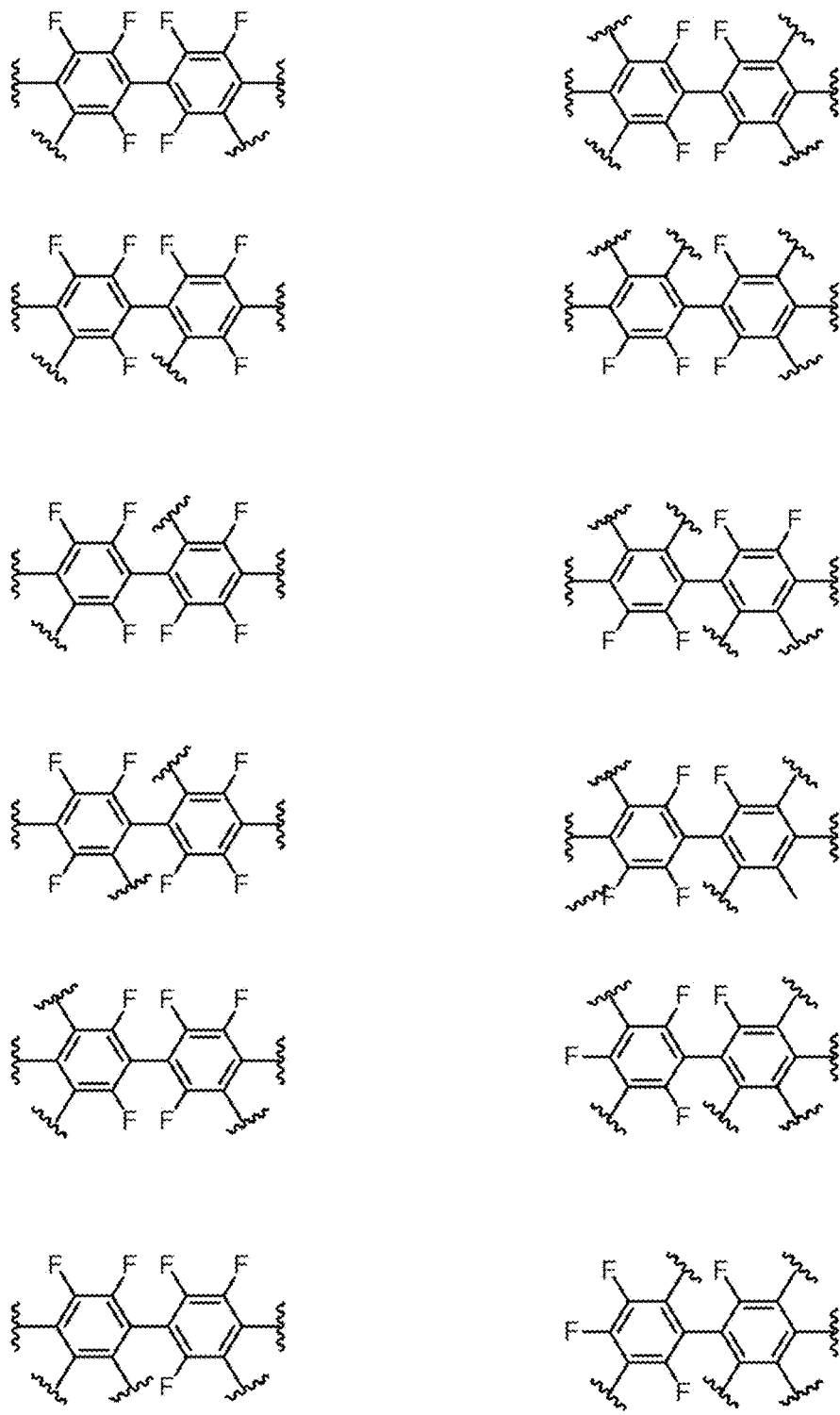
Figure 6:
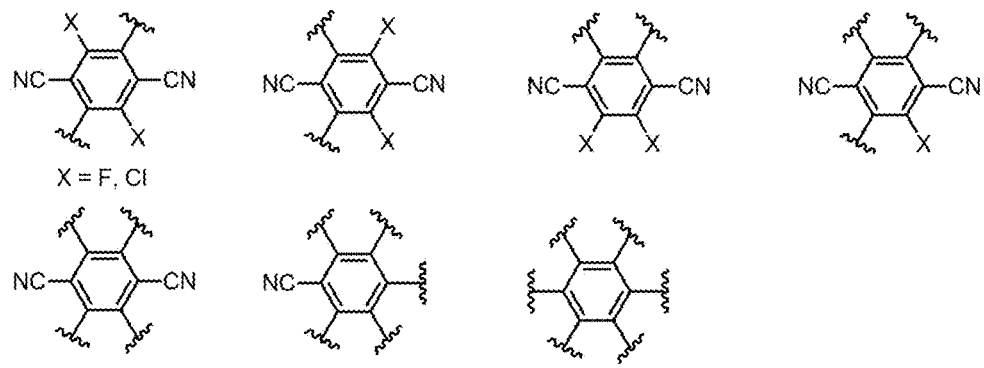
Figure 7:
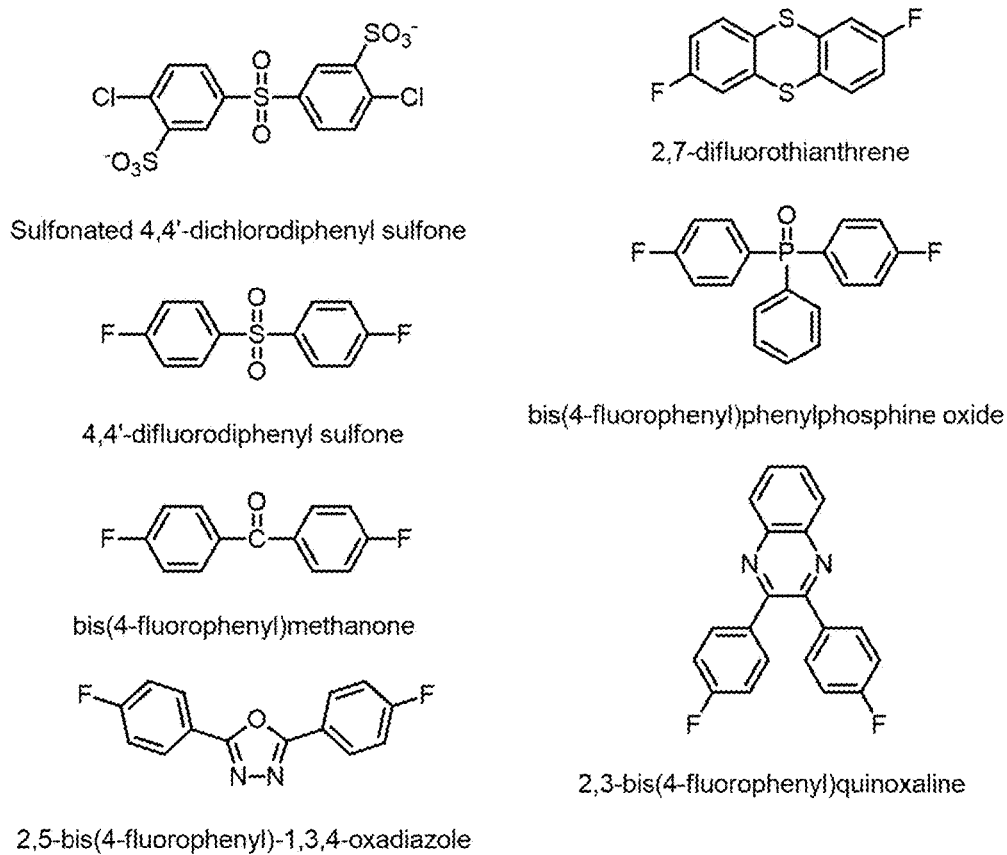
Figure 8:
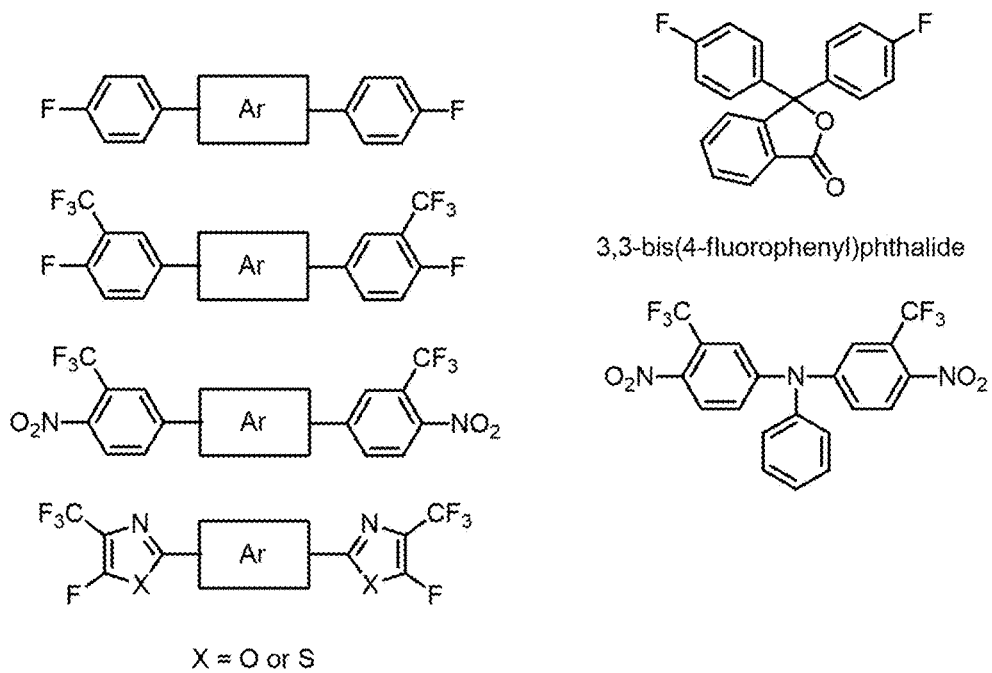
Figure 9:
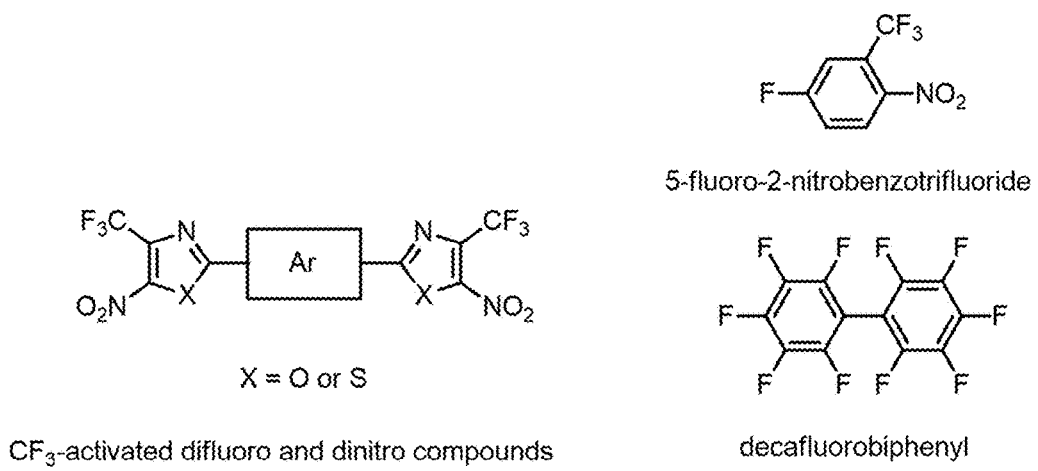

Examples of suitable aryl compounds that react to form aryl crosslinking moieties include the moieties shown in FIGS. 7-9, where Ar is an aryl moiety as defined herein. Two or more of the functional groups (e.g., halide, —NO2, and/or —CF3 groups) react to form an aryl crosslinking group. In particular embodiments, the aryl compound is tetrafluoroterephthalonitrile, decafluorobiphenyl, or octafluoronaphthalene.

Synthesis and Structural Characterization of β-CD Polymers

Figure 10:
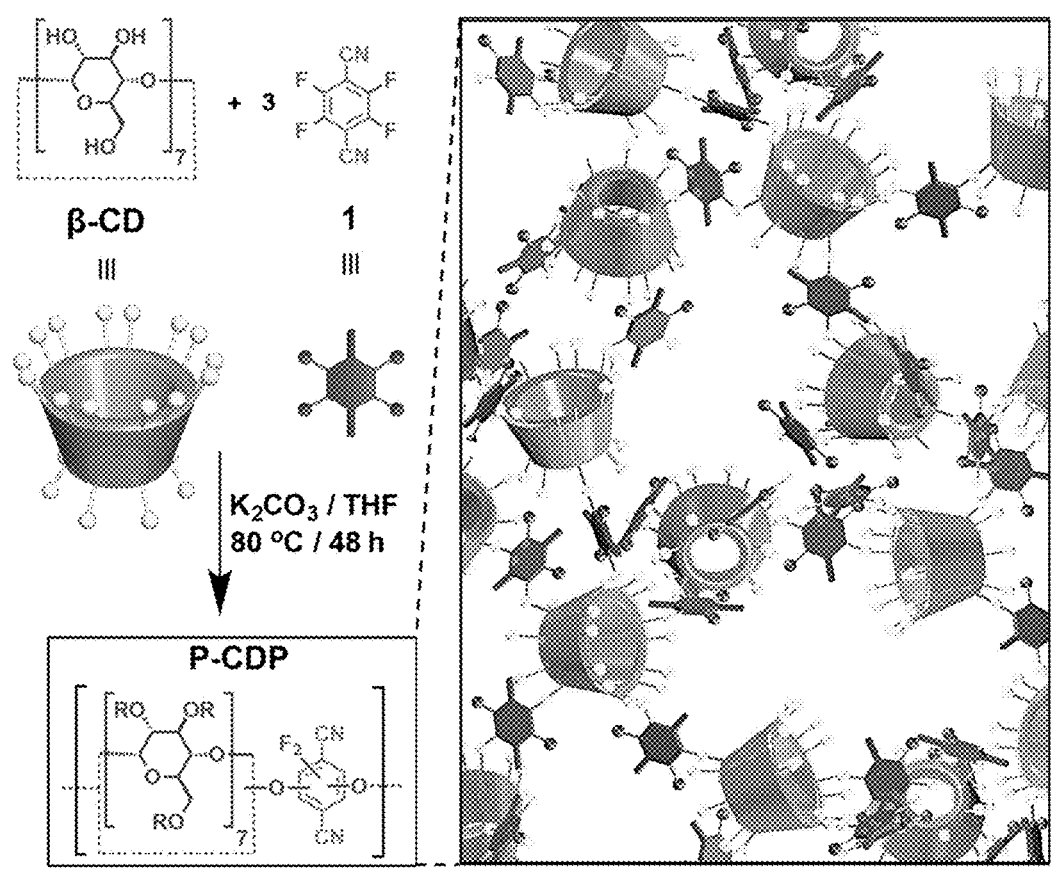
FIG. 10 is a depiction of the synthesis and structure of the mesoporous, high surface area β-CD polymer, P-CDP.
Figure 11:
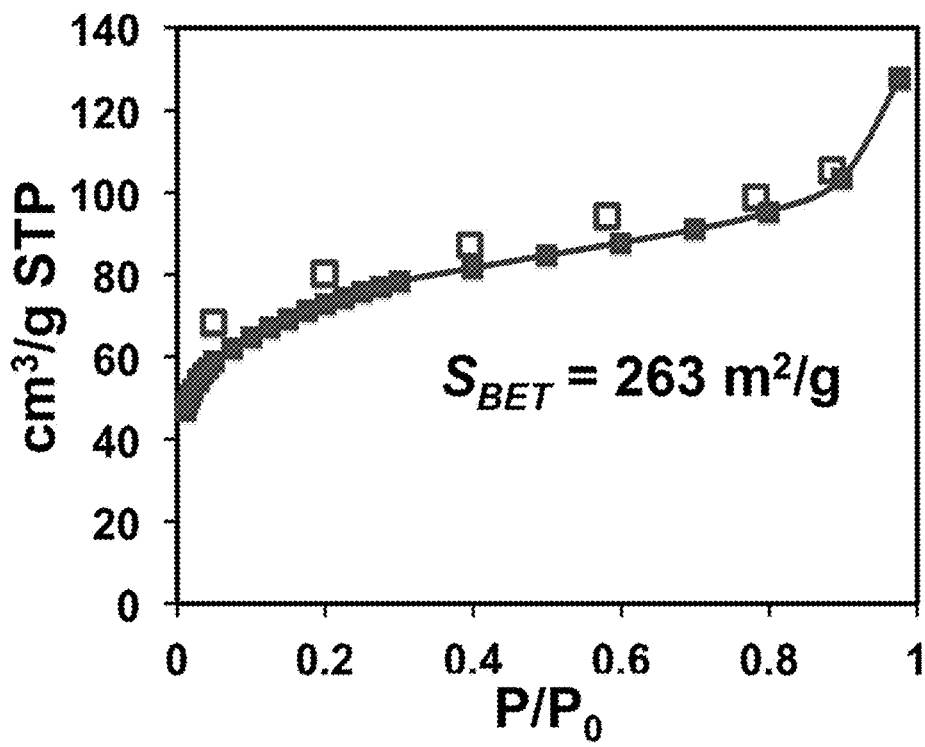
FIG. 11 is a graph of $N_2$ adsorption and desorption isotherms at 77K for a P-CDP.

In various embodiments, porous β-CD-containing polymers (P-CDPs) can be derived from nucleophilic aromatic substitution of tetrafluoroterephthalonitrile ("1," as referenced in the figures) by hydroxyl groups of β-CD. Although tetrafluoroterephthalonitrile has been copolymerized with bifunctional catechols previously, its reaction with aliphatic alkoxides does not appear to have been described. β-CD and tetrafluoroterephthalonitrile were polymerized in a suspension of K$_2$CO$_3$ in THF at 80° C. to provide a pale-yellow precipitate in 20% yield, which provided a mesoporous high surface area polymer with the expected chemical bonds as represented by FIG. 10. The yield was further improved to 45% by performing the polymerization in THF:DMF (9:1 v/v), in which β-CD is more soluble. Following activation under high vacuum, N$_2$ porosimetry of the P-CDPs provided type II isotherms indicative of mesoporosity, and their Brunauer-Emmett-Teller surface areas (S$_{BET}$) ranged from 35-263 m$^2$/g as shown in the Table 1 below, depending on the molar feed ratio of (1) tetrafluoroterephthalonitrile:β-CD employed in the polymerization as shown in FIG. 11. The closed squares in FIG. 11 represent the N$_2$ adsorption isotherms, and the open squares represent the N$_2$ desorption isotherms at 77 K of a P-CDP.

TABLE 1

| 1 (equiv) | Solvent | Temp (° C.) | Time (d) | $S_{BET}$ (m²/g) |
|---|---|---|---|---|
| 1 | THF | 80 | 2 | 35 |
| 3 | THF | 80 | 2 | 263 |
| 6 | THF | 80 | 2 | 97 |

Figure 12:
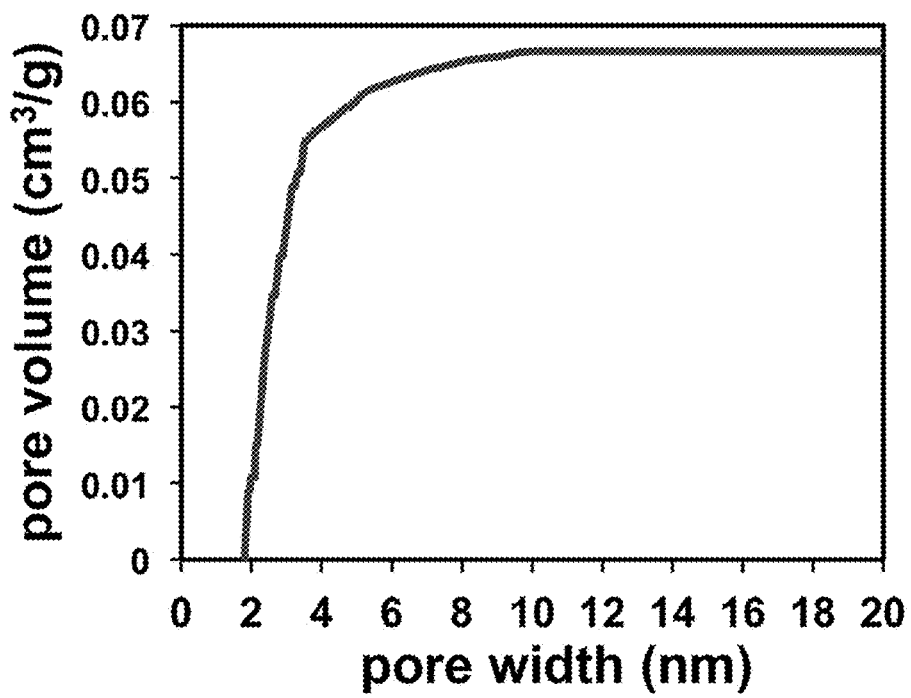
FIG. 12 is a chart showing pore size distributions of the P-CDPs.
Figure 13:
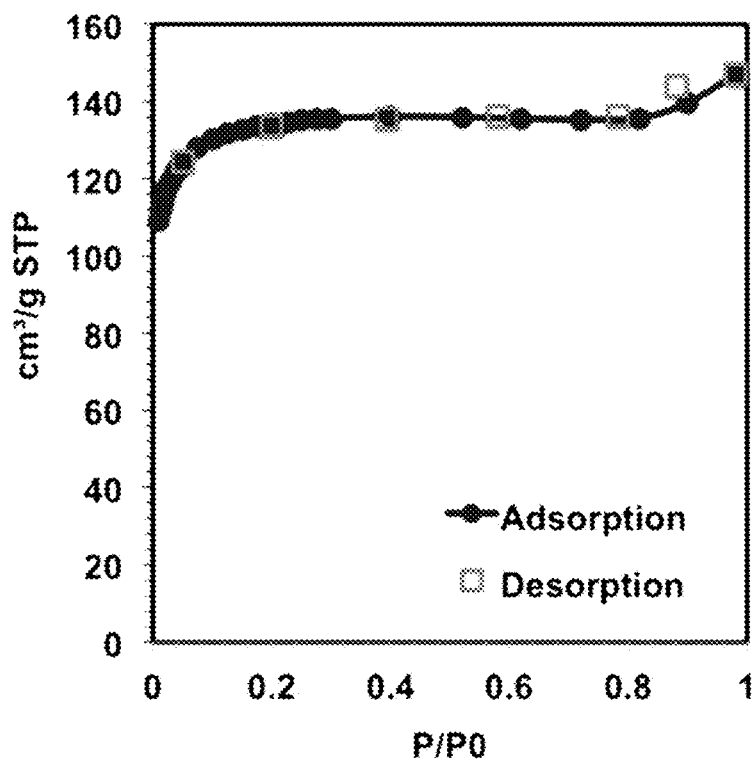
FIG. 13 is a graph of $N_2$ adsorption and desorption isotherms at 77K for Brita AC.
Figure 14:
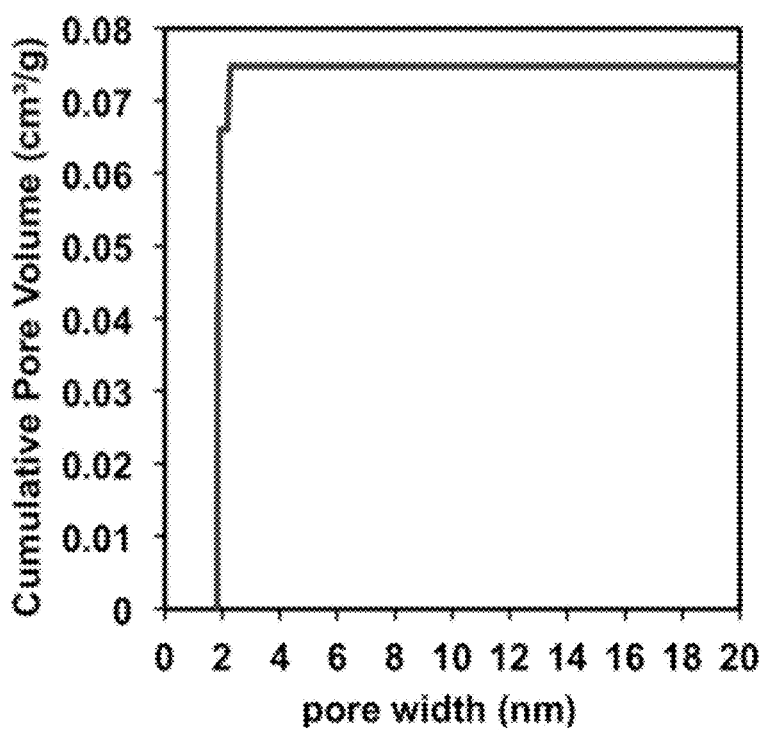
FIG. 14 is a graph of cumulative pore volume obtained by NLDFT analysis for Brita AC.
Figure 15:
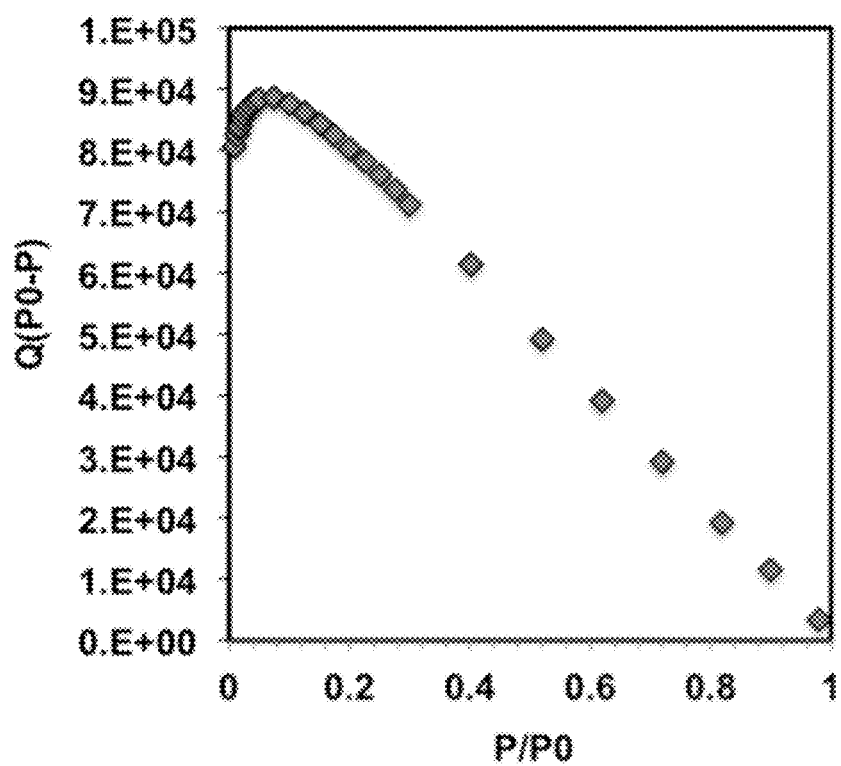
FIG. 15 is a surface area data analysis of Brita AC.
Figure 16:
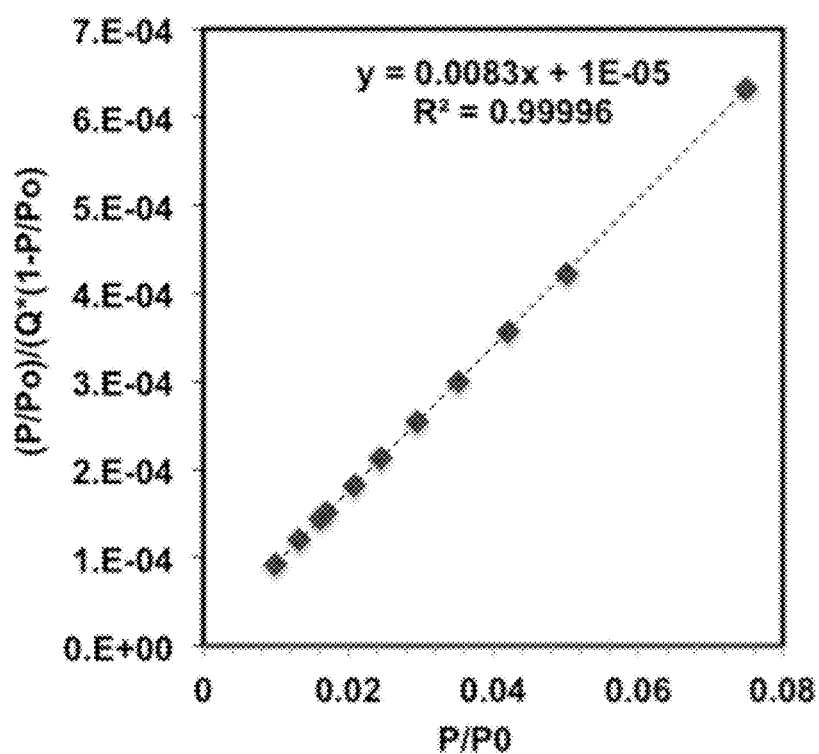
FIG. 16 is a surface area data analysis of Brita AC.
Figure 17:
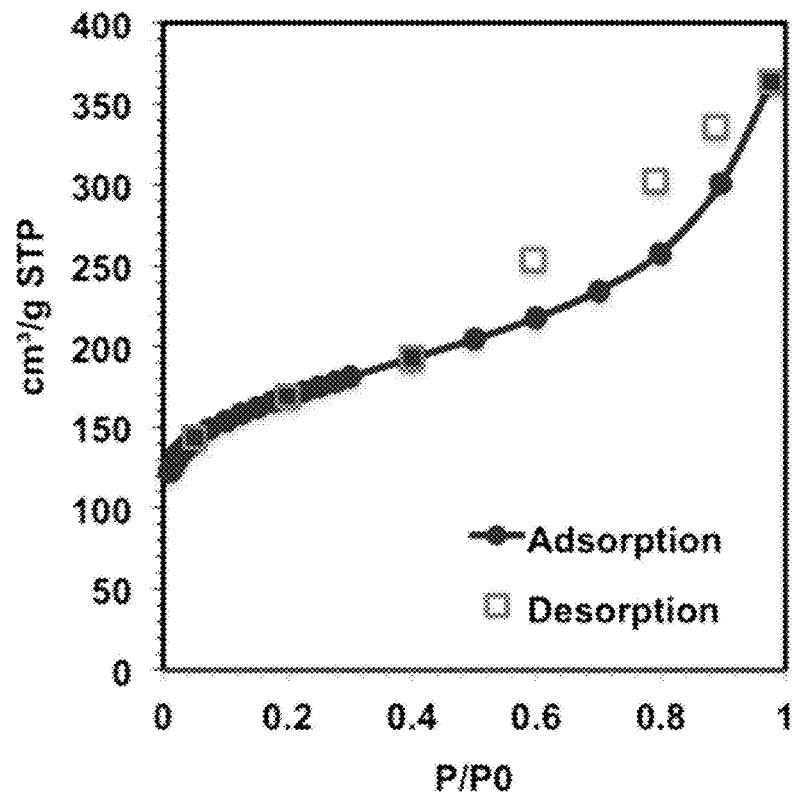
FIG. 17 is a graph of $N_2$ adsorption and desorption isotherms at 77K for GAC.
Figure 18:
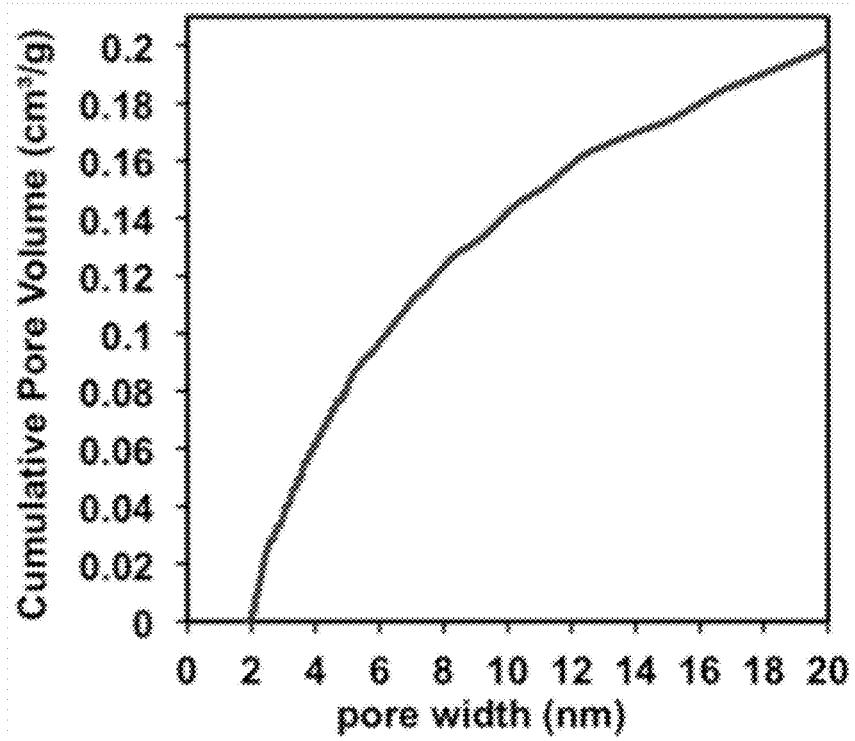
FIG. 18 is a graph of cumulative pore volume obtained by NLDFT analysis for GAC.
Figure 19:
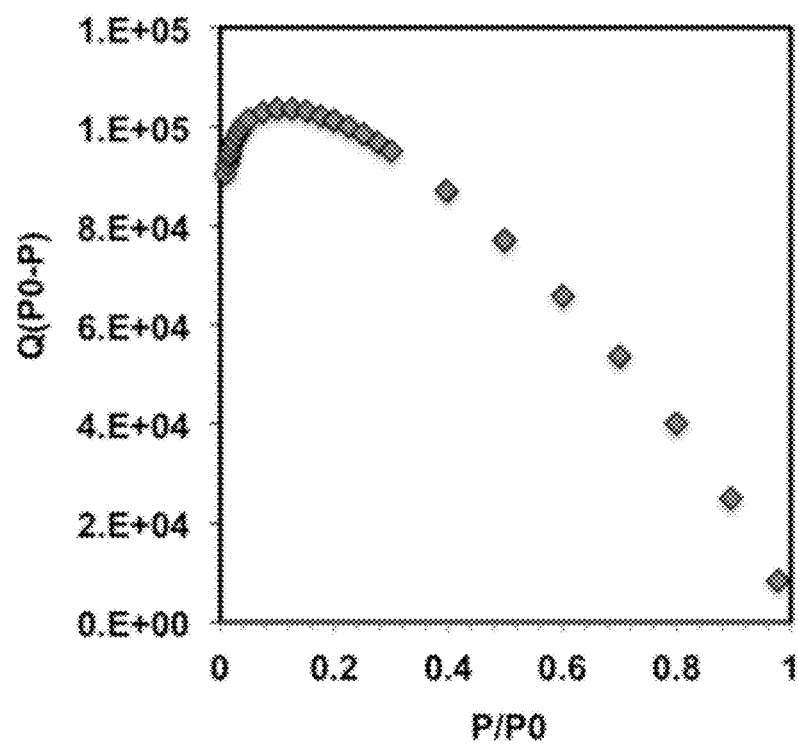
FIG. 19 is a surface area data analysis of GAC.
Figure 20:
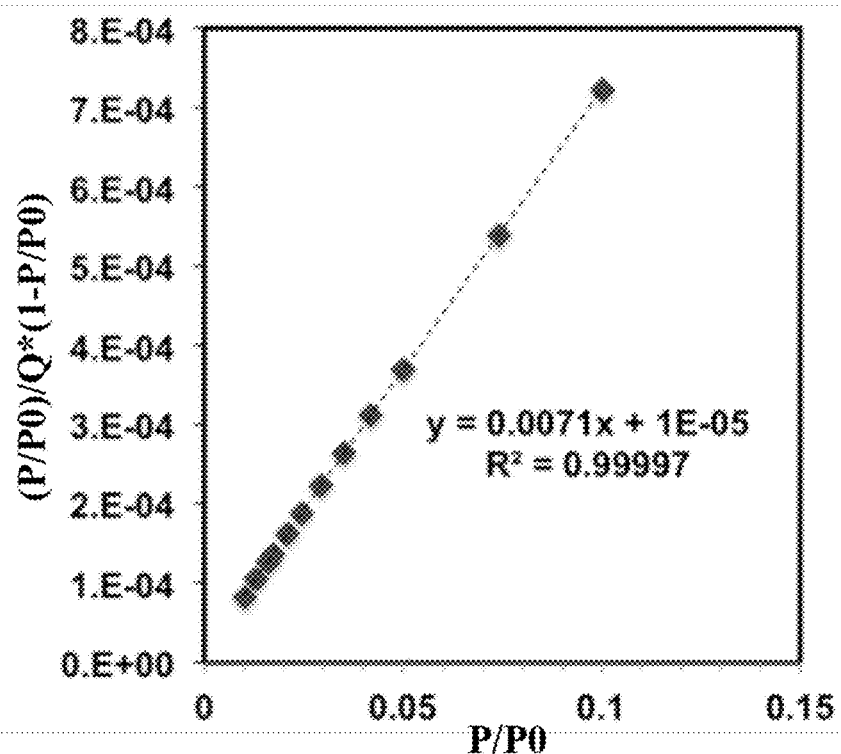
FIG. 20 is a surface area data analysis of GAC.
Figure 21:
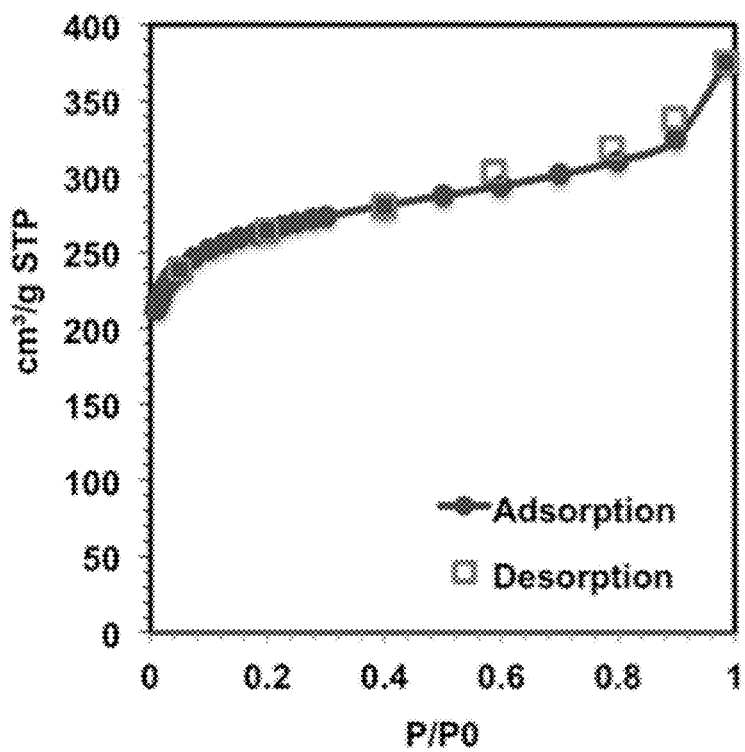
FIG. 21 is a graph of $N_2$ adsorption and desorption isotherms at 77K for NAC.
Figure 22:
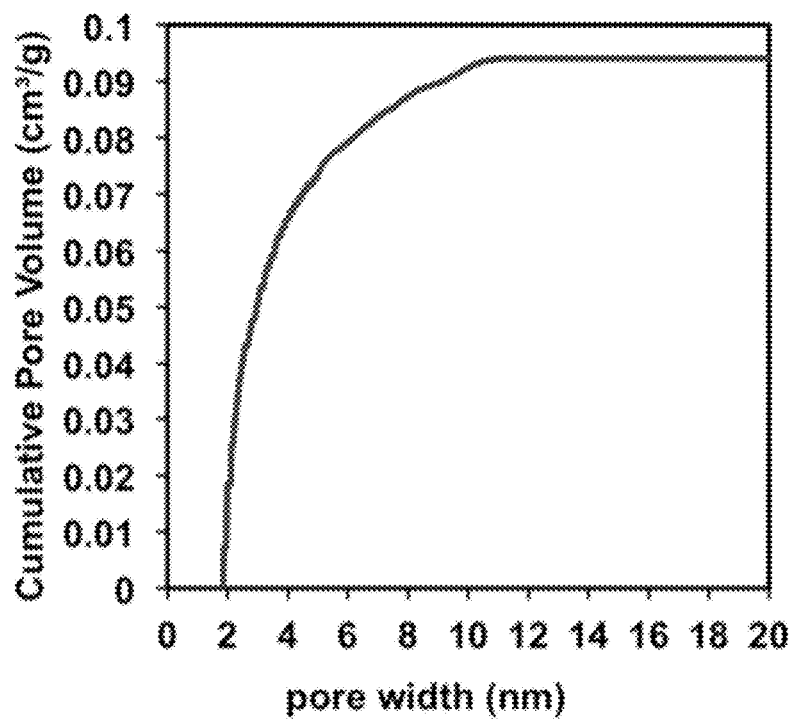
FIG. 22 is a graph of cumulative pore volume obtained by NLDFT analysis for NAC.
Figure 23:
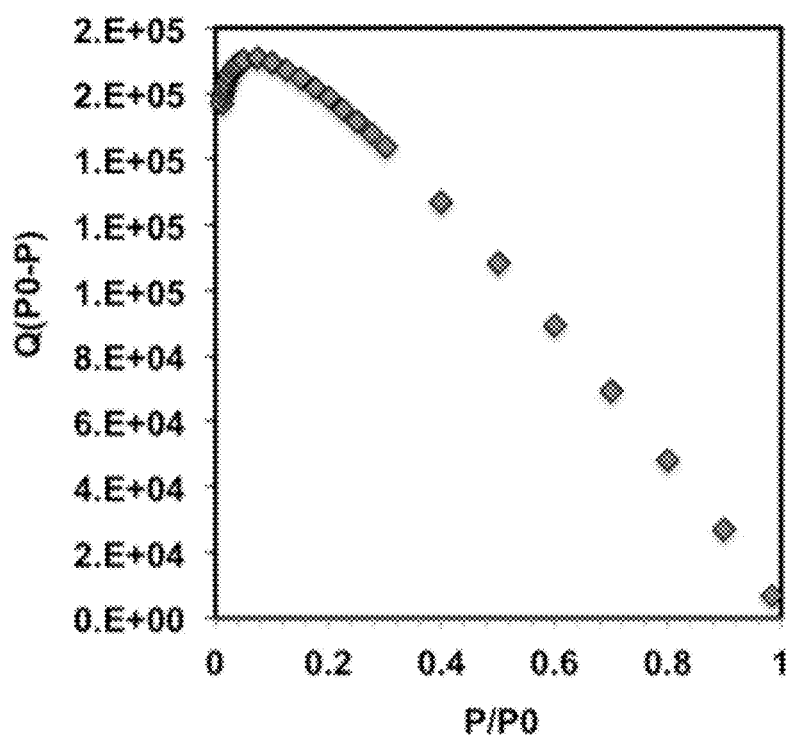
FIG. 23 is a surface area data analysis of NAC.
Figure 24:
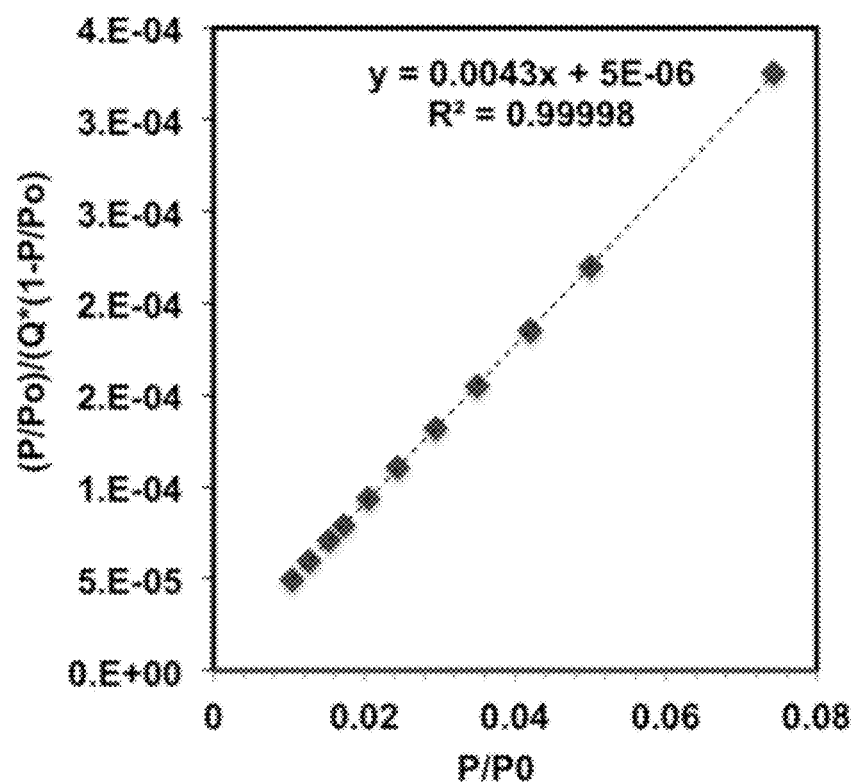
FIG. 24 is a surface area data analysis of NAC.

P-CDPs obtained from a tetrafluoroterephthalonitrile:β-CD ratio of 3:1 consistently exhibited the highest surface areas. The porosity and high surface area of P-CDP are robust and did not decrease when the polymer was dispersed in H₂O for several hours and reactivated. Non-local density functional theory (NLDFT) calculations applied to the isotherms indicate that 1.8-3.5 nm diameter pores comprise the majority of the P-CDPs free volume as shown in FIG. 11 and FIG. 12, much like the pore size distributions of ACs as shown in FIGS. 13-24. Alternative polymerization conditions, as shown below, (aqueous NaOH, 85° C.) produced a similar polymer that lacked permanent porosity (NP-CDP, $S_{BET}$=6 m²g⁻¹), which serves as a useful control to demonstrate the importance of surface area for rapid micropollutant removal.

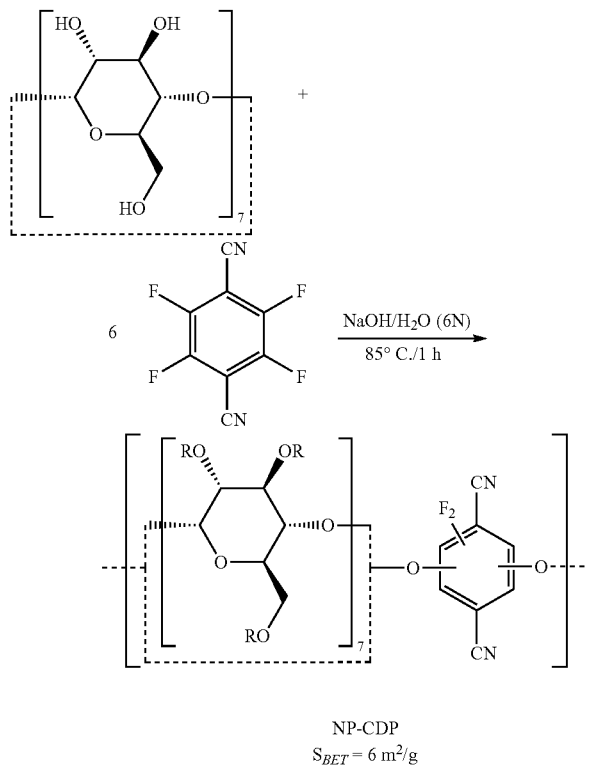

NP-CDP
$S_{BET}$ = 6 m²/g

Water regain analysis of P-CDP and NP-CDP also reflected the higher pore volume of P-CDP, which took up 265% of its weight when dispersed in H₂O as compared to 86% for NP-CDP as shown in Table 2, below.

TABLE 2

| | Dry pore volume (cm³/g) | H₂O regain (wt %) | Volumetric H₂O regain (cm³/g) |
|---|---|---|---|
| P-CDP | 0.112 | 265 | 2.65 |
| NP-CDP | 0.003 | 86 | 0.86 |

Nevertheless, NP-CDP swells to a much greater degree, as its H₂O uptake is approximately 300 times its dry pore volume, as compared to a factor of only 23 for P-CDP. P-CDPs' combination of high H₂O uptake and modest swelling are desirable as these parameters maximize adsorbent performance and minimize undesirable pressure drops associated with filtration processes.

Figure 25:
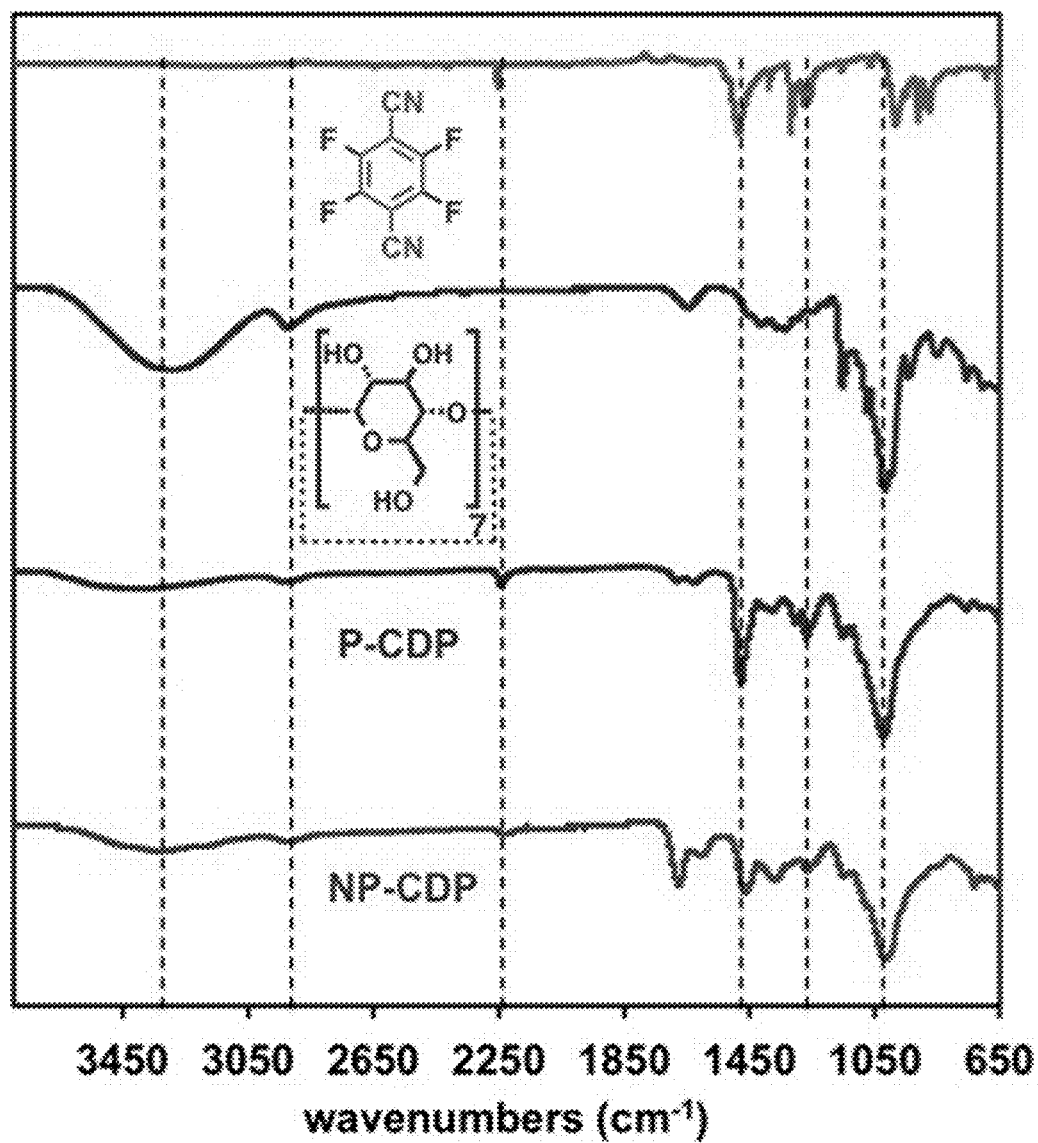
FIG. 25 shows FTIR spectra of 1, β-CD, P-CDP, and NP-CDP.
Figure 26:
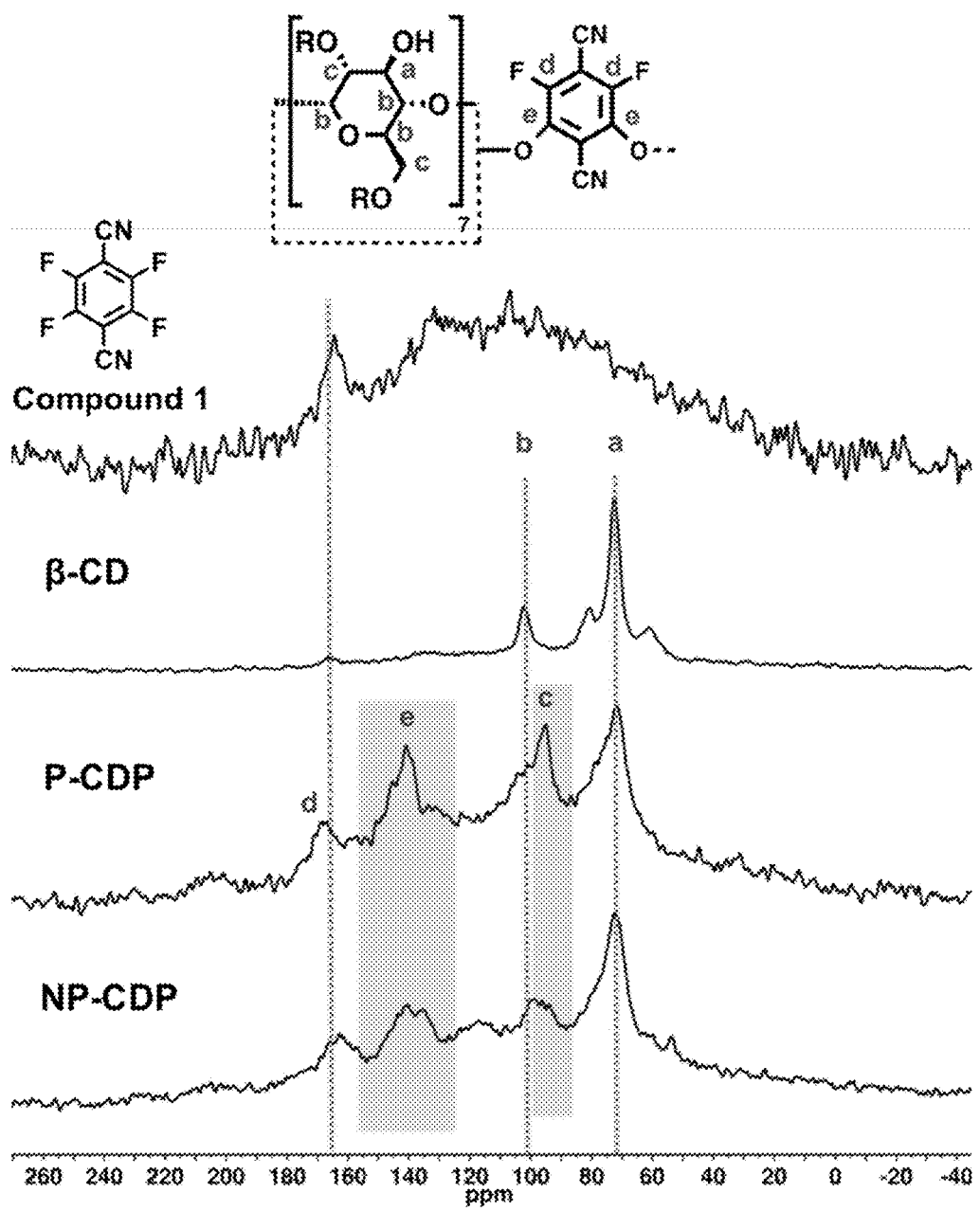
FIG. 26 shows $^{13}C$ CP-MAS SS-NMR spectra of 1, β-CD, P-CDP, and NP-CDP.

Compositional analysis and spectroscopic characterization of the P-CDP and NP-CDP networks indicated the presence of both tetrafluoroterephthalonitrile and β-CD moieties in the polymers. The ratio of tetrafluoroterephthalonitrile:β-CD in each polymer was determined by combustion analysis, with 6.1 equivalents of tetrafluoroterephthalonitrile per β-CD for P-CDP and 3.5 equivalents of tetrafluoroterephthalonitrile per β-CD for NP-CDP as shown in FIGS. 25 and 26 and the Table 3 below.

TABLE 3

| | P-CDP | NP-CDP |
|---|---|---|
| % C | 48.23 | 43.78 |
| % N | 7.37 | 5.11 |
| % H | 2.99 | 4.51 |
| % F | 9.66 | 6.31 |
| β-CD:1 | 1:6.1 | 1:3.5 |
| Substitution (1) | 2.1 | 2.2 |

Therefore P-CDP is more densely crosslinked than NP-CDP, which might be responsible for its permanent porosity; P-CDP samples synthesized with a lower tetrafluoroterephthalonitrile:β-CD feed ratio exhibited lower surface areas. The F:N ratio also indicates that the terephthalonitrile moieties in each polymer are substituted by 2.1 and 2.2 alkoxides on average, which are consistent with model studies, which suggest that the β-CD macrocycles are linked predominantly at both the small and large rims through disubstituted terephthalonitrile moieties. The FTIR spectra of each polymer showed absorbances at 2235 cm⁻¹, corresponding to the nitrile stretch, as well as 1670 and 1463 cm⁻¹, corresponding to C—C aromatic stretches. C—F stretches, which resonate at 1268 cm⁻¹, are present in the spectra of both polymers, and appear weaker compared to the spectrum of tetrafluoroterephthalonitrile, as expected for partial F substitution. Finally, the IR spectra of P-CDP and NP-CDP exhibited O—H stretches near 3330 cm⁻¹, aliphatic C—H stretches around 2930 cm⁻¹, and an intense C—O stretch at 1030 cm⁻¹, which are spectral features of intact β-CD a s shown in FIGS. 25 and 27. Solid-state ¹³C NMR spectra of P-CDP and NP-CDP exhibited resonances associated with β-CD at δ=72 and 100 ppm as shown in FIG. 26. Peaks at δ=95 and 140 ppm correspond to the newly formed alkoxy groups and aromatic carbons, respectively. These collective observations indicate that P-CDP and NP-CDP have the expected chemical composition and suggest that the higher crosslinking density of P-CDP contributes to its permanent mesoporosity.

The reaction of tetrafluoroterephthalonitrile with aliphatic alkoxides is previously unknown, which raises questions about the selectivity of its reaction with β-CD. It is unclear which of β-CDs seven primary and fourteen secondary hydroxyl groups participate in the polymerization. The average degree of substitution of tetrafluoroterephthalonitrile within each polymer is ~2, but tri- or tetrasubstituted terephthalonitriles might also be formed. Likewise, it is difficult to identify which of the disubstituted regioisomers are present in the polymer samples. Insight into the regioselectivity of the polymerization was gained by analyzing the outcomes of reactions of tetrafluoroterephthalonitrile with n-BuOH and trans-1,2-cyclohexanediol, which mimic β-CDs primary and secondary hydroxyl groups, respectively as shown below.

$S_{BET}=612$ m$^2$g$^{-1}$), and Norit RO 0.8 activated carbon (NAC, $S_{BET}=984$ m$^2$g$^{-1}$), which is a leading AC typically used for high-value water purification, as shown in FIGS. 13-24.

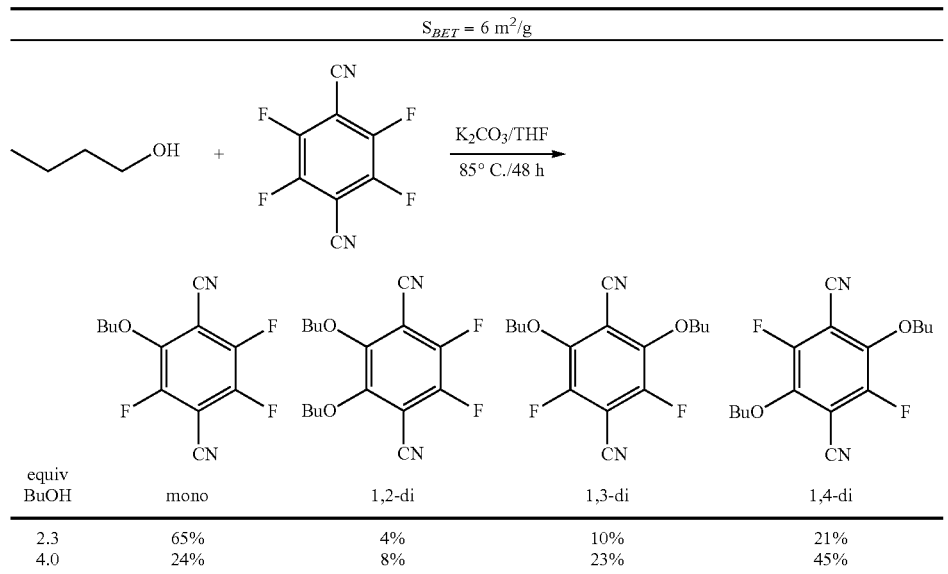

Figure 28:
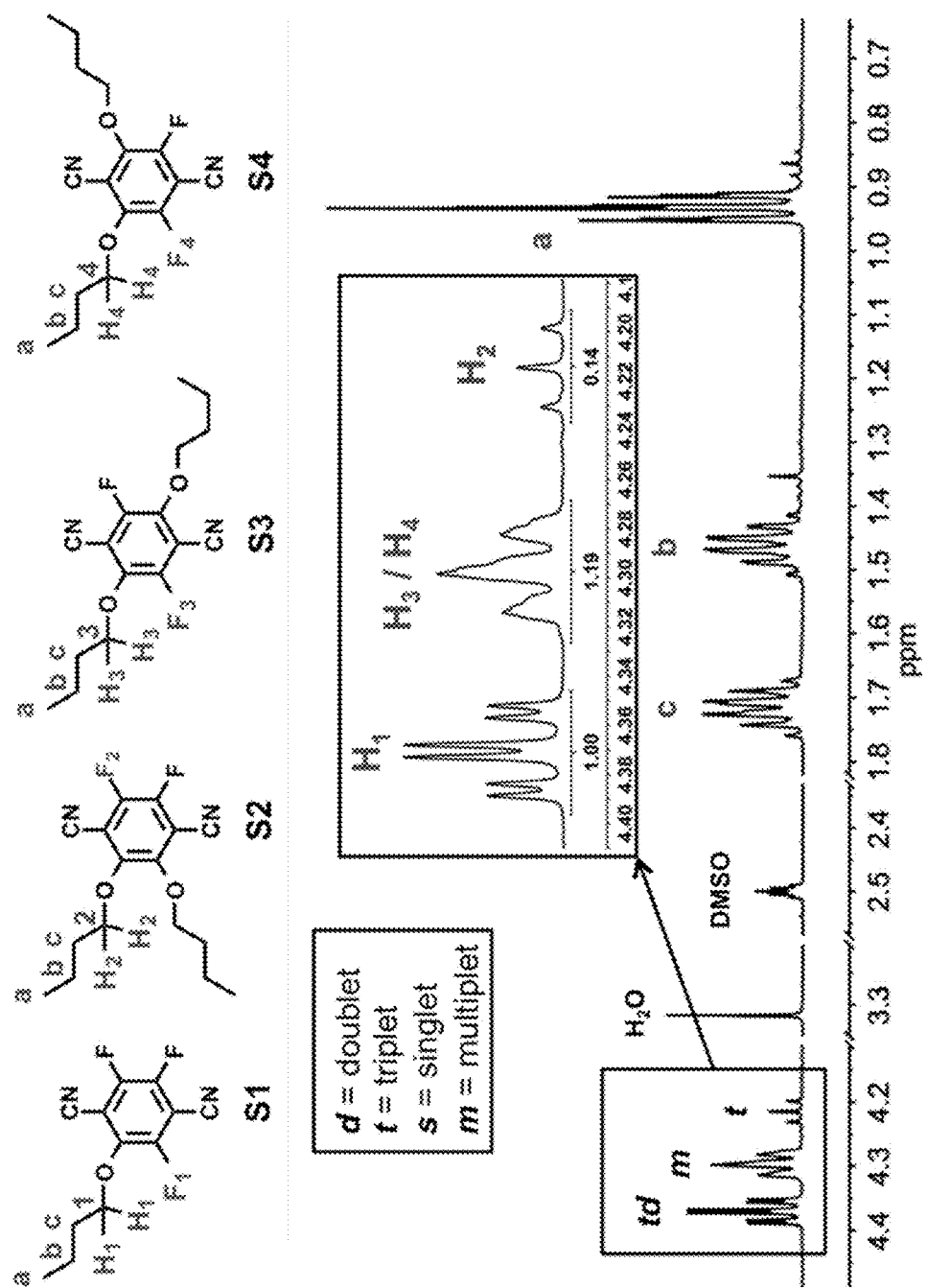
FIG. 28 is a $^1H$-NMR spectrum of the products of the reaction of 1 with 1-BuOH (S1, S2, S3, S4).
Figure 29:
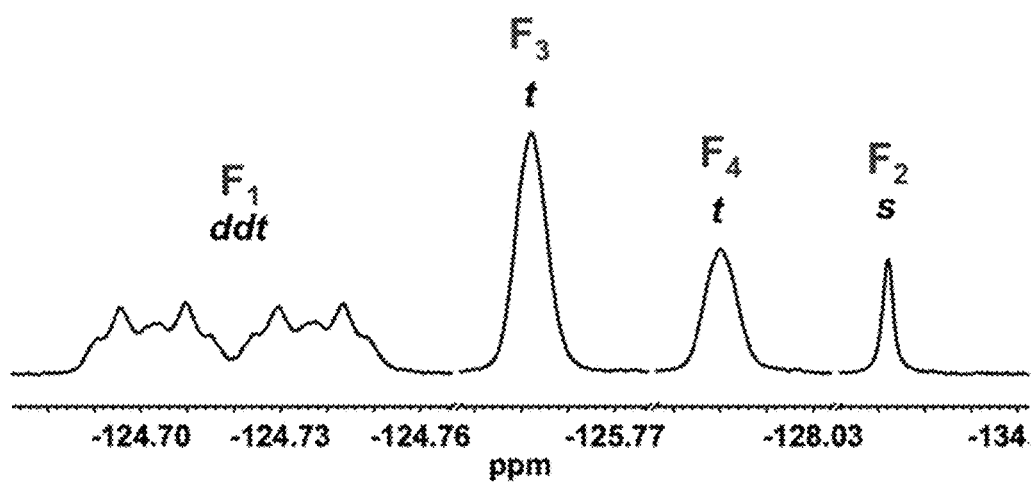
FIG. 29 is a $^{19}F$-NMR spectrum of the products of the reaction of 1 with 1-butanol (S1, S2, S3, S4). The labels above each peak refer to the chemical structures given in FIG. 28.
Figure 30:
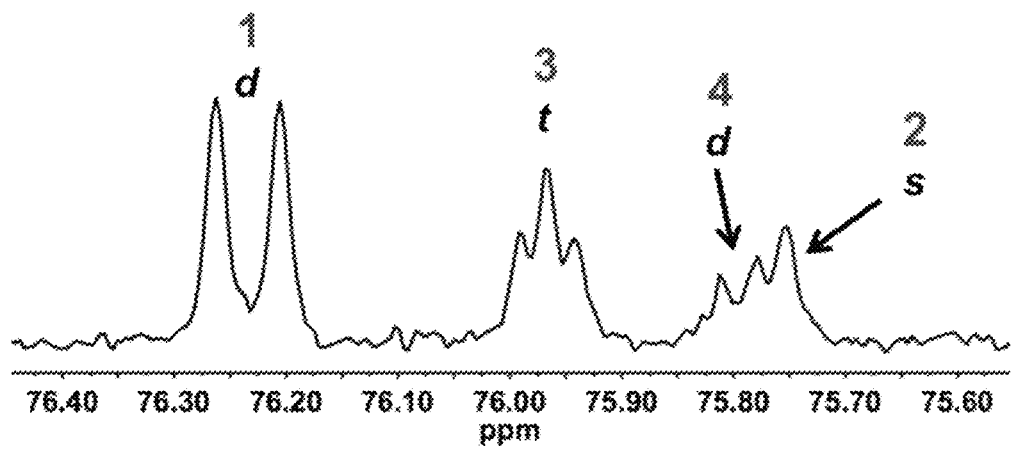
FIG. 30 is a $^{13}C$-NMR spectrum of the products of the reaction of 1 with 1-butanol (S1, S2, S3, S4). The labels above each peak refer to the chemical structures given in FIG. 28.
Figure 31:
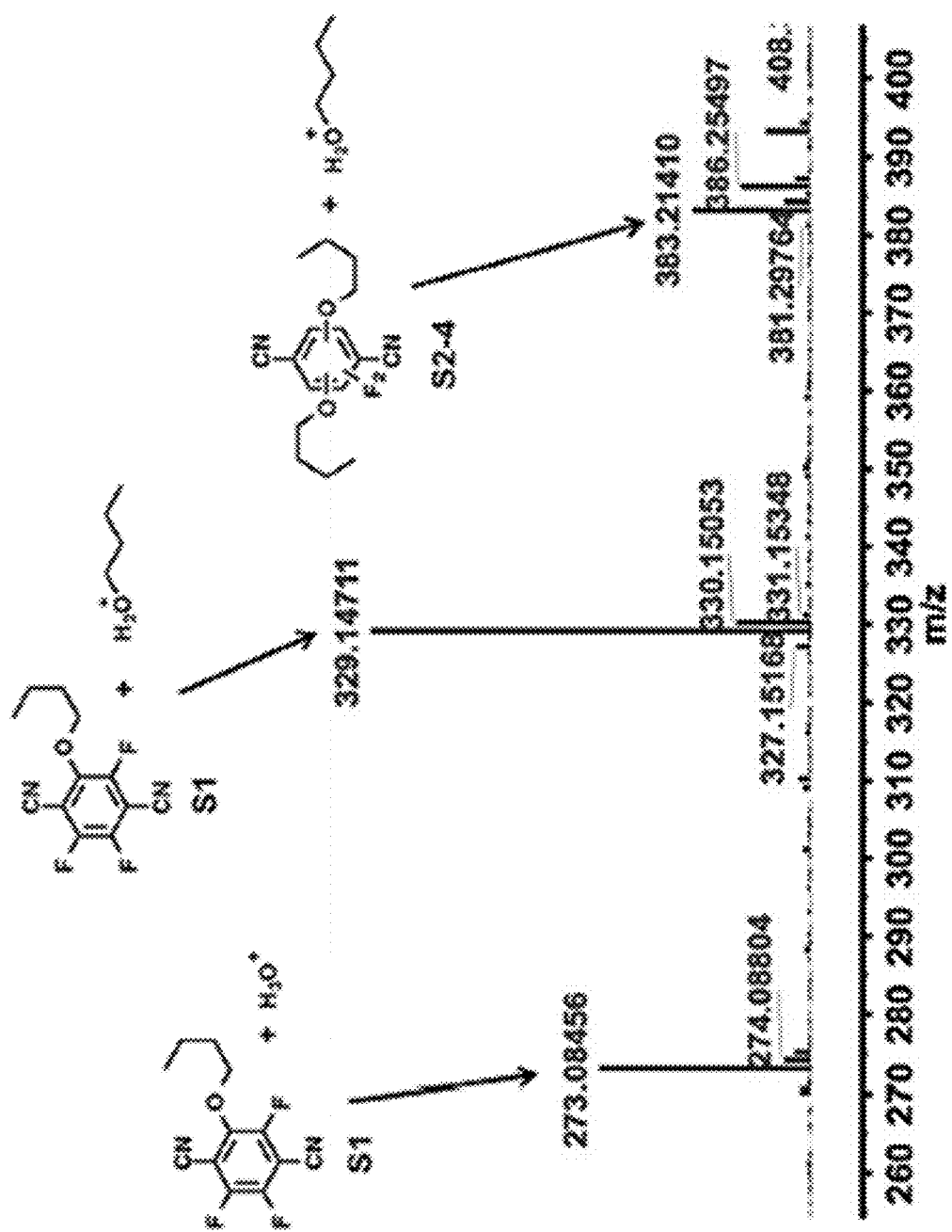
FIG. 31 is a mass spectrum of the products of the reaction of 1 with 1-butanol (S1, S2, S3, S4).

Both compounds form ether linkages under the polymerization conditions. The reaction of tetrafluoroterephthalonitrile with 2.3 equivalents of n-BuOH provided a 2:1 mixture of mono and disubstituted products, respectively, as revealed by NMR spectroscopy as shown in FIGS. 28-30 and mass spectrometry as shown in FIG. 31. The 1,4-, 1,3-, and 1,2-disubstituted products were formed at 6:3:1 ratio, respectively. A larger fraction of disubstituted products with a similar distribution of regioisomers was formed when 4 equivalents of n-BuOH were employed, yet tri- or tetrasubstituted products were still not observed as shown in FIG. 76. This experiment suggests that tri- and tetrasubstituted linkages are unlikely in the CD polymers. Finally, trans-1, 2-cyclohexanediol was found to form a 1,2-cyclic disubstitution product with tetrafluoroterephthalonitrile as shown in FIG. 77. A competition experiment in which both n-BuOH and trans-1,2-cyclohexanediol (2.3 equivalents each) were reacted with tetrafluoroterephthalonitrile provided a complex mixture of products that indicated that the two nucleophiles react at comparable rates as shown in FIG. 78. This experiment suggests that both the primary and secondary hydroxyl groups of β-CD might react with tetrafluoroterephthalonitrile. These model studies, along with the combustion analysis of the polymers, suggest that they are linked predominantly through disubstituted terephthaldehyde moieties at both the small and large rims of the β-CD macrocycles.

The high surface area and permanent porosity of P-CDP enable the rapid removal of organic contaminants from water. Bisphenol A (BPA), a component of plastics that has attracted attention as an endocrine disruptor, was chosen as a model pollutant to enable comparison to established adsorbents. The uptake of BPA by P-CDP, NP-CDP, and a non-porous β-CD polymer crosslinked with epichlorohydrin (EPI-CDP, $S_{BET}=23$ m$^2$g$^{-1}$) was compared. EPI-CDP is the most extensively studied β-CD polymer for water purification and has been commercialized. Three types of mesoporous ACs were tested: the hybrid AC/ion exchange resin used in commercial Brita point-of-use filters (Brita AC, $S_{BET}=507$ m$^2$g$^{-1}$), DARCO granular activated carbon (GAC, Each adsorbent (1 mg/mL) eventually removed most of the BPA from a 0.1 mM (22.8 mg/L) aqueous solution, corresponding to equilibrium uptakes of 19-24 mg BPA/g adsorbent as shown in FIGS. 32-43), with P-CDP near the high end of this range (22 mg/g). More importantly, P-CDP removed BPA more quickly than all other adsorbents, reaching ~95% of its equilibrium uptake in 10 s as shown in FIG. 44. In contrast, NP-CDP required 30 min to reach equilibrium and adsorbed only 46% of its equilibrium value in 10 s, indicating that the near-instantaneous adsorption of BPA by P-CDP is attributable to its porosity. Likewise, EPI-CDP required more than 1 h to reach equilibrium and only adsorbed 22% of its equilibrium value after 10 s, which is consistent with previous reports. Finally, the three ACs also showed slower BPA uptake with the Brita AC and GAC each requiring more than 1 h to reach equilibrium, while NAC required 10 min as shown in FIG. 44. NAC only adsorbed 53% of its equilibrium value in 10 s despite its nearly four times higher surface area than P-CDP.

Figure 32:
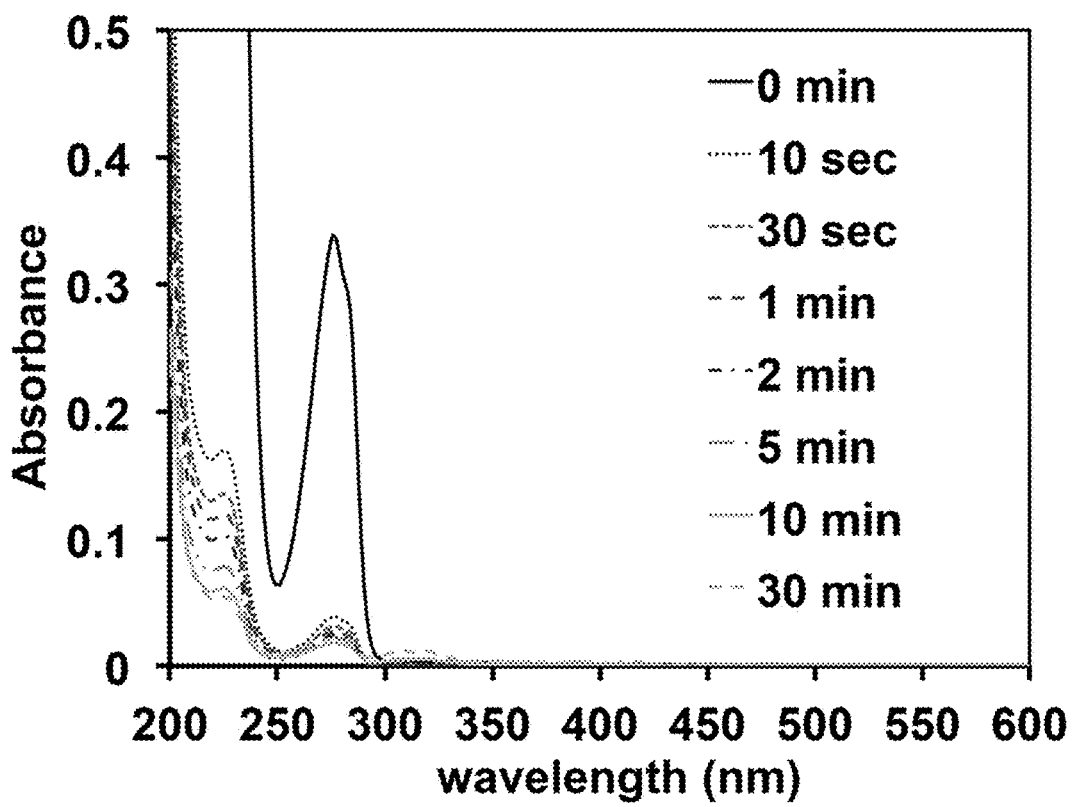
FIG. 32 shows UV-visible spectra that indicate the adsorption of BPA on P-CDP as a function of time.
Figure 33:
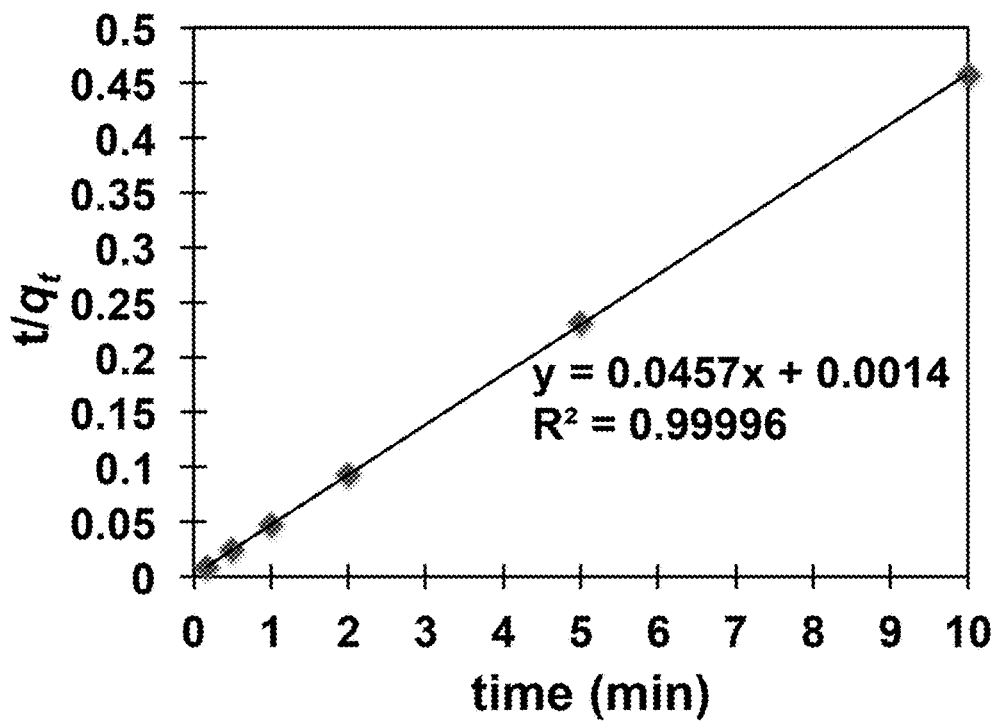
FIG. 33 shows a pseudo-second-order plot of BPA adsorption on P-CDP.
Figure 34:
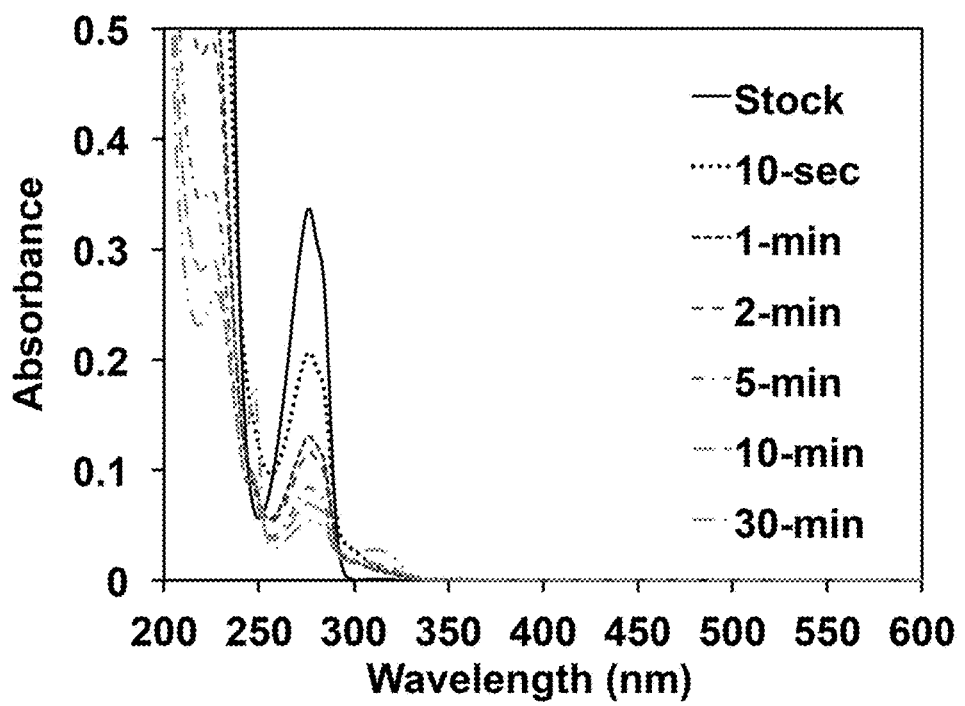
FIG. 34 shows UV-visible spectra that indicate the adsorption of BPA on NP-CDP as a function of time.
Figure 35:
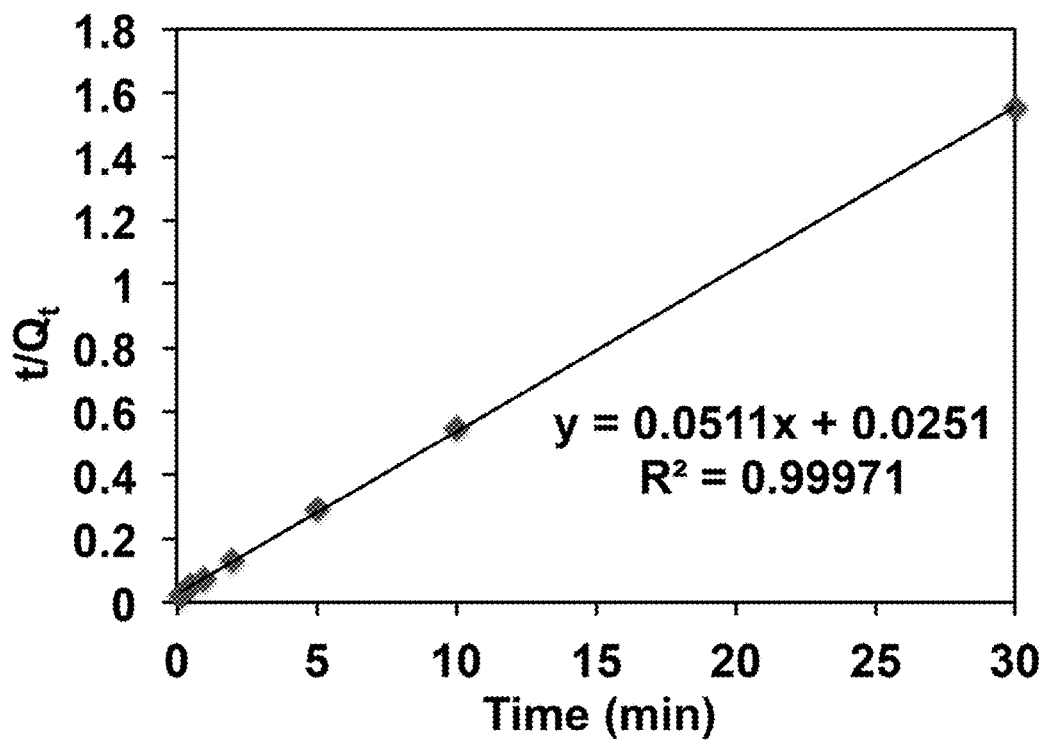
FIG. 35 shows a pseudo-second-order plot of BPA adsorption on NP-CDP.
Figure 36:
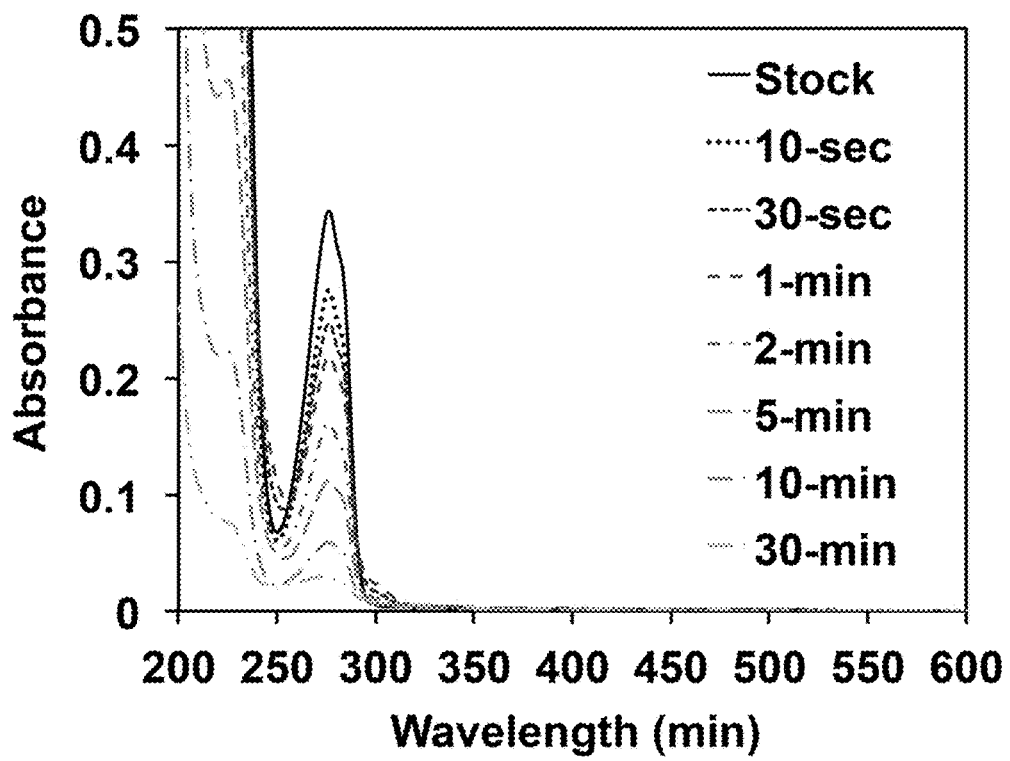
FIG. 36 shows UV-visible spectra that indicate the adsorption of BPA on EPI-CDP as a function of time.
Figure 37:
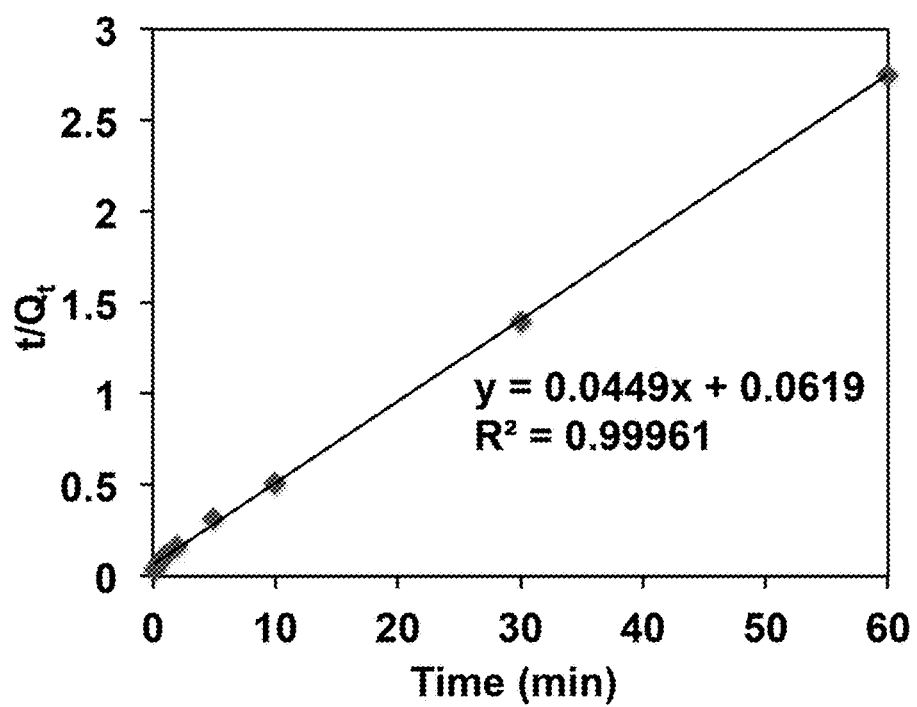
FIG. 37 shows a pseudo-second-order plot of BPA adsorption on EPI-CDP.
Figure 38:
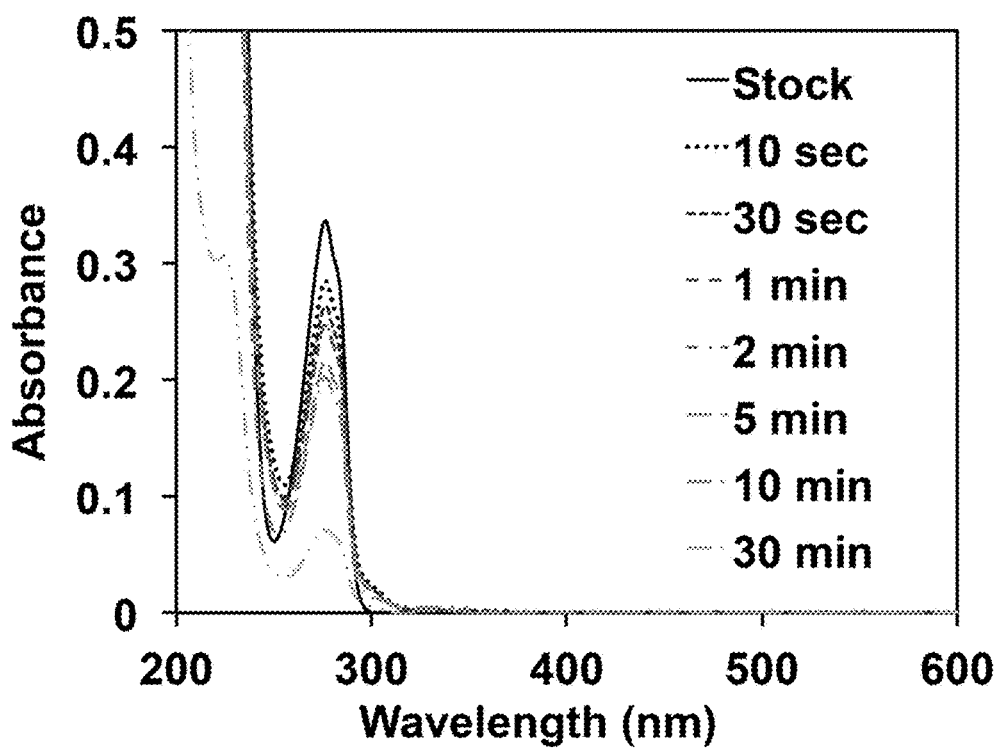
FIG. 38 shows UV-visible spectra that indicate the adsorption of BPA on BRITA AC as a function of time.
Figure 39:
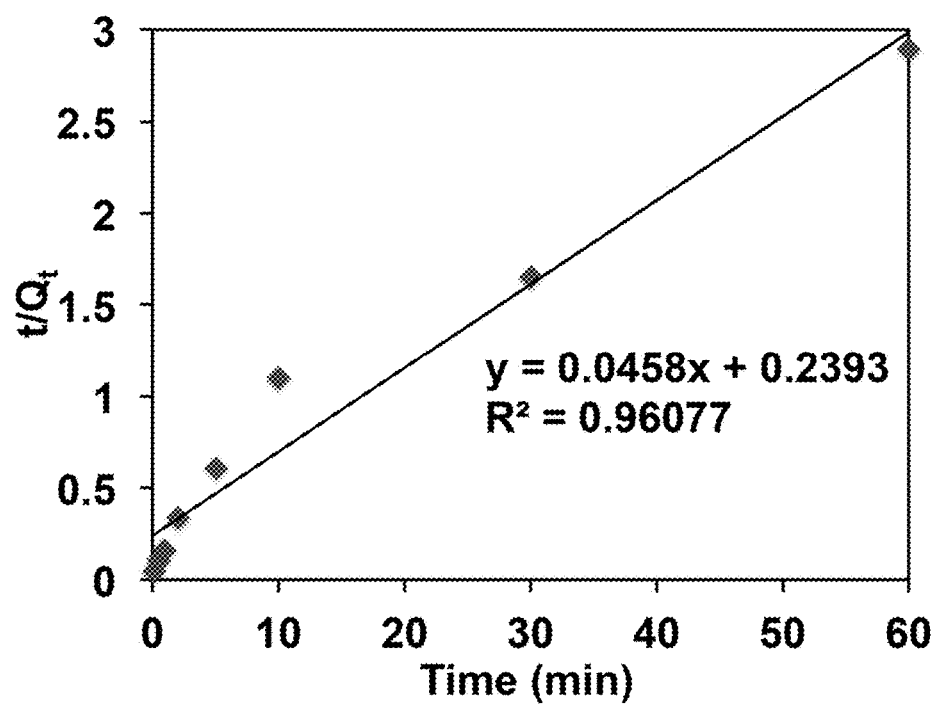
FIG. 39 shows a pseudo-second-order plot of BPA adsorption on Brita AC.
Figure 40:
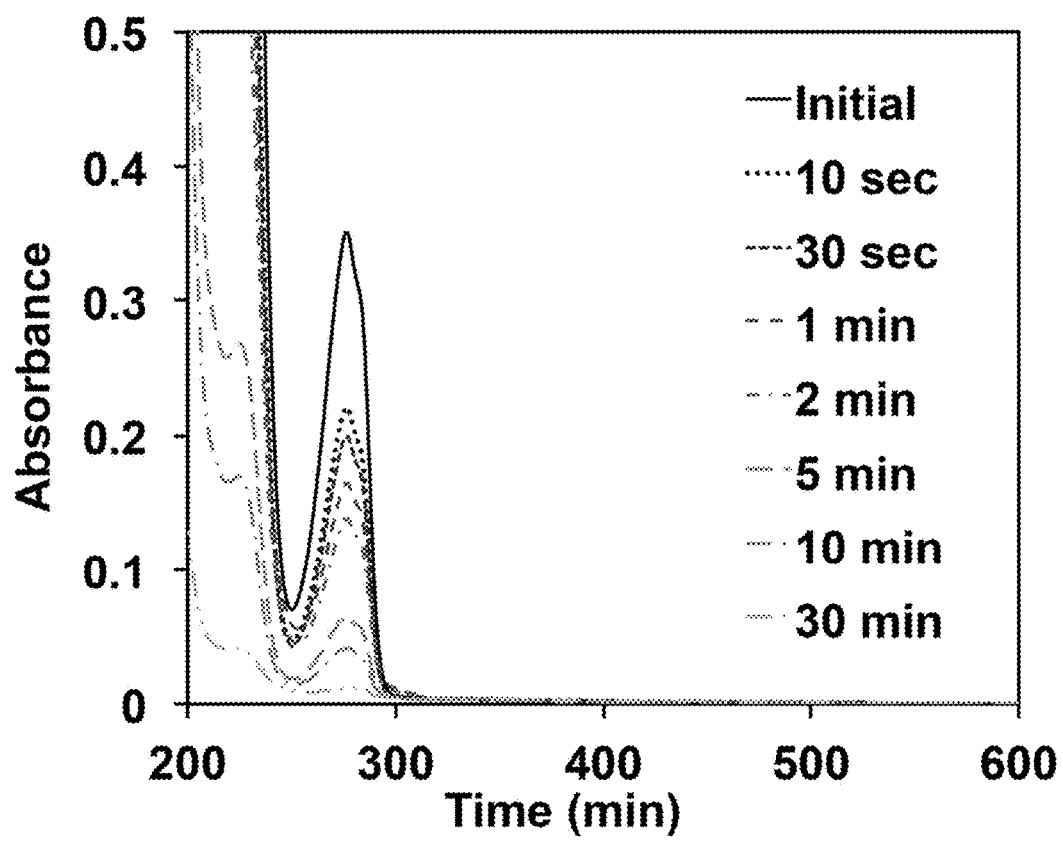
FIG. 40 shows UV-visible spectra that indicate the adsorption of BPA on GAC as a function of time.
Figure 41:
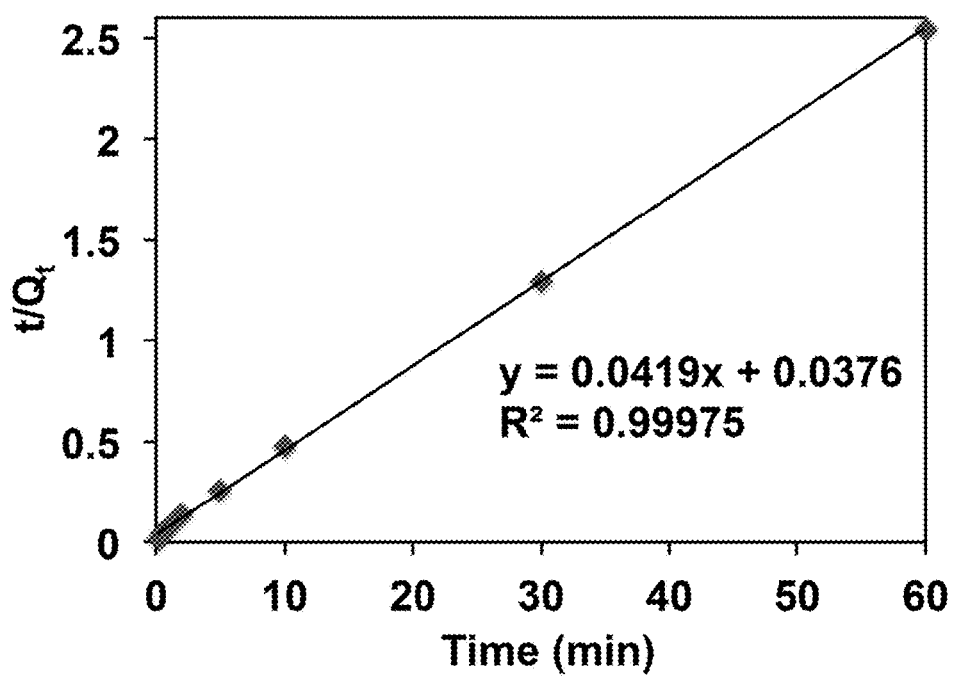
FIG. 41 shows a pseudo-second-order plot of BPA adsorption on GAC.
Figure 42:
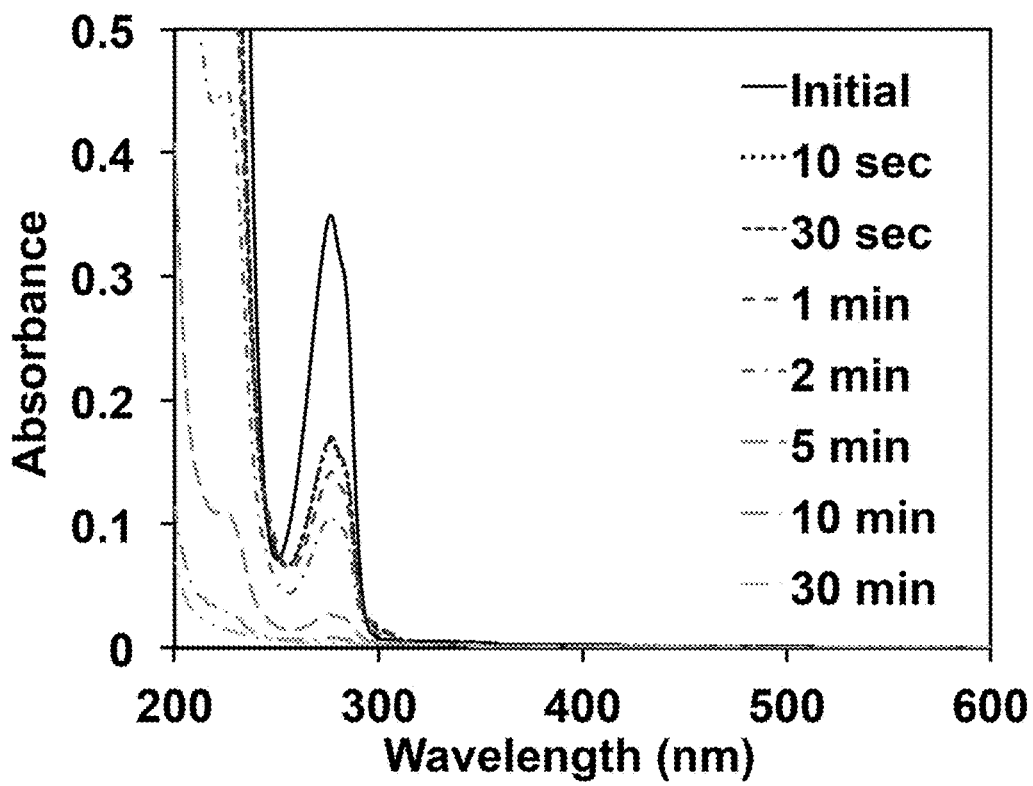

The apparent pseudo-second order rate constant ($k_{obs}$) of BPA (0.1 mM) adsorption to P-CDP is 1.5 mg g$^{-1}$ min$^{-1}$, which is 15 times higher than the high performance NAC and two or more orders of magnitude higher than the other studied adsorbents as shown in FIG. 32, FIG. 33, Table 4 and Table 5, below.

TABLE 4

| Sorbent | % Uptake in 10 sec | % Uptake at equilibrium | % Equilibrium in 10 sec[b] | $q_e$[c] |
|---|---|---|---|---|
| P-CDP | 89 | 95 | 94 | 22 |
| NP-CDP | 39 | 84 | 46 | 19 |
| EPI-CDP | 20 | 93[a] | 22 | 22[a] |
| NAC | 52 | 99 | 53 | 24 |
| GAC | 37 | 98[a] | 38 | 24[a] |
| Brita AC | 16 | 90[a] | 18 | 21[a] |

[a]This assumes that the equilibrium value is reached within 60 min.
[b]% equilibrium value that is achieved in 10 seconds.
[c]Amount of BPA adsorbed at equilibrium (mg BPA/g sorbent).

TABLE 5

| Adsorbent | BPA $k_{obs}$ (g mg$^{-1}$ min$^{-1}$) |
|---|---|
| P-CDP | 1.5 |
| NP-CDP | 0.1 |
| EPI-CDP | 0.03 |
| NAC | 0.09 |
| GAC | 0.05 |
| Brita AC | 0.009 |

To the knowledge of the present inventors, this rate constant is the highest reported for BPA or any other pollutant removed by ACs, mesoporous silicas, or carbohydrate-based adsorbents under similar experimental conditions. $k_{obs}$ amalgamates the performance of readily accessible binding sites (conceptualized as the outer surface of the adsorbent) and less accessible, slower binding sites (conceptualized as being within the adsorbent's interior). P-CDPs superior $k_{obs}$ for BPA adsorption indicates that nearly all of its β-CD binding sites are readily accessible, a feature not found in other adsorbents. The readily accessible binding sites of each adsorbent was investigated by determining the instantaneous uptake of BPA, or that achieved after very short contact times, as shown in FIG. 45. High instantaneous uptake is also desirable for rapid flow-through water purification. In these experiments, the adsorbent (~3 mg) was trapped as a thin layer on a 0.2 μm syringe filter, and aqueous BPA (3 mL, 0.1 mM) was passed rapidly through the filter at a flow rate of 9 mL/min. Under these conditions, P-CDP removed 80% of the BPA from the solution, corresponding to more than 85% of its equilibrium uptake as shown in FIG. 45, whereas NAC removed 59% of the BPA under the same conditions, indicative that half of its binding sites are not accessible on the 20 s time scale. The instantaneous BPA uptakes of other adsorbents track that seen at early time points in FIG. 44, but do not correspond perfectly to their $k_{obs}$ values, again reflecting that differences in both the affinity and accessibility of the binding sites factor into this parameter. The superior performance of P-CDP further indicates that most of its β-CD moieties are rapidly accessed by BPA. NACs higher instantaneous uptake compared to GAC and the other CD-containing polymers is reflective of its high surface area, four times higher than P-CDP. Nevertheless, this experiment indicates that half of its BPA binding sites are not accessible on the 20 s time scale. These experiments demonstrate the potential for rapid and energy efficient water purification protocols using P-CDP.

The thermodynamic parameters of P-CDPs BPA adsorption are consistent with the formation of β-CD inclusion complexes. P-CDPs equilibrium uptake at 20° C. as a function of [BPA]$_0$ fit the Langmuir model as shown in Table 6, below, suggesting 1:1 inclusion complex formation with an association constant (K) of 56000 M$^{-1}$, which is comparable to the values reported for other β-CD polymers.

TABLE 6

| Pollutant | Langmuir plot R$^2$ | $q_{max,e}$ (mg g$^{-1}$)$^a$ | K (Mol$^{-1}$)$^b$ | BPA/β-CD molar ratio at $q_{max,e}$ |
|---|---|---|---|---|
| BPA | 0.97665 | 88.5 | 56,500 | 0.9 |
| BPS | — | — | ~17,000$^c$ | — |
| metolachlor | — | — | ~35,000$^c$ | — |
| ethinyl estradiol | — | — | ~46,000$^c$ | — |

TABLE 6-continued

| Pollutant | Langmuir plot R$^2$ | $q_{max,e}$ (mg g$^{-1}$)$^a$ | K (Mol$^{-1}$)$^b$ | BPA/β-CD molar ratio at $q_{max,e}$ |
|---|---|---|---|---|
| propranolol hydrochloride | — | — | ~72,000$^c$ | — |
| 2-NO | — | — | ~30,000$^c$ | — |
| 1-NA | — | — | ~35,000$^c$ | — |
| DCP | — | — | ~17,000$^c$ | — |

$^a$Maximum adsorption capacity of pollutant on 1 g P-CDP at equilibrium.
$^b$Equilibrium constant.
$^c$Estimated from the equilibrium efficiency value from the batch kinetic studies.

Furthermore, the maximum adsorption capacity at equilibrium ($q_{e,max}$) was found to be 88 mg/g, which is similar to the highest reported value of an EPI-CDP (84 mg/g)[11], and corresponds to a BPA:β-CD molar ratio of 0.9. Therefore, most of the β-CD units in the polymer are able to form 1:1 complexes with BPA at equilibrium. At even higher concentrations of BPA, P-CDP achieves BPA:β-CD ratios greater than 1, presumably by binding BPA on the outside of the CD rings or through other nonspecific interactions. For example, 1 mg/mL of P-CDP adsorbs 200 mg/g of BPA from a 1 mM aqueous solution, indicating significant capacity beyond 1:1 CD inclusion complexes as shown in Table 7, below.

TABLE 7

| Stock BPA (mM) | P-CDP (mg/mL) | Equilibrium BPA conc (mM) | $q_e$ (mg g$^{-1}$)$^a$ | BPA/β-CD molar ratio at equilibrium |
|---|---|---|---|---|
| 0.048 | 1 | 0.0027 | 10.4 | 0.11 |
| 0.10 | 1 | 0.008 | 21.1 | 0.22 |
| 0.2 | 1 | 0.024 | 40.5 | 0.42 |
| 0.25 | 1 | 0.038 | 48.0 | 0.49 |
| 0.25 | 2 | 0.01 | 27.3 | 0.28 |
| 1.2 | 1 | 0.34 | 199.4 | 2.0 |
| 1.2 | 2 | 0.17 | 120.0 | 1.2 |

$^a$Amount of BPA (in mg) adsorbed on 1 g of P-CDP at equilibrium.

However, these results suggest that P-CDPs binding properties will reflect those of β-CD inclusion complex formation at concentrations relevant for water purification. In contrast to the energy intensive and degradative regeneration processes of ACs, BPA is easily removed from P-CDP by rinsing the polymer with methanol at room temperature. The recyclability was characterized by measuring P-CDPs equilibrium uptake from an aqueous BPA solution (0.1 mM), recovering the polymer by filtration, and dispersing it in MeOH (1 mg/mL) for 5 min. This procedure removes the BPA from the pores, as determined by the near-quantitative recovery of BPA from the MeOH solution and the subsequent ability of the reactivated polymer to adsorb additional BPA. Five consecutive BPA adsorption/desorption cycles were performed and the regenerated P-CDP exhibited almost no decrease in performance compared to the as-synthesized polymer as shown in FIG. 46.

Micropollutant Removal Study

In addition to BPA, the ability of P-CDP to remove pollutants of different size, functionality, and hydrophobicity that span simple aromatics, pharmaceuticals, and pesticides was evaluated as shown in FIG. 47. The molecular descriptor values for micropollutants used in the study are shown in FIG. 48. P-CDP rapidly removes many organic pollutants, including several pollutants of emerging concern that are not removed effectively by current water or wastewater treatment processes. Simple aromatics include: 2,4- dichlorophenol (DCP or 2,4-DCP), an intermediate in herbicide production and degradation product of the antibacterial agent triclosan; 1-naphthyl amine (1-NA), an azo dye precursor and known carcinogen; and 2-naphthol (2-NO), a model for various naphthol pollutants. The following anthropogenic contaminants were evaluated: bisphenol S (BPS), which has replaced BPA in many polycarbonates but also appears to be an endocrine disruptor with greater environmental persistence; metolachlor, one of the most common herbicides that is often detected in streams and groundwater; ethinyl estradiol, an estrogen mimic used in oral contraceptives that has caused the collapse of fish populations at concentrations as low as 5 ng/L; and propranolol, a beta-blocker used to treat hypertension, which is not removed efficiently by water or wastewater treatment protocols and has been detected in wastewater effluent streams at concentrations similar to blood serum levels of its users. Adsorption studies of each of these compounds were performed similarly as those for BPA (0.1 mM adsorbate, 1 mg/mL adsorbent), except ethinyl estradiol, which was tested at a lower concentration because of its low water solubility (0.04 mM adsorbate, 0.5 mg/mL adsorbent). Each organic contaminant is rapidly removed by P-CDP as shown in FIG. 49 and the time-dependent adsorption curves shown in FIGS. 50-70 are similar to that of BPA. These data also fit pseudo-second order kinetic models as shown in FIGS. 52, 55, 58, 61, 64, 67, and 70 and provided very high $k_{obs}$, ranging from 0.7-30 g mg' min' as shown in Table 6, and Tables 8 and 9, below.

TABLE 8

| Sorbent | % Uptake in 10 sec | % Uptake at equilibrium | % Equilibrium in 10 sec[b] | $q_e$[c] |
|---|---|---|---|---|
| P-CDP | 89 | 95 | 94 | 22 |
| NP-CDP | 39 | 84 | 46 | 19 |
| EPI-CDP | 20 | 93[a] | 22 | 22[a] |
| NAC | 52 | 99 | 53 | 24 |
| GAC | 37 | 98[a] | 38 | 24[a] |
| Brita AC | 16 | 90[a] | 18 | 21[a] |

[a]This assumes that the equilibrium value is reached within 60 min.
[b]% equilibrium value that is achieved in 10 seconds.
[c]Amount of BPA adsorbed at equilibrium (mg BPA/g sorbent).

TABLE 9

| Sorbent | $k_{obs}$ (g/mg min) | Correlation coefficient $R^2$ | Time to reach equilibrium (min) |
|---|---|---|---|
| P-CDP | 1.5 | 1.00 | 10 |
| NP-CDP | 0.10 | 1.00 | 30 |
| EPI-CDP | 0.032 | 1.00 | >60 |
| NAC | 0.090 | 1.00 | 10 |
| GAC | 0.047 | 1.00 | >60 |
| Brita AC | 0.0088 | 0.96 | >60 |

The binding constants of the tested pollutants were estimated from the binding efficiency at equilibrium, and all were approximately $10^4$ M$^{-1}$ as shown in Table 6. The instant uptake of these pollutants by P-CDP was also investigated as compared with EPI-CDP and high performance NAC as shown in FIG. 71. P-CDP shows excellent instant uptake of all pollutants, in stark contrast to the nonporous EPI-CDP, and it also outperforms NAC for all of the studied emerging contaminants. P-CDP even shows similar performance as NAC for the planar aromatic model compounds, which interact strongly with ACs. P-CDPs superior performance for anthropogenic contaminants indicates a major advantage of β-CD-based adsorbents: their three-dimensional cavities are a better match for non-planar compounds. Overall, these results show the broad scope and robust nature of the P-CDP for removing relevant emerging pollutants with diverse size, hydrophobicity, and pendant functionality.

The instant uptake of these pollutants was also investigated at environmentally relevant concentrations and in a mixture solution at concentrations between 2.5-100 μg/L, the range in which many polar organic pollutants are quantified in wastewater and drinking water resources. The aqueous mixture of pollutants (8 mL) was passed rapidly through a 0.2 μm syringe filter containing approximately 0.3 mg of P-CDP or NAC as shown in FIG. 72. On average, all of these emerging contaminants again showed equal or greater instant uptake by P-CDP over NAC. Two pollutants showed no instant uptake by NAC at low concentrations whereas all eight pollutants showed at least some removal by P-CDP. These results demonstrate that P-CDP can at least partially remove polar organic pollutants at environmental concentrations instantly and simultaneously when present in mixtures, suggesting that it can contribute to the removal of a wide range of micropollutants during water and wastewater treatment.

A. Reagents. β-cyclodextrin (β-CD) (>97%) and tetrafluoroterephthalonitrile (>99%) were purchased from Sigma Aldrich and used without further purification. Tetrahydrofuran (THF) was purified and dried in a custom-built activated alumina solvent purification system. Epichlorohydrin (>99%) was purchased from Sigma Aldrich and used as received. Aqueous solutions of pollutants were prepared using 18 MΩ deionized H$_2$O at neutral pH. Pollutant model compounds were obtained from commercial sources and used as received. Norit RO 0.8 activated carbon (NAC) pellets was purchased from Sigma Aldrich and ground into a fine powder before use. Brita AC was obtained from a "Brita Advanced Faucet" point-of-use water filter and was ground into fine powder before use. Granular activated carbon (GAC, DARCO 12-20 mesh) was purchased from Sigma Aldrich, and ground into fine powder before use.

B. Materials and Instrumentation. Pollutant removal experiments were performed at 25° C. on a stirring hot plate with a 250 rpm stirring rate. Aqueous suspensions of adsorption experiments were filtered in syringes equipped with Whatman 0.2 μm inorganic membrane filters. Instant pollutant removal experiments were also performed in syringes equipped with Whatman 0.2 μm inorganic membrane filters.

UV-Vis spectroscopy was performed on Cary 5000 Varian UV-Vis spectrometer. UV-Vis spectra were recorded at room temperature over the range of 200-600 nm, corrected against an appropriate background spectrum, and normalized to zero absorbance at 600 nm.

Quantification of analytes from the uptake of pollutant mixtures at μg/L concentrations was performed by mass spectrometry (HPLC-MS). The analytical method was adopted from one previously reported for ultratrace level screening of polar and semi-polar organic chemicals and involved high-performance liquid chromatography (HPLC) coupled with a quadrupole-orbitrap mass spectrometer (MS) (QExactive, ThermoFisher Scientific, Waltham, Mass.) and on-line solid phase extraction (EQuan Max Plus, ThermoFisher Scientific, Waltham, Mass.). Samples were injected at 5 mL volumes and were loaded onto an) XBridge (Waters, Milford, Mass.) C-18 Intelligent Speed (2.1 mm=20 mm, particle size 5 μm) trap column. Elution from the trap column and onto an XBridge (Waters, Milford, Mass.) C-18 analytical column (2.1 mm=50 mm, particle size 3.5 μm)

was performed using a gradient pump delivering 200 μL/min of a water and MeOH mobile phase, each containing 0.1% (volume) formic acid. The HPLC-MS was operated with electrospray ionization in positive and negative polarity modes. The MS acquired full-scan MS data within a mass-to-charge range of 100-1000 for each sample followed by a data-dependent acquisition of product ion spectra (MS/MS). Analytes were quantified from external calibration standards based on the analyte responses by linear least-squares regression. Limits of quantification for each analyte were determined as the lowest point in the external calibration curve at which at least 8 scans were measured across a chromatographic peak and the most intense MS/MS product ion was still detected. Exact molecular masses, ionization behavior, retention times, and limits of quantification used for the detection and quantification of each analyte are provided in FIGS. 80-82.

Infrared spectroscopy was performed on a Thermo Nicolet iS10 with a diamond ATR attachment. Solution-phase NMR experiments were performed on a Varian INOVA-400 using a standard $^1H\{^{13}C, ^{15}N\}$ Z-PFG probe with a 20 Hz sample spin rate. Solid-state NMR analyses were conducted on a Varian INOVA-400 spectrometer using an external Kalmus $^1H$ linear pulse amplifier blanked using a spare line. Samples were packed into 7 mm outside diameter silicon nitride rotors and inserted into a Varian HX magic angle spinning (MAS) probe.

Surface area measurements were conducted on a Micromeritics ASAP 2020 Accelerated Surface Area and Porosimetry Analyzer. Each sample (25-50 mg) was degassed at 90° C. for 24 h and then backfilled with $N_2$. $N_2$ isotherms were generated by incremental exposure to ultra high purity nitrogen up to 1 atm in a liquid nitrogen (77 K) bath, and surface parameters were determined using BET adsorption models included in the instrument software (Micromeritics ASAP 2020 V4.00).

Thermogravimetric (TGA) analysis was performed on a TA Instruments Q500 Thermogravimetric Analyzer. Parameters included a heating range of 20-600° C. using a 10° C./min ramp as shown in FIG. 73

FIG. 74 is a representative scanning electron micrograph of a P-CDP particle. Scanning electron microscopy was performed on a LEO 1550 FESEM (Keck SEM) operating at 2.00 kV and a working distance of 3-4 mm with an aperture size of 20 μm. Samples were prepared by adsorption onto a silicon wafer, which was then attached to a flat aluminum platform sample holder.

C. Synthetic Procedures.

Synthesis of the Porous β-cyclodextrin Polymer (P-CDP).

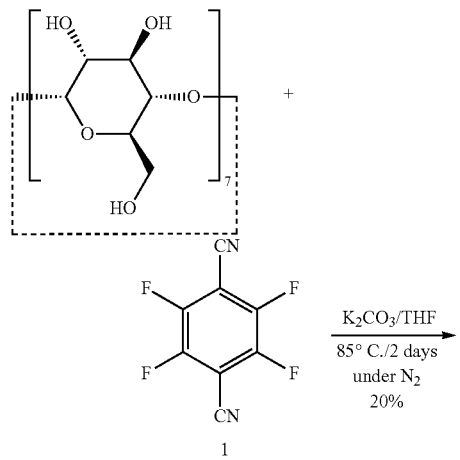

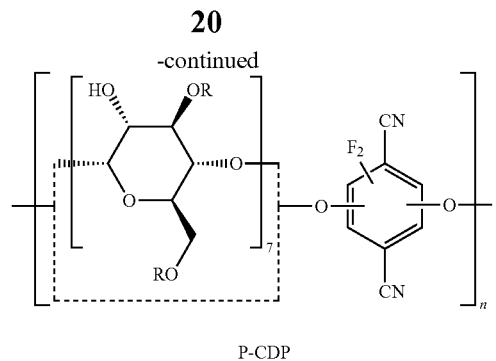

P-CDP

A flame dried 20 mL scintillation vial equipped with a magnetic stir bar was charged with β-CD (0.200 g, 0.176 mmol), (1) tetrafluoroterephthalonitrile (0.100 g, 0.500 mmol), and $K_2CO_3$ (0.300 g, 2.17 mmol). The vial was flushed with $N_2$ gas for 5 min, then dry THF (8 mL) was added and the vial was bubbled with $N_2$ for additional 2-3 min. The $N_2$ inlet was removed and the mixture was placed on a hot stirring plate (85° C.) and stirred at 500 rpm for 2 d. The orange suspension was cooled and then filtered, and the residual $K_2CO_3$ was removed by washing the solid on the filter paper with 1N HCl until $CO_2$ evolution stopped. The recovered light yellow solid was isolated and activated by soaking in $H_2O$ (2×10 mL) for 15 min, THF (2×10 mL) for 30 min and $CH_2Cl_2$ (1×15 mL) for 15 min. Finally, the solid was dried under high vacuum at 77 K in a liquid nitrogen bath for 10 min and then at room temperature for 2-3 days. P-CDP (0.055 g, 20% yield) was obtained as a pale yellow powder and subsequently characterized. $^{13}$C-MAS SS-NMR (400 MHz): δ 168.9, 157.2, 131.1, 103.9, 95.2, 71.8 ppm. IR (solid, ATR) 3368, 2937, 2243, 1684, 1625, 1478, 1376, 1304, 1270, 1153, 1030 cm$^{-1}$. Anal. Calcd. for $(C_{42}H_{70}O_{35})_1 \cdot (C_8F_2N_2)_{6.1} \cdot (CH_2Cl_2)_2 \cdot (H_2O)_2$: C, 47.95; H, 3.17; F, 9.97; N, 7.35. Found: C, 48.23; H, 2.99; F, 9.66; N, 7.37. FIG. 25 shows IR spectra of as-synthesized P-CDP. The assignments of the major IR peaks for the spectra shown in FIG. 25 are found in Table 10, below.

TABLE 10

| Peak (cm$^{-1}$) | Assignment |
|---|---|
| 3383 (m) | O—H stretch of residual hydroxyl groups (primary and secondary) on β-cyclodextrin residues |
| 2933 (m) | C—H stretch of $C_2$-$C_6$ on β-cyclodextrin residues |
| 2243 (m) | CN stretch of the nitrile groups on the terephthalonitrile residues |
| 1478 (s) | C=C aromatic stretch in the terephthalonitrile residues |
| 1269 (s) | C—F stretch aromatic |
| 1152 (s) | C—O stretch alcohols and acetal in β-cyclodextrin residues |
| 1030 (vs) | |

Synthesis of the Nonporous β-cyclodextrin Polymer (NP-CDP).

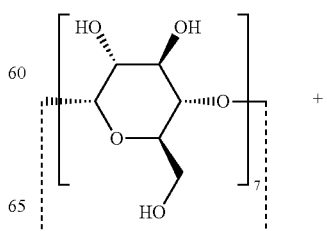

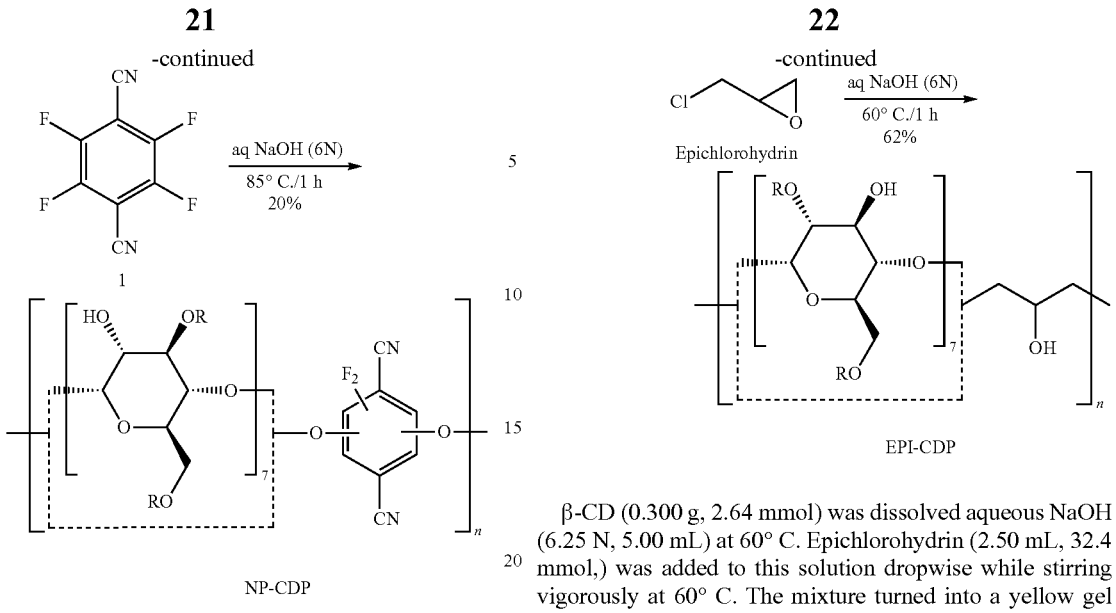

NP-CDP

β-CD (2.00 g, 1.76 mmol) and tetrafluoroterephthalonitrile (0.200 g, 1.00 mmol) were mixed vigorously in an aqueous NaOH solution (6.25 N, 2.00 mL) at 85° C. The mixture solidified within 1 h, after which deionized H$_2$O was added and the suspension was filtered. The solid was washed by soaking in deionized H$_2$O (2×150 mL) for 15 min, THF (3×15 mL) for 30 min and CH$_2$Cl$_2$ (1×15 mL) for 15 min. Finally, the solid was dried under high vacuum at room temperature for 2 days to give NP-CDP (0.746 g, 20.1% yield) as a yellow powder. $^{13}$C-MAS SS-NMR (400 MHz): δ 162.9, 143.3, 140.4, 135.1, 117.0, 99.0, 96.2, 94.1, 72.6 ppm. IR (solid, ATR) 3327, 2938, 2239, 1674, 1610, 1463, 1370, 1268, 1150, 1100, 1030 cm$^{-1}$. Anal. Calcd. For (C$_{42}$H$_{63}$O$_{35}$)$_1$.(C$_8$F$_{1.8}$N$_2$)3.5.(H$_2$O)$_{13}$: C, 43.88; H, 4.68; F, 6.25; N, 5.12. Found: C, 43.78; H, 4.51; F, 6.31; N, 5.11. FIG. 25 shows IR spectra of as-synthesized NP-CDP. The assignments of the major IR peaks for the spectra shown in FIG. 25 are found in Table 11, below.

TABLE 11

| Peak (cm$^{-1}$) | Assignment |
|---|---|
| 3330 (m) | O—H stretch of residual hydroxyl groups (primary and secondary) on β-cyclodextrin residues |
| 2929 (m) | C—H stretch of C$_2$-C$_6$ on β-cyclodextrin residues |
| 2236 (m) | CN stretch of the nitrile groups on the terephthalonitrile residues |
| 1463 (s) | C═C aromatic stretch in the terephthalonitrile residues |
| 1370 (s) | C—F stretch aromatic on terephthalonitrile residues |
| 1268 (s) | |
| 1152 (s) | C—O stretch alcohols and acetal in β-cyclodextrin residues |
| 1030 (vs) | |

Synthesis of Epichlorohydrin β-cyclodextrin Polymer (EPI-CDP).

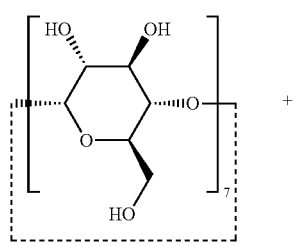

β-CD (0.300 g, 2.64 mmol) was dissolved aqueous NaOH (6.25 N, 5.00 mL) at 60° C. Epichlorohydrin (2.50 mL, 32.4 mmol,) was added to this solution dropwise while stirring vigorously at 60° C. The mixture turned into a yellow gel within 1 h, after which 10 mL of deionized H$_2$O was added, and the mixture was filtered on a Buchner funnel. The solid was washed by soaking in deionized H$_2$O (2×150 mL) for 15 min, THF (3×15 mL) for 30 min and CH$_2$Cl$_2$ (1×15 mL) for 15 min. The solid was finally dried under high vacuum for 2 d at room temperature to give EPI-CDP (3.11 g, 62% yield) as a white powder. $^{13}$C-MAS SS-NMR (400 MHz): β 100.1, 72.0 ppm. IR (solid, ATR) 3387, 2923, 2900, 1702, 1360, 1030 cm$^{-1}$. Anal. Calcd. For (C$_{42}$H$_{60}$O$_{35}$)$_1$.(C$_3$H$_6$O)$_{10}$.(H$_2$O)$_{4.5}$: C, 48.40; H, 7.28. Found: C, 48.23; H, 7.09. FIG. 79 shows the FT-IR spectrum of as-synthesized EPI-CDP.

D. FT-IR and solid-state $^{13}$C NMR characterization of P-CDP and NP-CDP. FTIR spectra of P-CDP and NP-CDP showed absorbances at 2235 cm$^{-1}$, corresponding to the nitrile stretch, as well as 1670 and 1463 cm$^{-1}$, corresponding to C-C aromatic stretches. C—F stretches, which resonate at 1268 cm$^{-1}$, are present in the spectra of both polymers and appear weaker compared to the spectrum of tetrafluoroterephthalonitrile, as expected for partial F substitution. Finally, the IR spectra of P-CDP and NP-CDP exhibited O–H stretches near 3330 cm$^{-1}$, aliphatic C–H stretches around 2930 cm$^{-1}$, and an intense C–O stretch at 1030 cm$^{-1}$, which are spectral features of intact β-CD as shown in FIG. 25. Solid-state $^{13}$C NMR spectra of P-CDP and NP-CDP exhibited resonances associated with β-CD at δ=72 and 100 ppm as shown in FIG. 26. Peaks at δ=95 and 140 ppm correspond to the newly formed alkoxy groups and aromatic carbons, respectively.

E. Water regain analysis. P-CDP or NP-CDP (100 mg) were dispersed in deionized H$_2$O (10 mL) for 1 h and then filtered using 11 μm Whatman filter paper. The solids were collected and blotted using additional Whatman filter paper, and weighed. The water regain (expressed as a weight percent) of each polymer was determined from the average of two measurements using the following equation:

$$\text{Water regain wt \%} = \frac{W_w - W_d}{W_d} \times 100$$

where $W_w$ (mg) and $W_d$ (mg) are the masses of the wet and dry polymer, respectively.

F. Batch adsorption kinetic studies. Adsorption kinetic studies were performed in 20 mL scintillation vials equipped with magnetic stir bars. All studies were conducted at ambient temperature on a stirring hot plate adjusted to provide a 250 rpm stirring rate.

In studies involving P-CDP and NP-CDP, the polymer (18 mg) was initially washed with $H_2O$ for 2-3 min and then filtered on 11 μm Whatman filter paper. The polymer was then transferred to a 20 mL scintillation vial and then a pollutant stock solution (18 mL) was added. The mixture was immediately stirred and 2 mL aliquots of the suspension were taken at certain intervals via syringe and filtered immediately by a Whatman 0.2 μm inorganic membrane filter. The residual concentration of the pollutant in each sample was determined by UV-Vis spectroscopy. In studies involving EPI-CDP, NAC, GAC and Brita AC, the adsorbent (6 mg) was added to a 20 mL scintillation vial and then a pollutant stock solution (6 mL) was added. The vial was stirred for a measured amount of time before the suspension was filtered using a Whatman 0.2 μm inorganic membrane filter.

The concentrations of pollutants in stock solutions as well as in the filtrates were characterized by UV/Vis spectroscopy, based on calibration with their measured molar extinction coefficients ($\epsilon$) ($M^{-1}cm^{-1}$), which were determined for bisphenol A (3343 at $\lambda_{max}$=276 nm), bisphenol S (20700 at $\lambda_{max}$=259 nm), 2-naphthol (4639 at $\lambda_{max}$=273 nm), 1-naphthyl amine (5185 at $\lambda_{max}$=305 nm), 2,4-dichlorophenol (2255 at $\lambda_{max}$=284 nm), and metolachlor (213 at $\lambda_{max}$=15330 nm) pollutants. c values of ethinyl estradiol (8430 at $\lambda_{max}$=220 nm) and propranolol hydrochloride (5310 at $\lambda_{max}$=290 nm) were reported elsewhere[31,32].

The efficiency of pollutant removal by the sorbent was determined by the following equation:

$$\text{Pollutant Removal Efficiency \%} = \frac{(C_0 - C_t)}{C_0} \times 100$$

where $C_0$ (mmol/L) and $C_t$ (mmol/L) are the initial and residual concentration of pollutant in the stock solution and filtrate, respectively.

The amount of pollutant bound to the sorbent was determined by the following equation:

$$q_t = \frac{(C_0 - C_t) \times M_w}{m}$$

where $q_t$ (mg/g) is amount of pollutant adsorbed per g of sorbent at time t (min). $C_0$ (mmol/L) and $C_t$ (mmol/L) are the initial and residual concentration of pollutant in the stock solution and filtrate, respectively. m (g) is the mass of sorbent used in the study. $M_w$ (g/mol) is the molar mass of the pollutant.

The pollutant uptake rate of each adsorbent was best described by Ho and McKay's pseudo-second order adsorption model, shown in the following equation in a common linearized form:

$$\frac{t}{q_t} = \frac{t}{q_e} + \frac{1}{k_{obs}q_e^2}$$

where $q_t$ and $q_e$ are the adsorbate uptakes (mg adsorbate/g polymer) at time t (min) and at equilibrium, respectively, and $k_{obs}$ is an apparent second-order rate constant (g $mg^{-1}$ $min^{-1}$).

G. Instant adsorption experiments. Individual pollutants at high (mM) concentrations: 3.0 mg of the adsorbent was stirred in 3 mL deionized $H_2O$ for 2-3 min, then the suspension was pushed by a syringe through a Whatman 0.2 μm inorganic membrane filter to form a thin layer of the adsorbent on the filter membrane. 3 mL of the pollutant stock solution was then pushed through the adsorbent during 20 seconds (8-9 mL/min flow rate).

The filtrate was then measured by UV-Vis spectroscopy to determine the pollutant removal efficiency.

Mixture of pollutants at environmentally relevant (μg/L) concentrations: 15 mg of the adsorbent (P-CDP or NAC) was added into a 20 mL vial and 5 mL nanopure water was added to prepare 3 g/L stock suspension. Then 0.1 mL of the suspension was pushed through a Whatman 0.2 μm inorganic membrane filter with a syringe to form a thin layer of the adsorbent on the membrane. 8 mL of the diluted mixture (100 μg/L BPA, 2.5 μg/L BPS, 50 μg/L ethinyl estradiol, 100 μg/L propranolol, 5 μg/L metolachlor, 5 μg/L 1-Na, 25 μg/L2-No, and 2.5 μg/L DCP) was then pushed through the adsorbent over approximately 20 seconds (25 mL/min flow rate). The experiments were conducted in triplicate. The filtrate was then measured by HPLC-MS and the results are shown in the Table 12, below.

TABLE 12

| Compound | Molecular Formula | Exact Mass | Ionization Mode | Retention Time, (min) | Quantification Limit, (μg/L) |
|---|---|---|---|---|---|
| BPA | $C_{15}H_{16}O_2$ | 228.1145 | negative | 14.1 | 20 |
| BPS | $C_{12}H_{10}O_4S$ | 250.0294 | positive | 10.83 | 0.05 |
| metolachlor | $C_{15}H_{22}ClNO_2$ | 283.1334 | positive | 16.47 | 0.1 |
| propranolol | $C_{16}H_{21}NO_2$ | 259.1567 | positive | 11.75 | 10 |
| Ethynyl estradiol | $C_{20}H_{24}O_2$ | 296.1771 | positive | 15.22 | 1 |
| 1-NA | $C_{10}H_9N$ | 143.0729 | positive | 10.35 | 0.1 |
| 2-NO | $C_{10}H_8O$ | 144.0569 | positive | 13.16 | 0.5 |
| 2,4-DCP | $C_6H_4Cl_2O$ | 161.9634 | negative | 14.6 | 0.05 |

H. Thermodynamic studies of adsorption. 4.0 mg of sorbent was initially washed with 3 mL of deionized $H_2O$ for 2-3 min and then filtered on a Whatman filter paper. Then the solid was transferred to 4 mL vial equipped with a stirring bar, and 2 mL (2 mg/mL studies) or 4 mL (1 mg/mL studies) of pollutant stock solution was added, and the suspension was stirred for 10 min to reach equilibrium. The suspension was then filtered on a Whatman 0.2 μm inorganic membrane filter, and the filtrate was measured by UV-Vis spectroscopy.

A Langmuir adsorption isotherm was generated by plotting $1/q_e$ vs $1/c$ in the following equation:

$$\frac{1}{q_e} = \frac{1}{q_{max,e}} + \frac{1}{q_{max,e} \times K \times c}$$

where qe (mg/g) is the amount of pollutant adsorbed at equilibrium. (mg/g) is the maximum adsorption capacity of adsorbent at equilibrium. c (mol/L) is the residual pollutant concentration at equilibrium. K ($mol^{-1}$) is the equilibrium constant.

I. P-CDP regeneration experiments. 10 mg of P-CDP was initially soaked in 5 mL deionized $H_2O$ for 5 min, and then filtered on a Whatman filter paper. The polymer was then transferred to a 20 mL scintillation vial equipped with a magnetic stir bar, to which a BPA stock solution (10 mL, 0.1 mM) was added. The mixture was stirred at room temperature for 10 min, and then filtered on a Whatman filter paper. The residual BPA concentration in the filtrate was measured by UV-Vis. P-CDP was regenerated by soaking in MeOH 10 mL) for 5 min and recovered by filtration. This adsorption/desorption cycle was performed five times to generate the plot shown in FIG. 46. The MeOH washing filtrate from the first cycle was concentrated under vacuum, and the residual solid was dissolved in 10 mL deionized $H_2O$ and measured by UV-Vis to determine the amount of recovered BPA that was adsorbed on the polymer.

Improved Synthesis of P-CDP

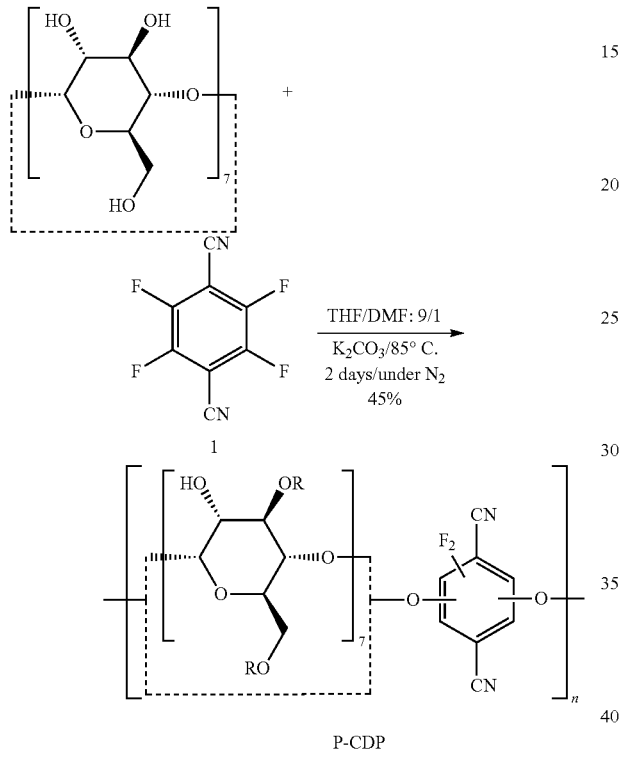

Figure 27:
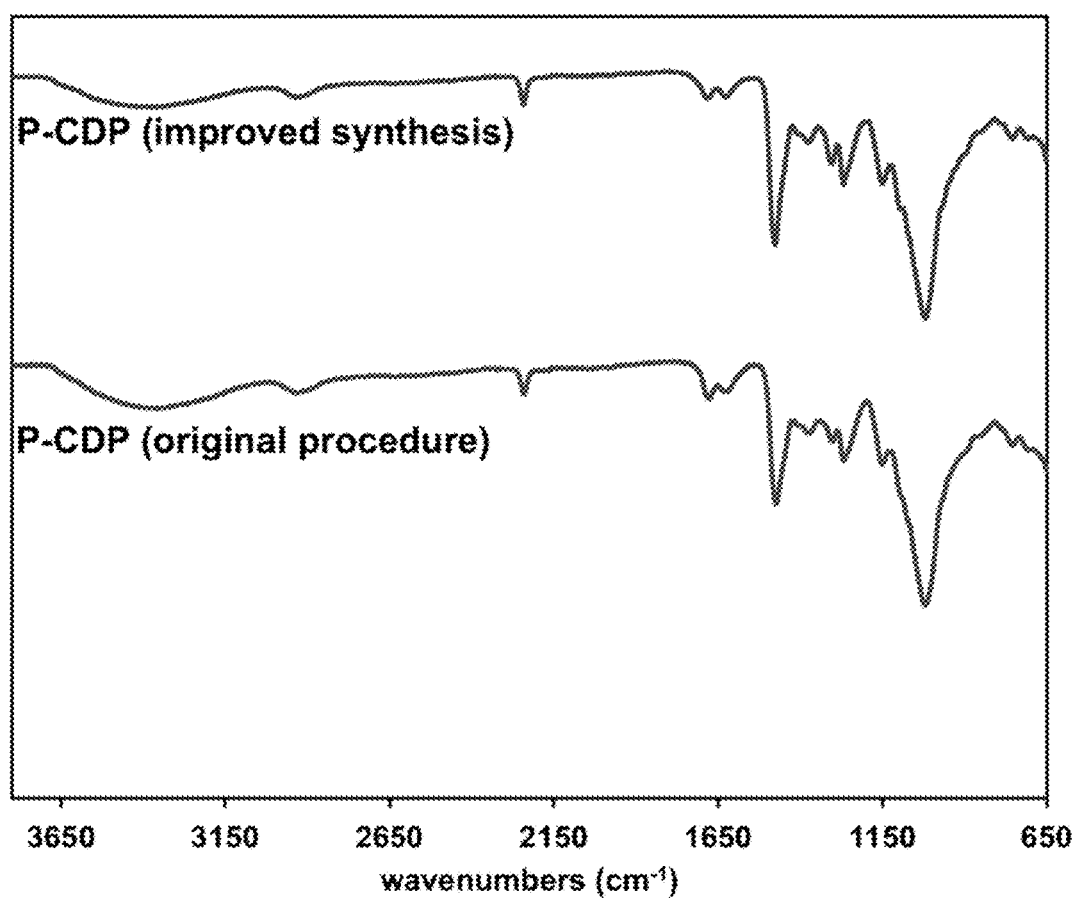
FIG. 27 shows FTIR spectra of P-CDP prepared using different synthetic methods.

A flame dried 20 mL scintillation vial equipped with a magnetic stir bar was charged with β-CD (0.205 g, 0.181 mmol), (1) tetrafluoroterephthalonitrile (0.100 g, 0.515 mmol), and $K_2CO_3$ (0.320 g, 2.32 mmol). The vial was flushed with $N_2$ gas for 5 min, then an anhydrous THF/DMF mixture (9:1 v/v, 8 mL) was added and the vial was sparged with $N_2$ for additional 2-3 min. The $N_2$ inlet was removed and the mixture was placed on a hot stirring plate (85° C.) and stirred at 500 rpm for 2 d. The orange suspension was cooled and then filtered, and the residual $K_2CO_3$ was removed by washing the solid on the filter paper with 1N HCl until $CO_2$ evolution stopped. The recovered light yellow solid was isolated and activated by soaking in $H_2O$ (2×10 mL) for 15 min, THF (2×10 mL) for 30 min and $CH_2Cl_2$ (1×15 mL) for 15 min. Finally, the solid was dried under high vacuum at 77 K in a liquid nitrogen bath for 10 min and then at room temperature for 2-3 days. P-CDP (0.125 g, 45% yield) was obtained as a pale yellow powder and subsequently characterized. Anal. Calcd. for $(C_{42}H_{65}O_{35})_1 \cdot (C_8F_{1.4}N_2)_5 \cdot (CH_2Cl_2)_5 \cdot (H_2O)_{13}$: C, 43.43; H, 4.55; F, 4.96; N, 5.22. Found: C, 43.74; H, 4.67; F, 4.83; N, 5.05. $S_{BET}$ ($N_2$ adsorption, 77K)=118 $m^2g^{-1}$. FT-IR spectra and BPA uptake performance are given below to compare materials derived from this improved procedure with those prepared in neat THF. The FTIR spectras of P-CDP prepared using the original (top) and higher yielding (bottom) improved procedures are shown in FIG. 27.

The instantaneous BPA uptake by P-CDP (1 mg/mL) prepared using the original (left) and higher yielding (right) synthetic procedures ([BPA]$_0$=0.1 mM, 9 mL/min flow rate) is shown in FIG. 75. The data are an average of three measurements and the error bars represent the minimum and maximum uptake.

Model Reaction S1

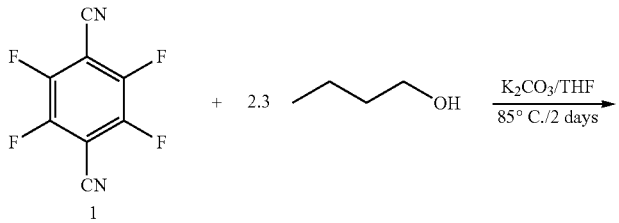

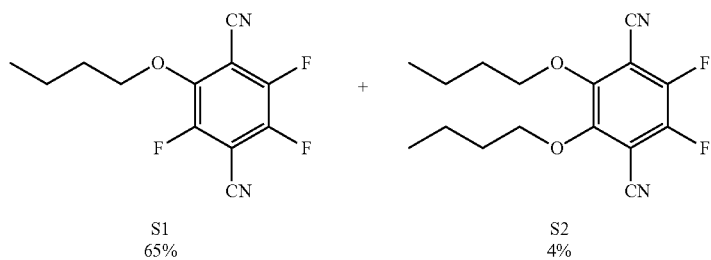

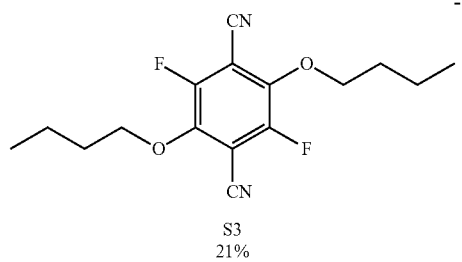

S3
21%

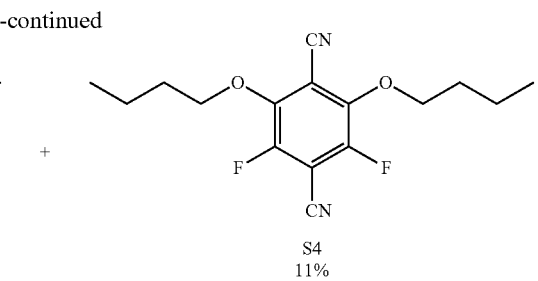

S4
11%

(1) tetrafluoroterephthalonitrile (1.00 g, 5.00 mmol), n-BuOH (1.10 mL, 12.0 mmol) and K$_2$CO$_3$ (2.76 g, 20.0 mmol) were added to a flame-dried 20 mL scintillation vial equipped with a magnetic stir bar. THF (16 mL) was then added and the vial was stirred at 85° C. for 2 d. The suspension was cooled to room temperature and filtered, from which a yellow solid was collected. THF was then removed under vacuum, and the remaining solid was suspended in hexanes, and the suspension was then filtered under vacuum. The filtrate was concentrated and thick yellow oil was isolated as a mixture of the above products, which were characterized by $^1$H, $^{19}$F and $^{13}$C NMR spectroscopy and Direct Analysis in Real Time (DART) mass spectrometry. FIGS. 28-30 show the partial NMR spectra (DMSO-d$_6$ 400 MHz, rt) of the crude product of model reaction 51. FIG. 28 shows the $^1$H NMR, FIG. 29 shows $^{19}$F NMR, and FIG. 30 shows the $^{13}$C NMR. The ESI spectrum of the crude product of model reaction S1 in positive ion mode is shown in FIG. 31.

(1) tetrafluoroterephthalonitrile (1.00 g, 5.00 mmol), n-BuOH (1.80 mL, 19.7 mmol) and K$_2$CO$_3$ (3.50 g, 25.3 mmol), THF (16 mL) were combined in a flame-dried 20 mL scintillation vial equipped with a magnetic stir bar. The mixture was stirred at 85° C. for 2d. The suspension was filtered, and the filtrate was collected and concentrated under vacuum. The crude mixture, which was collected from the filtrate, was then suspended in hexanes, and the suspension was then filtered under vacuum. The filtrate was concentrated and the resulting viscous yellow oil was isolated and subsequently characterized by $^1$H NMR spectroscopy. FIG. 76 shows the partial $^1$H NMR spectrum (DMSO-d$_6$, 400 MHz, rt) of the crude product of model reaction S2.

Model Reaction S2

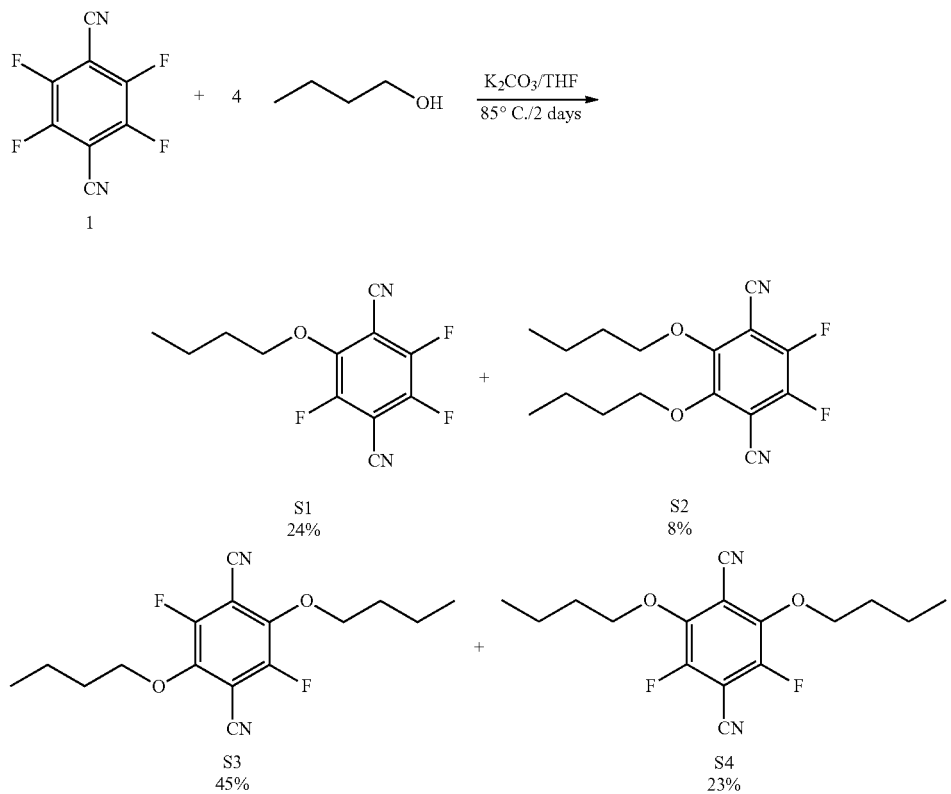

Model Reaction S3

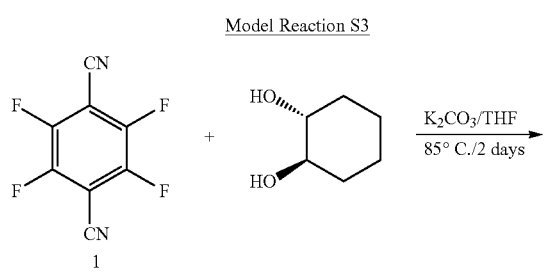

(1) tetrafluoroterephthalonitrile (200 mg, 1.00 mmol), trans-cyclohexane-1,2-diol (116 mg, 1.00 mmol) and $K_2CO_3$ (280 mg, 2.03 mmol) were added to a dry 20 mL scintillation vial. THF (16 mL) was then added and the mixture was stirred at 85° C. for 2 d. The mixture was filtered and then concentrated under vacuum. The crude yellow solid was characterized by $^1$H NMR as shown in FIG. 29, which revealed that the mono substituted product S5 was formed exclusively as shown in FIG. 77.

Competition Substitution Model Reaction S4

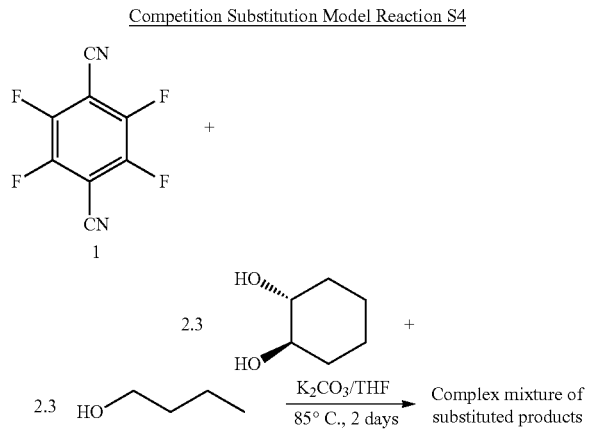

(1) tetrafluoroterephthalonitrile (200 mg, 1.00 mmol), trans-cyclohexane-1,2-diol (270 mg, 2.32 mmol), n-BuOH (0.213 mL, 2.33 mmol) and $K_2CO_3$ (610 mg, 4.41 mmol) were added to a dry 20 mL scintillation vial. THF (16 mL) was then added and the mixture was stirred at 85° C. for 2 d. Aliquots of the reaction were taken at certain intervals (4 h, 6 h, 24 h, and 2 d), which were filtered and concentrated under vacuum. The crude yellow solid was dissolved in DMSO-$d_6$ and characterized by $^1$H NMR spectroscopy. FIG. 78 shows the $^1$H NMR spectra (DMSO-$d_6$, 400 MHz, rt) of aliquots of the competition substitution model reaction S4 collected at various reaction times.

Three additional cyclodextrin polymers based on crosslinkers with increased fluorine content were synthesized under conditions slightly modified from those used to prepare the P-CDP described herein. Decafluorobiphenyl was used as the crosslinker for two materials, LX-105 (Scheme 1) and LX-113 (Scheme 2). LX-113 was synthesized using a higher reaction temperature compared to LX-105 and employed different solvents (a mixture of tetrahydrofuran (THF) and N,N-dimethylformamide (DMF) for LX-113 and N-methyl-2-pyrrolidone (NMP) for LX-105). These reaction conditions each provided polymers comprised of β-cyclodextrin crosslinked by fluorinated biphenyl groups, albeit with different surface area, fluorine content, and PFOA uptake (see below). LX-91 was synthesized under similar conditions as LX-113 but employed a different crosslinker, octafluoronaphthalene (Scheme 3).

Scheme 1. Synthesis of LX-105

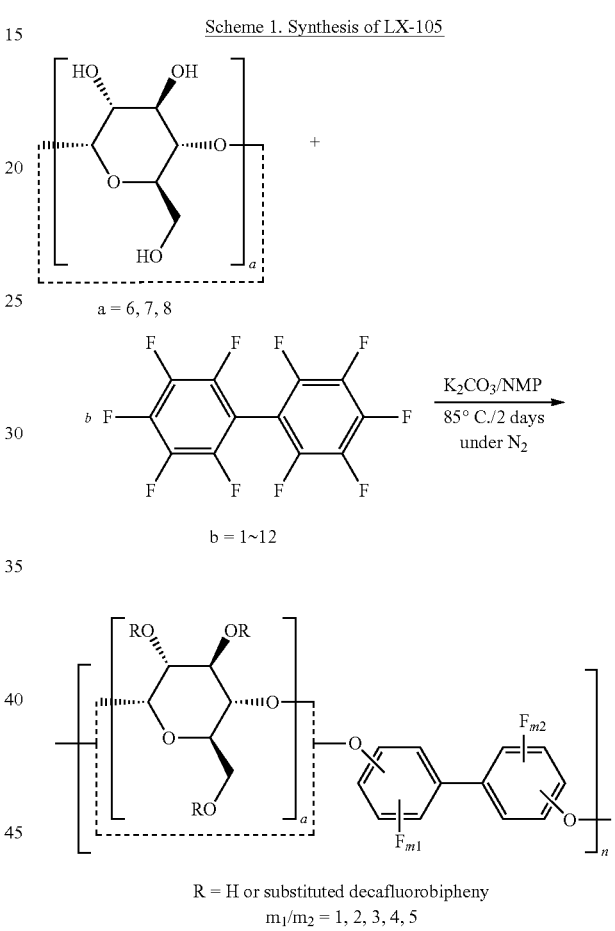

Scheme 2. Synthesis of LX-113

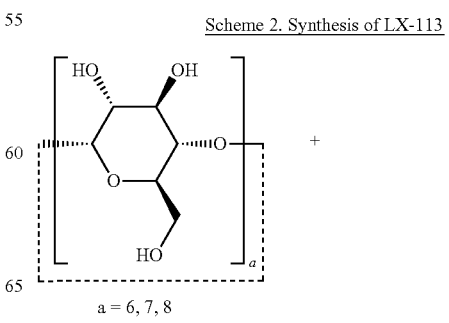

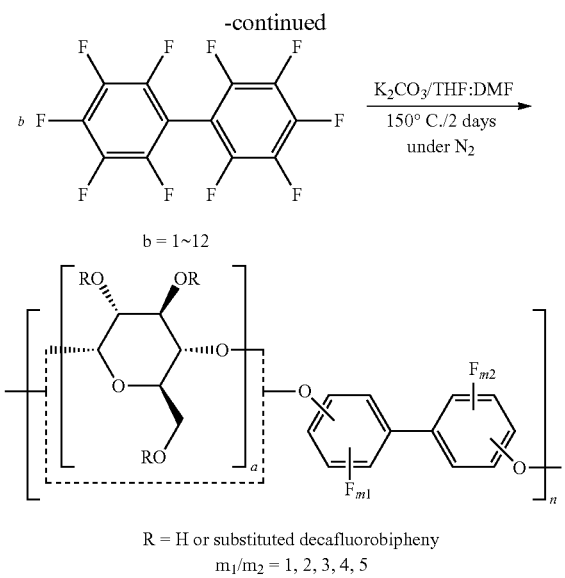

b = 1~12

R = H or substituted decafluorobipheny
$m_1/m_2$ = 1, 2, 3, 4, 5

Scheme 3. Synthesis of LX-91

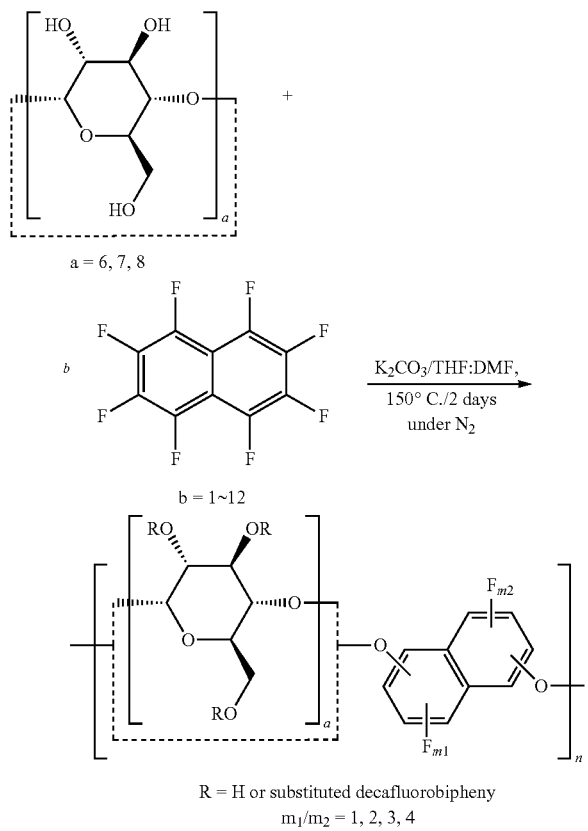

b = 1~12

R = H or substituted decafluorobipheny
$m_1/m_2$ = 1, 2, 3, 4

Each polymer sample was isolated from the reaction mixture by filtration, washed with solvents, and dried under vacuum. The surface area ($S_{BET}$) of each sample was characterized by $N_2$ adsorption performed at 77 K (Table 1). The fluorine content of each sample was measured by combustion analysis. Notably, both LX-91 and LX-105 provided surface areas that approach that of the P-CDP as well as increased fluorine content. Also, LX-113 did not exhibit permanent porosity, yet it had the highest fluorine content.

Identity, BET surface area ($S_{BET}$), and fluorine content of each polymer sample are shown in Table 13, below.

TABLE 13

| Sample | crosslinker | $S_{BET}$ (m²/g) | fluorine content (%) |
|---|---|---|---|
| P-CDP | tetrafluoroterephthalonitrile | 263 | 9.66* |
| LX-91 | octafluoronaphthelene | 169 | 13.50 |
| LX-105 | decafluorobiphenyl | 140 | 24.00 |
| LX-113 | decafluorobiphenyl | 0 | 31.59 |

The ability of each polymer to sequester perfluorooctanoic acid (PFOA), a model for perfluorinated compound pollutants in water, was evaluated using liquid chromatography mass spectrometry. Each polymer (10 mg/L) was introduced to a water sample containing PFOA (1 μg/L) for 4 days, after which an aliquot of the water sample was removed and the remaining concentration measured as shown in FIG. 83. The four-day contact time was chosen to characterize the equilibrium uptake of the PFOA. The PFOA uptake of each polymer ranged from poor (~10% for P-CDP) to high (100% for LX-113), which appears correlated to the fluorine content of each polymer. A time-dependent study of this behavior for LX-113 and P-CDP indicates that the excellent PFOA uptake of LX-113 is nearly complete after 15 hours and confirms the low uptake of P-CDP under the same conditions as shown in FIG. 84. Although this time scale is significantly slower than the rapid uptake of other pollutants observed for the P-CDP, as discussed above, it is conceivable that a high-fluorine content, high surface area variant of LX-113 might adsorb PFOA much more quickly.

Supported Porous Cyclodextrin Materials

The porous cyclodextrin polymer materials of the present disclosure can also be prepared on a support material, for example covalently bonded, adhesively bonded, or mechanically attached to a support such as a fibrous substrate. The support material can be any material that has one or more hydroxyl groups that can form a covalent bond with a crosslinking agent. For example, one end of a crosslinking agent is covalently bound to the substrate material and another end of the crosslinking agent is covalently bound to a glucose unit of a cyclodextrin. It is desirable that the support material not dissolve (e.g., to an observable extent by, for example, visual inspection, gravimetric methods, or spectroscopic methods) in aqueous media. Examples of support materials include, but are not limited to, polymer materials (e.g., acrylate materials, methacrylate materials, styrenic materials, polyester materials, nylon materials, and combinations thereof) or inorganic materials (e.g., silicates, silicones, metal oxides such as alumina, titania, zirconia, and hafnia, and combinations thereof). In various examples, the polymer materials are homopolymers, copolymers, or resins (e.g., resins comprising polymeric materials). The support material can be in the form a fiber, cloth, particulate (e.g., a powder), or a solid surface. In some embodiments, the fibrous substrate is a cellulosic substrate. Cellulosic substrates can comprise any suitable form of cellulose, such as cellulose derived from plant sources such as wood pulp (e.g., paper or paper fibers), cotton, regenerated cellulose, modified cellulosics such cellulose esters and/or ethers, and the like. The cellulosic substrate can be in the form of a fabric, such as a woven or nonwoven fabric, or as fibers, films, or any other suitable shape, particularly shapes that provide high surface area or porosity. In a particular embodiment, the porous cyclodextrin polymer materials of the present disclosure are bonded to fibers, for example, a cellulosic fiber or a fabric, such as cotton.

Synthesis of P-CDP on Cotton Fibers

Modification of cotton fabrics ("P-CDP@cotton") was accomplished through a nucleophilic aromatic substitution reaction between β-CD and tetrafluoroterephthalonitrile (TFP), using the following exemplary method.

Modification of the cotton fabric was carried out using a procedure similar to that used to prepare P-CDP. A 300 mL pressure vessel equipped with a magnetic stir bar was charged with TFP (2.2684 g, 11.31 mmol) and dry THF (145 mL), and the resulting solution was stirred for 10 minutes. In other flask β-CD (4.2570 g, 3.74 mmol) and $K_2CO_3$ (6.3688 g, 59.91 mmol) were suspended in 25 mL of deionized water and sonicated for 10 minutes, which was then added dropwise into the THF solution. Then 1.429 g of cotton 400 fabric was added to the reaction mixture, and the flask was bubbled with $N_2$ for 5 min. The $N_2$ inlet was removed, the flask was sealed and the mixture was placed on a hot stirring plate (85° C.) and stirred at 500 r.p.m. for 2 days. The resulting orange suspension was cooled and filtered, and the residual $K_2CO_3$ was removed by washing the cotton 400 fabric with 1 N HCl until $CO_2$ evolution stopped. The fabric was isolated from the solid formed and activated by soaking in 200 mL $H_2O$ for 1 day, then washed with methanol using a Soxhlet system for 1 day. The fabric was removed by filtration and dried under high vacuum at room temperature for 1 day, providing 1.472 g of a yellowish fabric. The fabric was characterized by SEM, XPS, and IR spectroscopy as shown in FIGS. 85-88.

The formation of the P-CDP and its grafting to the cotton fabrics are depicted in FIG. 89. As a result of the added mass of the P-CDP on the fabric, the weight of the fabric increases by 13.2%.

The capacity of the modified fabric to sequester bisphenol A (BPA) from aqueous solution was tested to compare the P-CDP@cotton to untreated cotton. FIG. 90 shows a clear difference in the BPA uptake as a function of time, and BPA concentration of the treated fabric in comparison with the untreated one. These data indicate that P-CDP modification of cotton enhances the capacity of the fabric to adsorb BPA by a factor of 10.

The kinetic studies based on the BPA uptake over time are shown in FIG. 90. The graph indicates a good agreement with a pseudo-second order adsorption rate law for the treated fabric and the control. Also the BPA adsorbed in the fabric at equilibrium shows a significant enhancement of the fabric capacity after the P-CDP@cotton compared to 0.37 mg BPA/g of untreated cotton. Two models were fit to the data as shown in FIG. 91. The Langmuir model fits the behavior of the P-CDP@cotton fabric well, yet does not describe the behavior of the control. The Freundlich model better describes the modest BPA uptake of the untreated fabric, which suggests that a more heterogeneous, poorly defined adsorption of the BPA occurs. Calculation of the constants and capacities for the Langmuir and Freundlich models shows higher values for the treated fabric in comparison with the control.

In order to compare the performance of the treated fabric with commercial examples, three commercially available products that uptake pollutants and odors were tested. The performance of the treated fabric, the untreated and commercial materials to uptake gas molecules was evaluated using styrene as a model compound. In these experiments the materials were exposed to a saturated atmosphere of styrene during different periods of time and the amount of the styrene adsorbed by the material was quantified. FIG. 92 shows that the best material to uptake styrene is the P-CDP@cotton, as it has a larger capacity in comparison with the untreated and the commercial materials. Additionally the stability of the P-CDP@cotton was evaluated as shown in FIG. 93. The similar uptake performance over four cycles indicates promise for the use of this modification for durable, long service time application.

Styrene uptake was also evaluated at lower relative vapor pressures. The fabrics were tested in sealed vials with styrene vapor pressures of 850 ppm, after which the quantity of the styrene on the fabric was evaluated the fabric. These experiments provided a maximum uptake of 0.48 mg styrene/g of P-CDP@cotton at 40 min of exposure, which represents an uptake of 43.1% of the total styrene injected in the chamber (850 ppm). In contrast, the uptake at 40 min of the untreated cotton is just 2.6%. As shown in FIG. 94, the use of the P-CDP@cotton can lower the styrene concentration to similar or lower than the maximum levels of styrene accepted by OSHA (600 ppm), unlike the untreated cotton that has a minimal effect on the styrene concentration.

As shown in FIG. 95, a survey of styrene, benzaldehyde and aniline performed to prove that performance of the P-CDP@cotton is general for other gases. From the results, the uptake of the treated fabric is better for the three gases in comparison with the untreated and the commercial materials, nevertheless the differences in uptake for aniline and benzaldehyde is lower due to a most stronger interaction of those gases with the cellulose in cotton.

Micropollutant Removal from Water

Chemicals. 83 micropollutants (MPs) were selected based on their environmental relevance, their previous investigation for adsorption onto activated carbon, and their broad range of physicochemical properties including polarity, charge state, and molecular volume. Detailed information on each MP can be found in FIG. 80. Stock solutions of each chemical were prepared at a concentration of 1 g/L using 100% HPLC-grade methanol with the exception of penciclovir which was prepared in Milli-Q water. The stock solutions were used to prepare two experimental mixes at a concentration of 100 mg/L using Milli-Q water. Mix-A contained all 83 MPs and was used for the kinetics experiments and the instantaneous uptake experiments. Mix-B contained 8 MPs and was used for the isotherm experiments. The stock solutions and the analytical mixes were stored in a freezer at −20° C. and a refrigerator at 4° C., respectively.

Adsorbents. Two adsorbents were investigated in this research: a porous 13-cyclodextrin-containing polymer (P-CDP) synthesized according to a published nucleophilic aromatic substitution method; and a coconut-shell based GAC (CCAC, AquaCarb 1230C, Westates Carbon, Siemens, Roseville, Minn.). To increase the similarity in particle size between the P-CDP and the CCAC and to enhance the adsorption rate of CCAC in isotherm experiments, the CCAC was pulverized with a mortar and pestle until >95% (mass) passed a 74-μm sieve (200 U.S. mesh). The CCAC that remained on the sieve was remixed with the CCAC that passed through the sieve to get an unbiased mixture. The P-CDP and the pulverized CCAC were dried under vacuum in a desiccator for one week and stored in a refrigerator at 4° C.

Kinetics experiments. The adsorption kinetics experiments were performed in 125 ml glass Erlenmeyer flasks with magnetic stir bars. For both P-CDP and CCAC, the experiments were conducted at 23° C. on a multi-position stirrer (VWR) with the stirring rate at 400 revolutions per minute (rpm). The adsorbent dose was 10 mg/L and the MPs were spiked to generate an initial adsorbate concentration of 1 µg/L. The adsorbent and MP doses were selected according to previous research investigating MP adsorption on the same CCAC. To activate the dried adsorbents, 10 mg of adsorbent (P-CDP or CCAC) was added into a 20 ml amber vial with 10 ml Milli-Q water to yield a 1 g/L suspension and then mixed with a vortex mixer (Fisher Scientific) for 30 seconds. The suspension was sonicated for 1 minute to break small aggregates and then stirred on a multi-position stirrer for 30 minutes at 360 rpm. Following the activation procedure, 98 ml of Milli-Q water, 1 ml of Mix-A (100 µg/L), and 1 ml of the activated adsorbent suspension were added to a flask successively. The adsorbent suspension was added after the addition of MPs to simulate the real situation in drinking water treatment. Samples were collected in 8 mL volumes at predetermined sampling times (0, 0.05, 0.17, 0.5, 1, 5, 10, 30, 60, 90, 120 minutes) and filtered with a 0.22 µm PVDF syringe filter (Restek). Control experiments were performed under the same condition with no addition of adsorbent and samples were collected at 120 minutes. All kinetics experiments (including controls) were performed with 5 replicates.

The concentration of MPs on the solid phase was determined by the following equation:

$$q_t = \frac{C_0 - C_t}{C_A}$$

where $q_t$ (mg g$^{-1}$) is the amount of a MP adsorbed on the solid phase at any time t; $C_0$ (ng l$^{-1}$) is the average concentration of a MP in the samples of the control experiments; $C_t$ (ng l$^{-1}$) is the concentration of a MP in the liquid phase at any sample time t; and $C_A$ (mg l$^{-1}$) is the concentration of adsorbent. The uptake rate of each adsorbent can then be described with Ho and McKay's pseudo-second-order adsorption model in a linearized form as the following equation:

$$\frac{t}{q_t} = \frac{t}{q_e} + \frac{1}{k_{obs} q_e^2}$$

where $q_e$ (mg g$^{-1}$) is the amount of a MP adsorbed on the solid phase at equilibrium; and $k_{obs}$ (g mg$^{-1}$ min$^{-1}$) is the rate constant of adsorption. The values for $k_{obs}$ at t=30 minutes were estimated for all MPs and for both adsorbents.

The MP removal efficiency was determined by the following equation:

$$MP\ Removal = \frac{C_0 - C_t}{C_0} \times 100$$

MP Removal was calculated for each of the five replicate experiments and is reported as the average value plus/minus the standard deviation.

Instantaneous uptake experiments. Instantaneous uptake experiments were performed with a 10 ml Luer-Lock tip glass syringe and Whatman 0.2 µm inorganic syringe filters at 23° C. with a constant flow rate of 25 ml/min as described in the preceding. The adsorbents were activated prior to conducting the instantaneous uptake experiments in the same way as was described for the kinetics experiments to generate an activated suspension of each adsorbent at a concentration of 1 g/L. The syringe filters were loaded with adsorbent by passing 0.3 mL of the activated suspension through the inorganic syringe filter to form a thin layer of 0.3 mg of adsorbent on the filter surface. Following loading of the filters with adsorbent, 8 mL of Mix-A (1 µg/L) was pushed through the adsorbent-loaded filter with constant pressure over 20 s. Control experiments were performed in the same way with no adsorbent on the filter to account for losses through the filter itself All instantaneous uptake experiments and controls were conducted in triplicate.

The instant removal of MPs (in %) was determined by the following equation:

$$MP\ Removal = \frac{C_0 - C_I}{C_0} \times 100$$

where $C_0$ (ng l$^{-1}$) is the average concentration of a MP in the samples of control experiments; and $C_I$ (ng l$^{-1}$) is the concentration of a MP in the filtrate. MP Removal was calculated for each of the three replicate experiments and is reported as the average value plus/minus the standard deviation.

Analytical methods. Quantification of analytes from kinetics and instantaneous uptake experiments was performed by high-performance liquid chromatography (HPLC) coupled with a quadrupole-orbitrap mass spectrometer (MS) (QExactive, ThermoFisher Scientific).

The analytical method was adopted from one previously reported for ultratrace level screening of polar and semipolar organic chemicals and involved HPLC-MS and on-line solid phase extraction (EQuan Max Plus, ThermoFisher Scientific). Samples were injected at 5 ml volumes and were loaded onto an XBridge (Waters) C-18 Intelligent Speed (2.1 mm×20 mm, particle size 5 µm) trap column. Elution from the trap column and onto an) XBridge (Waters) C-18 analytical column (2.1 mm×50 mm, particle size 3.5 µm) was performed using a gradient pump delivering 200 µl min$^{-1}$ of a water and MeOH mobile phase, each containing 0.1 vol.% formic acid. The HPLC-MS was operated with electrospray ionization in positive and negative polarity modes. The MS acquired full-scan MS data within a mass-to-charge range of 100-1,000 for each sample followed by a data-dependent acquisition of product ion spectra (MS/MS). Analytes were quantified from external calibration standards based on the analyte responses by linear least-squares regression. Limits of quantification for each analyte were determined as the lowest point in the external calibration curve at which at least 8 scans were measured across a chromatographic peak and the most intense MS/MS product ion was still detected. Exact molecular masses, ionization behavior, retention times, and limits of quantification used for the detection and quantification of each analyte are provided in FIG. 81.

Results & Discussion. The following sections describe the major results of the kinetics and instantaneous uptake experiments for the 83 MPs. All of the data are presented in the tables shown in FIG. 82.

Kinetics experiments. The estimated values of $k_{obs}$ for each MP for CCAC and P-CDP are presented in FIG. 82. The $k_{obs}$ describes the rate at which MP uptake is complete (i.e., the rate at which the system reaches equilibrium). This can lead to some misleading values for the magnitude of $k_{obs}$ for MPs that have little or no uptake. For example, 2,4-D is hardly removed by P-CDP, yet the estimated value for $k_{obs}$ is 72.9 g mg$^{-1}$ min$^{-1}$. On the other hand, 2,4-D is removed fairly well by CCAC and the estimated value for $k_{obs}$ is only 11.0 g mg$^{-1}$ min$^{-1}$. The $k_{obs}$ of 2,4-D is greater for the P-CDP, but only because it rapidly reaches an equilibrium condition of no removal. In other cases, little or no removal can lead to negative values of $k_{obs}$ when applying the model of Ho and McKay. Because of this, the $k_{obs}$ for all MPs that removed less than 5% are reported as zero with the estimated value based on the Ho and McKay model given in parentheses. Two MPs were removed to less than 5% for CCAC and 12 MPs were removed to less than 5% for the P-CDP.

To complement the estimated values for $k_{obs}$ and to enable more robust interpretation of uptake kinetics, the % removal for each MP after 5 minutes and 30 minutes for CCAC and P-CDP is provided in FIG. 82. These data provide insight into the extent of uptake at an early phase (5 minutes) and at equilibrium (30 minutes) for each adsorbent. Five groups of removal are defined into which each MP could be binned: group 1 (G1) contains compounds with removal between 80-100%; group 2 (G2) contains compounds with removal between 60-80%; group 3 (G3) contains compounds with removal between 20-60%; group 4(G4) contains compounds with removal between 5-20%; group 5 (G5) contains compounds with no removal.

For P-CDP at 5 minutes, 19 MPs were classified as G1, 13 MPs were classified as G2, 17 MPs were classified as G3, 23 MPs were classified as G4, and 11 were classified as G5. For P-CDP at 30 minutes, 23 MPs were classified as G1, 14 MPs were classified as G2, 16 MPs were classified as G3, 18 MPs were classified as G4, and 12 were classified as G5.

For CCAC at 5 minutes, 3 MPs were classified as G1, 13 MPs were classified as G2, 60 MPs were classified as G3, 5 MPs were classified as G4, and 2 were classified as G5. For CCAC at 30 minutes, 38 MPs were classified as G1, 28 MPs were classified as G2, 15 MPs were classified as G3, 0 MPs were classified as G4, and 2 were classified as G5.

This demonstrates that the P-CDP generally adsorbs more MPs to greater extents faster than CCAC (removal data at 5 minutes). CCAC is less selective and has an overall capacity for MPs that is greater than the P-CDP (removal data at 30 minutes). This latter finding is an artifact of the experimental design in which a fixed mass of adsorbent was used. Since the surface area of CCAC (1160 m$^2$/g) is more than 5 times the surface area of the P-CDP used (218 m$^2$/g), the CCAC sample incorporated more surface area for adsorption. However, the $k_{obs}$ values for 70 of the 71 MPs in G1-G4 for P-CDP at 30 minutes are all greater for P-CDP than CCAC (the exception is fluoxetine). Finally these results highlight nine MPs that are not effectively removed by CCAC that are removed well by P-CDP: albuterol, amphetamine, atenolol, atenolol acid, codeine, hydrocodone, morphine, tramadol and venlafaxine.

Instantaneous uptake experiments. The results of the instantaneous uptake experiments are provided in FIG. 82. A total of 47 MPs had greater instantaneous uptake on the P-CDP than on the CCAC. Remarkably, 35 MPs had instantaneous removal of greater than 80% on the P-CDP (31 of the MPs were greater than 90%) whereas no MPs had instantaneous removal greater than 80% for the CCAC. There were also 14 MPs that were removed to less than 10% for the P-CDP; all of these MPs were previously classified as G5 or G4 MPs in the kinetics experiments. For CCAC, all MPs were removed between 10-80% during the instantaneous uptake experiments, also aligning well with the previous classifications defined for the kinetics experiments.

Exemplary P-CDP Compositions

In some embodiments, the P-CDP is formed by crosslinking cyclodextrin that is selected from the group consisting of α-cyclodextrin, β-cyclodextrin, γ-cyclodextrin, randomly methylated β-cyclodextrin, hydroxypropyl-β-cyclodextrin, hydroxypropyl-γ-cyclodextrin, acetyl-γ-cyclodextrin, chlorotriazinyl-β-cyclodextrin, glucosyl-β-cyclodextrin, maltosyl-β-cyclodextrin, sulfobutyl-β-cyclodextrin, sulfated cyclodextrin, and combinations thereof. In these embodiments, the crosslinker is selected from the group consisting of tetrafluoroterephthalonitrile, octafluoronaphthelene, decafluorobiphenyl, and combinations thereof.

In one embodiment, the P-CDP is formed by crosslinking α-cyclodextrin with tetrafluoroterephthalonitrile. In one embodiment, the P-CDP is formed by crosslinking β-cyclodextrin with tetrafluoroterephthalonitrile. In one embodiment, the P-CDP is formed by crosslinking γ-cyclodextrin with tetrafluoroterephthalonitrile. In one embodiment, the P-CDP is formed by crosslinking randomly methylated β-cyclodextrin with tetrafluoroterephthalonitrile. In one embodiment, the P-CDP is formed by crosslinking hydroxypropyl-β-cyclodextrin with tetrafluoroterephthalonitrile. In one embodiment, the P-CDP is formed by crosslinking hydroxypropyl-γ-cyclodextrin with tetrafluoroterephthalonitrile. In one embodiment, the P-CDP is formed by crosslinking acetyl-γ-cyclodextrin with tetrafluoroterephthalonitrile. In one embodiment, the P-CDP is formed by crosslinking chlorotriazinyl-β-cyclodextrin with tetrafluoroterephthalonitrile. In one embodiment, the P-CDP is formed by crosslinking glucosyl-β-cyclodextrin with tetrafluoroterephthalonitrile. In one embodiment, the P-CDP is formed by crosslinking maltosyl-β-cyclodextrin with tetrafluoroterephthalonitrile. In one embodiment, the P-CDP is formed by crosslinking sulfobutyl-β-cyclodextrin with tetrafluoroterephthalonitrile. In one embodiment, the P-CDP is formed by crosslinking sulfated cyclodextrin with tetrafluoroterephthalonitrile.

In one embodiment, the P-CDP is formed by crosslinking α-cyclodextrin with octafluoronaphthelene. In one embodiment, the P-CDP is formed by crosslinking β-cyclodextrin with octafluoronaphthelene. In one embodiment, the P-CDP is formed by crosslinking γ-cyclodextrin with octafluoronaphthelene. In one embodiment, the P-CDP is formed by crosslinking randomly methylated β-cyclodextrin with octafluoronaphthelene. In one embodiment, the P-CDP is formed by crosslinking hydroxypropyl-β-cyclodextrin with octafluoronaphthelene. In one embodiment, the P-CDP is formed by crosslinking hydroxypropyl-γ-cyclodextrin with octafluoronaphthelene. In one embodiment, the P-CDP is formed by crosslinking acetyl-γ-cyclodextrin with octafluoronaphthelene. In one embodiment, the P-CDP is formed by crosslinking chlorotriazinyl-β-cyclodextrin with octafluoronaphthelene. In one embodiment, the P-CDP is formed by crosslinking glucosyl-β-cyclodextrin with octafluoronaphthelene. In one embodiment, the P-CDP is formed by crosslinking maltosyl-β-cyclodextrin with octafluoronaphthelene. In one embodiment, the P-CDP is formed by crosslinking sulfobutyl-β-cyclodextrin with octafluoronaphthelene. In one embodiment, the P-CDP is formed by crosslinking sulfated cyclodextrin with octafluoronaphthelene.

In one embodiment, the P-CDP is formed by crosslinking α-cyclodextrin with decafluorobiphenyl. In one embodiment, the P-CDP is formed by crosslinking β-cyclodextrin with decafluorobiphenyl. In one embodiment, the P-CDP is formed by crosslinking γ-cyclodextrin with decafluorobiphenyl. In one embodiment, the P-CDP is formed by crosslinking randomly methylated β-cyclodextrin with decafluorobiphenyl. In one embodiment, the P-CDP is formed by crosslinking hydroxypropyl-β-cyclodextrin with decafluorobiphenyl. In one embodiment, the P-CDP is formed by crosslinking hydroxypropyl-γ-cyclodextrin with decafluorobiphenyl. In one embodiment, the P-CDP is formed by crosslinking acetyl-γ-cyclodextrin with decafluorobiphenyl. In one embodiment, the P-CDP is formed by crosslinking chlorotriazinyl-β-cyclodextrin with decafluorobiphenyl. In one embodiment, the P-CDP is formed by crosslinking glucosyl-β-cyclodextrin with decafluorobiphenyl. In one embodiment, the P-CDP is formed by crosslinking maltosyl-β-cyclodextrin with decafluorobiphenyl. In one embodiment, the P-CDP is formed by crosslinking sulfobutyl-β-cyclodextrin with decafluorobiphenyl. In one embodiment, the P-CDP is formed by crosslinking sulfated cyclodextrin with decafluorobiphenyl.

Various embodiments of the present disclosure are provided herein, as follows:

A. A porous polymeric material comprising a plurality of cyclodextrin moieties crosslinked by one or more aryl moieties.

B. A porous polymeric material of embodiment A, wherein at least two of the plurality of the cyclodextrin moieties are crosslinked by two or more aryl moieties.

C. A porous polymeric material of embodiment A, wherein the molar ratio of cyclodextrin moieties to aryl moieties ranges from about 1:1 to about 1:X, wherein X is three times the average number of glucose subunits in the cyclodextrin moieties.

D. A porous polymeric material of embodiment A, wherein the cyclodextrin moieties comprise β-cyclodextrin.

E. A porous polymeric material of any of embodiments A-D, wherein the porous polymeric material is mesoporous.

F. A porous polymeric material of any of embodiments A-E, wherein the porous polymeric material has a surface area of 50 $m^2/g$ to 2000 $m^2/g$.

G. A porous polymeric material of any of embodiments A-F, wherein the cyclodextrin moieties comprise B-cyclodextrin and the ratio of β-cyclodextrin moieties to crosslinking moieties is 1:1 to 60:1.

H. A composition comprising the porous polymeric material of any of embodiments A-G.

I. A composition of embodiment H, further comprising a support material, wherein the porous polymeric material is covalently bonded to the support material.

J. A method of purifying a fluid sample comprising one or more pollutants, the method comprising contacting the fluid sample with the porous polymeric material of any of embodiments A-G or the composition of any of embodiments H-I whereby at least 50 wt. % of the total amount of the one or more pollutants in the fluid sample is adsorbed by the porous polymeric material.

K. A method of embodiment J, wherein the fluid sample flows across, around, or through the porous polymeric material.

L. A method of any of embodiments J-K, wherein the fluid sample is contacted with the porous polymeric material under static conditions for an incubation period and after the incubation period the fluid sample is separated from the porous polymeric material.

M. A method of any of embodiments J-M, wherein the fluid sample is drinking water, wastewater, ground water, aqueous extract from contaminated soil, or landfill leachate.

N. A method of any of embodiments J-L, wherein the fluid sample is in the vapor phase.

O. A method of embodiment N, wherein the fluid sample comprises one or more volatile organic compounds and air.

P. A method of determining the presence or absence of compounds in a fluid sample comprising:
a) contacting the sample with the porous polymeric material of any of embodiments A-G or the composition of any of embodiments H-I for an incubation period;
b) separating the porous polymeric material from a) from the sample; and
c) heating the porous polymeric material from b) or contacting the porous polymeric material from b) with a solvent such that at least a portion of the compounds are the released by the porous polymeric material; and
d) determining the presence or absence of any compounds, wherein the presence of one or more compounds correlates to the presence of the one or more compounds in the sample, or isolating the compounds.

Q. A method of embodiment P, wherein the determining is carried out by gas chromatography, liquid chromatograph, supercritical liquid chromatography, or mass spectrometry.

R. A method of any of embodiments P-Q, wherein the sample is a food or a fragrance and the compounds are volatile organic compounds.

S. A method of embodiment R, wherein the food is milk, wine, fruit juice, or an alcoholic beverage.

T. A method for removing compounds from a fluid sample comprising:
a) contacting the sample with the porous polymeric material of any of embodiments A-G or the composition of any of embodiments H-I for an incubation period such that at least some of the compounds are sequestered in the polymer;
b) separating the porous polymeric material from a) from the sample;
c) heating the porous polymeric material from b) or contacting the porous polymeric material from b) with a solvent such that at least part of the compounds are released by the porous polymeric material; and
d) optionally, isolating at least a portion of the compounds.

U. A method of embodiment T, wherein the sample is drinking water, wastewater, ground water, aqueous extract from contaminated soil, or landfill leachate.

V. A method of embodiment T, wherein the sample is in the vapor phase.

W. A method of embodiment V, wherein the sample comprises one or more volatile organic compounds and air.

X. An article of manufacture comprising the polymeric material of any of embodiments A-G or the composition of any of embodiments H-I.

Y. An article of manufacture of embodiment X, wherein the article of manufacture is protective equipment.

Z. A method of preparing the porous polymeric material of embodiment A, comprising reacting one or more cyclodextrins with at least an equimolar amount of one or more aryl fluorides in the presence of a base.

AA. A method of embodiment Z, wherein the molar ratio of cyclodextrin to aryl fluoride ranges from about 1:1 to about 1:X, wherein X is three times the average number of glucose subunits in the cyclodextrin.

BB. A method of any of embodiments Z-AA, wherein the cyclodextrin is selected from the group consisting of α-, β-, and γ-cyclodextrin, or derivatives thereof.

CC. A method of embodiment BB, wherein the cyclodextrin is β-cyclodextrin.

DD. A method of any of embodiments Z-CC, wherein the aryl fluoride is selected from the group consisting of tetrafluoroterephthalonitrile, decafluorobiphenyl, octafluoronaphthalene, and combinations thereof.

EE. A method of embodiment DD, wherein the aryl fluoride is tetrafluoroterephthalonitrile.

FF. A method of embodiment DD, wherein the aryl fluoride is decafluorobiphenyl.

GG. A method of any of embodiments Z-FF, wherein the molar ratio of cyclodextrin to aryl fluoride is about 1:3.

HH. A method of preparing the composition of embodiment H, comprising reacting one or more cyclodextrins with at least an equimolar amount of one or more aryl fluorides in the presence of a base and a cellulosic substrate.

II. A method of embodiment HH, wherein the cellulosic substrate comprises cotton.

JJ. A method of embodiment HH, wherein the cellulosic substrate comprises a cotton fabric.

KK. A method of any of embodiments HH-JJ, wherein the molar ratio of cyclodextrin to aryl fluoride ranges from about 1:1 to about 1:X, wherein X is three times the average number of glucose subunits in the cyclodextrin.

LL. A method of any of embodiments HH-KK, wherein the cyclodextrin is selected from the group consisting of α-, β-, and γ-cyclodextrin, or derivatives thereof.

MM. A method of embodiment LL, wherein the cyclodextrin is γ-cyclodextrin.

NN. A method of any of embodiments HH-MM, wherein the aryl fluoride is selected from the group consisting of tetrafluoroterephthalonitrile, decafluorobiphenyl, octafluoronaphthalene, and combinations thereof.

OO. A method of embodiment NN, wherein the aryl fluoride is tetrafluoroterephthalonitrile.

PP. A method of embodiment NN, wherein the aryl fluoride is decafluorobiphenyl.

QQ. A method of any of embodiments HH-PP, wherein the molar ratio of cyclodextrin to aryl fluoride is about 1:3.

Exemplary Uses

The following examples are presented to illustrate the present disclosure. It is not intended to be limiting in any manner. While the description provides specific examples of the present disclosure, those skilled in the art will recognize that routine modifications to these embodiments can be made which are intended to be within the scope of the present disclosure.

In an aspect, the present disclosure provides uses of the porous polymeric material. The described cyclodextrin polymer formulations rapidly remove chemical contaminants, micropollutants, and other contaminants from both liquid and gas phases. For example, the porous polymeric material can be used in water purification applications, food analysis applications, and remediation applications.

In some examples, the P-CDP is used in water treatment applications including in water filtration, purification, treatment or conditioning systems or processes, used in commercial, domestic, or municipal applications. These applications include municipal water treatment, point-of-use or other domestic filtration systems, water conditioning for businesses in the beverage, pharmaceutical, food service, hospital and health care industries. The P-CDP can be deployed in filters, columns, or other filtration mechanisms. In an alternative formulation, the adsorbent will be deployed as a chemically bonded coating on a fibrous material (e.g., cloth or membrane filter).

One of the most pressing problems in drinking water treatment is that chlorine, which is used to prevent microbial proliferation, reacts with naturally occurring organic compounds to produce toxic chlorination byproducts. In some examples, the P-CDP is used to adsorb chlorination byproducts. Almost all water treatment plants struggle to keep these chlorinated byproducts below limits set by the EPA. The P-CDP may remove many of these chlorination byproducts and/or the natural organic matter precursors.

In some examples, the P-CDP is used in the removal of fluorinated organic compounds (FOCs) from contaminated water in industrial, agricultural, military, or domestic installations. The P-CDP can be deployed in filters, columns, stagnation pools, or as a chemically bonded coating on a fibrous material (e.g., cloth or membrane filter).

In some examples, the P-CDP is used in point-of-use filtration. Point-of-use filtration is a large business in the US, with brand names such as Brita® and PUR and products such as batch water pitchers and continuous flow systems that attach to sinks. The P-CDP removes organic contaminants far more effectively and rapidly than the activated carbons used in these products. Point-of-use filtration is also used in the food industry to allow breweries and other food manufacturers to transform municipal water supplies into water sources that meet their needs. Point-of-use filtration is also important in the developing world, where this material might be used to remove pesticides from well water or other sources of contaminated water.

In some examples, the P-CDP is used in wastewater treatment systems or processes, including industrial, agricultural, municipal, military, or household installations. Once used in homes, factories, or for agriculture, water is contaminated with, for example, surfactants, industrial organic chemicals, dye stuffs, pesticides, and pharmaceuticals. This water is treated in wastewater treatment plants, but many compounds are not removed by this process, leading to so-called "emerging organic contaminants." The P-CDP rapidly removes many of these contaminants from water, including those not currently removed by existing methods. The P-CDP can be deployed in filters, columns, stagnation pools, or as a chemically bonded coating on a fibrous material (e.g., cloth or membrane filter).

In some examples, the P-CDP is used in environmental remediation applications including the removal by adsorption of contaminants from environmental media such as soil, groundwater, sediment or surface water. Many areas that are heavily contaminated from industrial pollution from many years ago contain high concentrations of organic compounds known as polychlorinated biphenyls (PCBs) and polybrominated aromatics (often used as flame retardants), and many other organic contaminants. Based at least in part on the speed of organic contaminant removal demonstrated by this material it is expected that it can be used to remove these compounds from contaminated soil. The P-CDP can be deployed in on-site or off-site systems through pump and treatment filtration methods, containment pools or the direct application of the polymer material to contaminated media in packets, membranes, or as a chemically-bonded coating on a fibrous material (e.g., cloth or membrane filter).

In some examples, the P-CDP is used in food science and fragrance applications. Food scientists spend significant effort and expense to quantify the presence of various volatile organic flavor components in milk, wine, orange juice, etc. This analysis can be done using solid-phase extraction, e.g., using SPME (Solid-Phase MicroExtraction), in which a sorbent is held in the headspace over the sample, where it adsorbs the volatile compounds (e.g. organics) from a liquid or a vapor phase, and is then connected to analysis equipment (e.g., gas chromatography/mass spectrometry). Conventional SPME materials require 10-30 minutes of contact time with the sample to achieve enough signal for analysis. Based on at least the rapid uptake of these materials, P-CDP significantly reduces the required contact time, e.g., to just a few seconds, allowing rapid analysis, and potentially, real-time analysis, of food samples during their manufacture or processing. In some examples, the P-CDP is used to test the composition of foods, beverages, soils, water samples, or the breath, urine, blood, stool, mucus, or other samples collected from humans or animals.

In some examples, the P-CDP is used in personal protective equipment applications including respiratory equipment to protect workers or soldiers operating in environments with, for example, organic contaminants or nerve agents. The P-CDP removes volatile organic compounds (VOCs) or other airborne contaminants in gas phase by vapor extraction through filters, respirators, protective clothing or as a chemically bonded coating on a fibrous material (e.g., cloth or membrane filter). The P-CDP can also be used in other air treatment applications, including industrial and consumer applications for removing objectionable odors from the air.

In some examples, the P-CDP is used in odor-reducing fabrics (e.g., cotton fabric that has been treated with cyclodextrin polymer formulations), including clothing constructed from such functionalized fabrics to remove odors (e.g., in clothing for hunting, camping, manual labor, or exercise) or contaminants (e.g., curtains that remove VOCs or other airborne contaminants from the vapor phase in the home or workplace).

In some examples, the P-CDP is used in enantioselective separation applications including the analytical or preparative separation of chemical mixtures (e.g., mixtures of compounds, constitutional isomers, and/or stereoisomers) in pharmaceutical, fine chemical, agricultural, analytical service, research, or other industries. Most pharmaceutical agents exist as so-called "left-handed" and "right-handed" forms, which are mirror images of one another. These compounds are known as "enantiomers". These enantiomers exhibit different biological activity—in extreme cases one form might have the desired effect and the other form might be toxic. Therefore, it is very important to be able to separate these forms, both to test them individually and to administer the desired form to patients. Chromatography is sometimes used for this purpose, in which the mixture of enantiomers are separated by passing them through a column packed with separation media. These columns are quite expensive (e.g., $500-$1000 each), despite containing only a very small amount of the separation medium. P-CDP deployed as a chromatographic stationary phase provides desirable performance in this application.

Exemplary Methods of Use

A nucleophilic aromatic substitution reaction is used to crosslink β-CD with a rigid aromatic group, providing the first mesoporous, high surface area β-CD organic polymer. This material combines the desirable molecular recognition properties and hydrophilicity of β-CD with the high surface area of ACs. β-CD can encapsulates pollutants to form well-defined host-guest complexes, but previously-produced, crosslinked β-CD polymers have low surface areas and poor removal performance compared to conventional ACs. The present invention includes, in various embodiments, crosslinked β-CD with rigid aromatic groups, providing the first high surface area, mesoporous β-CD polymer. These can rapidly sequester a variety of organic micropollutants with adsorption 2nd order rate constants 15-200 times greater than ACs and nonporous β-CD adsorbents. β-CD polymers produced according to the present invention can be regenerated several times by washing with alcohol solvents at room temperature with no loss in performance using a mild washing procedure, in contrast to the energy intensive and degradative regeneration procedures required for ACs. Finally, the β-CD polymer of the present disclosure outperformed a leading AC for the instant removal of a complex mixture of organic micropollutants at environmentally relevant concentrations. These findings demonstrate the promise of porous CD-based polymers of the present disclosure for rapid, flow-through water treatment.

In an embodiment, a method of purifying an aqueous sample comprises one or more organic compounds, the method comprising contacting the aqueous sample with a porous polymeric material disclosed herein such that, for example, at least 50% to at least 99% of the one or more pollutants is bound to one or more of the β-cyclodextrin moieties of the porous polymeric material. For example, the aqueous sample is flowed across, around, or through the porous polymeric material. In another example, the aqueous sample contacted with the porous polymeric material under static conditions for an incubation period and after the incubation period the aqueous sample is separated (e.g., by filtration) from the porous polymeric material. The method can be used to purify aqueous samples such as drinking water, wastewater, ground water, aqueous extracts from contaminated soils, and landfill leachates.

In an embodiment, a method of determining the presence or absence of compounds (e.g., organic compounds) in a sample comprises: a) contacting the sample with a porous polymeric material disclosed herein for an incubation period (e.g., 1 minute or less, 5 minutes or less, or 10 minutes or less); b) isolating the porous polymeric material from a) from the sample; and c) heating the porous polymeric material from b) or contacting the porous polymeric material from b) with a solvent (e.g., methanol) such that at least part of the compounds are then released by the porous polymeric material; and d) determining the presence or absence of any compounds, wherein the presence of one or more compounds correlates to the presence of the one or more compounds in the sample, or isolating (e.g., by filtration) the compounds. For example, the determining (e.g., analysis) is carried out by gas chromatography or mass spectrometry. For example, the sample is a food or beverage (e.g., milk, wine, fruit juice (e.g., orange juice, apple juice, and grape juice), or an alcoholic beverage (e.g., beer and spirits)) and the compounds are volatile organic compounds. The porous polymeric material (or a composition comprising the porous polymeric material) can be the extracting phase in a solid phase microextraction (SPME) device.

In an embodiment, a method for removing compounds (e.g., organic compounds) from a sample comprises: a) contacting the sample with a porous polymeric material disclosed herein for an incubation period such that at least some of the compounds are sequestered in the polymer; b) isolating the porous polymeric material from a) from the sample; c) heating the porous polymeric material from b) or contacting the porous polymeric material from b) with a solvent (e.g., methanol) such that at least part of the compounds are released by the porous polymeric material; and d) optionally, isolating at least a portion of the compounds.

A variety of compounds can be involved (e.g., sequestered, detected, and/or isolated) in the methods. The compounds can be organic compounds. The compounds can be desirable compounds such as flavorants (e.g., compounds that impact the palatability of foods) or pharmaceutical compounds (or pharmaceutical intermediates), contaminants (e.g., PCBs, PBAs, etc.), and/or adulterants.

The cyclodextrins are chiral. In an embodiment, a chiral compound is sequestered, detected, and/or isolated. In an embodiment, a chiral column (e.g., a preparative-scale or analytical-scale column is packed with a chiral porous polymeric material or composition comprising chiral porous polymeric material) is used to separate and detect or isolate (or at least significantly enrich the sample in one enantiomer) a single enantiomer of a compound.

In the methods, the porous polymeric material can be regenerated (e.g., for reuse in the methods). For, example, the porous polymeric material is regenerated by heating and/or exposure to solvent (e.g., alcohols such as methanol or ethanol, and aqueous mixtures thereof).

The steps of the methods described in the various embodiments and examples disclosed herein are sufficient to produce the porous polymeric material of the present disclosure. Thus, in an embodiment, the method consists essentially of a combination of the steps of the method disclosed herein. In another embodiment, the method consists of such steps.

In an aspect, the present disclosure provides an article of manufacture comprising one or more porous polymeric material or composition comprising one or more porous polymeric material disclosed herein.

In an embodiment, the article of manufacture is protective equipment. For example, the article of manufacture is clothing comprising one or more porous polymeric material or a composition comprising one or more porous polymeric material (e.g., clothing such as a uniform at least partially coated with the porous polymeric material or composition). In another example, the article is filtration medium comprising one or more porous polymeric material or a composition comprising one or more porous polymeric material. The filtration medium can be used in a gas mask. In an embodiment, the article is a gas mask comprising the filtration medium.

In another embodiment, the article is a solid phase microphase (SPME) extraction device comprising the porous polymeric material (or a composition comprising the porous polymeric material), where the porous polymeric material is the extracting phase the device.

In another embodiment, the article is a device for a solid-phase extraction of polar and semi-polar organic molecules. The device comprises the porous polymeric material (or a composition comprising the porous polymeric material) instead of HLB media (hydrophilic/lypophilic balanced). The article with the P-CDP outperforms the HLB media.

Linear Solvation Energy Relationships (LSERS)

LSER Model. Linear solvation energy relationships (LSERs) are models used to predict the distribution of an organic solute between aqueous and solid phases by using specific solvatochromic parameters. The form of the general LSER equation was developed by Abraham using 5 specific solvatochromic parameters and provided as:

$$\log SP = a\alpha^H + b\beta^H + p\pi^H + rR + vV + c$$

where SP is a response parameter of the solute in a specific solvent system and where the solvatochromic parameters are defined as follows: $\alpha^H$ is the overall or summation solute hydrogen bond acidity; $\beta^H$ is the overall or summation solute hydrogen bond basicity; $\pi^H$ is the combined dipolarity/polarizability descriptor; R is the excess molar refraction (the molar refraction of the solute minus the molar refraction of an alkane of equivalent volume); and V is McGowan's characteristic volume in units of ($cm^3$ $mol^{-1}/100$). The coefficients in the LSER equation ($\alpha$, b, p, r, v and c) can be estimated to describe the response parameter for a particular solute in a particular solvent system.

The LSER model was applied to a dataset that described the affinity (the response parameter) of a set of micropollutants (MPs) to a porous β-cyclodextrin polymer (P-CDP) in an aqueous solution. The form of the LSER then becomes:

$$\log K_\infty = a\alpha^H = b\beta^H = p\pi^H = rR = vV = c$$

where the response parameter, $K_\infty$, represents the affinity coefficient of an organic solute to the adsorbent (P-CDP) at infinite dilution which can be calculated for each micropollutant based on the equilibrium condition achieved with 100 mg/L of P-CDP.

Chemicals, Adsorbents & Analytical methods. The compounds, adsorbent (P-CDP), and analytical method are exactly the same as were described for the kinetics experiments and the instantaneous uptake experiments.

Affinity experiments. Affinity experiments were carried out using a P-CDP dose of 100 mg/L and initial MP concentrations of 1 µg/L per compound. The adsorbent and adsorbate doses were selected based on the results of kinetics experiments. Experiments were performed in 125 ml glass Erlenmeyer flasks with magnetic stir bars at 23° C. on a multi-position stirrer (VWR) with the stirring rate at 400 rpm.

In the affinity experiments, a 10 g/L adsorbent suspension was prepared and activated with the same procedures as described for the kinetics experiments. Aliquots of the activated adsorbent suspension were added to flasks containing a fixed volume of Mix-A (100 µg/L) and Milli-Q water to generate experimental solutions with initial MP concentrations of 1 µg/L per compound and a P-CDP dose of 100 mg/L. Experiments were mixed for 45 minutes to allow the suspension to reach equilibrium with the MPs. Samples were collected in 8 mL volumes at 45 minutes and filtered with a 0.22 µm PVDF syringe filter (Restek). Control experiments were performed under the same conditions with no addition of adsorbent and samples were collected at 45 minutes. Affinity experiments were performed in 5 replicates.

The equilibrium concentration of MPs on the solid phase was determined by the following equation:

$$q_e = \frac{C_0 - C_e}{C_A}$$

where $q_e$ (mg $g^{-1}$) is the amount of a MP adsorbed on the solid phase at equilibrium; $C_0$ (ng $l^{-1}$) is the average concentration of a MP in the samples of the control experiments; $C_e$ (ng $l^{-1}$) is the average concentration of a MP in the liquid phase at equilibrium; and $C_A$ (mg $l^{-1}$) is the concentration of adsorbent. $K_\infty$ can then be determined as:

$$K_\infty = \frac{q_e}{C_e}$$

Training data set. $K_\infty$ values were calculated for 79 MPs and 60 of them used in model training and verification are reported the table found in FIG. 96. The $K_\infty$ values from a representative set of 40 MPs were selected for model training.

Validation data set. Independent of the training data, 20 $K_\infty$ values were used as a validation data set to validate the generated model coefficients.

Solvatochromic Descriptors. The solvatochromix descriptors ($\alpha^H$, $\beta^H$, $\pi^H$, R, V) used to describe the properties of each individual MP were calculated with the software PaDEL-Descriptor developed by the National Singapore University through a group contribution approach. See FIG. 96 for the estimated values of each descriptor.

Multiple Linear Regression. Multiple linear regression (MLR) was performed to develop the equation between the sovatochromic descriptors and the affinity descriptor $K_\infty$ and to estimate the magnitude of the model coefficients. R Studio was used to fit equations and perform the analysis of variance (ANOVA). The regression model was evaluated by p-values. A p-value of the F test that was less than 0.01 indicates that at least one independent variable in the constructed model is useful in the prediction of $K_\infty$ at a 99% significant level. p-values less than 0.1 in ANOVA table indicated that the respective coefficients are non-zero at the 90% significant level. The part of the data set that can be explained by the parameters selected for this model was represented by the coefficient of determination ($r^2$). $r^2$ was also calculated for the validation data set to quantify the goodness of fit of the model predictions.

Reduced Model. Based on the ANOVA table for the full model fitted with all 5 descriptors, one descriptor $\beta^H$ was excluded because of its high p-value and a reduced model with only 4 sovatochromic descriptors ($\alpha^H$, $\pi^H$, R, V) was developed with MLR. ANOVA for the comparison between the full model and reduced model was performed to evaluate whether the descriptor $\beta^H$ can be excluded from the MLR model.

Affinity descriptors were calculated for 79 MPs based on the equilibrium distribution between the aqueous phase and 100 mg/L of P-CDP. A subset of 60 MPs were selected for the model training and validation. All of the data is presented in FIG. 96.

Development of LSER Model. The calculated values of log $K_\infty$ and solvatochromic descriptors for all 60 MPs are presented in FIG. 96. The coefficients of the LSER descriptors were determined with multiple linear regression between the independent variables (LSER descriptors) and dependent variables (log $K_\infty$). The equation generated with the training data set is presented as follows:

$$\log K_\infty = -(2.96 \pm 0.48) + (0.41 \pm 0.27)\alpha^H + (0.01 \pm 0.14)\beta^H +$$
$$(0.18 \pm 0.23)\pi^H + (0.26 \pm 0.21)R + (2.15 \pm 0.22)V$$

The model results including the fit of the training and validation data and the coefficient of determination are presented in FIG. 97. The p-value of the F test for this model was 1.531E-10 indicating that this model can be useful in the prediction of $K_\infty$ at a significance level much higher than 99%. Further, the magnitude of the coefficient of the V term was much higher than the coefficients of the other terms indicating that the McGowan's characteristic volume was the most influential descriptor in the LSER model for P-CDP and contributed the most to the goodness-of-fit of this model ($r^2$). The large and positive value of the coefficient for V indicates that MPs with large volumes tend to have higher affinity to P-CDP, though it is possible that MPs with large volumes will not bind to P-CDP due to other physicochemical properties that do not favor binding to P-CDP. Considering the uniform size of the adsorption sites of the P-CDP, the high selectivity of P-CDP to the actual volume of adsorbates can be explained.

FIG. 97 shows the full LSER model derived using the five LSER descriptors. The blue circle points are the 40 training MPs and the red square points are the 20 validation MPs.

In contrast, the magnitude of the coefficient of the $\beta^H$ suggested that the hydrogen bond basicity was the least significant descriptor in this model. To target a better model with fewer independent descriptors, this statistically insignificant descriptor $\beta^H$ was excluded and a reduced model with only four independent descriptors was generated with the same training data set. The equation is presented as follows:

$$\log K_\infty = -(2.96 \pm 0.47) + (0.41 \pm 0.27)\alpha^H +$$
$$(0.20 \pm 0.17)\pi^H + (0.25 \pm 0.20)R + (2.15 \pm 0.21)V$$

The model results including the fit of the training and validation data and the coefficient of determination are presented in FIG. 98. The p-value of the F test for this model was 2.499E-11 indicating that the significance of the reduced model was improved by excluding the term $\beta^H$ compared with the full model. Further, we determined that at over a 90% significance level, the existence of the term $\beta^H$ flu made no statistical difference on the LSER model for P-CDP. As a result, the LSER between MPs and P-CDP in aqueous solution can be described with a subset of solvatochromic descriptors with $\alpha^H$, $\pi^H$, R and V. The model we developed can be used to predict the affinity of other organic chemicals to the P-CDP based on the estimated values of these four solvatochromic descriptors.

FIG. 98 shows the reduced LSER model derived using the four LSER descriptors. The blue circle points are the 40 training MPs and the red square points are the 20 validation MPs.

The invention claimed is:

1. A mesoporous polymeric material comprising one or more cyclodextrins crosslinked with at least an equimolar amount of one or more aryl fluorides, wherein the aryl fluoride is an aryl fluoride of formula (I):

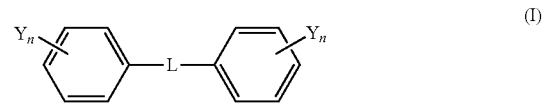

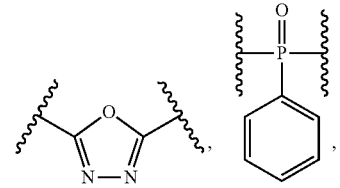

-continued

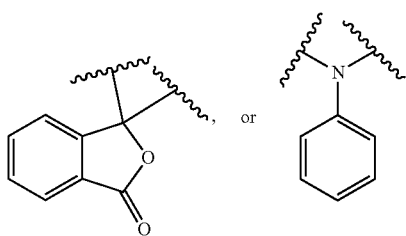 or wherein L is Aryl, —S(O)$_2$—, —C(O)—, bond,
and
wherein each Y is independently H, F, CF$_3$, SO$_3$H, or NO$_2$, with the proviso that n=0-5 and at least 2 of Y are F; or an aryl fluoride of formula (II):

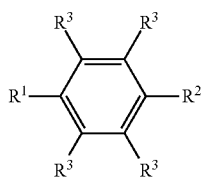

(II)

wherein R$^1$ is F or CN;
R$^2$ is F, CN, or NO$_2$; and
wherein each R$^3$ is independently H, F, or Cl, with the proviso at least 2 of R$^1$, R$^2$, or R$^3$ is F; or an aryl fluoride of formula (III):

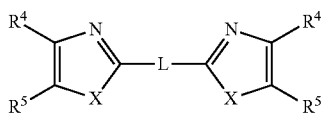

(III)

wherein L is Aryl;
X is O or S;
each R$^4$ is independently F or CF$_3$; and
each R$^5$ is independently F or NO$_2$, with the proviso that at least 2 of R$^4$ and R$^5$ are F; or an aryl fluoride of formula (IV):

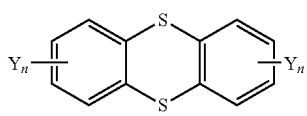

wherein each Y is independently H, F, Cl, CF$_3$, SO$_3$H, or NO$_2$, with the proviso that n=0-5 and at least 2 of Y are F.

2. The mesoporous polymeric material of claim 1, wherein the aryl fluorides of formula (I) are selected from the group consisting of:

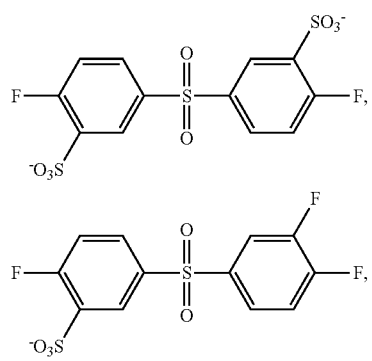

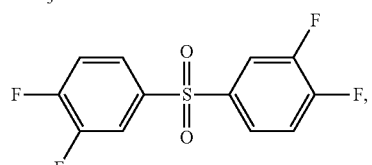

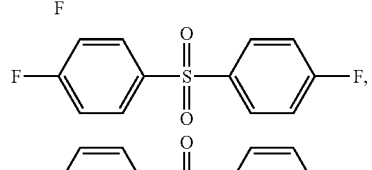

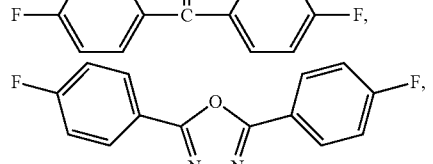

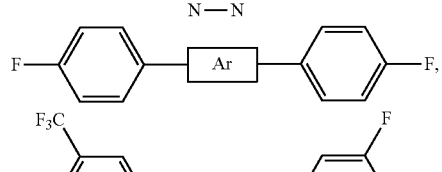

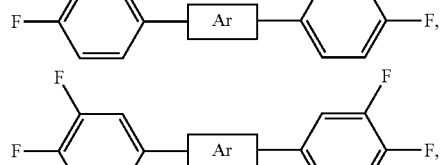

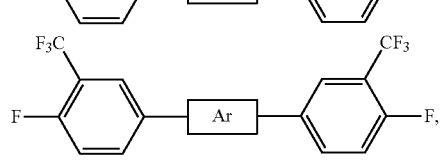

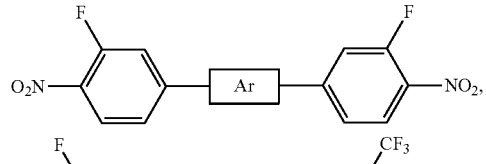

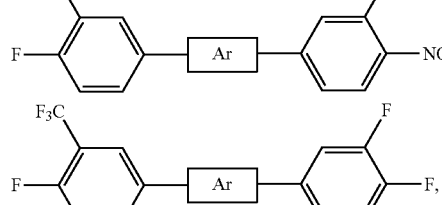

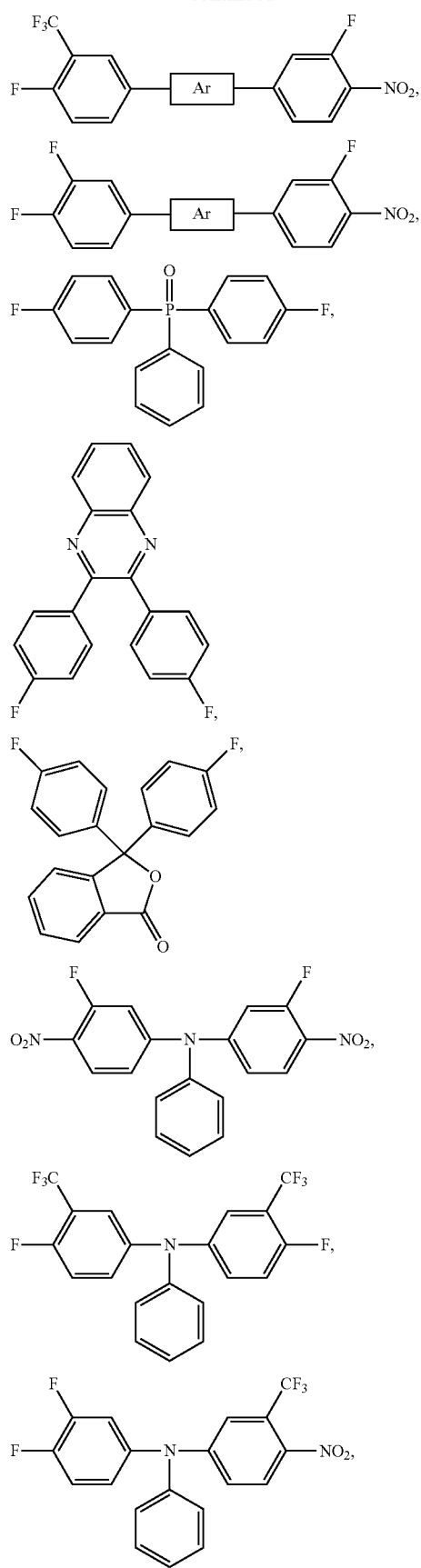
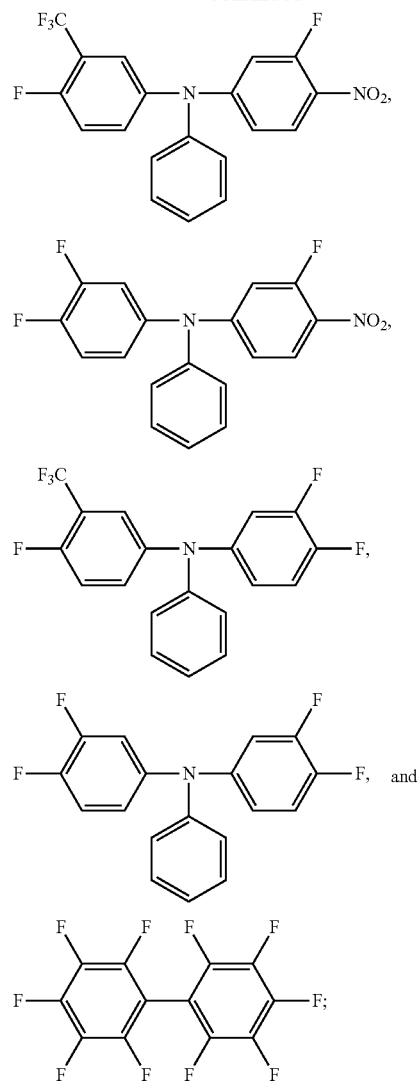
the aryl fluorides of formula (II) are selected from the group consisting of:
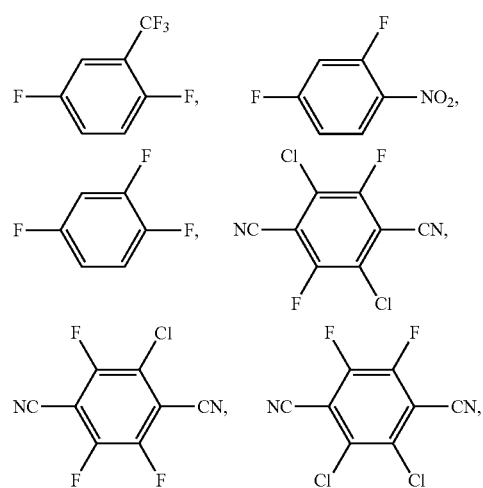

-continued
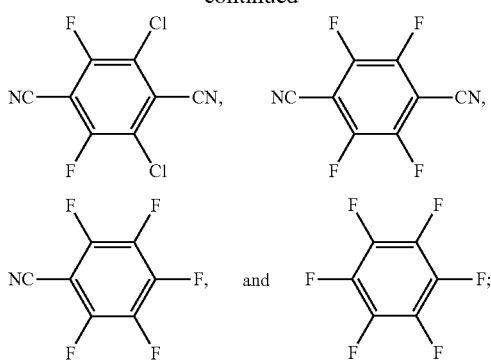
the aryl fluorides of formula (III) are selected from the group consisting of:
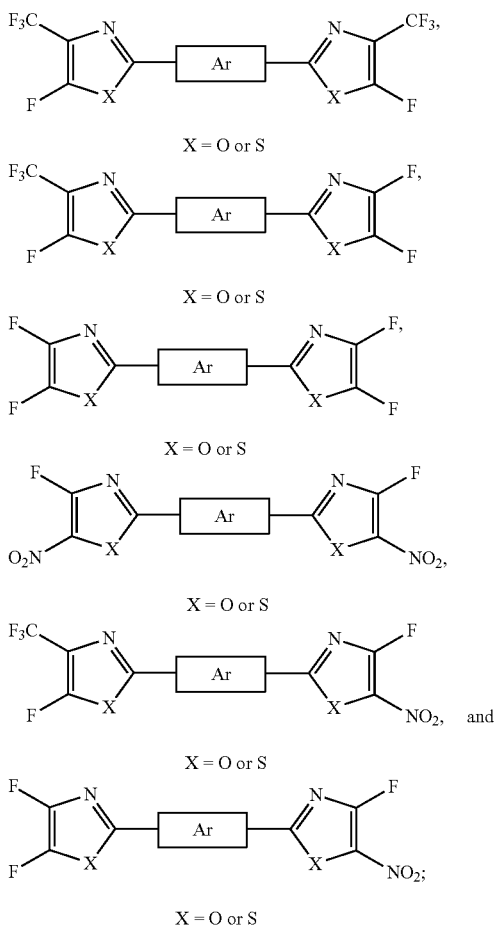
and
the aryl fluoride of formula (IV) is
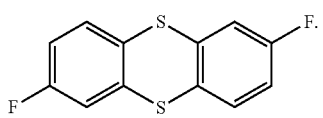
3. The mesoporous polymeric material of claim 1, wherein the aryl fluoride is an aryl fluoride of formula (I) and is selected from the group consisting of:
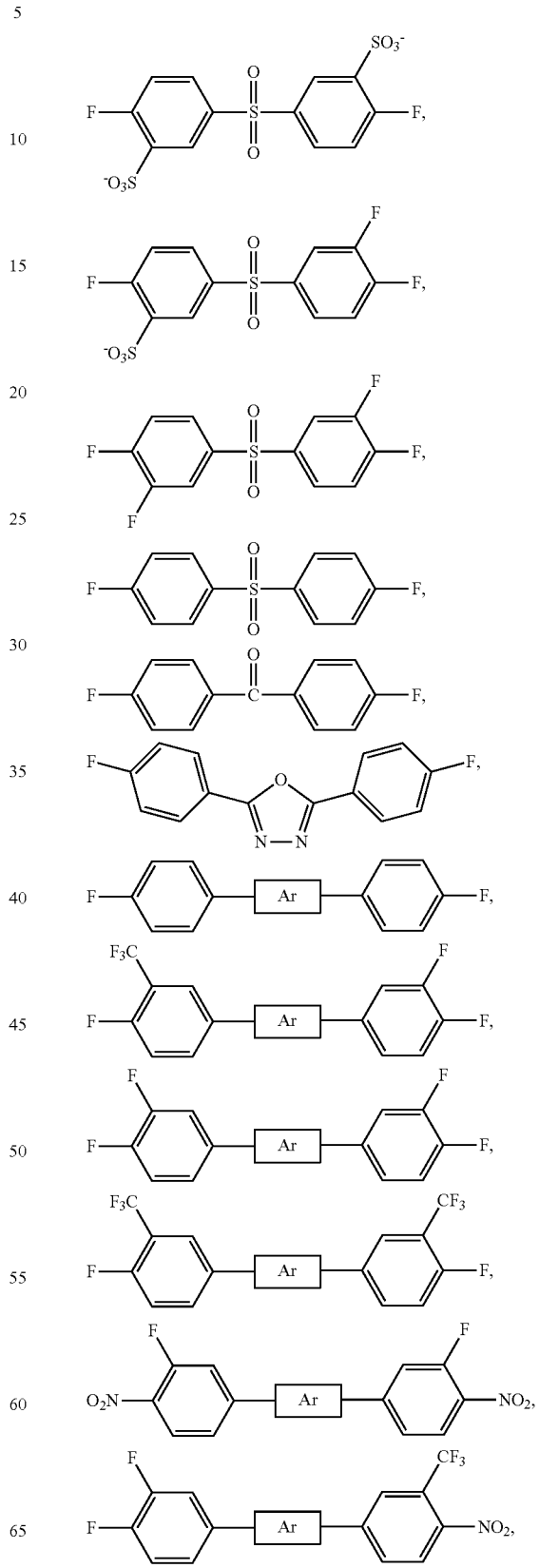

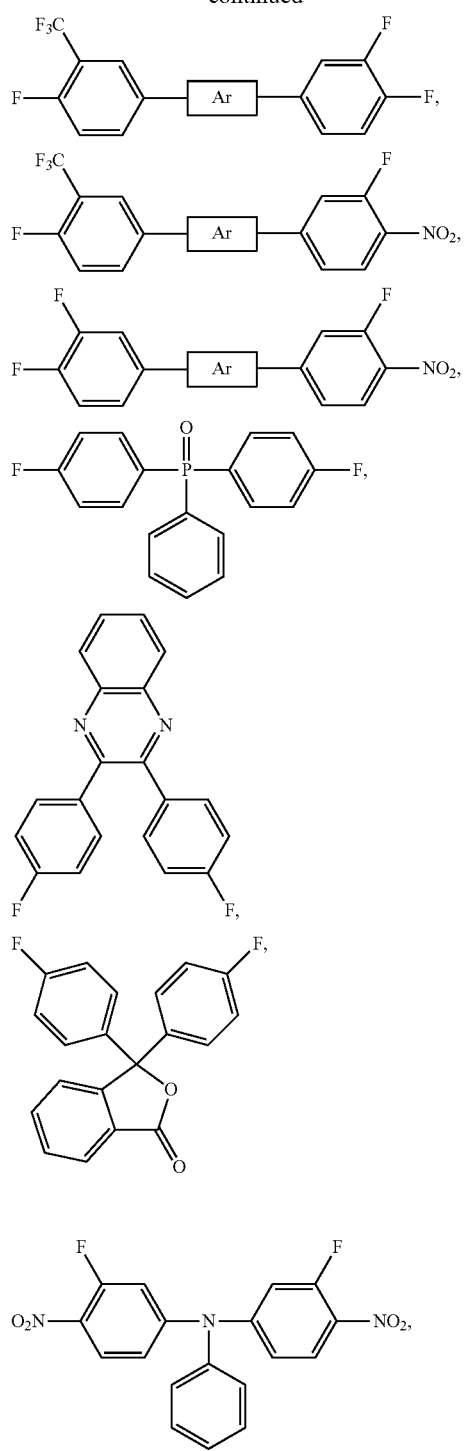
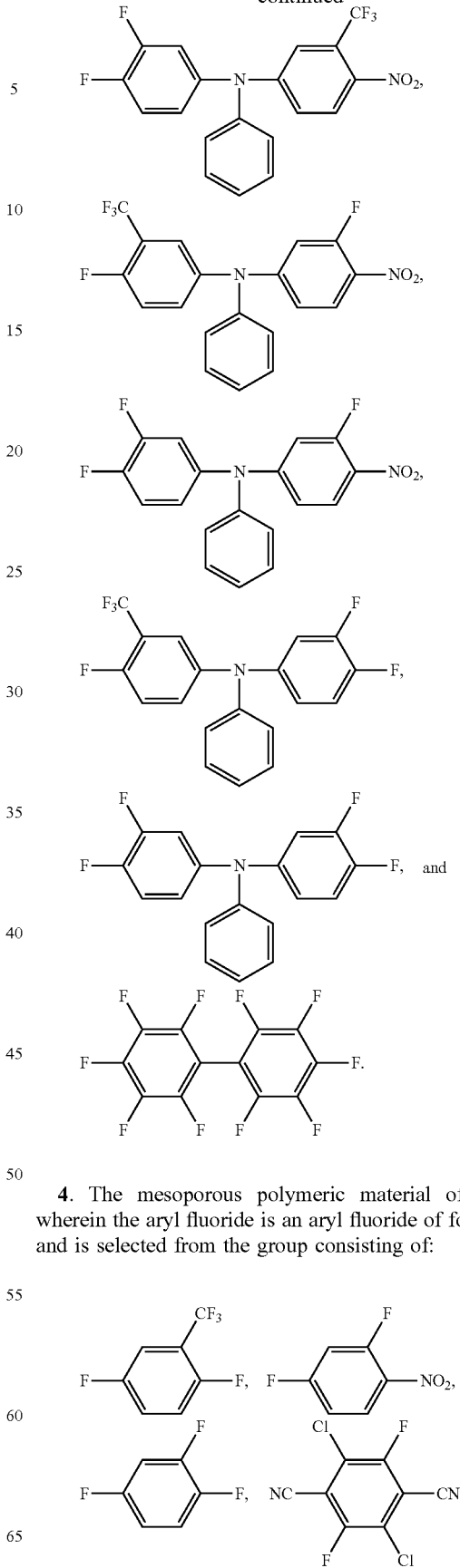
4. The mesoporous polymeric material of claim 1, wherein the aryl fluoride is an aryl fluoride of formula (II), and is selected from the group consisting of:

-continued

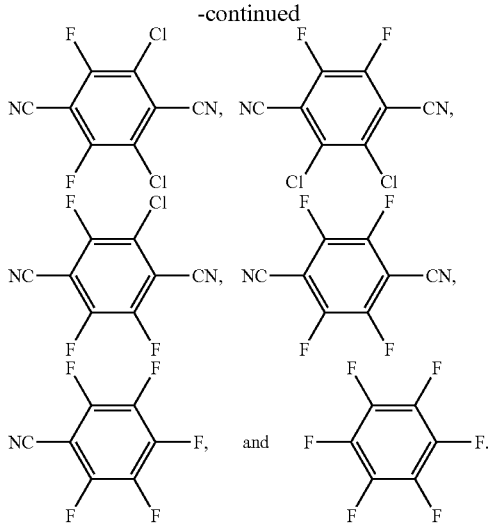

5. The mesoporous polymeric material of claim 1, wherein the aryl fluoride is an aryl fluoride of formula (III), and is selected from the group consisting of:

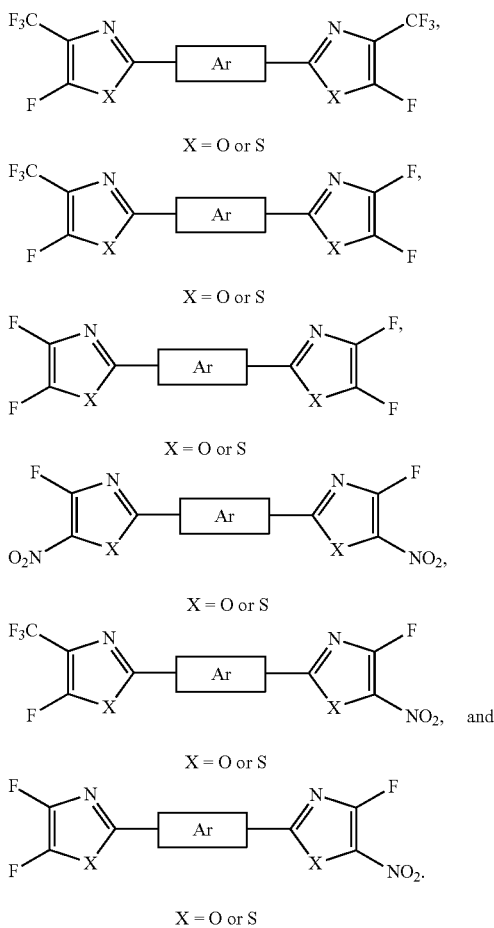

6. The mesoporous polymeric material of claim 1, wherein the molar ratio of cyclodextrin to aryl fluoride ranges from about 1:1 to about 1:X, wherein X is three times the average number of glucose subunits in the cyclodextrin.

7. The mesoporous polymeric material of claim 6, wherein the molar ratio of cyclodextrin to aryl fluoride is about 1:6.

8. The mesoporous polymeric material of claim 1, wherein the cyclodextrin is selected from the group consisting of α-, β-, γ-cyclodextrin, and combinations thereof.

9. The mesoporous polymeric material of claim 1, wherein the cyclodextrin is β-cyclodextrin.

10. The mesoporous polymeric material of claim 2, wherein the cyclodextrin is β-cyclodextrin.

11. The mesoporous polymeric material of claim 3, wherein the cyclodextrin is β-cyclodextrin.

12. The mesoporous polymeric material of claim 4, wherein the cyclodextrin is β-cyclodextrin.

13. The mesoporous polymeric material of claim 5, wherein the cyclodextrin is β-cyclodextrin.

14. The mesoporous polymeric material of claim 9, wherein the aryl fluoride is an aryl fluoride of formula (I), and the molar ratio of β-cyclodextrin to aryl fluoride is about 1:3.

15. The mesoporous polymeric material of claim 9, wherein the aryl fluoride is an aryl fluoride of formula (II), and the molar ratio of β-cyclodextrin to aryl fluoride is about 1:3.

16. The mesoporous polymeric material of claim 9, wherein the aryl fluoride is an aryl fluoride of formula (III), and the molar ratio of β-cyclodextrin to aryl fluoride is about 1:3.

17. A composition comprising the mesoporous polymeric material of claim 1 covalently bonded to a support.

18. The composition of claim 17, wherein the support is a cellulosic substrate.

19. The composition of claim 18, wherein the cellulosic substrate comprises cotton.

20. The composition of claim 19, wherein the cellulosic substrate is in the form of a fabric.

21. A method of purifying a fluid sample comprising one or more pollutants, the method comprising contacting the fluid sample with the mesoporous polymeric material of claim 1, whereby at least 50 wt. % of the total amount of the one or more pollutants in the fluid sample is adsorbed by the mesoporous polymeric material.

22. The method of claim 21, wherein the fluid sample flows across, around, or through the mesoporous polymeric material.

23. The method of claim 21, wherein the fluid sample is contacted with the mesoporous polymeric material under static conditions for an incubation period and after the incubation period the fluid sample is separated from the mesoporous polymeric material.

24. The method of claim 21, wherein the fluid sample is drinking water, wastewater, ground water, aqueous extract from contaminated soil, or landfill leachate.

25. The method of claim 21, wherein the fluid sample is in the vapor phase.

26. The method of claim 25, wherein the fluid sample comprises one or more volatile organic compounds and air.

27. A method of removing one or more compounds from a fluid sample or determining the presence or absence of one or more compounds in a fluid sample comprising: a) contacting the sample with the mesoporous polymeric material of claim 1 for an incubation period; b) separating the mesoporous polymeric material after the incubation period from the sample; and c) heating the porous polymeric material separated in step b), or contacting the porous polymeric material separated in step b) with a solvent, thereby releasing at least a portion of the compounds from the porous polymeric material; and d1) optionally isolating at least a portion of the compounds released in step c); or d2) determining the presence or absence of the compounds released in step c), wherein the presence of one or more compounds correlates to the presence of the one or more compounds in the sample.

28. The method of claim 27, wherein said determining is carried out by gas chromatography, liquid chromatography, supercritical fluid chromatography, or mass spectrometry.

29. The method of claim 27, wherein the sample is a food and the compounds are volatile organic compounds.

30. The method of claim 27, wherein the sample is a perfume or fragrance and the compounds are volatile organic compounds.

* * * * *

UNITED STATES PATENT AND TRADEMARK OFFICE
CERTIFICATE OF CORRECTION

PATENT NO. : 9,855,545 B2
APPLICATION NO. : 15/449206
DATED : January 2, 2018
INVENTOR(S) : Dichtel et al.

It is certified that error appears in the above-identified patent and that said Letters Patent is hereby corrected as shown below:

In the Claims

Column 48, Line 50, to Column 49, Line 15, In Claim 1, should read:

--    (I)

wherein L is Aryl, $-S(O)_2-$, $-C(O)-$, bond,

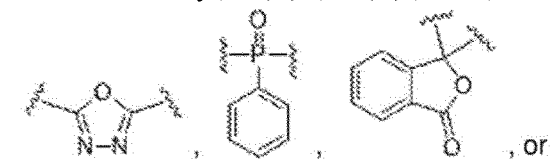, or

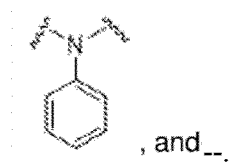, and --.

Signed and Sealed this
Twenty-first Day of August, 2018

Andrei Iancu
*Director of the United States Patent and Trademark Office*